United States Patent
Wasley et al.

(10) Patent No.: US 9,138,427 B2
(45) Date of Patent: *Sep. 22, 2015

(54) PYRROLE INHIBITORS OF S-NITROSOGLUTATHIONE REDUCTASE AS THERAPEUTIC AGENTS

(71) Applicant: N30 Pharmaceuticals, Inc., Boulder, CO (US)

(72) Inventors: Jan Wasley, Guilford, CT (US); Gary J. Rosenthal, Lafayette, CO (US); Xicheng Sun, Broomfield, CO (US); Sarah Strong, Louisville, CO (US); Jian Qiu, Longmont, CO (US)

(73) Assignee: Nivalis Therapeutics, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/204,849

(22) Filed: Mar. 11, 2014

(65) Prior Publication Data

US 2014/0194425 A1  Jul. 10, 2014

Related U.S. Application Data

(63) Continuation of application No. 13/057,171, filed as application No. PCT/US2009/053923 on Aug. 14, 2009, now Pat. No. 8,691,816.

(60) Provisional application No. 61/089,313, filed on Aug. 15, 2008, provisional application No. 61/116,982, filed on Nov. 21, 2008.

(51) Int. Cl.
| | |
|---|---|
| C07D 207/337 | (2006.01) |
| C07D 401/14 | (2006.01) |
| C07D 417/04 | (2006.01) |
| C07D 413/10 | (2006.01) |
| C07D 417/14 | (2006.01) |
| C07D 409/04 | (2006.01) |
| A61K 31/4178 | (2006.01) |
| C07D 207/327 | (2006.01) |
| C07D 401/04 | (2006.01) |
| C07D 401/10 | (2006.01) |
| C07D 401/12 | (2006.01) |
| C07D 403/04 | (2006.01) |
| C07D 403/10 | (2006.01) |
| C07D 403/12 | (2006.01) |
| C07D 403/14 | (2006.01) |
| C07D 405/04 | (2006.01) |
| C07D 405/10 | (2006.01) |
| C07D 405/12 | (2006.01) |
| C07D 409/10 | (2006.01) |
| C07D 409/12 | (2006.01) |
| C07D 409/14 | (2006.01) |
| C07D 413/04 | (2006.01) |
| C07D 413/12 | (2006.01) |
| C07D 413/14 | (2006.01) |
| C07D 417/10 | (2006.01) |
| A61K 31/402 | (2006.01) |
| A61K 31/4025 | (2006.01) |

(52) U.S. Cl.
CPC .......... *A61K 31/4178* (2013.01); *A61K 31/402* (2013.01); *A61K 31/4025* (2013.01); *C07D 207/327* (2013.01); *C07D 207/337* (2013.01); *C07D 401/04* (2013.01); *C07D 401/10* (2013.01); *C07D 401/12* (2013.01); *C07D 401/14* (2013.01); *C07D 403/04* (2013.01); *C07D 403/10* (2013.01); *C07D 403/12* (2013.01); *C07D 403/14* (2013.01); *C07D 405/04* (2013.01); *C07D 405/10* (2013.01); *C07D 405/12* (2013.01); *C07D 409/04* (2013.01); *C07D 409/10* (2013.01); *C07D 409/12* (2013.01); *C07D 409/14* (2013.01); *C07D 413/04* (2013.01); *C07D 413/10* (2013.01); *C07D 413/12* (2013.01); *C07D 413/14* (2013.01); *C07D 417/04* (2013.01); *C07D 417/10* (2013.01); *C07D 417/14* (2013.01)

(58) Field of Classification Search
None
See application file for complete search history.

(56) References Cited

U.S. PATENT DOCUMENTS

| | | |
|---|---|---|
| 3,168,527 A | 2/1965 | Short |
| 3,168,528 A | 2/1965 | Short |
| 3,168,529 A | 2/1965 | Short |
| 3,168,531 A | 2/1965 | Short |
| 3,168,532 A | 2/1965 | Short |
| 3,427,305 A | 2/1969 | Chinn |
| 3,752,826 A | 8/1973 | Carson et al. |
| 4,694,018 A | 9/1987 | Chinn |
| 4,792,568 A | 12/1988 | Auerbach |

(Continued)

FOREIGN PATENT DOCUMENTS

| | | |
|---|---|---|
| CN | 101006052 A | 7/2007 |
| FR | 1393615 | 3/1965 |

(Continued)

OTHER PUBLICATIONS de Belder et al. (May 1994) "Effects of S-nitroso-glutathione in the human forearm circulation; evidence for selective inhibition of platelet activation", *Cardiovasc Res.*, 28(5):691-694.
de Jesus-Berrios et al. (Nov. 2003) "Enzymes that Counteract Nitrosative Stress Promot Fungal Virulence", *Curr. Biol.*, 13:1963-1968.
European Search Opinion issued Dec. 4, 2012 in EP application serial No. 09807383.6. European Search Opinion issued Jul. 22, 2011 in EP application serial No. 09807382.8.
European Search Opinion issued Nov. 29, 2011 in EP application serial No. 09807378.6.

(Continued)

*Primary Examiner* — Kamal Saeed
(74) *Attorney, Agent, or Firm* — Swanson & Bratschun, L.L.C.

(57) ABSTRACT

The present invention is directed to inhibitors of S-nitrosoglutathione reductase (GSNOR), pharmaceutical compositions comprising such GSNOR inhibitors, and methods of making and using the same.

19 Claims, No Drawings

(56) References Cited

U.S. PATENT DOCUMENTS

| | | | |
|---|---|---|---|
| 4,826,869 | A | 5/1989 | Muchowski et al. |
| 5,189,051 | A | 2/1993 | Smith |
| 5,236,943 | A | 8/1993 | Heitsch et al. |
| 5,451,597 | A | 9/1995 | Bovy et al. |
| 5,789,440 | A | 8/1998 | Ellsworth et al. |
| 5,935,990 | A | 8/1999 | Khanna et al. |
| 6,008,368 | A | 12/1999 | Bovy et al. |
| 6,355,812 | B1 | 3/2002 | Ferro et al. |
| 6,391,064 | B1 | 5/2002 | Baudry et al. |
| 6,451,833 | B1 | 9/2002 | Bovy et al. |
| 6,590,119 | B2 | 7/2003 | Ferro et al. |
| 6,809,117 | B2 | 10/2004 | Enikolopov et al. |
| 7,186,716 | B2 | 3/2007 | Wei et al. |
| 7,223,791 | B2 | 5/2007 | Maekawa et al. |
| 8,470,857 | B2 | 6/2013 | Wasley et al. |
| 8,642,628 | B2 | 2/2014 | Wasley et al. |
| 8,673,961 | B2 | 3/2014 | Wasley et al. |
| 8,686,015 | B2 | 4/2014 | Wasley et al. |
| 8,691,816 | B2 | 4/2014 | Wasley et al. |
| 8,846,736 | B2 | 9/2014 | Wasley et al. |
| 8,957,105 | B2 | 2/2015 | Wasley et al. |
| 9,029,402 | B2 | 5/2015 | Wasley et al. |
| 2002/0107408 | A1 | 8/2002 | Ferro et al. |
| 2002/0128205 | A1 | 9/2002 | Stamler et al. |
| 2005/0014697 | A1 | 1/2005 | Stamler et al. |
| 2005/0187166 | A1 | 8/2005 | Stamler et al. |
| 2005/0215613 | A1 | 9/2005 | Teng et al. |
| 2005/0282843 | A1 | 12/2005 | Wang et al. |
| 2006/0148798 | A1 | 7/2006 | Lundstedt et al. |
| 2006/0270628 | A1 | 11/2006 | Das et al. |
| 2006/0293320 | A1 | 12/2006 | Schmistz et al. |
| 2007/0082912 | A1 | 4/2007 | Giblin et al. |
| 2008/0045542 | A1 | 2/2008 | Ronan et al. |
| 2008/0114022 | A1 | 5/2008 | Bala et al. |
| 2010/0286174 | A1 | 11/2010 | Stamler et al. |
| 2011/0136875 | A1 | 6/2011 | Wasley et al. |
| 2011/0136881 | A1 | 6/2011 | Wasley et al. |
| 2011/0144110 | A1 | 6/2011 | Wasley et al. |
| 2011/0144180 | A1 | 6/2011 | Wasley et al. |
| 2012/0245210 | A1 | 9/2012 | Sun |
| 2013/0253024 | A1 | 9/2013 | Wasley et al. |
| 2014/0057957 | A1 | 2/2014 | Sun et al. |
| 2014/0113938 | A1 | 4/2014 | Wasley et al. |
| 2014/0113945 | A1 | 4/2014 | Rosenthal et al. |
| 2014/0155447 | A1 | 6/2014 | Wasley et al. |
| 2014/0194481 | A1 | 7/2014 | Wasley et al. |
| 2015/0126570 | A1 | 5/2015 | Wasley et al. |

FOREIGN PATENT DOCUMENTS

| | | |
|---|---|---|
| GB | 1029915 | 6/1962 |
| GB | 997043 | 6/1963 |
| JP | 39012632 | 7/1964 |
| JP | 2006290791 | 10/2006 |
| WO | WO 2005/000229 | 1/2005 |
| WO | WO 2006/012642 | 2/2006 |
| WO | WO 2006/133926 | 12/2006 |
| WO | WO 2007/009083 | 1/2007 |
| WO | WO 2009/076665 | 6/2009 |
| WO | WO 2009/137071 | 11/2009 |
| WO | WO 2010/019903 | 2/2010 |
| WO | WO 2010/019905 | 2/2010 |
| WO | WO 2010/019909 | 2/2010 |
| WO | WO 2010/019910 | 2/2010 |
| WO | WO 2010/107476 | 9/2010 |
| WO | WO 2013/006635 | 1/2013 |

OTHER PUBLICATIONS

European Search Opinion issued Sep. 23, 2011 in EP application serial No. 09807379.4.
Foster et al. (Apr. 2003) "S-nitrosylation in health and disease", *Trends in Molecular Medicine*, 9(4):160-168.
Gaston et al. (Dec. 1993) "Endogenous nitrogen oxides and bronchodilator S-nitrosolthiols in human airways", *Proc. Natl. Acad. Sci. USA*, 90:10957-10961.
International Preliminary Report on Patentability issued in PCT/US2009/053923 mailed Feb. 24, 2011.
International Preliminary Report on Patentability issued in PCT/US2009/053925 mailed Feb. 24, 2011.
International Preliminary Report on Patentability issued in PCT/US2009/053929 mailed Feb. 24, 2011.
International Preliminary Report on Patentability issued in PCT/US2009/053931 mailed Feb. 24, 2011.
International Preliminary Report on Patentability issued in PCT/US2010/060303 mailed Jun. 28, 2012.
International Preliminary Report on Patentability issued in PCT/US2012/045434 mailed Jan. 16, 2014.
International Search Report and Written Opinion issued in PCT/US2009/053923 mailed Oct. 15, 2009.
International Search Report and Written Opinion issued in PCT/US2009/053925 mailed Oct. 15, 2009.
International Search Report and Written Opinion issued in PCT/US2009/053929 mailed Oct. 15, 2009.
International Search Report and Written Opinion issued in PCT/US2009/053931 mailed Oct. 9, 2009.
International Search Report and Written Opinion issued Sep. 26, 2012 in PCT/US2012/045434.
Jensen et al. (1998) "S-Nitrosoglutathione is a substrate for rat alcohol dehydrognease class III isoenzyme", *Biochem J.*,331:659-668.
Kaposzta et al. (2002) "S-Nitrosoglutathione Reduces Asymptomatic Embolization After Carotid Angioplasty", *Circulation*,106(24):3057-3062.
Kauffman et al. (2001) "QSAR and k-Nearest Neighbor Classification Analysis of Selective Cyclooxygenase-2 Inhibitors Using Topologically-Based Numerical Descriptors", *J. Chem. Inf. Comput. Sci*, 41(6):1553-1560.
Khanna et al. (1997) "1,2-Diarylpyrroles as Potent and Selective Inhibitors of Cyclooxygenase-2", *J. Med. Chem*, 40 (11):1619-1633.
Lipton et al. (Sep. 2001) "S-Nitrosothiols signal the ventilatory response to hypoxia", *Nature*, 413:171-174.
Liu et al. (Feb. 2004) "Essential Roles of S-Nitrosothiols in Vascular Homeostatsis and Endotoxic Shock", *Cell*, 116(4):617-628.
Liu et al. (Mar. 2001) "A metabolic enzyme for S-nitrosothiol conserved from bacterial to humans", *Nature*, 410:490-494.
Patani et al. (1996) Che. Rev. 96:3147-3176, "Bioisosterism: A Rational Approach in Drug Design".
Que et al. (Jun. 2005) "Protection from Experimental Asthma by an Endogenous Bronchodilator", *Science*, 308(5728):1618-1621.
Sanghani et al. (2000) "Kinetic Mechanism of Human Glutathioone-Dependent Formaldehyde Dehydrogenase", *Biochemistry*,39:10720-10729.
Sanghani et al. (2002) "Human Glutathione-Dependent Formaldehyde Dehydrognease. Structures of Apo, Binary, and Inhibitory Ternary Complexes", *Biochemistry*,41:10778-10786.
Schepetkin et al. (2006) "Novel Small-Molecule Inhibitors of Anthrax Lethal Factor Identified by High-Throughput Screening", *Journal of Medicinal Chemistry*, 49(17):5232-5244.
Staab et al. (2008) "Dual functions of alcohol dehydrogenase 3: implications with focus on formaldehyde dehydrogenase and S-nitroglutathione reductase activities", *Cell Mol. Life Sci*, 65:3950-3960.
Staab et al. (Jun. 15, 2009) "Medium-chain fatty acids and glutathione derivatives as inhibitors of S-nitrosoglutathione reduction mediated by alcohol dehydrogenase 3", Chemico-Biological Interactions 180(1):113-118.
Stamler et al. (Aug. 1992) "Nitric oxide circulates in mammalian plasma primarily as an S-nitrose adduct of serium albumin", *Proc. Natl. Acad. Sci. USA*, 89:7674-7677.
Uotila and Koivusalo (1989) Coenzymes and Cofactors vol. 3: Glutathione, part A., D. Dolphin, ed. pp. 517-551 (New York, John Wiley & Sons).
Zaman et al. (2001) "S-Nitrosoglutathione Increases Cystic Fibrosis Transmembrane Regulator Maturation", *Biochem Biophys Res Commun.*, 284:65-70.

US 9,138,427 B2

PYRROLE INHIBITORS OF S-NITROSOGLUTATHIONE REDUCTASE AS THERAPEUTIC AGENTS

RELATED APPLICATIONS

This application is a continuation of U.S. application Ser. No. 13/057,171, filed Feb. 2, 2011, entitled "Novel Pyrrole Inhibitors of S-Nitrosoglutathione Reductase as Therapeutic Agents." U.S. application Ser. No. 13/057,171 is a 35 U.S.C. §371 national phase application of PCT/US2009/053923, filed Aug. 14, 2009. PCT/US2009/053923 claims priority to U.S. Provisional Application Ser. No. 61/116,982, filed Nov. 21, 2008 and U.S. Provisional Application Ser. No. 61/089,313, filed Aug. 15, 2008. Each of these applications is incorporated herein by reference in its entirety.

FIELD OF THE INVENTION

The present invention is directed to novel pyrrole inhibitors of S-nitrosoglutathione reductase, pharmaceutical compositions comprising such inhibitors, and methods of making and using the same.

BACKGROUND OF THE INVENTION

The chemical compound nitric oxide is a gas with chemical formula NO. NO is one of the few gaseous signaling molecules known in biological systems, and plays an important role in controlling various biological events. For example, the endothelium uses NO to signal surrounding smooth muscle in the walls of arterioles to relax, resulting in vasodilation and increased blood flow to hypoxic tissues. NO is also involved in regulating smooth muscle proliferation, platelet function, neurotransmission, and plays a role in host defense. Although nitric oxide is highly reactive and has a lifetime of a few seconds, it can both diffuse freely across membranes and bind to many molecular targets. These attributes make NO an ideal signaling molecule capable of controlling biological events between adjacent cells and within cells.

NO is a free radical gas, which makes it reactive and unstable, thus NO is short lived in vivo, having a half life of 3-5 seconds under physiologic conditions. In the presence of oxygen, NO can combine with thiols to generate a biologically important class of stable NO adducts called S-nitrosothiols (SNO's). This stable pool of NO has been postulated to act as a source of bioactive NO and as such appears to be critically important in health and disease, given the centrality of NO in cellular homeostasis (Stamler et al., *Proc. Natl. Acad. Sci. USA*, 89:7674-7677 (1992)). Protein SNO's play broad roles in cardiovascular, respiratory, metabolic, gastrointestinal, immune and central nervous system function (Foster et al., 2003, Trends in Molecular Medicine Volume 9, Issue 4, April 2003, pages 160-168). One of the most studied SNO's in biological systems is S-nitrosoglutathione (GSNO) (Gaston et al., *Proc. Natl. Acad. Sci. USA* 90:10957-10961 (1993)), an emerging key regulator in NO signaling since it is an efficient trans-nitrosating agent and appears to maintain an equilibrium with other S-nitrosated proteins (Liu et al., 2001) within cells. Given this pivotal position in the NO—SNO continuum, GSNO provides a therapeutically promising target to consider when NO modulation is pharmacologically warranted.

In light of this understanding of GSNO as a key regulator of NO homeostasis and cellular SNO levels, studies have focused on examining endogenous production of GSNO and SNO proteins, which occurs downstream from the production of the NO radical by the nitric oxide synthetase (NOS) enzymes. More recently there has been an increasing understanding of enzymatic catabolism of GSNO which has an important role in governing available concentrations of GSNO and consequently available NO and SNO's.

Central to this understanding of GSNO catabolism, researchers have recently identified a highly conserved S-nitrosoglutathione reductase (GSNOR) (Jensen et al., *Biochem J.*, 331:659-668 (1998); Liu et al., *Nature*, 410:490-494 (2001)). GSNOR is also known as glutathione-dependent formaldehyde dehydrogenase (GS-FDH), alcohol dehydrogenase 3 (ADH-3) (Uotila and Koivusalo, *Coenzymes and Cofactors.*, D. Dolphin, ed. pp. 517-551 (New York, John Wiley & Sons, 1989)), and alcohol dehydrogenase 5 (ADH-5). Importantly GSNOR shows greater activity toward GSNO than other substrates (Jensen et al., 1998; Liu et al., 2001) and appears to mediate important protein and peptide denitrosating activity in bacteria, plants, and animals. GSNOR appears to be the major GSNO-metabolizing enzyme in eukaryotes (Liu et al., 2001). Thus, GSNO can accumulate in biological compartments where GSNOR activity is low or absent (e.g. airway lining fluid) (Gaston et al., 1993).

Yeast deficient in GSNOR accumulate S-nitrosylated proteins which are not substrates of the enzyme, which is strongly suggestive that GSNO exists in equilibrium with SNO-proteins (Liu et al., 2001). Precise enzymatic control over ambient levels of GSNO and thus SNO-proteins raises the possibility that GSNO/GSNOR may play roles across a host of physiological and pathological functions including protection against nitrosative stress wherein NO is produced in excess of physiologic needs. Indeed, GSNO specifically has been implicated in physiologic processes ranging from the drive to breathe (Lipton et al., *Nature*, 413:171-174 (2001)) to regulation of the cystic fibrosis transmembrane regulator (Zaman et al., *Biochem Biophys Res Commun*, 284: 65-70 (2001), to regulation of vascular tone, thrombosis and platelet function (de Belder et al., Cardiovasc Res. 1994 May; 28(5):691-4. (1994); Z. Kaposzta, A et al., Circulation; 106 (24): 3057-3062, 2002) as well as host defense (de Jesus-Berrios et al., *Curr. Biol.*, 13:1963-1968 (2003)). Other studies have found that GSNOR protects yeast cells against nitrosative stress both in vitro (Liu et al., 2001) and in vivo (de Jesus-Berrios et al., 2003).

Collectively data suggest GSNOR as a primary physiological ligand for the enzyme S-nitrosoglutathione reductase (GSNOR), which catabolizes GSNO and consequently reduces available SNO's and NO in biological systems (Liu et al., 2001), (Liu et al., Cell, (2004), 116(4), 617-628), and (Que et al., Science, 2005, 308, (5728):1618-1621). As such, this enzyme plays a central role in regulating local and systemic bioactive NO. Since perturbations in NO bioavailability has been linked to the pathogenesis of numerous disease states, including hypertension, atherosclerosis, thrombosis, asthma, gastrointestinal disorders, inflammation and cancer, agents that regulate GSNOR activity are candidate therapeutic agents for treating diseases associated with nitric oxide imbalance.

Currently, there is a great need in the art for diagnostics, prophylaxis, ameliorations, and treatments for medical conditions relating to increased NO synthesis and/or increased NO bioactivity. In addition, there is a significant need for novel compounds, compositions and methods for preventing, ameliorating, or reversing other NO-associated disorders. The present invention satisfies these needs.

SUMMARY OF THE INVENTION

The present invention provides novel pyrrole compounds useful as S-nitrosoglutathione reductase ("GSNOR") inhibitors. The invention encompasses pharmaceutically acceptable salts, prodrugs, and metabolites of the described GSNOR inhibitors. Also encompassed by the invention are pharmaceutical compositions comprising at least one GSNOR inhibitor and at least one pharmaceutically acceptable carrier.

The compositions of the present invention can be prepared in any suitable pharmaceutically acceptable dosage form.

The present invention provides a method for inhibiting S-nitrosoglutathione reductase in a subject in need thereof. Such a method comprises administering a therapeutically effective amount of a pharmaceutical composition comprising at least one GSNOR inhibitor or a pharmaceutically acceptable salt thereof, a prodrug or metabolite thereof, in combination with at least one pharmaceutically acceptable carrier. The GSNOR inhibitor can be a novel compound according to the invention, or it can be a known compound which previously was not known to be an inhibitor of GSNOR.

The present invention also provides a method of treating a disorder ameliorated by NO donor therapy in a subject in need thereof. Such a method comprises administering a therapeutically effective amount of a pharmaceutical composition comprising at least one GSNOR inhibitor or a pharmaceutically acceptable salt thereof, a prodrug, or metabolite thereof, in combination with at least one pharmaceutically acceptable carrier. The GSNOR inhibitor can be a novel compound according to the invention, or it can be a known compound which previously was not known to be an inhibitor of GSNOR.

The present invention also provides a method of treating a cell proliferative disorder in a subject in need thereof. Such a method comprises administering a therapeutically effective amount of a pharmaceutical composition comprising at least one GSNOR inhibitor or a pharmaceutically acceptable salt thereof, a prodrug, or metabolite thereof, in combination with at least one pharmaceutically acceptable carrier. The GSNOR inhibitor can be a novel compound according to the invention, or it can be a known compound which previously was not known to be an inhibitor of GSNOR.

The methods of the invention encompass administration with one or more secondary active agents. Such administration can be sequential or in a combination composition.

Although methods and materials similar or equivalent to those described herein can be used in the practice or testing of the present invention, suitable methods and materials are described below. All publicly available publications, patent applications, patents, and other references mentioned herein are incorporated by reference in their entirety. In the case of conflict, the present specification, including definitions, will control.

Both the foregoing summary and the following detailed description are exemplary and explanatory and are intended to provide further details of the compositions and methods as claimed. Other objects, advantages, and novel features will be readily apparent to those skilled in the art from the following detailed description.

DETAILED DESCRIPTION OF THE PREFERRED EMBODIMENTS

A. Overview of the Invention

Until recently, S-nitrosoglutathione reductase (GSNOR) was known to oxidize the formaldehyde glutathione adduct, S-hydroxymethylglutathione. GSNOR has since been identified in a variety of bacteria, yeasts, plants and animals and is well conserved. The proteins from E. coli, S. cerevisiae and mouse macrophages share over 60% amino acid sequence identity. GSNOR activity (i.e., decomposition of S-nitrosoglutathione when NADH is present as a required cofactor) has been detected in E. coli, in mouse macrophages, in mouse endothelial cells, in mouse smooth muscle cells, in yeasts, and in human HeLa, epithelial and monocyte cells. Human GSNOR nucleotide and amino acid sequence information can be obtained from the National Center for Biotechnology Information (NCBI) databases under Accession Nos. M29872, NM_000671. Mouse GSNOR nucleotide and amino acid sequence information can be obtained from NCBI databases under Accession Nos. NM_007410. In the nucleotide sequence, the start site and stop site are underlined. CDS designates coding sequence. SNP designates single nucleotide polymorphism. Other related GSNOR nucleotide and amino acid sequences, including those of other species, can be found in U.S. Patent Application 2005/0014697.

In accord with the present invention, GSNOR has been shown to function in vivo and in vitro to metabolize S-nitrosoglutathione (GSNO) and protein S-nitrosothiols (SNOs) to modulate NO bioactivity, by controlling the intracellular levels of low mass NO donor compounds and preventing protein nitrosylation from reaching toxic levels.

Based on this, it follows that inhibition of this enzyme potentiates bioactivity in all diseases in which NO donor therapy is indicated, inhibits the proliferation of pathologically proliferating cells, and increases NO bioactivity in diseases where this is beneficial.

The present invention provides pharmaceutical agents that are potent inhibitors of GSNOR. In particular, provided are substituted pyrrole analogs that are inhibitors of GSNOR having the structures depicted below (Formula I-Formula IV), or a pharmaceutically acceptable salt, stereoisomer, or prodrug thereof.

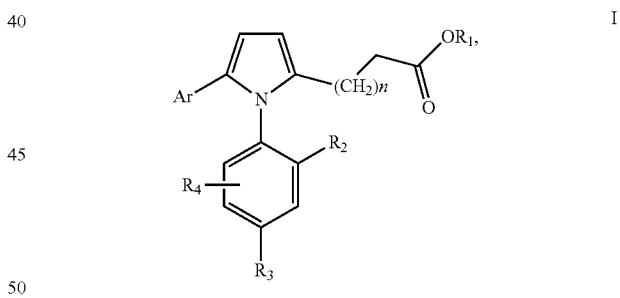

I

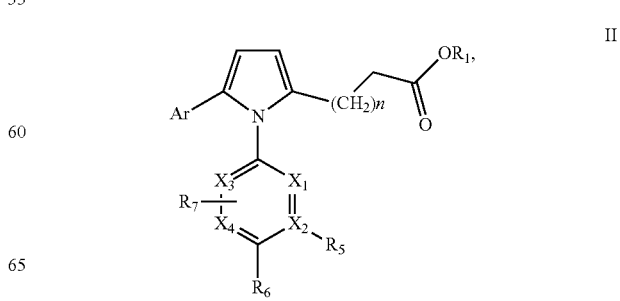

II

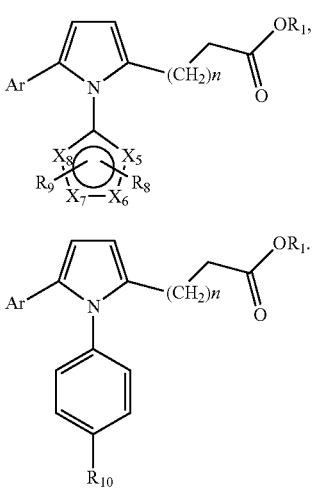

Tri-substituted pyrrole analogs are potent inhibitors of GSNOR. As used in this context, the term "analog" refers to a compound having similar chemical structure and function as compounds of formula I that retains the pyrrole ring.

Some pyrrole analogs of the invention can also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of a compound including tautomeric forms of the compound.

Illustrative compounds having asymmetric centers can exist in different enantiomeric and diastereomeric forms. A compound can exist in the form of an optical isomer or a diastereomer. Accordingly, the invention encompasses compounds in the forms of their optical isomers, diastereomers and mixtures thereof, including racemic mixtures.

It should be noted that if there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereoisomers of the described compound.

In accordance with the invention, the levels of the S-nitrosoglutathione reductase in the biological sample can be determined by the methods described in U.S. Patent Application Publication No. 2005/0014697. The term "biological sample" includes, but is not limited to, samples of blood (e.g., serum, plasma, or whole blood), urine, saliva, sweat, breast milk, vaginal secretions, semen, hair follicles, skin, teeth, bones, nails, or other secretions, body fluids, tissues, or cells.

B. Definitions

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The term "acyl" includes compounds and moieties that contain the acetyl radical ($CH_3CO-$) or a carbonyl group to which a straight or branched chain lower alkyl residue is attached.

The term "alkyl" as used herein refers to a straight or branched chain, saturated hydrocarbon having the indicated number of carbon atoms. For example, ($C_1$-$C_6$) alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents as described herein.

The term "alkenyl" as used herein refers to a straight or branched chain unsaturated hydrocarbon having the indicated number of carbon atoms and at least one double bond. Examples of a ($C_2$-$C_8$) alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein.

The term "alkynyl" as used herein refers to a straight or branched chain unsaturated hydrocarbon having the indicated number of carbon atoms and at least one triple bond. Examples of a ($C_2$-$C_8$) alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein.

The term "alkoxy" as used herein refers to an —O-alkyl group having the indicated number of carbon atoms. For example, a ($C_1$-$C_6$) alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aminoalkyl" as used herein, refers to an alkyl group (typically one to six carbon atoms) wherein one or more of the $C_1$-$C_6$ alkyl group's hydrogen atoms is replaced with an amine of formula —$N(R^c)_2$, wherein each occurrence of $R^c$ is independently —H or ($C_1$-$C_6$) alkyl. Examples of aminoalkyl groups include, but are not limited to, —$CH_2NH_2$, —$CH_2CH_2NH_2$—, —$CH_2CH_2CH_2NH_2$, —$CH_2CH_2CH_2CH_2NH_2$, —$CH_2CH_2CH_2CH_2CH_2NH_2$, —$CH_2CH_2CH_2CH_2CH_2CH_2NH_2$, —$CH_2CH_2CH_2N(CH_3)_2$, t-butylaminomethyl, isopropylaminomethyl and the like.

The term "aryl" as used herein refers to a 5- to 14-membered monocyclic, bicyclic or tricyclic aromatic ring system. Examples of an aryl group include phenyl and naphthyl. An aryl group can be unsubstituted or optionally substituted with one or more substituents as described herein below. Examples of aryl groups include phenyl or aryl heterocycles such as, pyrrole, furan, thiophene, thiazole, isothiazole, imidazole, triazole, tetrazole, pyrazole, oxazole, isoxazole, pyridine, pyrazine, pyridazine, and pyrimidine, and the like.

As used herein, the term "bioactivity" indicates an effect on one or more cellular or extracellular process (e.g., via binding, signaling, etc.) which can impact physiological or pathophysiological processes.

The term "carbonyl" or "carboxy" or "carboxyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "$C_m$-$C_n$" means "m" number of carbon atoms to "n" number of carbon atoms. For example, the term "$C_1$-$C_6$" means one to six carbon atoms ($C_1$, $C_2$, $C_3$, $C_4$, $C_5$ or $C_6$). The term "$C_2$-$C_6$" includes two to six carbon atoms ($C_2$, $C_3$, $C_4$, $C_5$ or $C_6$). The term "$C_3$-$C_6$" includes three to six carbon atoms ($C_3$, $C_4$, $C_5$ or $C_6$).

The term "cycloalkyl" as used herein refers to a 3- to 14-membered saturated or unsaturated non-aromatic monocyclic, bicyclic or tricyclic hydrocarbon ring system. Included in this class are cycloalkyl groups which are fused to a benzene ring. Representative cycloalkyl groups include, but are not limited to, cyclopropyl, cyclobutyl, cyclobutenyl, cyclopentyl, cyclopentenyl, cyclopentadienyl, cyclohexyl, cyclohexenyl, 1,3-cyclohexadienyl, cycloheptyl, cycloheptenyl, 1,3-cycloheptadienyl, 1,4-cycloheptadienyl, -1,3,5-cycloheptatrienyl, cyclooctyl, cyclooctenyl, 1,3-cyclooctadienyl, 1,4-cyclooctadienyl, -1,3,5-cyclooctatrienyl, decahydronaphthalene, octahydronaphthalene, hexahydronaphthalene, octahydroindene, hexahydroindene, tetrahydroinden, decahydrobenzocycloheptene, octahydrobenzocycloheptene, hexahydrobenzocycloheptene, tetrahydrobenzocycloheptene, dodecahydroheptalene, decahydroheptalene, octahydroheptalene, hexahydroheptalene, and tetrahydroheptalene, (1s,3s)-bicyclo[1.1.0]butane, bicyclo[1.1.1]pentane, bicyclo[2.1.1]hexane, Bicyclo[2.2.1]heptane, bicyclo[2.2.2]octane, bicyclo[3.1.1]heptane, bicyclo[3.2.1]octane, bicyclo[3.3.1]nonane, bicyclo[3.3.2]decane, bicyclo[3.3.]undecane, bicyclo[4.2.2]decane, bicyclo[4.3.1]decane. A cycloalkyl group can be unsubstituted or optionally substituted with one or more substituents as described herein below.

The term "halogen" includes fluorine, bromine, chlorine, iodine, etc.

The term "haloalkyl" as used herein, refers to a $C_1$-$C_6$ alkyl group wherein from one or more of the $C_1$-$C_6$ alkyl group's hydrogen atom is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "heteroalkyl" by itself or in combination with another term, means, unless otherwise stated, a stable straight or branched chain alkyl, or combinations thereof, consisting of carbon atoms and from one to three heteroatoms selected from the group consisting of O, N and S, and wherein the nitrogen and sulfur atoms may optionally be oxidized and the nitrogen heteroatom may optionally be quaternized. The heteroatom(s) O, N and S can be placed at any position of the heteroalkyl group. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$S(O)—$CH_3$, —$CH_2$—$CH_2$S(O)$_2$—$CH_3$, and —$CH_2$—CH=N—$OCH_3$. Up to two heteroatoms can be consecutive, such as, for example, —$CH_2$—NH—$OCH_3$. When a prefix such as ($C_2$-$C_8$) is used to refer to a heteroalkyl group, the number of carbons (2 to 8, in this example) is meant to include the heteroatoms as well. For example, a $C_2$-heteroalkyl group is meant to include, for example, —$CH_2OH$ (one carbon atom and one heteroatom replacing a carbon atom) and —$CH_2SH$.

To further illustrate the definition of a heteroalkyl group, where the heteroatom is oxygen, a heteroalkyl group can be an oxyalkyl group. For instance, ($C_2$-$C_5$) oxyalkyl is meant to include, for example —$CH_2$—O—$CH_3$ (a $C_3$-oxyalkyl group with two carbon atoms and one oxygen replacing a carbon atom), —$CH_2CH_2CH_2CH_2OH$, —$OCH_2CH_2OCH_2CH_2OH$, —$OCH_2CH(OH)CH_2OH$, and the like.

The term "heteroaryl" as used herein refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thienyl(thiophen-yl), benzothienyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, quinoxalinyl and oxazolyl. A heteroaryl group can be unsubstituted or optionally substituted with one or more substituents as described herein below.

As used herein, the term "heteroatom" is meant to include oxygen (O), nitrogen (N), and sulfur (S).

As used herein, the term "heterocycle" refers to 3- to 14-membered ring systems which are either saturated, unsaturated, or aromatic, and which contains from 1 to 4 heteroatoms independently selected from nitrogen, oxygen and sulfur, and wherein the nitrogen and sulfur heteroatoms can be optionally oxidized, and the nitrogen heteroatom can be optionally quaternized, including, including monocyclic, bicyclic, and tricyclic ring systems. The bicyclic and tricyclic ring systems may encompass a heterocycle or heteroaryl fused to a benzene ring. The heterocycle can be attached via any heteroatom or carbon atom, where chemically acceptable. Heterocycles include heteroaryls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, dioxanyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thienyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl and quinazolinyl. A heterocycle group can be unsubstituted or optionally substituted with one or more substituents as described herein below.

The term "heterocycloalkyl" by itself or in combination with other terms, represents, unless otherwise stated, cyclic versions of "heteroalkyl." Additionally, a heteroatom can occupy the position at which the heterocycle is attached to the remainder of the molecule. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "hydroxyalkyl" as used herein, refers to an alkyl group having the indicated number of carbon atoms wherein one or more of the hydrogen atoms in the alkyl group is replaced with an —OH group. Examples of hydroxyalkyl groups include, but are not limited to, —$CH_2OH$, —$CH_2CH_2OH$, —$CH_2CH_2CH_2OH$, —$CH_2CH_2CH_2CH_2OH$, —$CH_2CH_2CH_2CH_2CH_2OH$, —$CH_2CH_2CH_2CH_2CH_2CH_2OH$, and branched versions thereof.

The term "hydroxy" or "hydroxyl" includes groups with an —OH or —$O^-$.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. In some embodiments, a stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

As used herein, "protein" is used synonymously with "peptide," "polypeptide," or "peptide fragment." A "purified" polypeptide, protein, peptide, or peptide fragment is substantially free of cellular material or other contaminating proteins from the cell, tissue, or cell-free source from which the amino acid sequence is obtained, or substantially free from chemical precursors or other chemicals when chemically synthesized.

As used herein, "modulate" is meant to refer to an increase or decrease the levels of a peptide or a polypeptide, or to increase or decrease the stability or activity of a peptide or a polypeptide. The term "inhibit" is meant to refer to a decrease in the levels of a peptide or a polypeptide or to decrease in the stability or activity of a peptide or a polypeptide. In preferred embodiments, the peptide which is modulated or inhibited is S-nitrosoglutathione (GSNO) or protein S-nitrosothiols (SNOs).

As used here, the terms "nitric oxide" and "NO" encompass uncharged nitric oxide and charged nitric oxide species, particularly including nitrosonium ion ($NO^+$) and nitroxyl ion ($NO^-$). The reactive form of nitric oxide can be provided by gaseous nitric oxide. Compounds having the structure $X-NO_y$, wherein X is a nitric oxide releasing, delivering or transferring moiety, including any and all such compounds which provide nitric oxide to its intended site of action in a form active for their intended purpose, and Y is 1 or 2.

As utilized herein, the term "pharmaceutically acceptable" means approved by a regulatory agency of a federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils.

A "pharmaceutically acceptable salt" or "salt" of a GSNOR inhibitor is a product of the disclosed compound that contains an ionic bond, and is typically produced by reacting the disclosed compound with either an acid or a base, suitable for administering to a subject. A pharmaceutically acceptable salt can include, but is not limited to, acid addition salts including hydrochlorides, hydrobromides, phosphates, sulphates, hydrogen sulphates, alkylsulphonates, arylsulphonates, arylalkylsulfonates, acetates, benzoates, citrates, maleates, fumarates, succinates, lactates, and tartrates; alkali metal cations such as Li, Na, K, alkali earth metal salts such as Mg or Ca, or organic amine salts.

A "pharmaceutical composition" is a formulation comprising the disclosed compounds in a form suitable for administration to a subject. A pharmaceutical composition of the invention is preferably formulated to be compatible with its intended route of administration. Examples of routes of administration include, but are not limited to, oral and parenteral, e.g., intravenous, intradermal, subcutaneous, inhalation, topical, transdermal, transmucosal, and rectal administration.

The term "substituted" as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Ring double bonds, as used herein, are double bonds that are formed between two adjacent ring atoms (e.g., C=C, C=N, or N=N).

Substituents for the groups referred to as alkyl, heteroalkyl, alkylene, alkenyl, alkynyl, cycloalkyl, heterocycloalkyl, cycloalkenyl and heterocycloalkenyl can be selected from a variety of groups including $-OR^{d\prime}$, $=O$, $=NR^{d\prime}$, $=N-OR^{d\prime}$, $-NR^{d\prime}R^{d\prime\prime\prime}$, $-SR^{d\prime}$, -halo, $-SiR^{d\prime}R^{d\prime\prime}R^{d\prime\prime\prime}$, $-OC(O)R^{d\prime}$, $-C(O)R^{d\prime}$, $-CO_2R^{d\prime}$, $-CONR^{d\prime}R^{d\prime\prime}$, $-OC(O)NR^{d\prime}R^{d\prime\prime}$, $-NR^{d\prime\prime}C(O)R^{d\prime}$, $-NR^{d\prime\prime}C(O)NR^{d\prime}R^{d\prime\prime}$, $-NR^{d\prime\prime\prime}SO_2NR^{d\prime}R^{d\prime\prime}$, $-NR^{d\prime\prime}CO_2R^{d\prime}$, $-NHC(NH_2)=NH$, $-NR^{d\prime}C(NH_2)=NH$, $-NHC(NH_2)=NR^{d\prime}$, $-S(O)R^{d\prime}$, $-SO_2R^{d\prime}$, $-SO_2NR^{d\prime}R^{d\prime\prime}$, $-NR^{d\prime\prime}SO_2R^{d\prime}$, $-CN$ and $-NO_2$, in a number ranging from zero to three, with those groups having zero, one or two substituents being exemplary.

$R^{d\prime}$, $R^{d\prime\prime}$ and $R^{d\prime\prime\prime}$ each independently refer to hydrogen, unsubstituted $(C_1-C_8)$alkyl, unsubstituted hetero$(C_1-C_8)$ alkyl, unsubstituted aryl and aryl substituted with one to three substituents selected from -halo, unsubstituted alkyl, unsubstituted alkoxy, unsubstituted thioalkoxy and unsubstituted aryl$(C_1-C_4)$alkyl. When $R^{d\prime}$ and $R^{d\prime\prime}$ are attached to the same nitrogen atom, they can be combined with the nitrogen atom to form a 5-, 6- or 7-membered ring. For example, $-NR^{d\prime}R^{d\prime\prime}$ can represent 1-pyrrolidinyl or 4-morpholinyl.

Typically, an alkyl or heteroalkyl group will have from zero to three substituents, with those groups having two or fewer substituents being exemplary of the present invention. An alkyl or heteroalkyl radical can be unsubstituted or monosubstituted. In some embodiments, an alkyl or heteroalkyl radical will be unsubstituted.

Exemplary substituents for the alkyl and heteroalkyl radicals include but are not limited to $-OR^{d\prime\prime}$, $=O$, $=NR^{d\prime}$, $=N-OR^{d\prime}$, $-NR^{d\prime}R^{d\prime\prime}$, $-SR^{d\prime}$, -halo, $-SiR^{d\prime}R^{d\prime\prime}R^{d\prime\prime\prime}$, $-OC(O)R^{d\prime}$, $-C(O)R^{d\prime}$, $-CO_2R^{d\prime}$, $-CONR^{d\prime}R^{d\prime\prime}$, $-OC(O)NR^{d\prime}NR^{d\prime\prime}$, $-NR^{d\prime\prime}C(O)R^{d\prime}$, $-NR^{d\prime\prime}C(O)NR^{d\prime}R^{d\prime\prime}$, $-NR^{d\prime\prime\prime}SO_2NR^{d\prime}R^{d\prime\prime}$, $-NR^{d\prime\prime}CO_2R^{d\prime}$, $-NHC(NH_2)=NH$, $-NR^{d\prime}C(NH_2)=NH$, $-NHC(NH_2)=NR^{d\prime}$, $-S(O)R^{d\prime}$, $-SO_2R^{d\prime}$, $-SO_2NR^{d\prime}R^{d\prime\prime}$, $-NR^{d\prime\prime}SO_2R^{d\prime}$, $-CN$ and $-NO_2$, where $R^{d\prime}$, $R^{d\prime\prime}$ and $R^{d\prime\prime\prime}$ are as defined above. Typical substituents can be selected from: $-OR^{d\prime}$, $=O$, $-NR^{d\prime}R^{d\prime\prime}$, -halo, $-OC(O)R^{d\prime}$, $-CO_2R^{d\prime}$, $-C(O)NR^{d\prime}R^{d\prime\prime}$, $-OC(O)NR^{d\prime}R^{d\prime\prime}$, $-NR^{d\prime\prime}C(O)R^{d\prime}$, $-NR^{d\prime\prime}CO_2R^{d\prime}$, $-NR^{d\prime\prime\prime}SO_2NR^{d\prime}R^{d\prime\prime}$, $-SO_2R^{d\prime}$, $-SO_2NR^{d\prime}R^{d\prime\prime}$, $-NR^{d\prime\prime}SO_2R^{d\prime}$ $-CN$ and $-NO_2$.

Similarly, substituents for the aryl and heteroaryl groups are varied and selected from: -halo, $-OR^{e\prime}$, $-OC(O)R^{e\prime}$, $-NR^{e\prime}R^{e\prime\prime}$, $-SR^{e\prime}$, $-R^{e\prime}$, $-CN$, $-NO_2$, $-CO_2R^{e\prime}$, $-C(O)NR^{e\prime}R^{e\prime\prime}$, $-C(O)R^{e\prime}$, $-OC(O)NR^{e\prime}R^{e\prime\prime}$, $-NR^{e\prime\prime}C(O)R^{e\prime}$, $-NR^{e\prime\prime}CO_2R^{e\prime}$, $-NR^{e\prime\prime\prime}C(O)NR^{e\prime}R^{e\prime\prime}$, $-NR^{e\prime\prime\prime}SO_2NR^{e\prime}R^{e\prime\prime}$, $-NHC(NH_2)=NH$, $-NR^{e\prime}C(NH_2)=NH$, $-NH-C(NH_2)=NR^{e\prime}$, $-S(O)R^{e\prime}$, $-SO_2R^{e\prime}$, $-SO_2NR^{e\prime}R^{e\prime\prime}$, $-NR^{e\prime\prime}SO_2R^{e\prime}$, $-N_3$, $-CH(Ph)_2$, perfluoroalkoxy and perfluoro$(C_1-C_4)$alkyl, in a number ranging from zero to the total number of open valences on the aromatic ring system.

$R^{e\prime}$, $R^{e\prime\prime}$ and $R^{e\prime\prime\prime}$ are independently selected from hydrogen, unsubstituted $(C_1-C_8)$ alkyl, unsubstituted hetero$(C_1-C_8)$ alkyl, unsubstituted aryl, unsubstituted heteroaryl, unsubstituted aryl$(C_1-C_4)$ alkyl and unsubstituted aryloxy $(C_1-C_4)$ alkyl. Typically, an aryl or heteroaryl group will have from zero to three substituents, with those groups having two or fewer substituents being exemplary in the present invention. In one embodiment of the invention, an aryl or heteroaryl group will be unsubstituted or monosubstituted. In another embodiment, an aryl or heteroaryl group will be unsubstituted.

Two of the substituents on adjacent atoms of an aryl or heteroaryl ring in an aryl or heteroaryl group as described herein may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -J-(CH$_2$)$_r$—K—, wherein J and K are independently —CH$_2$—, —O—, —NH—, —S—, —S(O)—, —S(O)$_2$—, —S(O)$_2$NR$^{fi}$— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR$^{fi}$, —S—, —S(O)—, —S(O)$_2$—, or —S(O)$_2$NR$^{a1}$—. The substituent R$^{fi}$ in —NR$^{fi}$— and —S(O)$_2$NR$^{fi}$— is selected from hydrogen or unsubstituted (C$_1$-C$_6$) alkyl.

"Stable compound" and "stable structure" are meant to indicate a compound that is sufficiently robust to survive isolation to a useful degree of purity from a reaction mixture, and formulation into an efficacious therapeutic agent.

As used herein the term "therapeutically effective amount" generally means the amount necessary to ameliorate at least one symptom of a disorder to be prevented, reduced, or treated as described herein. The phrase "therapeutically effective amount" as it relates to the GSNOR inhibitors of the present invention shall mean the GSNOR inhibitor dosage that provides the specific pharmacological response for which the GSNOR inhibitor is administered in a significant number of subjects in need of such treatment. It is emphasized that a therapeutically effective amount of a GSNOR inhibitor that is administered to a particular subject in a particular instance will not always be effective in treating the conditions/diseases described herein, even though such dosage is deemed to be a therapeutically effective amount by those of skill in the art.

C. S-Nitrosoglutathione Reductase Inhibitors

1. Inventive Compounds

In one of its aspects the present invention provides a compound having a structure shown in Formula I, or a pharmaceutically acceptable salt, stereoisomer, or prodrug thereof:

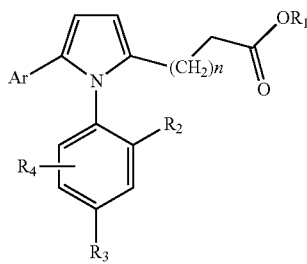

I wherein
Ar is selected from the group consisting of aryl, substituted aryl, heteroaryl and substituted heteroaryl;

R$_1$ is selected from the group consisting of hydrogen, C$_1$-C$_6$ alkyl, C$_3$-C$_6$ cycloalkyl, aryl, substituted aryl, heteroaryl, and substituted heteroaryl;

R$_2$ is selected from the group consisting of halogen, C$_1$-C$_6$ alkyl, C$_3$-C$_6$ cycloalkyl, cyano, nitro, CF$_3$, carbamoyl, C$_1$-C$_6$ alkylcarbamoyl, amino, C$_1$-C$_6$ alkylamino, C$_1$-C$_6$ dialkylamino, C$_1$-C$_6$ alkoxyl, and C$_3$-C$_6$ cycloalkoxyl;

R$_3$ is selected from the group consisting of hydroxyl, carbamoyl, C$_1$-C$_6$ alkylcarbamoyl, sulfamoyl, C$_1$-C$_6$ alkylsulfamoyl, C$_3$-C$_6$ cycloalkyl, cyano, nitro, carboxyl, amino, aminomethyl, acetamido, acetamido-2-methyl, 2-methoxyacetamido, propionamido, tetrahydrofuran-2-ylmethoxy, CF$_3$, carboxyl, ureido, sulfamoylamino, C$_1$-C$_6$ alkylsulfonamido, 2-amino-2-oxoethyl, C$_1$-C$_6$ alkylamino, C$_1$-C$_6$ dialkylamino, arylamino, heteroarylamino, C$_1$-C$_6$ alkoxyl, C$_3$-C$_6$ cycloalkoxyl, 1H-imidazol-2-yl, oxazol-2-yl, thiazol-2-yl, methylcarbamoyl, dimethycarbamoyl, methoxyethylcarbamoyl, hydroxyethylcarbamoyl, (dimethylamino)ethylcarbamoyl, pyridin-3-ylcarbamoyl, pyridin-4-yl-carbamoyl, 6-methoxypyridin-3-ylcarbamoyl, pyridazin-4-ylcarbamoyl, and pyrimidin-5-ylcarbamoyl;

R$_4$ is selected from the group consisting of hydrogen, hydroxyl, halogen, C$_1$-C$_6$ alkyl, C$_3$-C$_6$ cycloalkyl, cyano, nitro, carbamoyl, C$_1$-C$_6$ alkylcarbamoyl, sulfamoyl, C$_1$-C$_6$ alkyl sulfamoyl, amino, C$_1$-C$_6$ alkylamino, C$_1$-C$_6$ dialkylamino, C$_1$-C$_6$ alkoxyl, and C$_3$-C$_6$ cycloalkoxyl;

n is 0-3;

wherein Ar excludes substituted or unsubstituted indazol-3-yl and substituted or unsubstituted 1H-pyrazolo[3,4-b]pyridyl;

with the following provisos:
proviso Ia: when R$_3$ is carboxyl, methylsulfonamido, or sulfamoyl, then Ar cannot be phenyl, substituted or unsubstituted phenyl-(C$_1$-C$_3$)-alkyl, or phenyl-(C$_2$-C$_6$)-alkenyl; and
proviso Ib: when R$_2$ and R$_3$ are both methoxy, then Ar cannot be phenyl, 4-methyl-phenyl, 4-methoxy-phenyl, 4-halo-phenyl, or thiophen-yl.

In a further aspect of the invention of formula I, Ar is selected from the group consisting of phenyl, substituted phenyl, thiophen-yl, substituted thiophen-yl, pyridinyl, substituted pyridinyl, thiazolyl, substituted thiazolyl, pyrimidinyl, substituted pyrimidinyl, furanyl, substituted furanyl, bicyclic aryl, substituted bicyclic aryl, bicyclic heteroaryl, and substituted bicyclic heteroaryl;

R$_1$ is selected from the group consisting of hydrogen and C$_1$-C$_6$ alkyl;

R$_2$ is selected from the group consisting of halogen, C$_1$-C$_6$ alkyl, and CF$_3$;

R$_3$ is selected from the group consisting of hydroxyl, carbamoyl, sulfamoyl, sulfamoylamino, C$_1$-C$_6$ alkoxy, amino, aminomethyl, acetamido, acetamido-2-methyl, 2-methoxyacetamido, propionamido, tetrahydrofuran-2-ylmethoxy, methylsulfamido, carboxyl, C$_1$-C$_6$ alkylamino, 1H-imidazol-2-yl, oxazol-2-yl, thiazol-2-yl, methylcarbamoyl, dimethycarbamoyl, methoxyethylcarbamoyl, hydroxyethylcarbamoyl, (dimethylamino)ethylcarbamoyl, pyridin-3-ylcarbamoyl, pyridin-4-yl-carbamoyl, 6-methoxypyridin-3-ylcarbamoyl, pyridazin-4-ylcarbamoyl, and pyrimidin-5-ylcarbamoyl;

R$_4$ is selected from the group consisting of hydrogen and C$_1$-C$_6$ alkyl; and
n is 1.

In a further aspect of the invention of formula I, Ar is selected from the group consisting of phenyl, substituted phenyl, aryl-phenyl, substituted aryl-phenyl, heteroaryl-phenyl, substituted heteroaryl-phenyl, thiophen-yl, substituted thiophen-yl, aryl-thiophen-yl, substituted aryl-thiophen-yl, heteroaryl-thiophen-yl, substituted heteroaryl-thiophen-yl, pyridinyl, substituted pyridinyl, aryl-pyridinyl, substituted aryl-pyridinyl, heteroaryl-pyridinyl, substituted heteroaryl-pyridinyl, thiazolyl, substituted thiazolyl, aryl-thiazolyl; substituted aryl-thiozolyl; heteroaryl-thiazolyl; substituted heteroaryl-thiazolyl, pyrimidinyl, substituted pyrimidinyl, aryl-pyrimidinyl, substituted aryl-pyrimidinyl, heteroaryl-pyrimidinyl, substituted heteroaryl-pyrimidinyl, furanyl, substituted furanyl, aryl-furanyl, substituted aryl-furanyl, heteroaryl-furanyl, and substituted heteroaryl-furanyl.

In a further aspect of the invention of formula I, Ar is phenyl, thiophen-yl, thiazolyl, pyridinyl, pyrimidinyl, or furanyl having 0, 1, 2, or 3 substitutions, wherein such substitutions are independently selected from the group consisting of hydrogen, hydroxyl, halogen, $C_1$-$C_6$ alkoxy, amino, cyano, $C_1$-$C_6$ alkyl, imidazolyl, methyl imidazolyl, ethyl imidazolyl, furanyl, methylthio, nitro, triazolyl, tetrazolyl, carbamoyl, pyrazolyl, trifluoromethoxy, trifluoromethyl, 2-amino-2oxoethoxy, ureido, morpholino, pyridinyl, pyrrolyl, methyl sulfonamido, carbamoyl phenyl, 6-oxo-1,6-dihydropyridinyl, 3,5-dimethylisoxazolyl, carboxymethoxy, hydroxyacetamido, methoxyacetamido, sulfamoyl, piperazinyl, oxoimidazolidinyl, methylsulfinyl, methylsulfonyl, pyrrolidinyl, piperidinyl, methylpyrazolyl, phenyl, thiazolyl, hydroxycarbamoyl, cyclopropylimidazolyl, carboxy, methylamino, methoxymethyl, dimethylamino, hydroxymethylimidazolyl, oxooxazolidinyl, formamido, hydroxyphenyl, and thiophen-yl.

In a further aspect of the invention of formula I, Ar is selected from the group consisting of 4-(1H-imidazol-1-yl)phenyl, 5-(1H-imidazol-1-yl)thiophen-2-yl, 4-(2-methyl-1H-imidazol-1-yl)phenyl, thiazol-5-yl, 4-hydroxyphenyl, 5-bromothiophen-2-yl, 4-methoxyphenyl, 4-aminophenyl, 4-bromophenyl, 4-(furan-3-yl)phenyl, phenyl, 3-chloro-4-methoxyphenyl, 3-fluoro-4-methoxyphenyl, 4-cyanophenyl, 3-chloro-4-hydroxyphenyl, 4-methoxy-3-methylphenyl, 4-iodophenyl, 3-methoxyphenyl, 6-methoxypyridin-3-yl, benzo[d]thiazol-6-yl, 4-(methylthio)phenyl, 4-nitrophenyl, 4-(4H-1,2,4-triazol-4-yl)phenyl, 4-(2H-tetrazol-5-yl)phenyl, benzo[d][1,3]dioxol-5-yl, 6-(1H-imidazol-1-yl)pyridin-3-yl, 5-carbamoylthiophen-2-yl, 4-(1H-pyrazol-4-yl)phenyl, 4-(trifluoromethoxy)phenyl, 4-carbamoylphenyl, 4-(trifluoromethyl)phenyl, 4-(1H-1,2,4-triazol-1-yl)phenyl, 4-(1H-pyrazol-1-yl)phenyl, 4-(2-amino-2-oxoethoxy)phenyl, 4-(1-methyl-1H-pyrazol-4-yl)phenyl, 4-(1H-tetrazol-1-yl)phenyl, 4-(4-methyl-1H-imidazol-1-yl)phenyl, 4-ureidophenyl, 4-morpholinophenyl, 4-(2H-tetrazol-5-yl)phenyl, 4-(pyridin-4-yl)phenyl, 4-(1H-pyrrol-1-yl)phenyl, 4-(methylsulfonamido)phenyl, 1H-1,2,3-triazol-1-yl)phenyl, naphthalen-2-yl, 3'-carbamoylbiphenyl-4-yl, 4-(6-oxo-1,6-dihydropyridin-3-yl)phenyl, 4-(3,5-dimethylisoxazol-4-yl)phenyl, 4-(pyridin-3-yl)phenyl, 4-(carboxymethoxy)phenyl, 4-(2-hydroxyacetamido)phenyl, 4-(2-methoxyacetamido)phenyl, 4-sulfamoylphenyl, 4-(piperazin-1-yl)phenyl, 4-(2-oxoimidazolidin-1-yl)phenyl, 4-ethoxyphenyl, 4-(methylsulfinyl)phenyl, 4-(2-ethyl-1H-imidazol-1-yl)phenyl, 4-(furan-2-yl)phenyl, 4-(methylsulfonyl)phenyl, 4-(pyrrolidin-1-yl)phenyl, 4-(piperidin-1-yl)phenyl, 4-(1-methyl-1H-pyrazol-5-yl)phenyl, 5-(2-methyl-1H-imidazol-1-yl)thiophen-2-yl, 4-(furan-3-yl)phenyl, 2-methoxypyrimidin-5-yl, 2-methyl-4-(methylsulfonamido)phenyl, 4-amino-3-chlorophenyl, 3,4-difluorophenyl, 2,4-difluorophenyl, 4-chlorophenyl, 4-bromothiophen-2-yl, biphenyl-4-yl, 2-(1H-imidazol-1-yl)pyrimidin-5-yl, 4-fluoro-3-methoxyphenyl, 3-cyano-4-fluorophenyl, 4-carbamoyl-2-methylphenyl, 4-methoxy-2-methylphenyl, 4-chloro-2-fluorophenyl, 4-fluorophenyl, 4-fluoro-2-methylphenyl, 4-chloro-2-(trifluoromethyl)phenyl, 4-chloro-2-methoxyphenyl, 4-cyano-3-fluorophenyl, 2-chloro-4-methoxyphenyl, 4-(1H-imidazol-1-yl)thiophen-2-yl, 3,5-dimethyl-4-nitrophenyl, 4-amino-3,5-dimethylphenyl, 2-(1H-imidazol-1-yl)thiazol-4-yl, 2-ethoxy-4-fluorophenyl, 4-methoxy-2-(trifluoromethyl)phenyl, 4-fluoro-2-methoxyphenyl, 4-(thiazol-5-yl)phenyl, 4-chloro-3-fluorophenyl, 4-(hydroxycarbamoyl)phenyl, 3-fluoro-4-(1H-imidazol-1-yl)phenyl, 3-fluoro-4-(2-methyl-1H-imidazol-1-yl)phenyl, 4-chloro-2-ethoxyphenyl, 5-bromo-2-methoxyphenyl, 4-(2-cyclopropyl-1H-imidazol-1-yl)phenyl, 4-(2-methyl-1H-imidazol-1-yl)thiophen-2-yl, 4-bromo-2-methoxyphenyl, 2-methoxy-4-(2-methyl-1H-imidazol-1-yl)phenyl, 4-chloro-2-hydroxyphenyl, 5-bromothiophen-3-yl, 4-hydroxy-3-methylphenyl, 2-carbamoyl-4-chlorophenyl, 2-acetamido-4-chlorophenyl, 2-methoxyphenyl, benzoic acid, 2,4-dimethoxyphenyl, 4-chloro-2-propoxyphenyl, 4-chloro-2-(2-methoxyacetamido)phenyl, 4-chloro-2-(methylsulfonamido)phenyl, 4-chloro-2-(methylamino)phenyl, 4-chloro-2-(methoxymethyl)phenyl, 4-hydroxy-2-methoxyphenyl, 4-chloro-2-(dimethylamino)phenyl, 4-(2-(hydroxymethyl)-1H-imidazol-1-yl)phenyl, 4-(2-oxooxazolidin-3-yl)phenyl)-1H-pyrrol-2-yl, 4-(1H-imidazol-1-yl)-2-methoxyphenyl, 5-(2-methyl-1H-imidazol-1-yl)thiophen-3-yl, 5-chlorothiophen-2-yl, 5-bromothiazol-2-yl, 4-bromothiazol-2-yl, 5-(2-ethyl-1H-imidazol-1-yl)thiophen-2-yl, 4-chloro-2-formamidophenyl, 3-chlorothiophen-2-yl, 4-formamido-2-methoxyphenyl, 3-bromo-5-methoxythiophen-2-yl, 5-(4-hydroxyphenyl)thiophen-2-yl, 4-(thiophen-3-yl)phenyl, 5-(1H-imidazol-1-yl)furan-2-yl, 4-chlorothiophen-2-yl, 5-bromo-4-chlorothiophen-2-yl, 5-(2-methyl-1H-imidazol-1-yl)furan-2-yl, and 5-bromofuran-2-yl.

In a further aspect of the invention of formula I, Ar is selected from the group consisting of 4-(1H-imidazol-1-yl)phenyl, 5-(1H-imidazol-1-yl)thiophen-2-yl, 4-(2-methyl-1H-imidazol-1-yl)phenyl, thiazol-5-yl, 4-hydroxyphenyl, 5-bromothiophen-2-yl, 4-methoxyphenyl, 4-aminophenyl, 4-bromophenyl, 4-(furan-3-yl)phenyl, 3-chloro-4-methoxyphenyl, 3-fluoro-4-methoxyphenyl, 4-cyanophenyl, 3-chloro-4-hydroxyphenyl, 4-methoxy-3-methylphenyl, 4-iodophenyl, 3-methoxyphenyl, 6-methoxypyridin-3-yl, benzo[d]thiazol-6-yl, 4-(methylthio)phenyl, 4-nitrophenyl, 4-(4H-1,2,4-triazol-4-yl)phenyl, 4-(2H-tetrazol-5-yl)phenyl, benzo[d][1,3]dioxol-5-yl, 6-(1H-imidazol-1-yl)pyridin-3-yl, 5-carbamoylthiophen-2-yl, 4-(1H-pyrazol-4-yl)phenyl, 4-(trifluoromethoxy)phenyl, 4-carbamoylphenyl, 4-(trifluoromethyl)phenyl, 4-(1H-1,2,4-triazol-1-yl)phenyl, 4-(1H-pyrazol-1-yl)phenyl, 4-(2-amino-2-oxoethoxy)phenyl, 4-(1-methyl-1H-pyrazol-4-yl)phenyl, 4-(1H-tetrazol-1-yl)phenyl, 4-(4-methyl-1H-imidazol-1-yl)phenyl, 4-ureidophenyl, 4-morpholinophenyl, 4-(2H-tetrazol-5-yl)phenyl, 4-(pyridin-4-yl)phenyl, 4-(1H-pyrrol-1-yl)phenyl, 4-(methylsulfonamido)phenyl, 1H-1,2,3-triazol-1-yl)phenyl, naphthalen-2-yl, 3'-carbamoylbiphenyl-4-yl, 4-(6-oxo-1,6-dihydropyridin-3-yl)phenyl, 4-(3,5-dimethylisoxazol-4-yl)phenyl, 4-(pyridin-3-yl)phenyl, 4-(carboxymethoxy)phenyl, 4-(2-hydroxyacetamido)phenyl, 4-(2-methoxyacetamido)phenyl, 4-sulfamoylphenyl, 4-(piperazin-1-yl)phenyl, 4-(2-oxoimidazolidin-1-yl)phenyl, 4-ethoxyphenyl, 4-(methylsulfinyl)phenyl, 4-(2-ethyl-1H-imidazol-1-yl)phenyl, 4-(furan-2-yl)phenyl, 4-(methylsulfonyl)phenyl, 4-(pyrrolidin-1-yl)phenyl, 4-(piperidin-1-yl)phenyl, 4-(1-methyl-1H-pyrazol-5-yl)phenyl, 5-(2-methyl-1H-imidazol-1-yl)thiophen-2-yl, 4-(furan-3-yl)phenyl, 2-methoxypyrimidin-5-yl, 2-methyl-4-(methylsulfonamido)phenyl, 4-amino-3-chlorophenyl, 3,4-difluorophenyl, 2,4-difluorophenyl, 4-chlorophenyl, 4-bromothiophen-2-yl, biphenyl-4-yl, 2-(1H-imidazol-1-yl)pyrimidin-5-yl, 4-fluoro-3-methoxyphenyl, 3-cyano-4-fluorophenyl, 4-carbamoyl-2-methylphenyl, 4-methoxy-2-methylphenyl, 4-chloro-2-fluorophenyl, 4-fluorophenyl, 4-fluoro-2-methylphenyl, 4-chloro-2-(trifluoromethyl)phenyl, 4-chloro-2-methoxyphenyl, 4-cyano-3-fluorophenyl, 2-chloro-4-methoxyphenyl, 4-(1H-imidazol-1-yl)thiophen-2-yl, 3,5-dimethyl-4-nitrophenyl, 4-amino-3,5-dimethylphenyl, 2-(1H-imidazol-1-yl)thiazol-4-yl, 2-ethoxy-4-fluorophenyl, 4-methoxy-2-(trifluoromethyl)phenyl, 4-fluoro-2-methoxyphenyl, 4-(thiazol-5-yl)phenyl, 4-chloro-3-fluorophenyl, 4-(hydroxycarbamoyl)phenyl, 3-fluoro-4-(1H-imidazol-1-yl)phenyl, 3-fluoro-4-(2-methyl-1H-imidazol-1-yl)phenyl, 4-chloro-2-ethoxyphenyl, 5-bromo-2-methoxyphenyl, 4-(2-cyclopropyl-1H-imidazol-1-yl)phenyl, 4-(2-methyl-1H-imidazol-1-yl)thiophen-2-yl, 4-bromo-2-methoxyphenyl, 2-methoxy-4-(2-methyl-1H-imidazol-1-yl)phenyl, 4-chloro-2-hydroxyphenyl, 5-bromothiophen-3-yl, 4-hydroxy-3-methylphenyl, 2-carbamoyl-4-chlorophenyl, 2-acetamido-4-chlorophenyl, 2-methoxyphenyl, benzoic acid, 2,4-dimethoxyphenyl, 4-chloro-2-propoxyphenyl, 4-chloro-2-(2-methoxyacetamido)phenyl, 4-chloro-2-(methylsulfonamido)phenyl, 4-chloro-2-(methylamino)phenyl, 4-chloro-2-(methoxymethyl)phenyl, 4-hydroxy-2-methoxyphenyl, 4-chloro-2-(dimethylamino)phenyl, 4-(2-(hydroxymethyl)-1H-imidazol-1-yl)phenyl, 4-(2-oxooxazolidin-3-yl)phenyl)-1H-pyrrol-2-yl, 4-(1H-imidazol-1-yl)-2-methoxyphenyl, 5-(2-methyl-1H-imidazol-1-yl)thiophen-3-yl, 5-chlorothiophen-2-yl, 5-bromothiazol-2-yl, 4-bromothiazol-2-yl, 5-(2-ethyl-1H-imidazol-1-yl)thiophen-2-yl, 4-chloro-2-formamidophenyl, 3-chlorothiophen-2-yl, 4-formamido-2-methoxyphenyl, 3-bromo-5-methoxythiophen-2-yl, 5-(4-hydroxyphenyl)thiophen-2-yl, 4-(thiophen-3-yl)phenyl, 5-(1H-imidazol-1-yl)furan-2-yl, 4-chlorothiophen-2-yl, 5-bromo-4-chlorothiophen-2-yl, 5-(2-methyl-1H-imidazol-1-yl)furan-2-yl, and 5-bromofuran-2-yl.

In a further aspect of the invention of formula I, Ar is selected from the group consisting of aryl, substituted aryl, heteroaryl and substituted heteroaryl;
$R_1$ is selected from the group consisting of hydrogen, $C_1$-$C_6$ alkyl, $C_3$-$C_6$ cycloalkyl, aryl, substituted aryl, heteroaryl, and substituted heteroaryl;
$R_2$ is selected from the group consisting of halogen, hydroxyl, $C_1$-$C_6$ alkyl, $C_3$-$C_6$ cycloalkyl, cyano, nitro, $CF_3$, carbamoyl, $C_1$-$C_6$ alkylcarbamoyl, amino, $C_1$-$C_6$ alkylamino, $C_1$-$C_6$ dialkylamino, $C_1$-$C_6$ alkoxyl, and $C_3$-$C_6$ cycloalkoxyl;
$R_3$ is selected from the group consisting of halogen, hydroxyl, carbamoyl, substituted carbamoyl, $C_1$-$C_6$ alkylcarbamoyl, sulfamoyl, $C_1$-$C_6$ alkylsulfamoyl, $C_1$-$C_6$ alkyl, $C_3$-$C_6$ cycloalkyl, cyano, nitro, carboxyl, amino, aminomethyl, acetamido, acetamido-2-methyl, 2-methoxyacetamido, propionamido, tetrahydrofuran-2-ylmethoxy, $CF_3$, carboxyl, ureido, sulfamoylamino, $C_1$-$C_6$ alkylsulfonamido, 2-amino-2-oxoethyl, $C_1$-$C_6$ alkylamino, $C_1$-$C_6$ dialkylamino, arylamino, heteroarylamino, $C_1$-$C_6$ alkoxyl, $C_3$-$C_6$ cycloalkoxyl, aryl, substituted aryl, heteroaryl, and substituted heteroaryl;
$R_4$ is selected from the group consisting of hydrogen, hydroxyl, halogen, $C_1$-$C_6$ alkyl, $C_3$-$C_6$ cycloalkyl, cyano, nitro, carbamoyl, $C_1$-$C_6$ alkylcarbamoyl, sulfamoyl, $C_1$-$C_6$ alkyl sulfamoyl, amino, $C_1$-$C_6$ alkylamino, $C_1$-$C_6$ dialkylamino, $C_1$-$C_6$ alkoxyl, and $C_3$-$C_6$ cycloalkoxyl;
n is 0-3;

with the following provisos:
proviso Ia: Ar excludes substituted or unsubstituted indazol-3-yl and substituted or unsubstituted 1H-pyrazolo[3,4-b]pyridyl; and
proviso Ib: when one of $R_2$, $R_3$, or $R_4$, are carboxyl, methylsulfonamido, hydroxycarbamoyl, methoxycarbamoyl, benzyloxycarbamoyl, sulfamoyl, 1-H-tetrazol, 1-H-tetrazol-5-ylcarbamoyl, 2-(trifluoromethylsulfonyl)hydrazinecarbonyl, 1-carboxy-2-phenylethylcarbamoyl, 2-(carboxy)pyrrolidine-1-carbonyl, substituted or unsubstituted 3-(carboxy)thiophen-2-yl, substituted or unsubstituted 3-(carboxy)furan-2-yl, substituted or unsubstituted 3-(carboxy)-1H-pyrrol-2-yl, 5-(trifluoromethyl)-1H-1,2,4-triazol-2-yl, 5-substituted-1H-1,2,3-triazol-4-yl, Ar cannot be phenyl, substituted or unsubstituted phenyl-($C_1$-$C_3$)-alkyl, or phenyl-($C_2$-$C_6$)-alkenyl; and
proviso Ic: when $R_2$ and $R_3$ are independently selected from the group consisting of halogen or methyl, Ar cannot be 4-hydroxyphenyl or 4-$C_1$-$C_6$ acyl-oxy-phenyl; and
proviso Id: when $R_2$ is hydroxyl, $R_3$ or $R_4$ cannot be Cl; and
proviso Ie: when $R_2$ and $R_3$ are independently selected from the group consisting of Cl, methyl, and methoxy, then Ar cannot be phenyl, 4-methyl-phenyl, 4-methoxy-phenyl, 4-halo-phenyl, or thiophen-yl.

In one of its aspects the present invention provides a compound having a structure shown in Formula II, or a pharmaceutically acceptable salt, stereoisomer, or prodrug thereof:

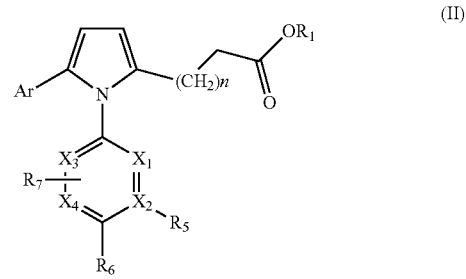

(II)

wherein
Ar is selected from the group consisting of aryl, substituted aryl, heteroaryl and substituted heteroaryl;
$R_1$ is selected from the group consisting of hydrogen, $C_1$-$C_6$ alkyl, $C_3$-$C_6$ cycloalkyl, aryl, substituted aryl, heteroaryl, and substituted heteroaryl;
$X_1$-$X_4$ is independently selected from the group consisting of C and N;
$R_5$ is selected from the group consisting of hydrogen, hydroxyl, halogen, $C_1$-$C_6$ alkyl, $C_3$-$C_6$ cycloalkyl, cyano, nitro, carbamoyl, $C_1$-$C_6$ alkylcarbamoyl, carboxyl, $C_1$-$C_6$ alkylhydroxy, sulfamoyl, $C_1$-$C_6$ alkylsulfamoyl, amino, $C_1$-$C_6$ alkylamino, $C_1$-$C_6$ dialkylamino, $C_1$-$C_6$ alkoxyl, and $C_3$-$C_6$ cycloalkoxyl;
$R_6$ is selected from the group consisting of halogen, hydroxyl, carbamoyl, substituted carbamoyl, $C_1$-$C_6$ alkylcarbamoyl, sulfamoyl, $C_1$-$C_6$ alkylsulfamoyl, $C_1$-$C_6$ alkyl, $C_3$-$C_6$ cycloalkyl, cyano, nitro, amino, $CF_3$, carboxyl, ureido, sulfamoylamino, 2-amino-2-oxoethyl, $C_1$-$C_6$ alkylamino, $C_1$-$C_6$ dialkylamino, arylamino, heteroarylamino, $C_1$-$C_6$ alkoxyl, $C_3$-$C_6$ cycloalkoxyl, 1H-imidazol-1-yl, and 2-methyl-1H-imidazol-1-yl;
or alternatively $R_5$ and $R_6$ together form a substituted or unsubstituted 5 or 6 membered heterocyclic ring containing up to 2 heteroatoms chosen from O, N or S;
$R_7$ is selected from the group consisting of hydrogen, hydroxyl, halogen, $C_1$-$C_6$ alkyl, $C_3$-$C_6$ cycloalkyl, cyano, nitro, carbamoyl, $C_1$-$C_6$ alkylcarbamoyl, sulfamoyl, $C_1$-$C_6$ alkylsulfamoyl, amino, $C_1$-$C_6$ alkylamino, $C_1$-$C_6$ dialkylamino, $C_1$-$C_6$ alkoxyl, and $C_3$-$C_6$ cycloalkoxyl;

n is 0-3;

wherein $R_5$ can be hydrogen only when at least one of $X_1$-$X_4$ is N;

and further wherein, $X_1$ and $X_3$ must be CH or N unless $R_5$ and $R_6$ together form a 5 or 6 membered heterocyclic ring or at least one of $X_1$-$X_4$ is N;

and wherein Ar excludes substituted or unsubstituted indazol-3-yl and substituted or unsubstituted 1H-pyrazolo[3,4-b]pyridyl;

with the following provisos:

proviso IIa: when all X are C and one of $R_5$, $R_6$, or $R_7$ are carboxyl, methylsulfonamido, or sulfamoyl, then Ar cannot be phenyl, substituted or unsubstituted phenyl-($C_1$-$C_3$)-alkyl, or phenyl-($C_2$-$C_6$)-alkenyl; and proviso IIb: when all X are C and one of $R_5$, $R_6$, or $R_7$ are independently selected from the group consisting of halogen or methyl, then Ar cannot be 4-hydroxyphenyl or 4-$C_1$-$C_6$ acyl-oxy-phenyl; and proviso IIc: when all X are C and $R_5$ is methyl, Cl, hydroxyl, trifluoromethyl and $R_6$ is methyl, methyoxy, carboxyethyl, Cl, or carboxypropyl, and n is 1, then Ar cannot be phenyl, 4-methyl-phenyl, 4-methoxy-phenyl, 4-halo-phenyl, or thiophen-yl; and proviso IId: when all X are C and $R_5$ and $R_6$ together form a heterocyclic ring and the resulting bicyclic ring system is benzo[d]thiazol substituted at the 2 position with $C_1$-$C_3$ alkyl, then Ar cannot be phenyl, 4-F-phenyl, 4-methoxy-phenyl, or thiophen-yl.

In a further aspect of the invention of formula II, Ar is selected from the group consisting of phenyl, substituted phenyl, thiophen-yl, substituted thiophen-yl, pyridinyl, substituted pyridinyl, thiazolyl, and substituted thiazolyl.

In a further aspect of the invention of formula II, Ar is selected from the group consisting of aryl, substituted aryl, heteroaryl and substituted heteroaryl;

$R_1$ is selected from the group consisting of hydrogen, $C_1$-$C_6$ alkyl, $C_3$-$C_6$ cycloalkyl, aryl, substituted aryl, heteroaryl, and substituted heteroaryl;

$X_1$-$X_4$ is independently selected from the group consisting of C and N;

$R_5$ is selected from the group consisting of hydrogen, hydroxyl, halogen, $C_1$-$C_6$ alkyl, $C_3$-$C_6$ cycloalkyl, cyano, nitro, carbamoyl, $C_1$-$C_6$ alkylcarbamoyl, carboxyl, $C_1$-$C_6$ alkylhydroxy, sulfamoyl, $C_1$-$C_6$ alkylsulfamoyl, amino, $C_1$-$C_6$ alkylamino, $C_1$-$C_6$ dialkylamino, $C_1$-$C_6$ alkoxyl, and $C_3$-$C_6$ cycloalkoxyl;

$R_6$ is selected from the group consisting of halogen, hydroxyl, carbamoyl, substituted carbamoyl, $C_1$-$C_6$ alkylcarbamoyl, sulfamoyl, $C_1$-$C_6$ alkylsulfamoyl, $C_1$-$C_6$ alkyl, $C_3$-$C_6$ cycloalkyl, cyano, nitro, amino, $CF_3$, carboxyl, ureido, sulfamoylamino, 2-amino-2-oxoethyl, $C_1$-$C_6$ alkylamino, $C_r$-$C_6$ dialkylamino, arylamino, heteroarylamino, $C_1$-$C_6$ alkoxyl, $C_3$-$C_6$ cycloalkoxyl, aryl, substituted aryl, heteroaryl, and substituted heteroaryl;

or alternatively $R_5$ and $R_6$ together form a substituted or unsubstituted 5 or 6 membered heterocyclic ring containing up to 2 heteroatoms chosen from O, N or S;

$R_7$ is selected from the group consisting of hydrogen, hydroxyl, halogen, $C_1$-$C_6$ alkyl, $C_3$-$C_6$ cycloalkyl, cyano, nitro, carbamoyl, $C_1$-$C_6$ alkylcarbamoyl, sulfamoyl, $C_1$-$C_6$ alkylsulfamoyl, amino, $C_1$-$C_6$ alkylamino, $C_1$-$C_6$ dialkylamino, $C_1$-$C_6$ alkoxyl, and $C_3$-$C_6$ cycloalkoxyl;

n is 0-3;

wherein $R_5$ can be hydrogen only when at least one of $X_1$-$X_4$ is N;

and further wherein, $X_1$ and $X_3$ must be CH or N unless $R_5$ and $R_6$ together form a 5 or 6 membered heterocyclic ring or at least one of $X_1$-$X_4$ is N;

with the following provisos:

proviso IIa: Ar excludes substituted or unsubstituted indazol-3-yl and substituted or unsubstituted 1H-pyrazolo[3,4-b]pyridyl; and proviso IIb: when all X are C and one of $R_5$, $R_6$, or $R_7$ are carboxyl, methylsulfonamido, hydroxycarbamoyl, methoxycarbamoyl, benzyloxycarbamoyl, sulfamoyl, 1-H-tetrazol, 1-H-tetrazol-5-ylcarbamoyl, 2-(trifluoromethylsulfonyl)hydrazinecarbonyl, 1-carboxy-2-phenylethylcarbamoyl, 2-(carboxy)pyrrolidine-1-carbonyl, substituted or unsubstituted 3-(carboxy)thiophen-2-yl, substituted or unsubstituted 3-(carboxy)furan-2-yl, substituted or unsubstituted 3-(carboxy)-1H-pyrrol-2-yl, 5-(trifluoromethyl)-1H-1,2,4-triazol-2-yl, 5-substituted-1H-1,2,3-triazol-4-yl, Ar cannot be phenyl, substituted or unsubstituted phenyl-($C_1$-$C_3$)-alkyl, or phenyl-($C_2$-$C_6$)-alkenyl; and proviso IIc: when all X are C and one of $R_5$, $R_6$, or $R_7$ are independently selected from the group consisting of halogen or methyl, Ar cannot be 4-hydroxyphenyl or 4-$C_1$-$C_6$ acyl-oxy-phenyl; and proviso IId: when all X are C and $R_5$ is methyl, Cl, hydroxyl, trifluoromethyl and $R_6$ is methyl, methyoxy, carboxyethyl, Cl, or carboxypropyl, and n is 1, then Ar cannot be phenyl, 4-methyl-phenyl, 4-methoxy-phenyl, 4-halo-phenyl, or thiophen-yl; and proviso IIe: when all X are C and $R_5$ and $R_6$ together form a heterocyclic ring and the resulting bicyclic ring system is benzo[d]thiazol substituted at the 2 position with $C_1$-$C_3$ alkyl, then Ar cannot be phenyl, 4-F-phenyl, 4-methoxy-phenyl, or thiophen-yl.

In one of its aspects the present invention provides a compound having a structure shown in Formula III, or a pharmaceutically acceptable salt, stereoisomer, or prodrug thereof:

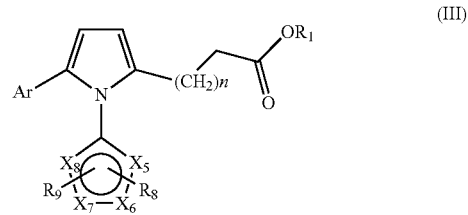

(III)

Ar is selected from the group consisting of aryl, substituted aryl, heteroaryl and substituted heteroaryl;

$R_1$ is selected from the group consisting of hydrogen, $C_1$-$C_6$ alkyl, $C_3$-$C_6$ cycloalkyl, aryl, substituted aryl, heteroaryl, and substituted heteroaryl;

$X_5$-$X_8$ are independently selected from the group consisting of N, C and S, wherein at least one X must be N or S;

$R_8$ and $R_9$ are independently selected from the group consisting of hydrogen, halogen, hydroxyl, carbamoyl, substituted carbamoyl, sulfamoyl, substituted sulfamoyl, $C_1$-$C_6$ alkyl, $C_3$-$C_6$ cycloalkyl, cyano, nitro, amino, $CF_3$, carboxyl, ureido, sulfamoylamino, 2-amino-2-oxoethyl, $C_1$-$C_6$ alkylamino, $C_1$-$C_6$ dialkylamino, arylamino, heteroarylamino, $C_1$-$C_6$ alkoxyl, $C_3$-$C_6$ cycloalkoxyl, aryl, aryloxyl, substituted aryl, heteroaryl, substituted heteroaryl, and null if $X_5$-$X_8$ are all N;

n is 0-3;

wherein Ar excludes substituted or unsubstituted indazol-3-yl and substituted or unsubstituted 1H-pyrazolo[3,4-b]pyridyl.

In a further aspect of the invention of formula III, Ar is selected from the group consisting of phenyl, substituted phenyl, thiophen-yl, substituted thiophen-yl, pyridinyl, substituted pyridinyl, thiazolyl, substituted thiazolyl, bicyclic aryl, substituted bicyclic aryl, bicyclic heteroaryl, and substituted bicyclic heteroaryl.

In one of its aspects the present invention provides a compound having a structure shown in Formula IV, or a pharmaceutically acceptable salt, stereoisomer, or prodrug thereof:

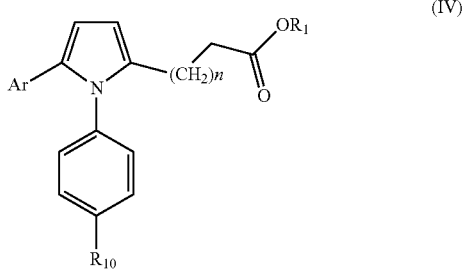

(IV)

wherein
Ar is selected from the group consisting of aryl, substituted aryl, heteroaryl and substituted heteroaryl;
$R_1$ is selected from the group consisting of hydrogen, $C_1$-$C_6$ alkyl, $C_3$-$C_6$ cycloalkyl, aryl, substituted aryl, heteroaryl, and substituted heteroaryl;
$R_{10}$ is hydroxyl, carbamoyl, ureido, sulfamoylamino, 2-amino-2-oxoethyl, acetyl, hydroxyethyl, pyridin-3-ylamino, piridin-4-ylamino, 1-methylpyrrolidin-3-yloxy, trifluoroacetyl, imidazol-1-yl, acetamido, methylsulfamido, 2-oxooxazolidin-3-yl, 2-hydroxyethylamino, and methylcarbamoyl;
n is 0-3;
wherein Ar excludes substituted or unsubstituted indazol-3-yl and substituted or unsubstituted 1H-pyrazolo[3,4-b]pyridyl; with the following proviso:
proviso IVa: when $R_{10}$ is hydroxyl or carbamoyl, Ar cannot be phenyl, 4-methyl-phenyl, 4-methoxy-phenyl, 4-halo-phenyl, or thiophen-yl when n is 0 or 1.

In a further aspect of the invention of formula IV, Ar is selected from the group consisting of phenyl, substituted phenyl, thiophen-yl, substituted thiophen-yl, pyridinyl, substituted pyridinyl, thiazolyl, and substituted thiazolyl.

In yet a further aspect of the invention of formula IV, Ar is selected from phenyl, 3-methoxyphenyl, 4-methoxyphenyl, 4-chloro-2-methoxyphenyl, 2-methoxy-4-(2-methyl-1H-imidazol-1-yl)phenyl, 1H-imidazol-1-yl-phenyl, 2-methyl-1H-imidazol-1-yl-phenyl, 1H-imidazol-1-yl-thiophen-2-yl, and 2-methyl-1H-imidazol-1-yl-thipheny-2-yl.

In a further aspect of the invention of formula IV, Ar is selected from the group consisting of aryl, substituted aryl, heteroaryl and substituted heteroaryl;
$R_1$ is selected from the group consisting of hydrogen, $C_1$-$C_6$ alkyl, $C_3$-$C_6$ cycloalkyl, aryl, substituted aryl, heteroaryl, and substituted heteroaryl;
$R_{10}$ is hydroxyl, carbamoyl, ureido, sulfamoylamino, 2-amino-2-oxoethyl, acetyl, hydroxyethyl, pyridin-3-ylamino, piridin-4-ylamino, 1-methylpyrrolidin-3-yloxy, trifluoroacetyl, imidazol-1-yl, acetamido, methylsulfamido, 2-oxooxazolidin-3-yl, 2-hydroxyethylamino, and methylcarbamoyl;
n is 0-3;
with the following provisos:
proviso IVa: Ar excludes substituted or unsubstituted indazol-3-yl and substituted or unsubstituted 1H-pyrazolo[3,4-b]pyridyl; and
proviso IVb: when $R_{10}$ is hydroxyl or carbamoyl, Ar cannot be phenyl, 4-methyl-phenyl, 4-methoxy-phenyl, 4-halo-phenyl, or thiophen-yl when n is 0 or 1.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present invention.

It is to be understood that isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

2. Representative GSNOR Inhibitors

Table 1 below lists representative novel pyrrole analogs of Formula I useful as GSNOR inhibitors of the invention. The synthetic methods that can be used to prepare each compound, identified in Table 1 (i.e. Scheme 1, Scheme 2, etc.) are detailed below. In some cases, if the starting material or intermediate of a scheme is not commercially available, then a corresponding method (called Method 1, Method 2, etc.) describes the synthesis of that starting material or intermediate. Table 1 provides Scheme number, defines starting materials shown in Schemes, and where necessary provides the method number which corresponds to synthesis of an intermediate or starting material. Supporting mass spectrometry data for each compound is also included in Table 1. GSNOR inhibitor activity was determined by the assay described in Example 2 and $IC_{50}$ values were obtained. GSNOR inhibitor compounds 1-198 of Table 1 had an $IC_{50}$ of about <100 µM. GSNOR inhibitor compounds 1-42, 69-71, 73-77, 79-81, 84-86, 92-103, 105-108, 110, 112-118, 120, 123-142, 144-164, 166-168, 170-172, 175-181, 183, 185-198 of Table 1 had an $IC_{50}$ of about less than 5.0 µM. GSNOR inhibitor compounds 1-25, 69, 75-76, 80, 84-86, 92-94, 96-99, 101-103, 105-106, 110, 112-116, 118, 120, 124-126, 128-131, 133-137, 139-141, 144, 146, 149-150, 152, 154-157, 162-163, 166-168, 170-172, 175-180, 186-192, 194, and 196-197 of Table 1 had an $IC_{50}$ of about less than 1.0 µM.

TABLE 1

| # | Structure | Compound name | Chemical formula | Molecular weight | Mass Spec | Scheme #/Method # |
|---|---|---|---|---|---|---|
| 1 | 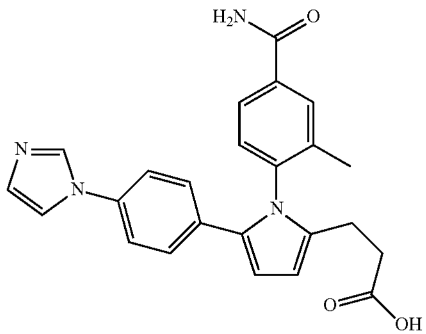 | 3-(5-(4-((1H-imidazol-1-yl)phenyl)-1-(4-carbamoyl-2-methylphenyl)-1H-pyrrol-2-yl)propanoic acid | C24H22N4O3 | 414.5 | 415.1 | Scheme 5, Ar1 = 4-carbamoyl-2-methylphenyl, R = H |
| 2 | 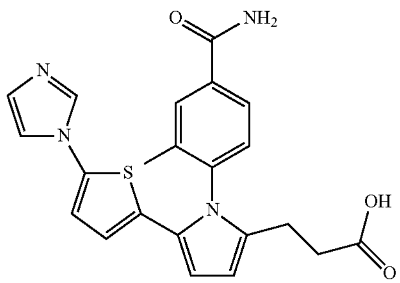 [SMILES: Cc1cc(C(N)=O)ccc1-n1c(CCC(=O)O)ccc1-c1ccc(-n2ccnc2)s1] | 3-(5-(5-(1H-imidazol-1-yl)thiophen-2-yl)-1-(4-carbamoyl-2-methylphenyl)-1H-pyrrol-2-yl)propanoic acid | C22H20N4O3S | 420.5 | 421.1 | Scheme 9b, Ar = 1H-imidazol-1-yl |
| 3 | 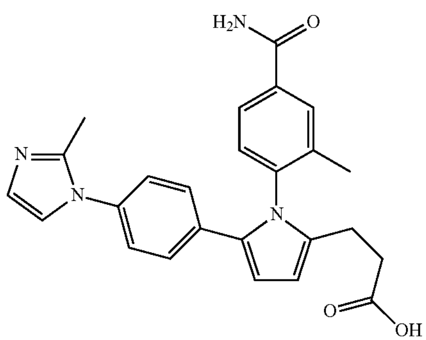 [SMILES: Cc1cc(C(N)=O)ccc1-n1c(CCC(=O)O)ccc1-c1ccc(-n2ccnc2C)cc1] | 3-(1-(4-carbamoyl-2-methylphenyl)-5-(4-(2-methyl-1H-imidazol-1-yl)phenyl)-1H-pyrrol-2-yl)propanoic acid | C25H24N4O3 | 428.5 | 429.1 | Scheme 9a, Ar = 2-methyl-1H-imidazol-1-yl |

TABLE 1-continued

| # | Structure | Compound name | Chemical formula | Molecular weight | Mass Spec | Scheme #/Method # |
|---|---|---|---|---|---|---|
| 4 | 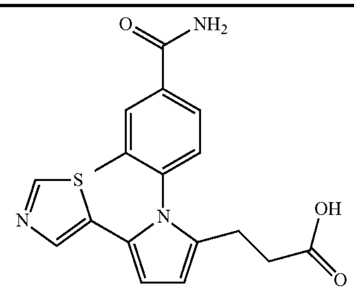 | 3-(1-(4-carbamoyl-2-methylphenyl)-5-(thiazol-5-yl)-1H-pyrrol-2-yl)propanoic acid | C18H17N3O3S | 355.4 | 356.1 | Scheme 1, R2 = thiazol-5-yl, R1 = 4-carbamoyl-2-methylphenyl |
| 5 | 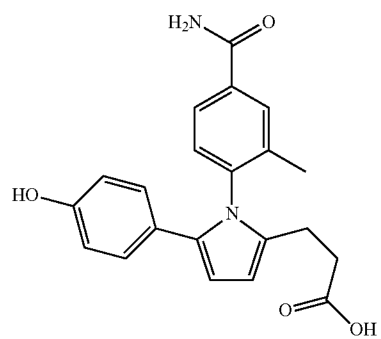 | 3-(1-(4-carbamoyl-2-methylphenyl)-5-(4-hydroxyphenyl)-1H-pyrrol-2-yl)propanoic acid | C21H20N2O4 | 364.4 | 365.1 | Scheme 1, R2 = 4-hydroxyphenyl, R1 = 4-carbamoyl-2-methylphenyl |
| 6 | 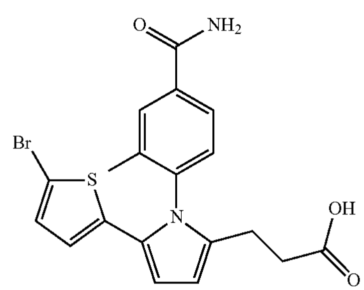 [SMILES: Cc1cc(C(N)=O)ccc1-n1c(CCC(=O)O)ccc1-c1ccc(Br)s1] | 3-(5-(5-bromothiophen-2-yl)-1-(4-carbamoyl-2-methylphenyl)-1H-pyrrol-2-yl)propanoic acid | C19H17BrN2O3S | 433.3 | 433, 435 | Scheme 1, R2 = 5-bromothiophen-2-yl, R1 = 4-carbamoyl-2-methylphenyl |

TABLE 1-continued

| # | Structure | Compound name | Chemical formula | Molecular weight | Mass Spec | Scheme #/Method # |
|---|---|---|---|---|---|---|
| 7 | 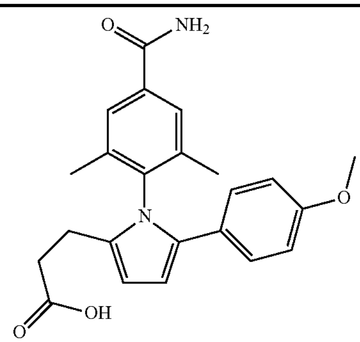 | 3-(1-(4-carbamoyl-2,6-dimethylphenyl)-5-(4-methoxyphenyl)-1H-pyrrol-2-yl)propanoic acid | C23H24N2O4 | 392.4 | 393.1 | Scheme 1, R2 = 4-methoxyphenyl, R1 = 4-carbamoyl-2,6-dimethylphenyl |
| 8 | 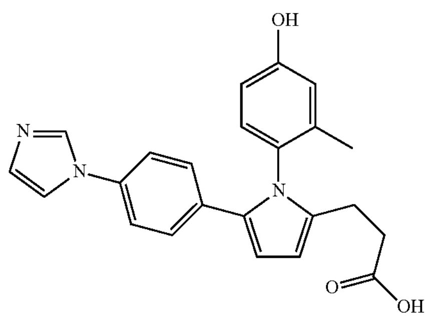 [SMILES: Cc1cc(O)ccc1-n1c(CCC(=O)O)ccc1-c1ccc(-n2ccnc2)cc1] | 3-(5-(4-(1H-imidazol-1-yl)phenyl)-1-(4-hydroxy-2-methylphenyl)-1H-pyrrol-2-yl)propanoic acid | C23H21N3O3 | 387.4 | 388.2 | Scheme 5, Ar1 = 4-hydroxy-2-methylphenyl, R = H |
| 9 | 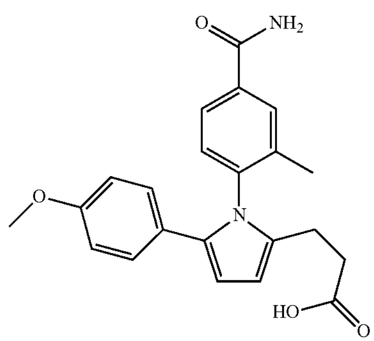 [SMILES: COc1ccc(-c2ccc(CCC(=O)O)n2-c2ccc(C(N)=O)cc2C)cc1] | 3-(1-(4-carbamoyl-2-methylphenyl)-5-(4-methoxyphenyl)-1H-pyrrol-2-yl)propanoic acid | C22H22N2O4 | 378.4 | 379.1 | Scheme 1, R2 = 4-methoxyphenyl, R1 = 4-carbamoyl-2-methylphenyl |

TABLE 1-continued

| # | Structure | Compound name | Chemical formula | Molecular weight | Mass Spec | Scheme #/Method # |
|---|---|---|---|---|---|---|
| 10 | 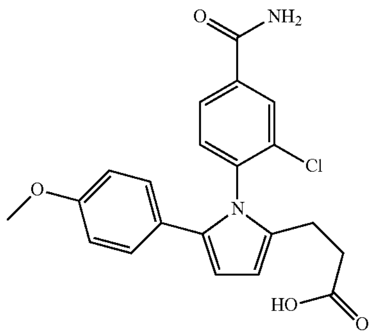 [SMILES: COc1ccc(-c2ccc(CCC(=O)O)n2-c2ccc(C(N)=O)cc2Cl)cc1] | 3-(1-(4-carbamoyl-2-chlorophenyl)-5-(4-methoxyphenyl)-1H-pyrrol-2-yl)propanoic acid | C21H19ClN2O4 | 398.8 | 398.9 | Scheme 1, R2 = 4-methoxyphenyl, R1 = 4-carbamoyl-2-chlorophenyl/Method 1 |
| 11 | 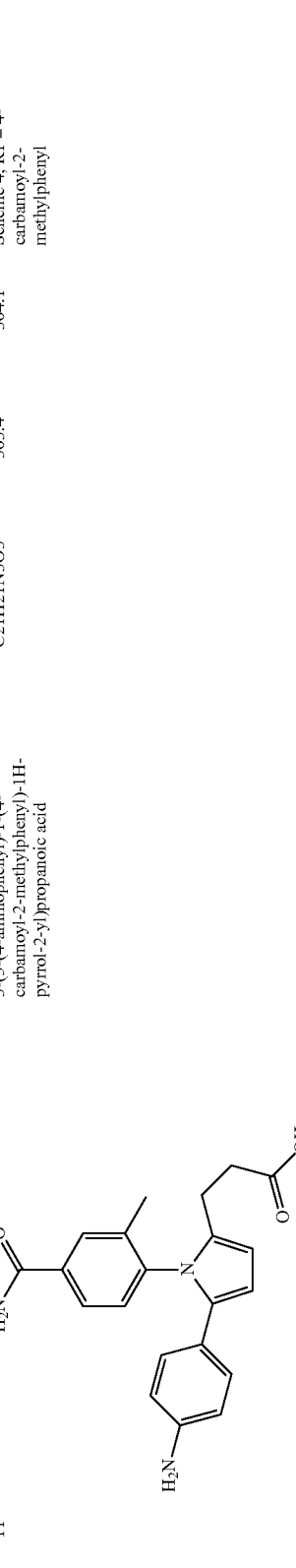 | 3-(5-(4-aminophenyl)-1-(4-carbamoyl-2-methylphenyl)-1H-pyrrol-2-yl)propanoic acid | C21H21N3O3 | 363.4 | 364.1 | Scheme 4, R1 = 4-carbamoyl-2-methylphenyl |
| 12 | 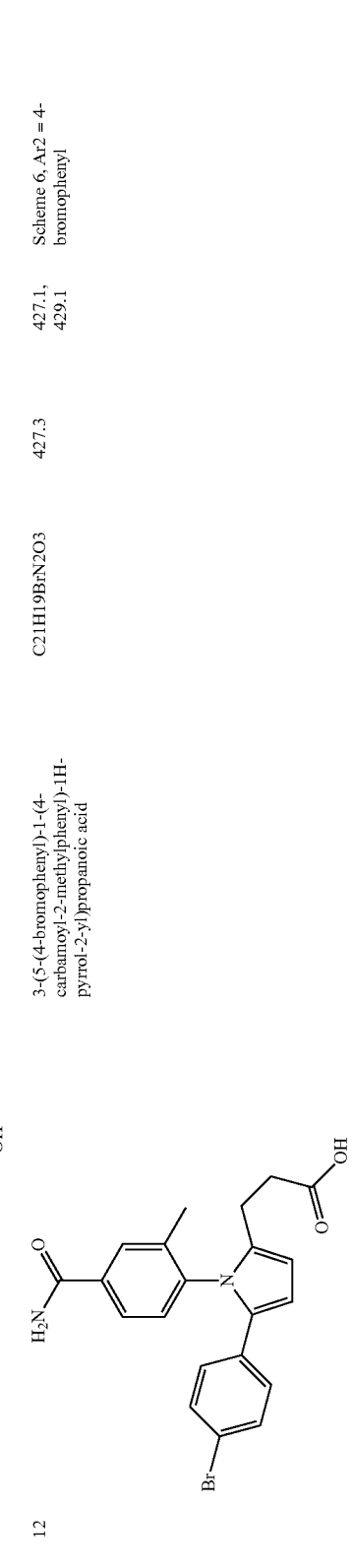 | 3-(5-(4-bromophenyl)-1-(4-carbamoyl-2-methylphenyl)-1H-pyrrol-2-yl)propanoic acid | C21H19BrN2O3 | 427.3 | 427.1, 429.1 | Scheme 6, Ar2 = 4-bromophenyl |

TABLE 1-continued

| # | Structure | Compound name | Chemical formula | Molecular weight | Mass Spec | Scheme #/Method # |
|---|---|---|---|---|---|---|
| 13 | 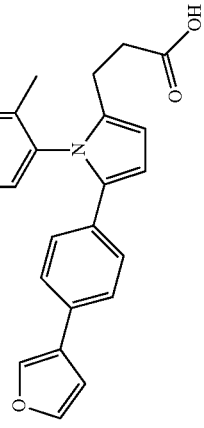 | 3-(1-(4-carbamoyl-2-methylphenyl)-5-(4-(furan-3-yl)phenyl)-1H-pyrrol-2-yl)propanoic acid | C25H22N2O4 | 414.5 | 415.1 | Scheme 3, R8 = furan-3-yl, R1 = 4 carbamoyl-2-methylphenyl |
| 14 | 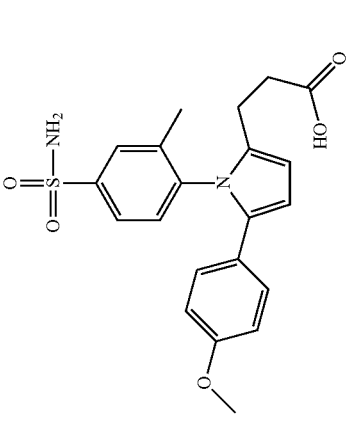 | 3-(5-(4-methoxyphenyl)-1-(2 methyl-4-sulfamoylphenyl)-1H-pyrrol-2-yl)propanoic acid | C21H22N2O5S | 414.5 | (M − H+)− 413.1 | Scheme 1, R2 = 4-methoxyphenyl, R1 = 2-methyl-4-sulfamoylphenyl |
| 15 | 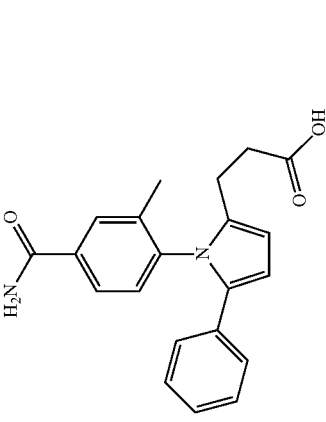 | 3-(1-(4-carbamoyl-2-methylphenyl)-5-phenyl-1H-pyrrol-2-yl)propanoic acid | C21H20N2O3 | 348.4 | 349.2 | Scheme 1, R2 = phenyl, R1 = 4-carbamoyl-2-methylphenyl |

TABLE 1-continued

| # | Structure | Compound name | Chemical formula | Molecular weight | Mass Spec | Scheme #/Method # |
|---|---|---|---|---|---|---|
| 16 | 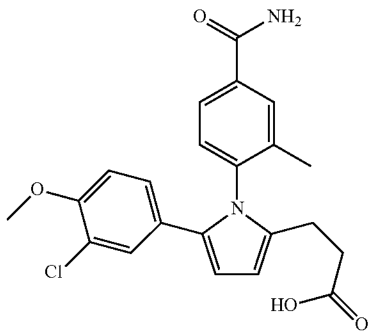 [SMILES: COc1ccc(-c2ccc(CCC(=O)O)n2-c2ccc(C(N)=O)cc2C)cc1Cl] | 3-(1-(4-carbamoyl-2-methylphenyl)-5-(3-chloro-4-methoxyphenyl)-1H-pyrrol-2-yl)propanoic acid | C22H21ClN2O4 | 412.9 | 413.1 | Scheme 6, Ar2 = 3-chloro-4-methoxyphenyl |
| 17 | 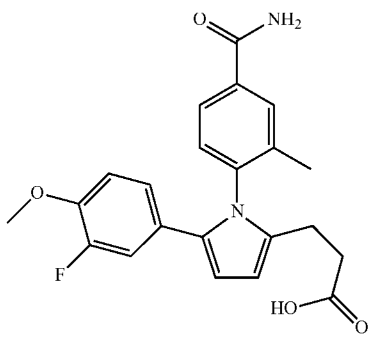 [SMILES: COc1ccc(-c2ccc(CCC(=O)O)n2-c2ccc(C(N)=O)cc2C)cc1F] | 3-(1-(4-carbamoyl-2-methylphenyl)-5-(3-fluoro-4-methoxyphenyl)-1H-pyrrol-2-yl)propanoic acid | C22H21FN2O4 | 396.4 | 397.1 | Scheme 6, Ar2 = 3-fluoro-4-methoxyphenyl |
| 18 | 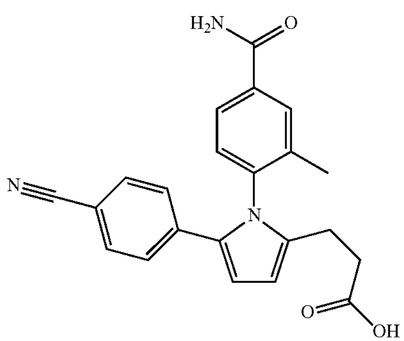 [SMILES: Cc1cc(C(N)=O)ccc1-n1c(CCC(=O)O)ccc1-c1ccc(C#N)cc1] | 3-(1-(4-carbamoyl-2-methylphenyl)-5-(4-cyanophenyl)-1H-pyrrol-2-yl)propanoic acid | C22H19N3O3 | 373.4 | 374.1 | Scheme 1, R2 = 4-cyanophenyl, R1 = 4-carbamoyl-2-methylphenyl |

TABLE 1-continued

| # | Structure | Compound name | Chemical formula | Molecular weight | Mass Spec | Scheme #/Method # |
|---|---|---|---|---|---|---|
| 19 | 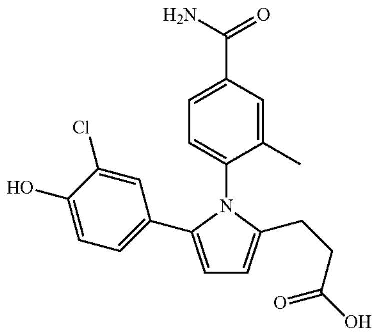 [SMILES: Cc1cc(C(N)=O)ccc1-n1c(CCC(=O)O)ccc1-c1ccc(O)c(Cl)c1] | 3-(1-(4-carbamoyl-2-methylphenyl)-5-(3-chloro-4-hydroxyphenyl)-1H-pyrrol-2-yl)propanoic acid | C21H19ClN2O4 | 398.8 | 399.1 | Scheme 1, R2 = 3-chloro-4-hydroxyphenyl, R1 = 4-carbamoyl-2-methylphenyl |
| 20 | 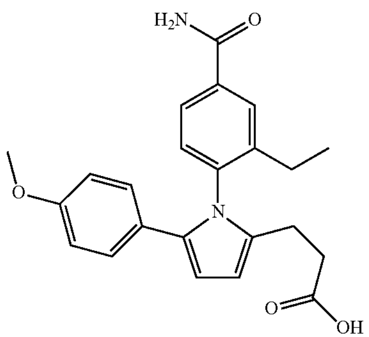 [SMILES: CCc1cc(C(N)=O)ccc1-n1c(CCC(=O)O)ccc1-c1ccc(OC)cc1] | 3-(1-(4-carbamoyl-2-ethylphenyl)-5-(4-methoxyphenyl)-1H-pyrrol-2-yl)propanoic acid | C23H24N2O4 | 392.4 | 393.1 | Scheme 1, R2 = 4-methoxyphenyl, R1 = 4-carbamoyl-2-ethylphenyl |
| 21 | 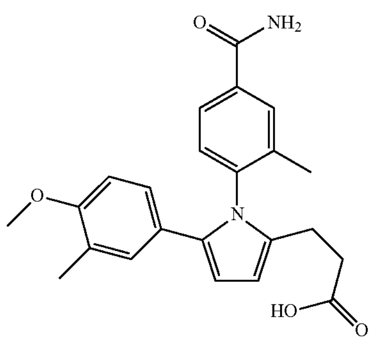 | 3-(1-(4-carbamoyl-2-methylphenyl)-5-(4-methoxy-3-methylphenyl)-1H-pyrrol-2-yl)propanoic acid | C23H24N2O4 | 392.4 | 393.2 | Scheme 6, Ar2 = 4-methoxy-3-methylphenyl |

TABLE 1-continued

| # | Structure | Compound name | Chemical formula | Molecular weight | Mass Spec | Scheme #/Method # |
|---|---|---|---|---|---|---|
| 22 | 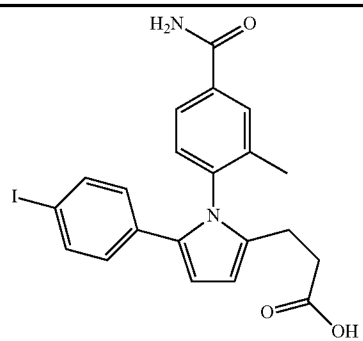 | 3-(1-(4-carbamoyl-2-methylphenyl)-5-(4-iodophenyl)-1H-pyrrol-2-yl)propanoic acid | C21H19IN2O3 | 474.3 | 475.0 | Scheme 1, R2 = 4-iodophenyl, R1 = 4-carbamoyl-2-methylphenyl |
| 23 | 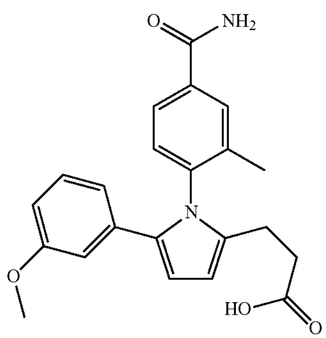 [SMILES: COc1cccc(-c2ccc(CCC(=O)O)n2-c2ccc(C(N)=O)cc2C)c1] | 3-(1-(4-carbamoyl-2-methylphenyl)-5-(3-methoxyphenyl)-1H-pyrrol-2-yl)propanoic acid | C22H22N2O4 | 378.4 | 379.1 | Scheme 1, R2 = 3-methoxyphenyl, R1 = 4-carbamoyl-2-methylphenyl |
| 24 | 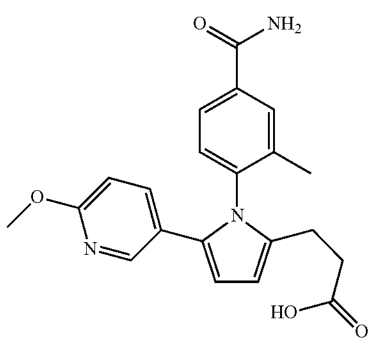 | 3-(1-(4-carbamoyl-2-methylphenyl)-5-(6-methoxypyridin-3-yl)-1H-pyrrol-2-yl)propanoic acid | C21H21N3O4 | 379.4 | 380.1 | Scheme 2, R2 = 6-methoxypyridin-3-yl, R1 = 4-carbamoyl-2-methylphenyl |

TABLE 1-continued

| # | Structure | Compound name | Chemical formula | Molecular weight | Mass Spec | Scheme #/Method # |
|---|---|---|---|---|---|---|
| 25 | 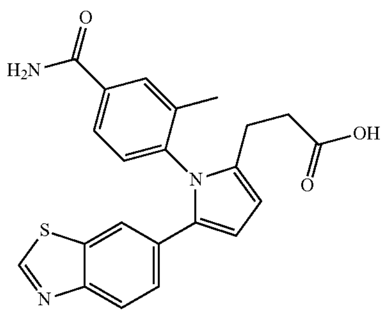 [SMILES: Cc1cc(C(N)=O)ccc1-n1c(CCC(=O)O)ccc1-c1ccc2ncsc2c1] | 3-(5-(benzo[d]thiazol-6-yl)-1-(4-carbamoyl-2-methylphenyl)-1H-pyrrol-2-yl)propanoic acid | C22H19N3O3S | 405.5 | 406.1 | Scheme 19, Ar2 = benzo[d]thiazol-6-yl |
| 26 | 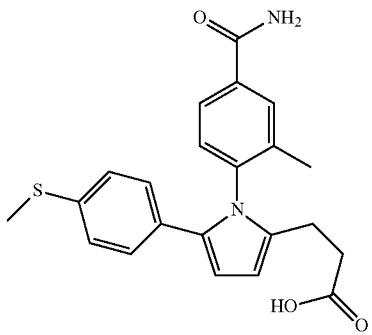 | 3-(1-(4-carbamoyl-2-methylphenyl)-5-(4-(methylthio)phenyl)-1H-pyrrol-2-yl)propanoic acid | C22H22N2O3S | 394.5 | 395.1 | Scheme 6, Ar2 = 4-(methylthio)phenyl |
| 27 | 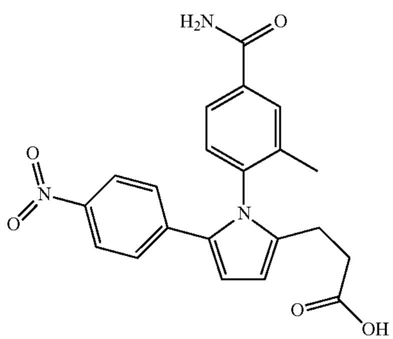 [SMILES: Cc1cc(C(N)=O)ccc1-n1c(CCC(=O)O)ccc1-c1ccc([N+](=O)[O-])cc1] | 3-(1-(4-carbamoyl-2-methylphenyl)-5-(4-nitrophenyl)-1H-pyrrol-2-yl)propanoic acid | C21H19N3O5 | 393.4 | 394.1 | Scheme 1, R2 = 4-nitrophenyl, R1 = 4-carbamoyl-2-methylphenyl |

TABLE 1-continued

| # | Structure | Compound name | Chemical formula | Molecular weight | Mass Spec | Scheme #/Method # |
|---|---|---|---|---|---|---|
| 28 | 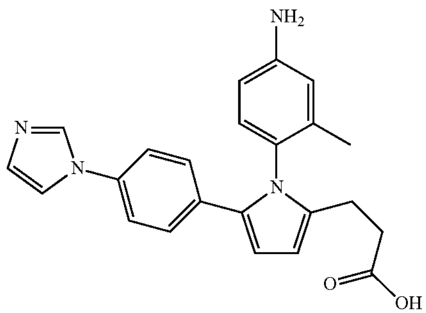 | 3-(5-(4-(1H-imidazol-1-yl)phenyl)-1-(4-amino-2-methylphenyl)-1H-pyrrol-2-yl)propanoic acid | C23H22N4O2 | 386.4 | 387.2 | Scheme 20, (Step 1, compound 20B, Ar2 = 4-(1H-imidazol-1-yl)phenyl), where 20A is compound #1 in this table |
| 29 | 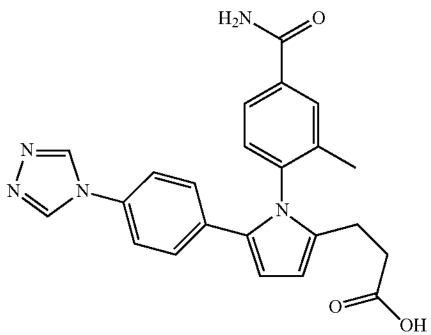 | 3-(5-(4-(4H-1,2,4-triazol-4-yl)phenyl)-1-(4-carbamoyl-2-methylphenyl)-1H-pyrrol-2-yl)propanoic acid | C23H21N5O3 | 415.4 | 416.2 | Scheme 11 |
| 30 | 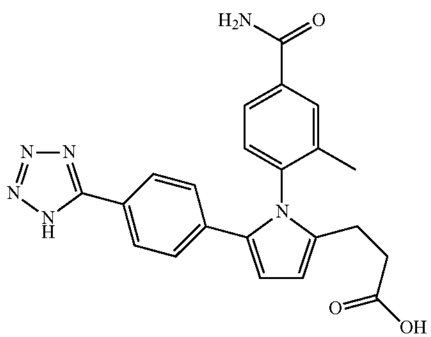 [SMILES: Cc1cc(C(N)=O)ccc1-n1c(CCC(=O)O)ccc1-c1ccc(-c2nnn[nH]2)cc1] | 3-(5-(4-(2H-tetrazol-5-yl)phenyl)-1-(4-carbamoyl-2-methylphenyl)-1H-pyrrol-2-yl)propanoic acid | C22H20N6O3 | 416.4 | 417.1 | Scheme 26, (26C) |

TABLE 1-continued

| # | Structure | Compound name | Chemical formula | Molecular weight | Mass Spec | Scheme #/Method # |
|---|---|---|---|---|---|---|
| 31 | 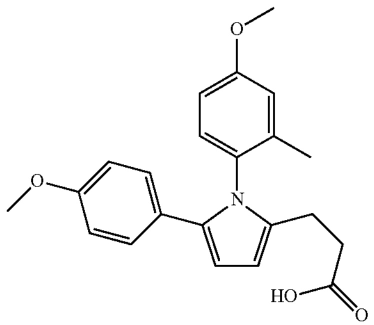 [SMILES: COc1ccc(-c2ccc(CCC(=O)O)n2-c2ccc(OC)cc2C)cc1] | 3-(1-(4-methoxy-2-methylphenyl)-5-(4-methoxyphenyl)-1H-pyrrol-2-yl)propanoic acid | C22H23NO4 | 365.4 | 366.1 | Scheme 1, R2 = 4-methoxyphenyl, R1 = 4-methoxy-2-methylphenyl |
| 32 | 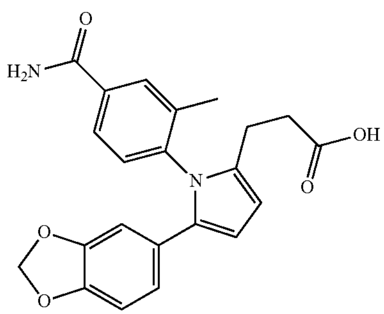 [SMILES: Cc1cc(C(N)=O)ccc1-n1c(CCC(=O)O)ccc1-c1ccc2c(c1)OCO2] | 3-(5-(benzo[d][1,3]dioxol-5-yl)-1-(4-carbamoyl-2-methylphenyl)-1H-pyrrol-2-yl)propanoic acid | C22H20N2O5 | 392.4 | (M − H)− 391.0 | Scheme 6, Ar2 = benzo[d][1,3]dioxol-5-yl |
| 33 | 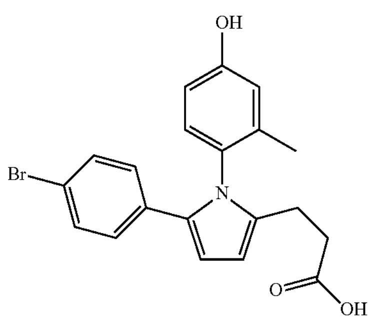 [SMILES: Cc1cc(O)ccc1-n1c(CCC(=O)O)ccc1-c1ccc(Br)cc1] | 3-(5-(4-bromophenyl)-1-(4-hydroxy-2-methylphenyl)-1H-pyrrol-2-yl)propanoic acid | C20H18BrNO3 | 400.3 | 400.1, 402.1 | Scheme 5 to 5C (Ar1 = 4-hydroxy-2-methylphenyl), followed by final step of Scheme 5 |

TABLE 1-continued

| # | Structure | Compound name | Chemical formula | Molecular weight | Mass Spec | Scheme #/Method # |
|---|---|---|---|---|---|---|
| 34 | 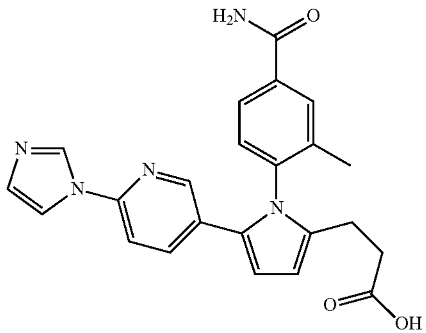 | 3-(5-(6-(1H-imidazol-1-yl)pyridin-3-yl)-1-(4-carbamoyl-2-methylphenyl)-1H-pyrrol-2-yl)propanoic acid | C23H21N5O3 | 415.4 | 416.0 | Scheme 2, R2 = 6-(1H-imidazol-1-yl)pyridin-3-yl, R1 = 4-carbamoyl-2-methylphenyl/Method 2 |
| 35 | 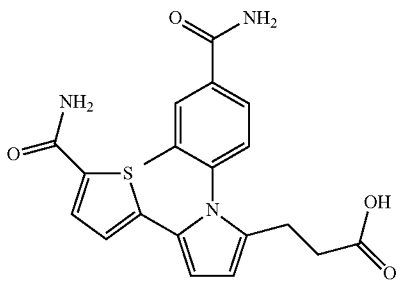 [SMILES: Cc1cc(C(N)=O)ccc1-n1c(CCC(=O)O)ccc1-c1ccc(C(N)=O)s1] | 3-(1-(4-carbamoyl-2-methylphenyl)-5-(5-carbamoylthiophen-2-yl)-1H-pyrrol-2-yl)propanoic acid | C20H19N3O4S | 397.4 | 398.0 | Scheme 2, R2 = 5-carbamoylthiophen-2-yl, R1 = 4-carbamoyl-2-methylphenyl |
| 36 | 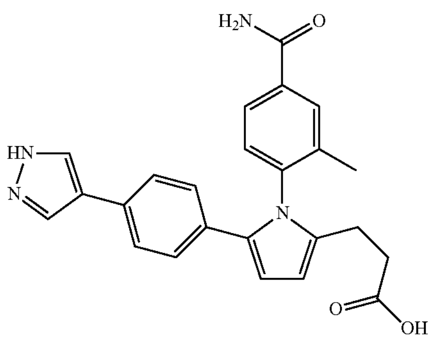 [SMILES: Cc1cc(C(N)=O)ccc1-n1c(CCC(=O)O)ccc1-c1ccc(-c2cn[nH]c2)cc1] | 3-(5-(4-(1H-pyrazol-4-yl)phenyl)-1-(4-carbamoyl-2-methylphenyl)-1H-pyrrol-2-yl)propanoic acid | C24H22N4O3 | 414.5 | 415.1 | Scheme 3, R8 = 1H-pyrazol-4-yl, R1 = 4-carbamoyl-2-methylphenyl |

TABLE 1-continued

| # | Structure | Compound name | Chemical formula | Molecular weight | Mass Spec | Scheme #/Method # |
|---|---|---|---|---|---|---|
| 37 | 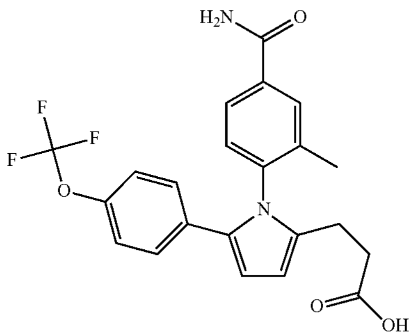 [SMILES: Cc1cc(C(N)=O)ccc1-n1c(CCC(=O)O)ccc1-c1ccc(OC(F)(F)F)cc1] | 3-(1-(4-carbamoyl-2-methylphenyl)-5-(4-(trifluoromethoxy)phenyl)-1H-pyrrol-2-yl)propanoic acid | C22H19F3N2O4 | 432.4 | 433.1 | Scheme 6, Ar2 = 4-(trifluoromethoxy)phenyl |
| 38 | 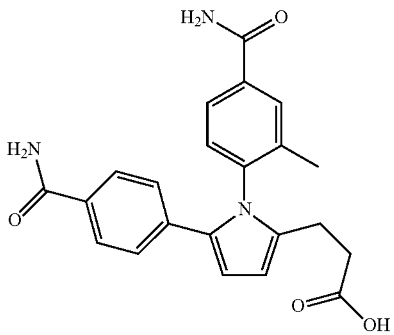 | 3-(1-(4-carbamoyl-2-methylphenyl)-5-(4-carbamoylphenyl)-1H-pyrrol-2-yl)propanoic acid | C22H21N3O4 | 391.4 | (M − H+)−390.1 | Scheme 2, R2 = 4-carbamoylphenyl, R1 = 4-carbamoyl-2-methylphenyl |
| 39 | 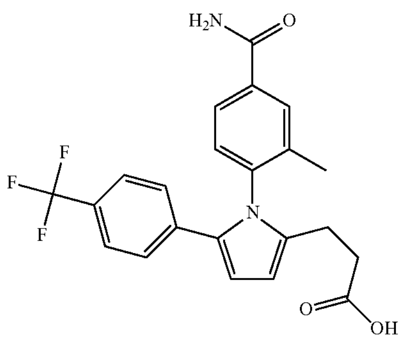 [SMILES: Cc1cc(C(N)=O)ccc1-n1c(CCC(=O)O)ccc1-c1ccc(C(F)(F)F)cc1] | 3-(1-(4-carbamoyl-2-methylphenyl)-5-(4-(trifluoromethyl)phenyl)-1H-pyrrol-2-yl)propanoic acid | C22H19F3N2O3 | 416.4 | 417.0 | Scheme 6, Ar2 = 4-(trifluoromethyl)phenyl |

TABLE 1-continued

| # | Structure | Compound name | Chemical formula | Molecular weight | Mass Spec | Scheme #/Method # |
|---|---|---|---|---|---|---|
| 40 | 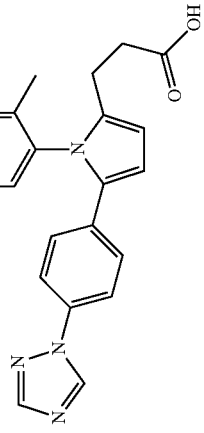 | 3-(5-(4-(1H-1,2,4-triazol-1-yl)phenyl)-1-(4-carbamoyl-2-methylphenyl)-1H-pyrrol-2-yl)propanoic acid | C23H21N5O3 | 415.4 | 416.1 | Scheme 9a, Ar = 1H-1,2,4-triazol-1-yl |
| 41 | 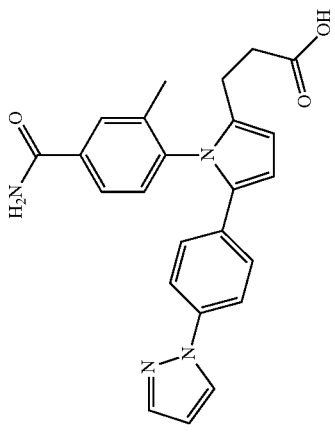 | 3-(5-(4-(1H-pyrazol-1-yl)phenyl)-1-(4-carbamoyl-2-methylphenyl)-1H-pyrrol-2-yl)propanoic acid | C24H22N4O3 | 414.5 | 415.1 | Scheme 9a, Ar = 1H-pyrazol-1-yl |
| 42 | 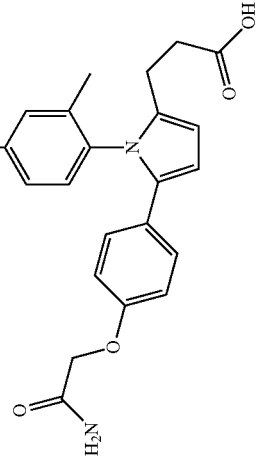 | 3-(5-(4-(2-amino-2-oxoethoxy)phenyl)-1-(4-carbamoyl-2-methylphenyl)-1H-pyrrol-2-yl)propanoic acid | C23H23N3O5 | 421.4 | 422.1 | Scheme 7, R1 = 4-carbamoyl-2-methylphenyl |

TABLE 1-continued

| # | Structure | Compound name | Chemical formula | Molecular weight | Mass Spec | Scheme #/Method # |
|---|---|---|---|---|---|---|
| 43 | 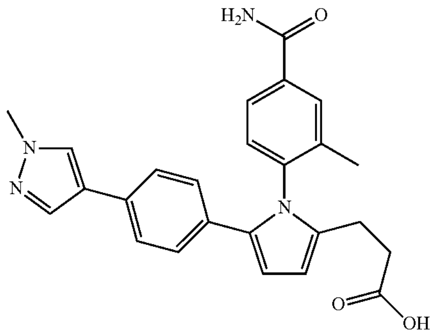 [SMILES: Cc1cc(C(N)=O)ccc1-n1c(CCC(=O)O)ccc1-c1ccc(-c2cnn(C)c2)cc1] | 3-(1-(4-carbamoyl-2-methylphenyl)-5-(4-(1-methyl-1H-pyrazol-4-yl)phenyl)-1H-pyrrol-2-yl)propanoic acid | C25H24N4O3 | 428.5 | 429.2 | Scheme 3, R8 = 1-methyl-1H-pyrazol-4-yl, R1 = 4-carbamoyl-2-methylphenyl |
| 44 | 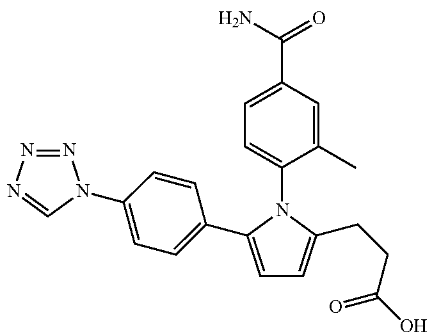 [SMILES: Cc1cc(C(N)=O)ccc1-n1c(CCC(=O)O)ccc1-c1ccc(-n2cnnn2)cc1] | 3-(5-(4-(1H-tetrazol-1-yl)phenyl)-1-(4-carbamoyl-2-methylphenyl)-1H-pyrrol-2-yl)propanoic acid | C22H20N6O3 | 416.4 | 417.0 | Scheme 12 |
| 45 | 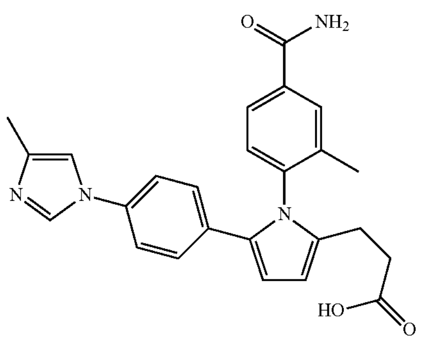 [SMILES: Cc1cn(-c2ccc(-c3ccc(CCC(=O)O)n3-c3ccc(C(N)=O)cc3C)cc2)cn1] | 3-(1-(4-carbamoyl-2-methylphenyl)-5-(4-(4-methyl-1H-imidazol-1-yl)phenyl)-1H-pyrrol-2-yl)propanoic acid | C25H24N4O3 | 428.5 | 429.1 | Scheme 9a, Ar = 4-methyl-1H-imidazol-1-yl |

TABLE 1-continued

| # | Compound name | Chemical formula | Molecular weight | Mass Spec | Scheme #/Method # |
|---|---|---|---|---|---|
| 46 | 3-(1-(4-carbamoyl-2-methylphenyl)-5-(4-ureidophenyl)-1H-pyrrol-2-yl)propanoic acid | C22H22N4O4 | 406.4 | 407.0 | Scheme 13 |
| 47 | 4-(2-(benzo[d][1,3]dioxol-5-yl)-5-(2-carboxyethyl)-1H-pyrrol-1-yl)-3-methylbenzoic acid | C22H19NO6 | 393.4 | (M − H+)− 392.0 | Scheme 21, Ar2 = benzo[d][1,3]dioxol-5-yl |
| 48 | 3-(1-(4-amino-2-methylphenyl)-5-(4-bromophenyl)-1H-pyrrol-2-yl)propanoic acid | C20H19BrN2O2 | 399.3 | 399.1, 401.1 | Scheme 22 |

TABLE 1-continued

| # | Structure | Compound name | Chemical formula | Molecular weight | Mass Spec | Scheme #/Method # |
|---|---|---|---|---|---|---|
| 49 | 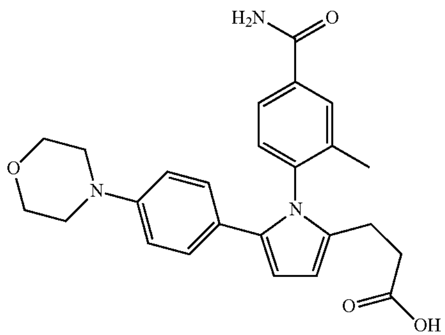 [SMILES: Cc1cc(C(N)=O)ccc1-n1c(CCC(=O)O)ccc1-c1ccc(N2CCOCC2)cc1] | 3-(1-(4-carbamoyl-2-methylphenyl)-5-(4-morpholinophenyl)-1H-pyrrol-2-yl)propanoic acid | C25H27N3O4 | 433.5 | 434.1 | Scheme 10, R = morpholino |
| 50 | 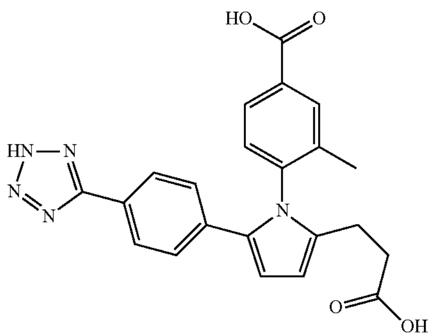 [SMILES: Cc1cc(C(=O)O)ccc1-n1c(CCC(=O)O)ccc1-c1ccc(-c2nn[nH]n2)cc1] | 4-(2-(4-(2H-tetrazol-5-yl)phenyl)-5-(2-carboxyethyl)-1H-pyrrol-1-yl)-3-methylbenzoic acid | C22H19N5O4 | 417.4 | 418.1 | Scheme 26, (26D) |
| 51 | 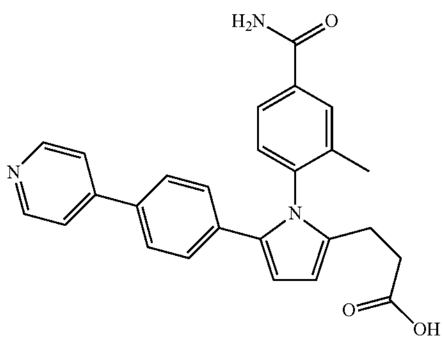 [SMILES: Cc1cc(C(N)=O)ccc1-n1c(CCC(=O)O)ccc1-c1ccc(-c2ccncc2)cc1] | 3-(1-(4-carbamoyl-2-methylphenyl)-5-(4-(pyridin-4-yl)phenyl)-1H-pyrrol-2-yl)propanoic acid | C26H23N3O3 | 425.5 | 426.1 | Scheme 3, R8 = pyridin-4-yl, R1 = 4-carbamoyl-2-methylphenyl |

TABLE 1-continued

| # | Structure | Compound name | Chemical formula | Molecular weight | Mass Spec | Scheme #/Method # |
|---|---|---|---|---|---|---|
| 52 | 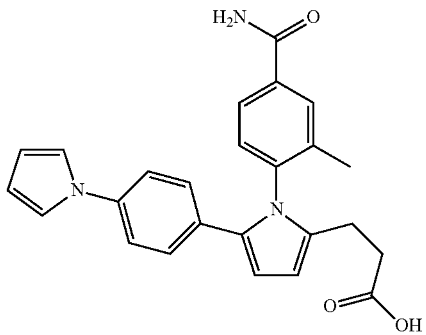 | 3-(5-(4-(1H-pyrrol-1-yl)phenyl)-1-(4-carbamoyl-2-methylphenyl)-1H-pyrrol-2-yl)propanoic acid | C25H23N3O3 | 413.5 | 414.1 | Scheme 9a, Ar = 1H-pyrrol-1-yl |
| 53 | 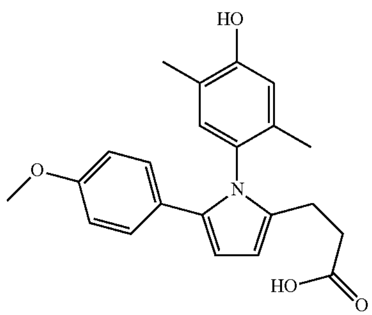 [SMILES: COc1ccc(-c2ccc(CCC(=O)O)n2-c2cc(C)c(O)cc2C)cc1] | 3-(1-(4-hydroxy-2,5-dimethylphenyl)-5-(4-methoxyphenyl)-1H-pyrrol-2-yl)propanoic acid | C22H23NO4 | 365.4 | 366.1 | Scheme 1, R2 = 4-methoxyphenyl, R1 = 4-hydroxy-2,5-dimethylphenyl |
| 54 | 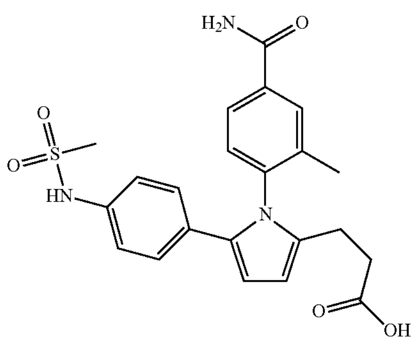 [SMILES: Cc1cc(C(N)=O)ccc1-n1c(CCC(=O)O)ccc1-c1ccc(NS(C)(=O)=O)cc1] | 3-(1-(4-carbamoyl-2-methylphenyl)-5-(4-(methylsulfonamido)phenyl)-1H-pyrrol-2-yl)propanoic acid | C22H23N3O5S | 441.5 | 442.1 | Scheme 14 |

TABLE 1-continued

| # | Structure | Compound name | Chemical formula | Molecular weight | Mass Spec | Scheme #/Method # |
|---|---|---|---|---|---|---|
| 55 | 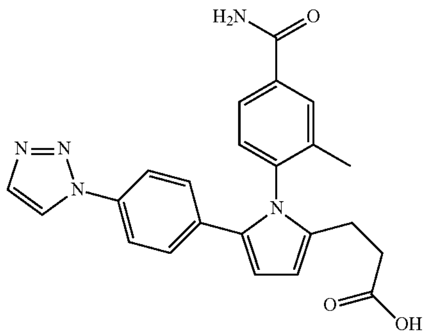 | 3-(5-(4-(1H-1,2,3-triazol-1-yl)phenyl)-1-(4-carbamoyl-2-methylphenyl)-1H-pyrrol-2-yl)propanoic acid | C23H21N5O3 | 415.4 | 416.0 | Scheme 15 |
| 56 | 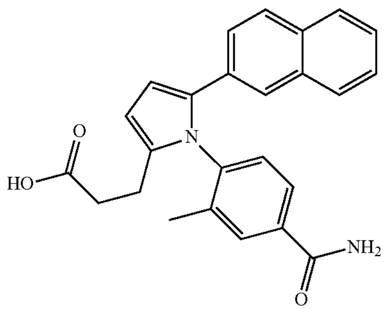 [SMILES: Cc1cc(C(N)=O)ccc1-n1c(CCC(=O)O)ccc1-c1ccc2ccccc2c1] | 3-(1-(4-carbamoyl-2-methylphenyl)-5-(naphthalen-2-yl)-1H-pyrrol-2-yl)propanoic acid | C25H22N2O3 | 398.5 | 399.0 | Scheme 1, R2 = naphthalen-2-yl, R1 = 4-carbamoyl-2-methylphenyl |
| 57 | 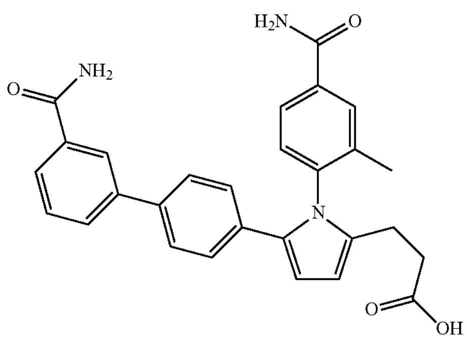 [SMILES: Cc1cc(C(N)=O)ccc1-n1c(CCC(=O)O)ccc1-c1ccc(-c2cccc(C(N)=O)c2)cc1] | 3-(1-(4-carbamoyl-2-methylphenyl)-5-(3-carbamoylbiphenyl-4-yl)-1H-pyrrol-2-yl)propanoic acid | C28H25N3O4 | 467.5 | 468.1 | Scheme 3, R8 = 3-carbamoylphenyl, R1 = 4-carbamoyl-2-methylphenyl |

TABLE 1-continued

| # | Structure | Compound name | Chemical formula | Molecular weight | Mass Spec | Scheme #/Method # |
|---|---|---|---|---|---|---|
| 58 | 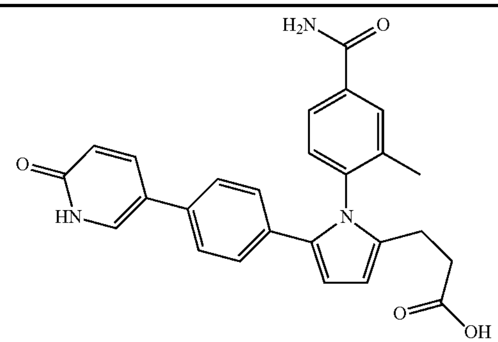 | 3-(1-(4-carbamoyl-2-methylphenyl)-5-(4-(6-oxo-1,6-dihydropyridin-3-yl)phenyl)-1H-pyrrol-2-yl)propanoic acid | C26H23N3O4 | 441.5 | 442.1 | Scheme 3, R8 = 6-oxo-1,6-dihydropyridin-3-yl, R1 = 4-carbamoyl-2-methylphenyl |
| 59 | 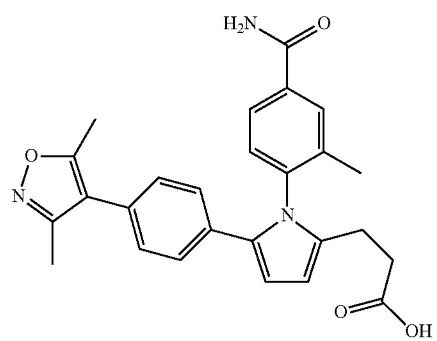 [SMILES: Cc1cc(C(N)=O)ccc1-n1c(CCC(=O)O)ccc1-c1ccc(-c2c(C)noc2C)cc1] | 3-(1-(4-carbamoyl-2-methylphenyl)-5-(4-(3,5-dimethylisoxazol-4-yl)phenyl)-1H-pyrrol-2-yl)propanoic acid | C26H25N3O4 | 443.5 | 444.1 | Scheme 3, R8 = 3,5-dimethylisoxazol-4-yl, R1 = 4-carbamoyl-2-methylphenyl |
| 60 | 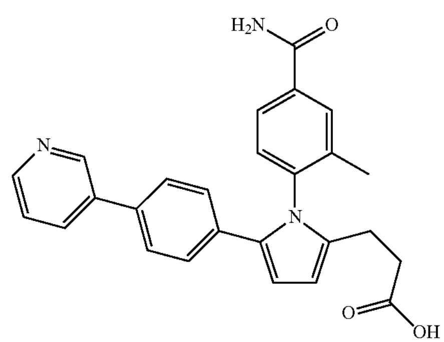 | 3-(1-(4-carbamoyl-2-methylphenyl)-5-(4-(pyridin-3-yl)phenyl)-1H-pyrrol-2-yl)propanoic acid | C26H23N3O3 | 425.5 | 426.2 | Scheme 3, R8 = pyridin-3-yl, R1 = 4-carbamoyl-2-methylphenyl |

TABLE 1-continued

| # | Structure | Compound name | Chemical formula | Molecular weight | Mass Spec | Scheme #/Method # |
|---|---|---|---|---|---|---|
| 61 | 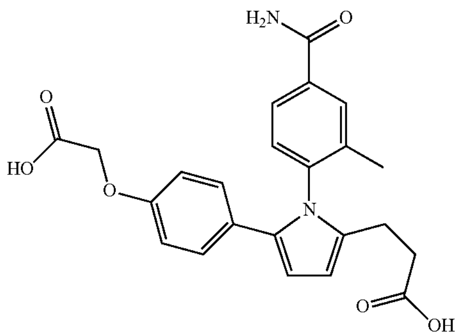 [SMILES: Cc1cc(C(N)=O)ccc1-n1c(CCC(=O)O)ccc1-c1ccc(OCC(=O)O)cc1] | 3-(1-(4-carbamoyl-2-methylphenyl)-5-(4-(carboxymethoxy)phenyl)-1H-pyrrol-2-yl)propanoic acid | C23H22N2O6 | 422.4 | 423.6 | Scheme 16 |
| 62 | 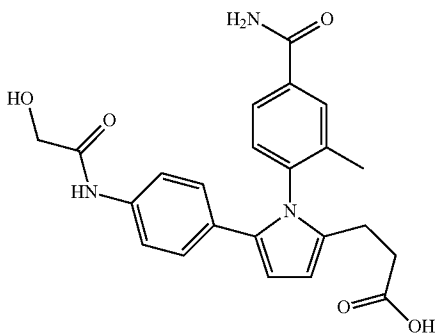 [SMILES: Cc1cc(C(N)=O)ccc1-n1c(CCC(=O)O)ccc1-c1ccc(NC(=O)CO)cc1] | 3-(1-(4-carbamoyl-2-methylphenyl)-5-(4-(2-H-hydroxyacetamido)phenyl)-1H-pyrrol-2-yl)propanoic acid | C23H23N3O5 | 421.4 | 422.0 | Scheme 18 |
| 63 | 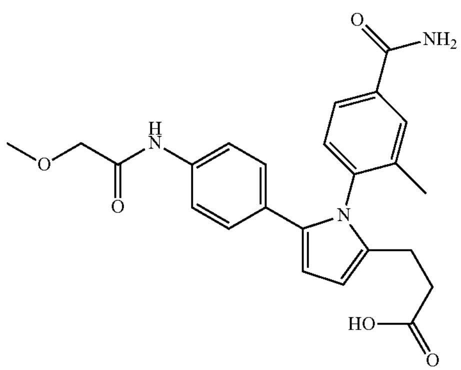 [SMILES: COCC(=O)Nc1ccc(-c2ccc(CCC(=O)O)n2-c2ccc(C(N)=O)cc2C)cc1] | 3-(1-(4-carbamoyl-2-methylphenyl)-5-(4-(2-methoxyacetamido)phenyl)-1H-pyrrol-2-yl)propanoic acid | C24H25N3O5 | 435.5 | 436.2 | Scheme 17 |

TABLE 1-continued

| # | Structure | Compound name | Chemical formula | Molecular weight | Mass Spec | Scheme #/Method # |
|---|---|---|---|---|---|---|
| 64 | 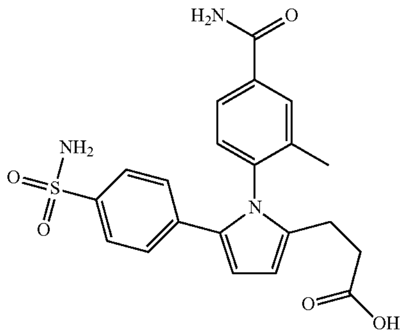 [SMILES: Cc1cc(C(N)=O)ccc1-n1c(CCC(=O)O)ccc1-c1ccc(S(N)(=O)=O)cc1] | 3-(1-(4-carbamoyl-2-methylphenyl)-5-(4-sulfamoylphenyl)-1H-pyrrol-2-yl)propanoic acid | C21H21N3O5S | 427.5 | 428.1 | Scheme 1, R2 = 4-sulfamoylphenyl, R1 = 4-carbamoyl-2-methylphenyl |
| 65 | 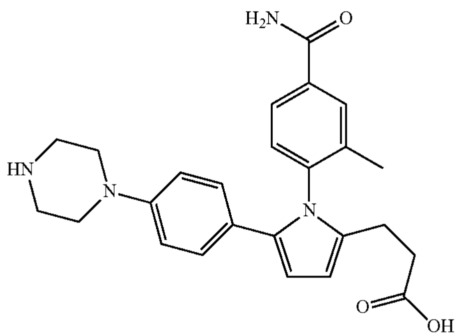 [SMILES: Cc1cc(C(N)=O)ccc1-n1c(CCC(=O)O)ccc1-c1ccc(N2CCNCC2)cc1] | 3-(1-(4-carbamoyl-2-methylphenyl)-5-(4-(piperazin-1-yl)phenyl)-1H-pyrrol-2-yl)propanoic acid | C25H28N4O3 | 432.5 | 433.2 | Scheme 10, R = piperazin-1-yl |
| 66 | 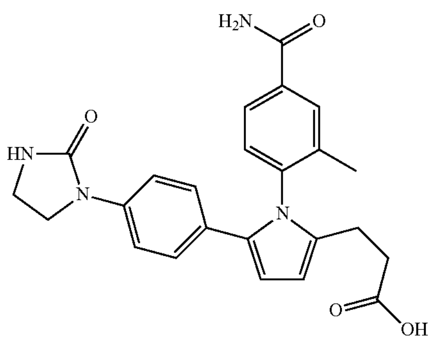 [SMILES: Cc1cc(C(N)=O)ccc1-n1c(CCC(=O)O)ccc1-c1ccc(N2CCNC2=O)cc1] | 3-(1-(4-carbamoyl-2-methylphenyl)-5-(4-(2-oxoimidazolidin-1-yl)phenyl)-1H-pyrrol-2-yl)propanoic acid | C24H24N4O4 | 432.5 | 433.1 | Scheme 8, R = 2-oxoimidazolidin-1-yl |

TABLE 1-continued

| # | Structure | Compound name | Chemical formula | Molecular weight | Mass Spec | Scheme #/Method # |
|---|---|---|---|---|---|---|
| 67 | 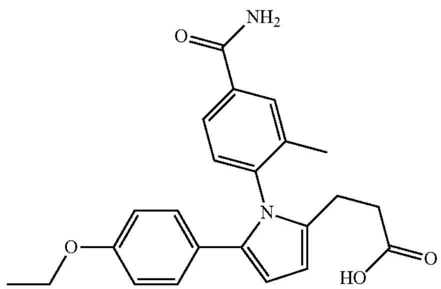 [SMILES: CCOc1ccc(-c2ccc(CCC(=O)O)n2-c2ccc(C(N)=O)cc2C)cc1] | 3-(1-(4-carbamoyl-2-methylphenyl)-5-(4-ethoxyphenyl)-1H-pyrrol-2-yl)propanoic acid | C23H24N2O4 | 392.4 | 393.1 | Scheme 6, Ar2 = 4-ethoxyphenyl |
| 68 | 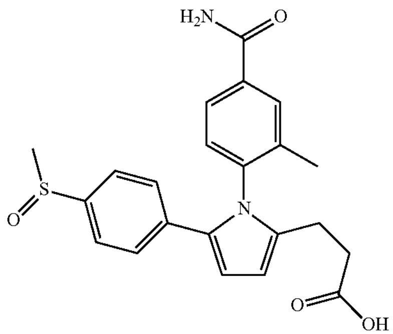 | 3-(1-(4-carbamoyl-2-methylphenyl)-5-(4-(methylsulfinyl)phenyl)-1H-pyrrol-2-yl)propanoic acid | C22H22N2O4S | 410.5 | 411.1 | Scheme 23 |
| 69 | 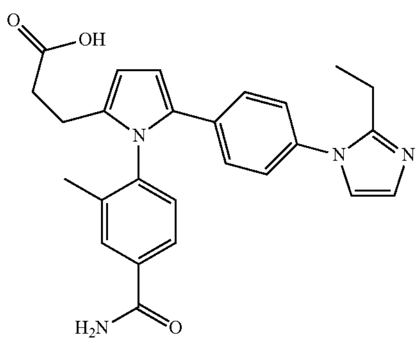 [SMILES: CCc1nccn1-c1ccc(-c2ccc(CCC(=O)O)n2-c2ccc(C(N)=O)cc2C)cc1] | 3-(1-(4-carbamoyl-2-methylphenyl)-5-(4-(2-ethyl-1H-imidazol-1-yl)phenyl)-1H-pyrrol-2-yl)propanoic acid | C26H26N4O3 | 442.5 | 443.2 | Scheme 5, Ar1 = 4-carbamoyl-2-methylphenyl, R = ethyl |

TABLE 1-continued

| # | Structure | Compound name | Chemical formula | Molecular weight | Mass Spec | Scheme #/Method # |
|---|---|---|---|---|---|---|
| 70 | 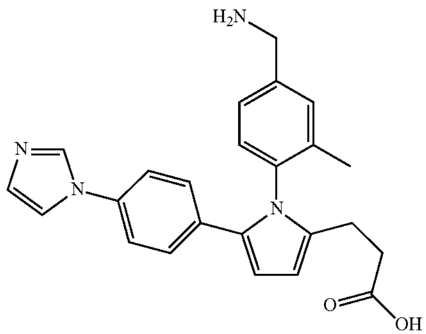 [SMILES: Cc1cc(CN)ccc1-n1c(CCC(=O)O)ccc1-c1ccc(-n2ccnc2)cc1] | 3-(5-(4-(1H-imidazol-1-yl)phenyl)-1-(4-(aminomethyl)-2-methylphenyl)-1H-pyrrol-2-yl)propanoic acid | C24H24N4O2 | 400.5 | 401.1 | Scheme 30 |
| 71 | 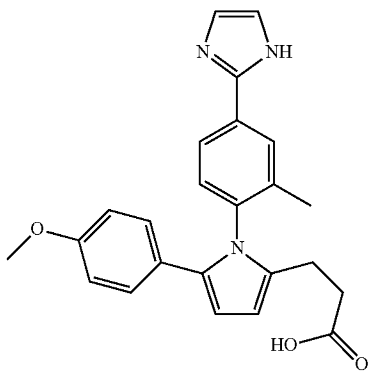 [SMILES: COc1ccc(-c2ccc(CCC(=O)O)n2-c2ccc(-c3ncc[nH]3)cc2C)cc1] | 3-(1-(4-(1H-imidazol-2-yl)-2-methylphenyl)-5-(4-methoxyphenyl)-1H-pyrrol-2-yl)propanoic acid | C24H23N3O3 | 401.5 | 402.2 | Scheme 25, Ar 1 = 4-(1H-imidazol-2-yl)-2-methylphenyl |
| 72 | 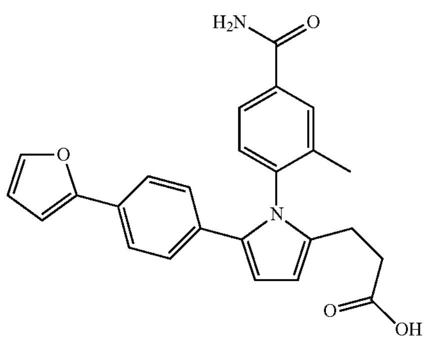 [SMILES: Cc1cc(C(N)=O)ccc1-n1c(CCC(=O)O)ccc1-c1ccc(-c2ccco2)cc1] | 3-(1-(4-carbamoyl-2-methylphenyl)-5-(4-(furan-2-yl)phenyl)-1H-pyrrol-2-yl)propanoic acid | C25H22N2O4 | 414.5 | 415.2 | Scheme 3, step 1, R8 = furan-2-yl, R1 = 4-carbamoyl-2-methylphenyl, followed by the final step of scheme 5 |

TABLE 1-continued

| # | Structure | Compound name | Chemical formula | Molecular weight | Mass Spec | Scheme #/Method # |
|---|---|---|---|---|---|---|
| 73 | 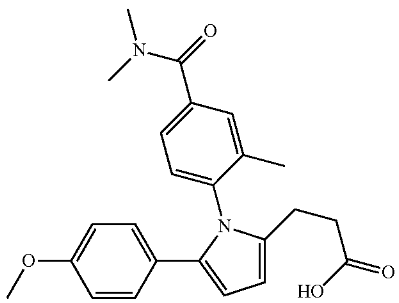 [SMILES: COc1ccc(-c2ccc(CCC(=O)O)n2-c2ccc(C(=O)N(C)C)cc2C)cc1] | 3-(1-(4-(dimethylcarbamoyl)-2-methyl)phenyl)-5-(4-methoxyphenyl)-1H-pyrrol-2-yl)propanoic acid | C24H26N2O4 | 406.5 | 407.1 | Scheme 27, Y = CH3, X1 = X2 = CH3 |
| 74 | 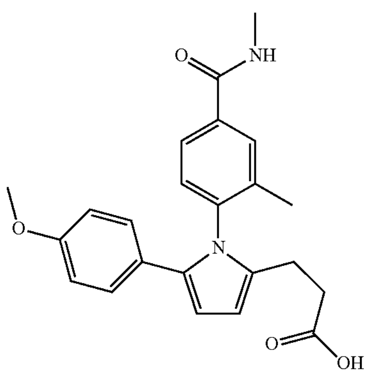 [SMILES: CNC(=O)c1ccc(-n2c(CCC(=O)O)ccc2-c2ccc(OC)cc2)c(C)c1] | 3-(5-(4-methoxyphenyl)-1-(2-methyl-4-(methylcarbamoyl)phenyl)-1H-pyrrol-2-yl)propanoic acid | C23H24N2O4 | 392.4 | 393.1 | Scheme 27, Y = CH3, X1 = CH3, X2 = H |

TABLE 1-continued

| # | Structure | Compound name | Chemical formula | Molecular weight | Mass Spec | Scheme #/Method # |
|---|---|---|---|---|---|---|
| 75 | 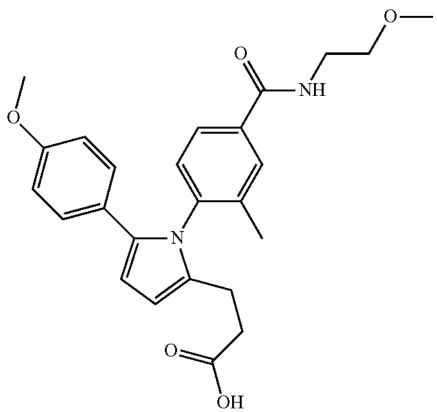 [SMILES: COCCNC(=O)c1ccc(-n2c(CCC(=O)O)ccc2-c2ccc(OC)cc2)c(C)c1] | 3-(1-(4-(2-methoxyethylcarbamoyl)-2-methylphenyl)-5-(4-methoxyphenyl)-1H-pyrrol-2-yl)propanoic acid | C25H28N2O5 | 436.5 | 437.2 | Scheme 27, Y = CH3, X1 = (CH2)2OMe, X2 = H |
| 76 | 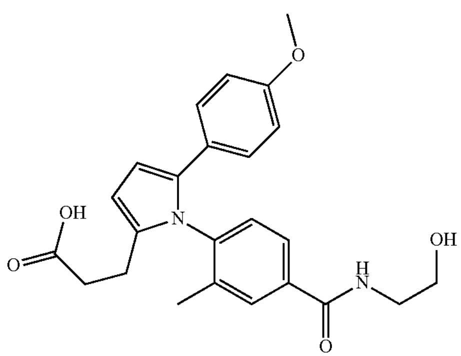 [SMILES: COc1ccc(-c2ccc(CCC(=O)O)n2-c2ccc(C(=O)NCCO)cc2C)cc1] | 3-(1-(4-(2-hydroxyethylcarbamoyl)-2-methylphenyl)-5-(4-methoxyphenyl)-1H-pyrrol-2-yl)propanoic acid | C24H26N2O5 | 422.5 | 423.1 | Scheme 27, Y = CH3, X1 = (CH2)2OH, X2 = H |

TABLE 1-continued

| # | Structure | Compound name | Chemical formula | Molecular weight | Mass Spec | Scheme #/Method # |
|---|---|---|---|---|---|---|
| 77 | 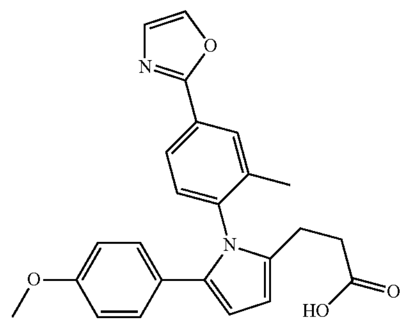 [SMILES: COc1ccc(-c2ccc(CCC(=O)O)n2-c2ccc(-c3ncco3)cc2C)cc1] | 3-(5-(4-methoxyphenyl)-1-(2-methyl-4-(oxazol-2-yl)phenyl)-1H-pyrrol-2-yl)propanoic acid | C24H22N2O4 | 402.4 | 403.0 | Scheme 25, Ar 1 = 2-methyl-4-(oxazol-2-yl)phenyl/Method 4 |
| 78 | 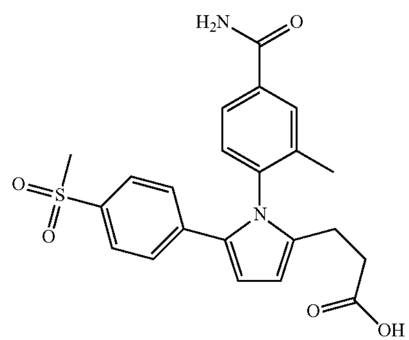 [SMILES: Cc1cc(C(N)=O)ccc1-n1c(CCC(=O)O)ccc1-c1ccc(S(C)(=O)=O)cc1] | 3-(1-(4-carbamoyl-2-methylphenyl)-5-(4-(methylsulfonyl)phenyl)-1H-pyrrol-2-yl)propanoic acid | C22H22N2O5S | 426.5 | 427.0 | Scheme 28 |
| 79 | 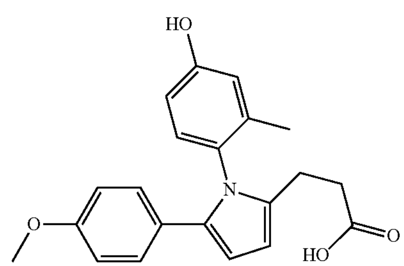 [SMILES: COc1ccc(-c2ccc(CCC(=O)O)n2-c2ccc(O)cc2C)cc1] | 3-(1-(4-hydroxy-2-methylphenyl)-5-(4-methoxyphenyl)-1H-pyrrol-2-yl)propanoic acid | C21H21NO4 | 351.4 | 352.1 | Scheme 1, R2 = 4-methoxyphenyl, R1 = 4-hydroxy-2-methylphenyl |

TABLE 1-continued

| # | Structure | Compound name | Chemical formula | Molecular weight | Mass Spec | Scheme #/Method # |
|---|---|---|---|---|---|---|
| 80 | 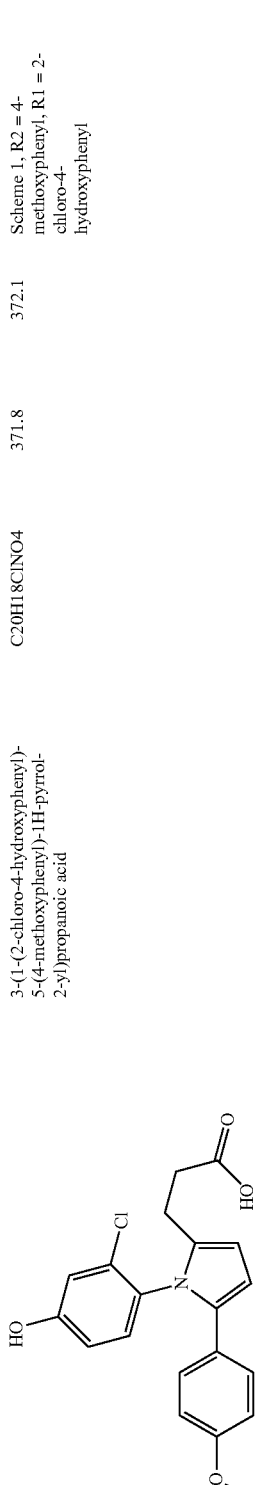 | 3-(1-(2-chloro-4-hydroxyphenyl)-5-(4-methoxyphenyl)-1H-pyrrol-2-yl)propanoic acid | C20H18ClNO4 | 371.8 | 372.1 | Scheme 1, R2 = 4-methoxyphenyl, R1 = 2-chloro-4-hydroxyphenyl |
| 81 | 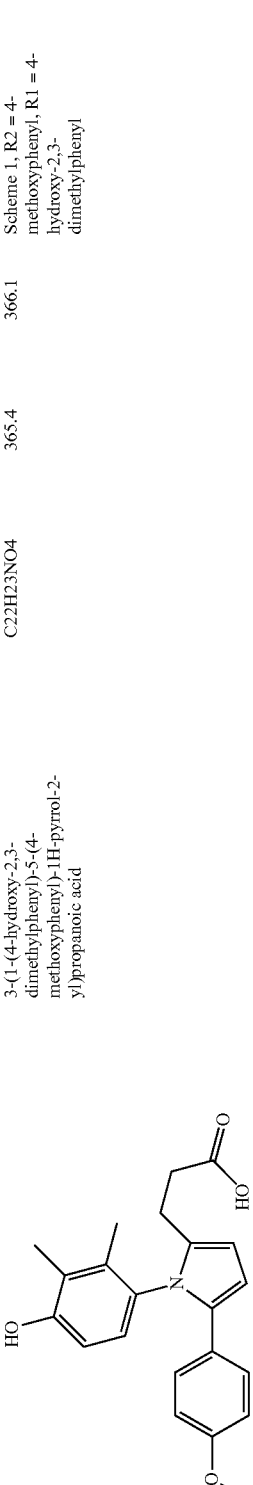 | 3-(1-(4-hydroxy-2,3-dimethylphenyl)-5-(4-methoxyphenyl)-1H-pyrrol-2-yl)propanoic acid | C22H23NO4 | 365.4 | 366.1 | Scheme 1, R2 = 4-methoxyphenyl, R1 = 4-hydroxy-2,3-dimethylphenyl |
| 82 | 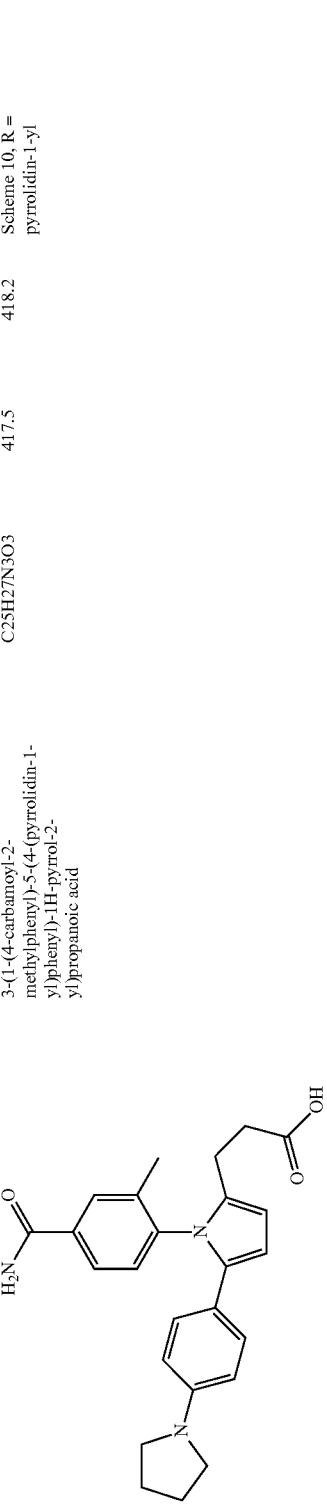 | 3-(1-(4-carbamoyl-2-methylphenyl)-5-(4-(pyrrolidin-1-yl)phenyl)-1H-pyrrol-2-yl)propanoic acid | C25H27N3O3 | 417.5 | 418.2 | Scheme 10, R = pyrrolidin-1-yl |

TABLE 1-continued

| # | Structure | Compound name | Chemical formula | Molecular weight | Mass Spec | Scheme #/Method # |
|---|---|---|---|---|---|---|
| 83 | 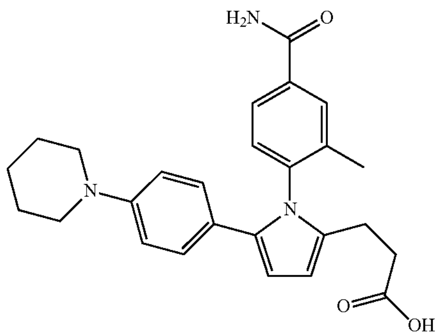 [SMILES: Cc1cc(C(N)=O)ccc1-n1c(CCC(=O)O)ccc1-c1ccc(N2CCCCC2)cc1] | 3-(1-(4-carbamoyl-2-methylphenyl)-5-(4-(piperidin-1-yl)phenyl)-1H-pyrrol-2-yl)propanoic acid | C26H29N3O3 | 431.5 | 432.2 | Scheme 10, R = piperidin-1-yl |
| 84 | 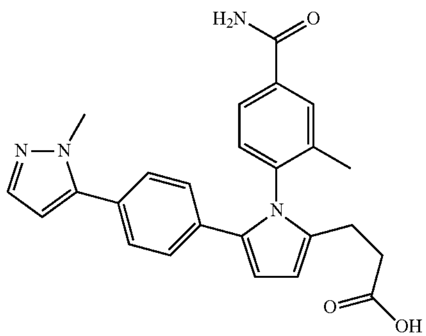 [SMILES: Cc1cc(C(N)=O)ccc1-n1c(CCC(=O)O)ccc1-c1ccc(-c2ccnn2C)cc1] | 3-(1-(4-carbamoyl-2-methylphenyl)-5-(4-(1-methyl-1H-pyrazol-5-yl)phenyl)-1H-pyrrol-2-yl)propanoic acid | C25H24N4O3 | 428.5 | 429.1 | Scheme 3 step 1, R8 = 1-methyl-1H-pyrazol-5-yl, R1 = 4-carbamoyl-2-methylphenyl |
| 85 | 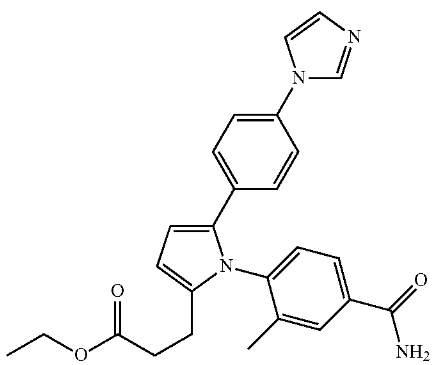 [SMILES: CCOC(=O)CCc1ccc(-c2ccc(-n3ccnc3)cc2)n1-c1ccc(C(N)=O)cc1C] | ethyl 3-(5-(4-(1H-imidazol-1-yl)phenyl)-1-(4-carbamoyl-2-methylphenyl)-1H-pyrrol-2-yl)propanoate | C26H26N4O3 | 442.5 | 443.7 | Scheme 5 (first 4 steps), Ar1 = 4-carbamoyl-2-methylphenyl, R = H |

TABLE 1-continued

| # | Structure | Compound name | Chemical formula | Molecular weight | Mass Spec | Scheme #/Method # |
|---|---|---|---|---|---|---|
| 86 | 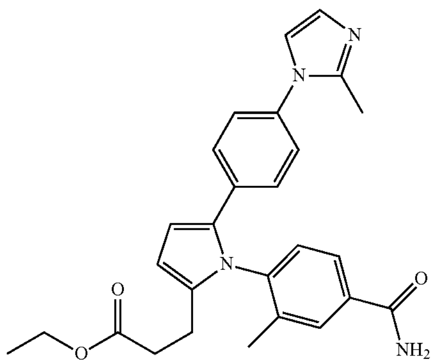 [SMILES: CCOC(=O)CCc1ccc(-c2ccc(-n3ccnc3C)cc2)n1-c1ccc(C(N)=O)cc1C] | ethyl 3-(1-(4-carbamoyl-2-methylphenyl)-5-(4-(2-methyl-1H-imidazol-1-yl)phenyl)-1H-pyrrol-2-yl)propanoate | C27H28N4O3 | 456.5 | 457.2 | Scheme 9a step 1, Ar = 2-methyl-1H-imidazol-1-yl |
| 87 | 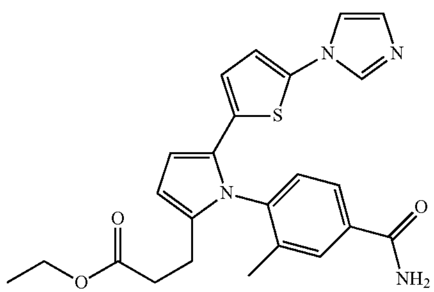 [SMILES: CCOC(=O)CCc1ccc(-c2ccc(-n3ccnc3)s2)n1-c1ccc(C(N)=O)cc1C] | ethyl 3-(1-(4-carbamoyl-2-methylphenyl)-5-(5-(2-methyl-1H-imidazol-1-yl)thiophen-2-yl)-1H-pyrrol-2-yl)propanoate | C24H24N4O3S | 448.5 | 449.1 | Scheme 9b step 1, Ar = 1H-imidazol-1-yl |
| 88 | 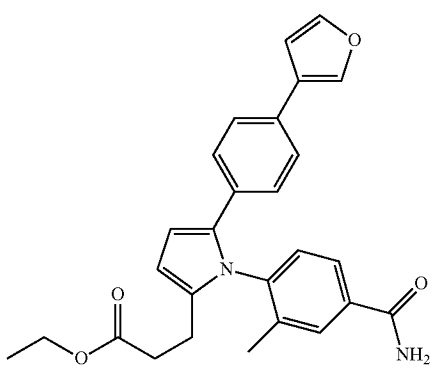 | ethyl 3-(1-(4-carbamoyl-2-methylphenyl)-5-(4-(furan-3-yl)phenyl)-1H-pyrrol-2-yl)propanoate | C27H26N2O4 | 442.5 | 443.2 | Scheme 3 (step 1), R8 = furan-3-yl, R1 = 4-carbamoyl-2-methylphenyl |

TABLE 1-continued

| # | Structure | Compound name | Chemical formula | Molecular weight | Mass Spec | Scheme #/Method # |
|---|---|---|---|---|---|---|
| 89 | 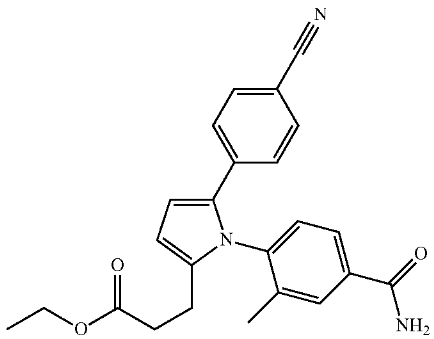 [SMILES: CCOC(=O)CCc1ccc(-c2ccc(C#N)cc2)n1-c1ccc(C(N)=O)cc1C] | ethyl 3-(1-(4-carbamoyl-2-methylphenyl)-5-(4-cyanophenyl)-1H-pyrrol-2-yl)propanoate | C24H23N3O3 | 401.5 | 402.2 | Scheme 1 (first three steps), R2 = 4-cyanophenyl, R1 = 4-carbamoyl-2-methylphenyl |
| 90 | 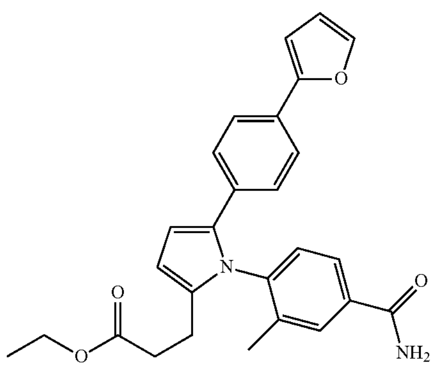 [SMILES: CCOC(=O)CCc1ccc(-c2ccc(-c3ccco3)cc2)n1-c1ccc(C(N)=O)cc1C] | ethyl 3-(1-(4-carbamoyl-2-methylphenyl)-5-(4-(furan-2-yl)phenyl)-1H-pyrrol-2-yl)propanoate | C27H26N2O4 | 442.5 | 443.0 | Scheme 3, step1, R8 = furan-2-yl, R1 = 4-carbamoyl-2-methylphenyl |

TABLE 1-continued

| # | Structure | Compound name | Chemical formula | Molecular weight | Mass Spec | Scheme #/Method # |
|---|---|---|---|---|---|---|
| 91 | 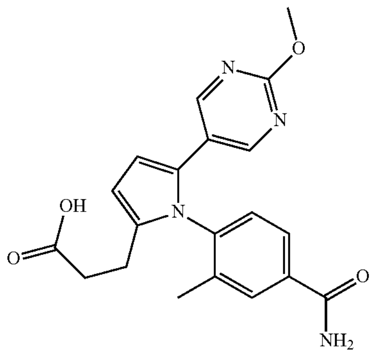 [SMILES: COc1ncc(-c2ccc(CCC(=O)O)n2-c2ccc(C(N)=O)cc2C)cn1] | 3-(1-(4-carbamoyl-2-methylphenyl)-5-(2-methoxypyrimidin-5-yl)-1H-pyrrol-2-yl)propanoic acid | C20H20N4O4 | 380.4 | 381.1 | Scheme 6, Ar2 = 2-methoxypyrimidin-5-yl/ method #11 |
| 92 | 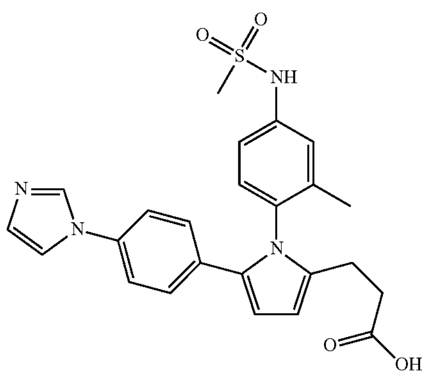 [SMILES: Cc1cc(NS(C)(=O)=O)ccc1-n1c(CCC(=O)O)ccc1-c1ccc(-n2ccnc2)cc1] | 3-(5-(4-(1H-imidazol-1-yl)phenyl)-1-(2-methyl-4-(methylsulfonamido)phenyl)-1H-pyrrol-2-yl)propanoic acid | C24H24N4O4S | 464.5 | 465.0 | Scheme 20, Ar2 = 4-(1H-imidazol-1-yl)phenyl/where 20A is compound #1 in this table |

TABLE 1-continued

| # | Structure | Compound name | Chemical formula | Molecular weight | Mass Spec | Scheme #/Method # |
|---|---|---|---|---|---|---|
| 93 | 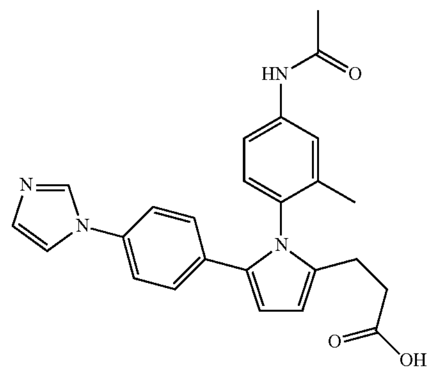 [SMILES: CC(=O)Nc1ccc(-n2c(CCC(=O)O)ccc2-c2ccc(-n3ccnc3)cc2)c(C)c1] | 3-(5-(4-(1H-imidazol-1-yl)phenyl)-1-(4-acetamido-2-methylphenyl)-1H-pyrrol-2-yl)propanoic acid | C25H24N4O3 | 428.5 | 429.2 | Scheme 31, where acylating agent is acetic anhydride in glacial acetic acid at room temp, R1 = methyl. |
| 94 | 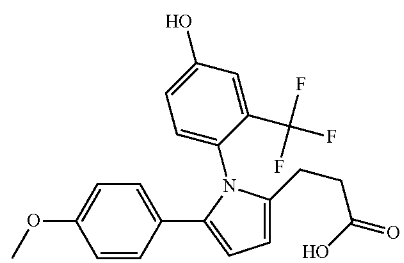 [SMILES: COc1ccc(-c2ccc(CCC(=O)O)n2-c2ccc(O)cc2C(F)(F)F)cc1] | 3-(1-(4-hydroxy-2-(trifluoromethyl)phenyl)-5-(4-methoxyphenyl)-1H-pyrrol-2-yl)propanoic acid | C21H18F3NO4 | 405.4 | 406.0 | Scheme 1 (first three steps), R2 = 4-methoxyphenyl, R1 = 4-hydroxy-2-(trifluoromethyl)phenyl, then Scheme 5, 5D-> 5E |
| 95 | 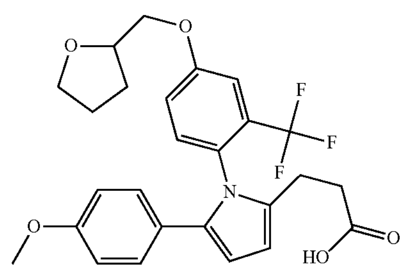 [SMILES: COc1ccc(-c2ccc(CCC(=O)O)n2-c2ccc(OCC3CCCO3)cc2C(F)(F)F)cc1] | 3-(5-(4-methoxyphenyl)-1-(4-((tetrahydrofuran-2-yl)methoxy)-2-(trifluoromethyl)phenyl)-1H-pyrrol-2-yl)propanoic acid | C26H26F3NO5 | 489.5 | 489.9 | Scheme 1 (first three steps), R2 = 4-methoxyphenyl, R1 = 4-((tetrahydrofuran-2-yl)methoxy)-2-(trifluoromethyl)phenyl, then Scheme 5, 5D-> 5E |

TABLE 1-continued

| # | Structure | Compound name | Chemical formula | Molecular weight | Mass Spec | Scheme #/Method # |
|---|---|---|---|---|---|---|
| 96 | 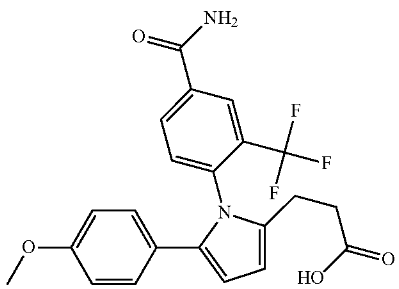 [SMILES: COc1ccc(-c2ccc(CCC(=O)O)n2-c2ccc(C(N)=O)cc2C(F)(F)F)cc1] | 3-(1-(4-carbamoyl-2-(trifluoromethyl)phenyl)-5-(4-methoxyphenyl)-1H-pyrrol-2-yl)propanoic acid | C22H19F3N2O4 | 432.4 | 432.8 | Scheme 27, Y = CF3, X1 = X2 = H, where the amine in step 2 is NH4OAc |
| 97 | 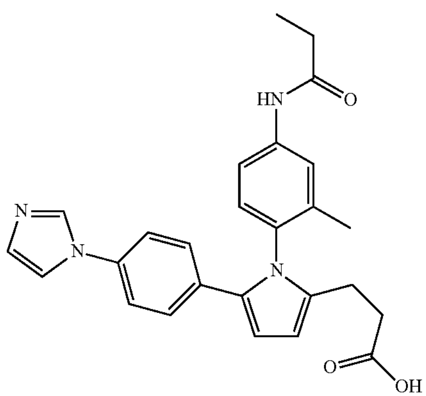 [SMILES: CCC(=O)Nc1ccc(-n2c(CCC(=O)O)ccc2-c2ccc(-n3ccnc3)cc2)c(C)c1] | 3-(5-(4-(1H-imidazol-1-yl)phenyl)-1-(2-methyl-4-propionamidophenyl)-1H-pyrrol-2-yl)propanoic acid | C26H26N4O3 | 442.5 | 443.0 | Scheme 31, R1 = ethyl |

TABLE 1-continued
| # | Compound name | Structure | Chemical formula | Molecular weight | Mass Spec | Scheme #/Method # |
|---|---|---|---|---|---|---|
| 98 | 3-(5-(4-(1H-imidazol-1-yl)phenyl)-1-(4-(2-methoxyacetamido)-2-methylphenyl)-1H-pyrrol-2-yl)propanoic acid | 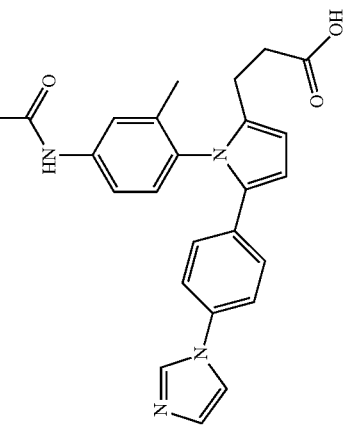 | C26H26N4O4 | 458.5 | 459.0 | Scheme 31, R1 = methoxy methyl |
| 99 | 3-(5-(4-amino-3-chlorophenyl)-1-(4-carbamoyl-2-methylphenyl)-1H-pyrrol-2-yl)propanoic acid | 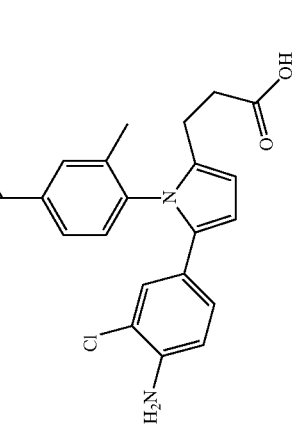 | C21H20ClN3O3 | 397.9 | 398.0 | Scheme 6, Ar2 = 4-amino-3-chlorophenyl/method 12 |

TABLE 1-continued

| # | Structure | Compound name | Chemical formula | Molecular weight | Mass Spec | Scheme #/Method # |
|---|---|---|---|---|---|---|
| 100 | 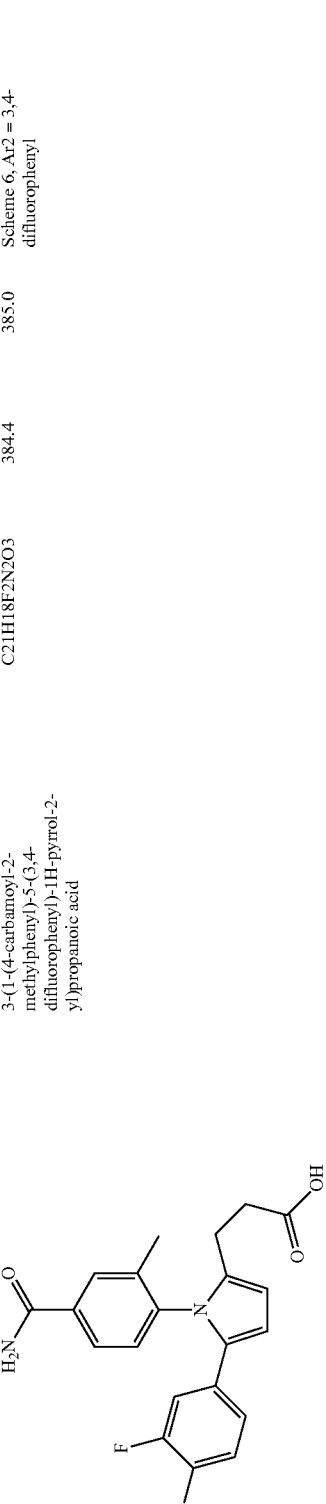 | 3-(1-(4-carbamoyl-2-methylphenyl)-5-(3,4-difluorophenyl)-1H-pyrrol-2-yl)propanoic acid | C21H18F2N2O3 | 384.4 | 385.0 | Scheme 6, Ar2 = 3,4-difluorophenyl |
| 101 | 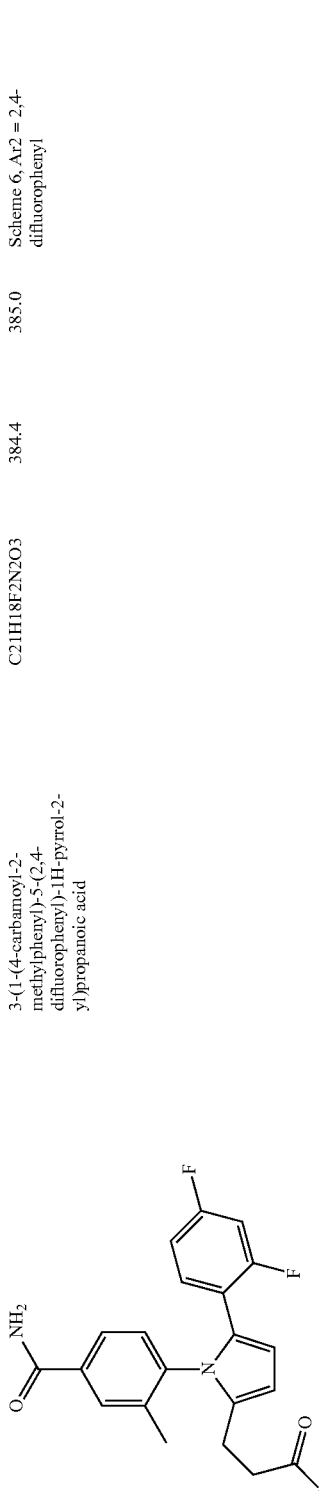 | 3-(1-(4-carbamoyl-2-methylphenyl)-5-(2,4-difluorophenyl)-1H-pyrrol-2-yl)propanoic acid | C21H18F2N2O3 | 384.4 | 385.0 | Scheme 6, Ar2 = 2,4-difluorophenyl |
| 102 | 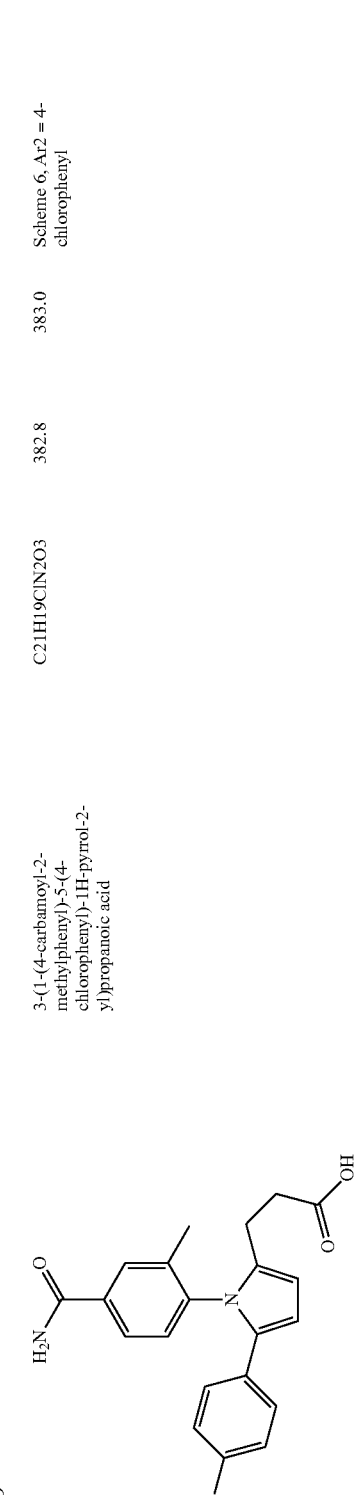 | 3-(1-(4-carbamoyl-2-chlorophenyl)-5-(4-chlorophenyl)-1H-pyrrol-2-yl)propanoic acid | C21H19ClN2O3 | 382.8 | 383.0 | Scheme 6, Ar2 = 4-chlorophenyl |

TABLE 1-continued

| # | Structure | Compound name | Chemical formula | Molecular weight | Mass Spec | Scheme #/Method # |
|---|---|---|---|---|---|---|
| 103 | 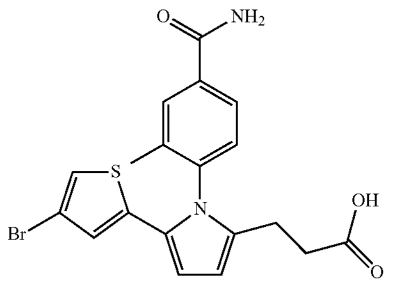 [SMILES: Cc1cc(C(N)=O)ccc1-n1c(CCC(=O)O)ccc1-c1cc(Br)cs1] | 3-(5-(4-bromothiophen-2-yl)-1-(4-carbamoyl-2-methylphenyl)-1H-pyrrol-2-yl)propanoic acid | C19H17BrN2O3S | 433.3 | 433.0, 434.8 | Scheme 1, R2 = 4-bromothiophen-2-yl, R1 = 4-carbamoyl-2-methylphenyl |
| 104 | 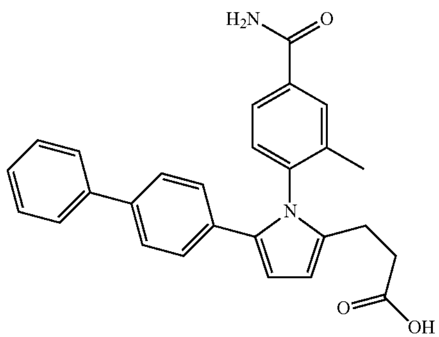 [SMILES: Cc1cc(C(N)=O)ccc1-n1c(CCC(=O)O)ccc1-c1ccc(-c2ccccc2)cc1] | 3-(5-(biphenyl-4-yl)-1-(4-carbamoyl-2-methylphenyl)-1H-pyrrol-2-yl)propanoic acid | C27H24N2O3 | 424.5 | 425.1 | Scheme 3, R8 = phenyl, R1 = 4-carbamoyl-2-methylphenyl |
| 105 | 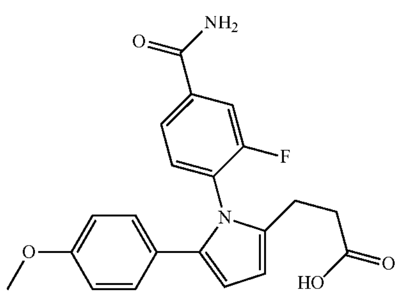 [SMILES: COc1ccc(-c2ccc(CCC(=O)O)n2-c2ccc(C(N)=O)cc2F)cc1] | 3-(1-(4-carbamoyl-2-fluorophenyl)-5-(4-methoxyphenyl)-1H-pyrrol-2-yl)propanoic acid | C21H19FN2O4 | 382.4 | 383.1 | Scheme 1 (first three steps), R2 = 4-methoxyphenyl, R1 = 4-carbamoyl-2-fluorophenyl, followed by last step of Scheme 5 |

TABLE 1-continued
| # | Structure | Compound name | Chemical formula | Molecular weight | Mass Spec | Scheme #/Method # |
|---|---|---|---|---|---|---|
| 106 | 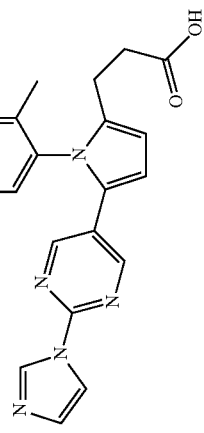 | (5-(2-(1H-imidazol-1-yl)pyrimidin-5-yl)-1-(4-carbamoyl-2-methylphenyl)-1H-pyrrol-2-yl)propanoic acid | C22H20N6O3 | 416.4 | 417.0 | Scheme 42 |
| 107 | 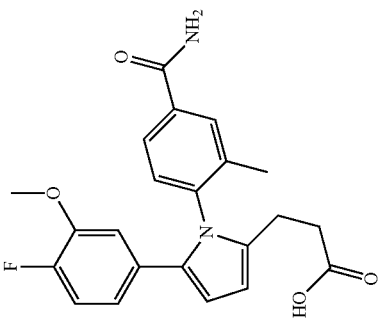 | 3-(1-(4-carbamoyl-2-methylphenyl)-5-(4-fluoro-3-methoxyphenyl)-1H-pyrrol-2-yl)propanoic acid | C22H21FN2O4 | 396.4 | 397.2 | Scheme 6, Ar2 = 4-fluoro-3-methoxyphenyl |

TABLE 1-continued

| # | Structure | Compound name | Chemical formula | Molecular weight | Mass Spec | Scheme #/Method # |
|---|---|---|---|---|---|---|
| 108 | 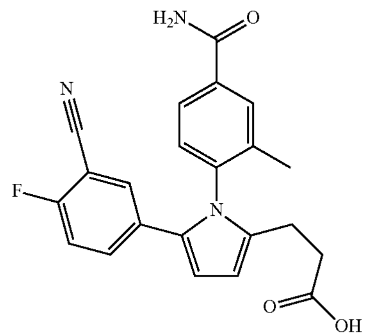 [SMILES: Cc1cc(C(N)=O)ccc1-n1c(CCC(=O)O)ccc1-c1ccc(F)c(C#N)c1] | 3-(1-(4-carbamoyl-2-methylphenyl)-5-(3-cyano-4-fluorophenyl)-1H-pyrrol-2-yl)propanoic acid | C22H18FN3O3 | 391.4 | 392.2 | Scheme 6, Ar2 = 3-cyano-4-fluorophenyl |
| 109 | 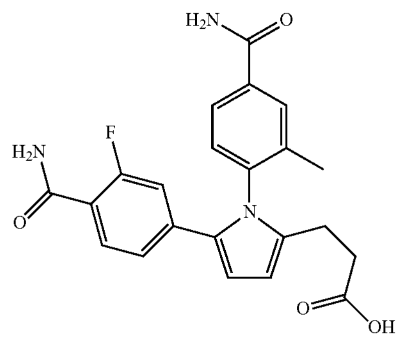 [SMILES: Cc1cc(C(N)=O)ccc1-n1c(CCC(=O)O)ccc1-c1ccc(C(N)=O)c(F)c1] | 3-(1-(4-carbamoyl-2-methylphenyl)-5-(4-carbamoyl-3-fluorophenyl)-1H-pyrrol-2-yl)propanoic acid | C22H20FN3O4 | 409.4 | 410.2 | Scheme 6, Ar2 = 4-carbamoyl-3-fluorophenyl |
| 110 | 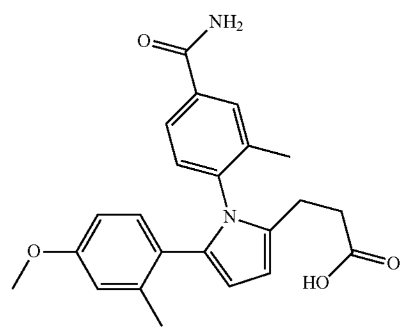 [SMILES: COc1ccc(-c2ccc(CCC(=O)O)n2-c2ccc(C(N)=O)cc2C)c(C)c1] | 3-(1-(4-carbamoyl-2-methylphenyl)-5-(4-methoxy-2-methylphenyl)-1H-pyrrol-2-yl)propanoic acid | C23H24N2O4 | 392.4 | 393.2 | Scheme 6, Ar2 = 4-methoxy-2-methylphenyl |

TABLE 1-continued

| # | Structure | Compound name | Chemical formula | Molecular weight | Mass Spec | Scheme #/Method # |
|---|---|---|---|---|---|---|
| 111 | 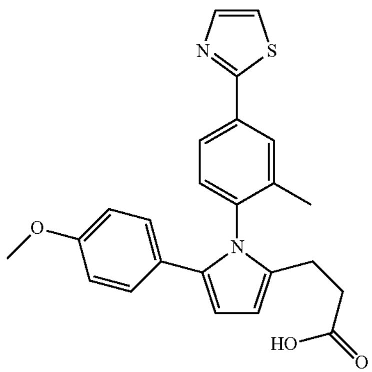 [SMILES: COc1ccc(-c2ccc(CCC(=O)O)n2-c2ccc(-c3nccs3)cc2C)cc1] | 3-(5-(4-methoxyphenyl)-1-(2-methyl-4-(thiazol-2-yl)phenyl)-1H-pyrrol-2-yl)propanoic acid | C24H22N2O3S | 418.5 | 419.0 | Scheme 1, R2 = 4-methoxyphenyl, R1 = 2-methyl-4-(thiazol-2-yl)phenyl, where conversion of 1 B to 1 C used μ-wave conditions described in prep. of 29A/method 13 |
| 112 | 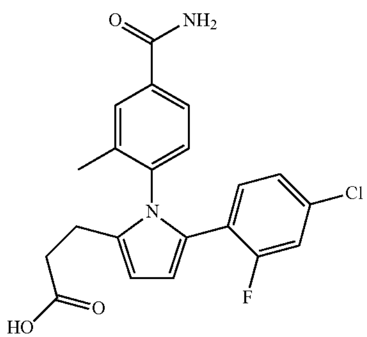 [SMILES: Cc1cc(C(N)=O)ccc1-n1c(CCC(=O)O)ccc1-c1ccc(Cl)cc1F] | 3-(1-(4-carbamoyl-2-methylphenyl)-5-(4-chloro-2-fluorophenyl)-1H-pyrrol-2-yl)propanoic acid | C21H18ClFN2O3 | 400.8 | 401.0 | Scheme 6, Ar2 = 4-chloro-2-fluorophenyl |
| 113 | 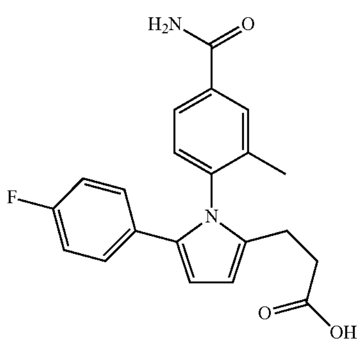 [SMILES: Cc1cc(C(N)=O)ccc1-n1c(CCC(=O)O)ccc1-c1ccc(F)cc1] | 3-(1-(4-carbamoyl-2-methylphenyl)-5-(4-fluorophenyl)-1H-pyrrol-2-yl)propanoic acid | C21H19FN2O3 | 366.4 | 367.0 | Scheme 6, Ar2 = 4-fluorophenyl |

TABLE 1-continued

| # | Structure | Compound name | Chemical formula | Molecular weight | Mass Spec | Scheme #/Method # |
|---|---|---|---|---|---|---|
| 114 | 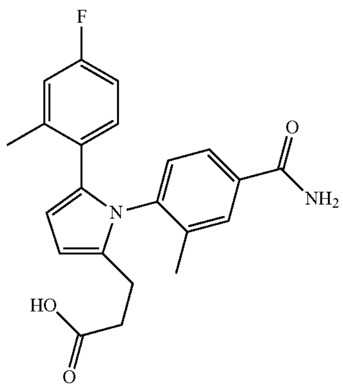 [SMILES: Cc1cc(F)ccc1-c1ccc(CCC(=O)O)n1-c1ccc(C(N)=O)cc1C] | 3-(1-(4-carbamoyl-2-methylphenyl)-5-(4-fluoro-2-methylphenyl)-1H-pyrrol-2-yl)propanoic acid | C22H21FN2O3 | 380.4 | 381.1 | Scheme 6, Ar2 = 4-fluoro-2-methylphenyl |
| 115 | 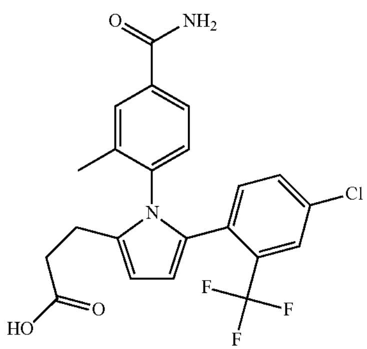 [SMILES: Cc1cc(C(N)=O)ccc1-n1c(CCC(=O)O)ccc1-c1ccc(Cl)cc1C(F)(F)F] | 3-(1-(4-carbamoyl-2-methylphenyl)-5-(4-chloro-2-(trifluoromethyl)phenyl)-1H-pyrrol-2-yl)propanoic acid | C22H18ClF3N2O3 | 450.8 | 451.1 | Scheme 6, Ar2 = 4-chloro-2-(trifluoromethyl)phenyl |

TABLE 1-continued

| # | Structure | Compound name | Chemical formula | Molecular weight | Mass Spec | Scheme #/Method # |
|---|---|---|---|---|---|---|
| 116 | 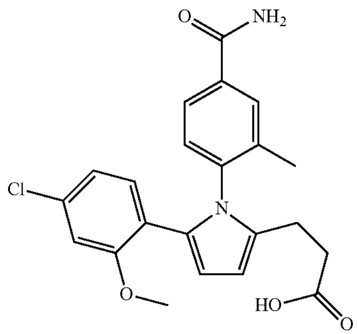 [SMILES: COc1cc(Cl)ccc1-c1ccc(CCC(=O)O)n1-c1ccc(C(N)=O)cc1C] | 3-(1-(4-carbamoyl-2-methylphenyl)-5-(4-chloro-2-methoxyphenyl)-1H-pyrrol-2-yl)propanoic acid | C22H21ClN2O4 | 412.9 | 413.0 | Scheme 33, R1 = 4-carbamoyl-2-methylphenyl, R2 = 4-chloro, R3 = methyl |
| 117 | 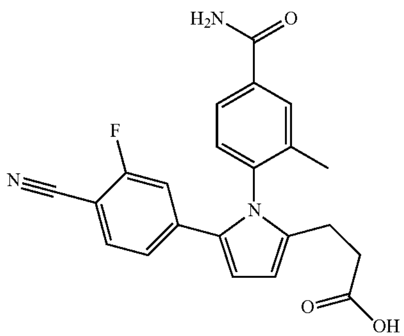 [SMILES: Cc1cc(C(N)=O)ccc1-n1c(CCC(=O)O)ccc1-c1ccc(C#N)c(F)c1] | 3-(1-(4-carbamoyl-2-methylphenyl)-5-(4-cyano-3-fluorophenyl)-1H-pyrrol-2-yl)propanoic acid | C22H18FN3O3 | 391.4 | 392.0 | Scheme 6, Ar2 = 4-cyano-3-fluorophenyl |
| 118 | 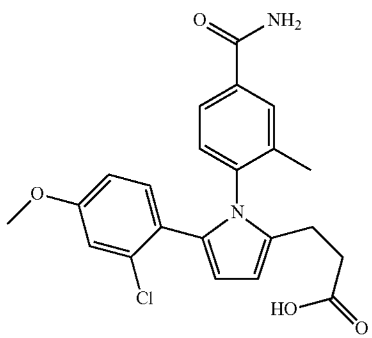 [SMILES: COc1ccc(-c2ccc(CCC(=O)O)n2-c2ccc(C(N)=O)cc2C)c(Cl)c1] | 3-(1-(4-carbamoyl-2-methylphenyl)-5-(2-chloro-4-methoxyphenyl)-1H-pyrrol-2-yl)propanoic acid | C22H21ClN2O4 | 412.9 | 414.0 | Scheme 6, Ar2 = 2-chloro-4-methoxyphenyl |

TABLE 1-continued

| # | Structure | Compound name | Chemical formula | Molecular weight | Mass Spec | Scheme #/Method # |
|---|---|---|---|---|---|---|
| 119 | 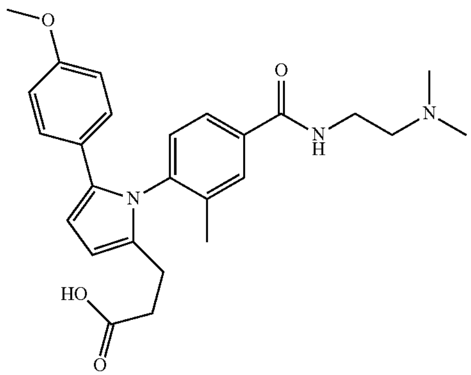 | 3-(1-(4-(2-(dimethylamino)ethylcarbamoyl)-2-methylphenyl)-5-(4-methoxyphenyl)-1H-pyrrol-2-yl)propanoic acid | C26H31N3O4 | 449.5 | 450.1 | Scheme 27, Y = CF3, X1 = H, and X2 = N HCH2CH2N(CH3)2 |
| 120 | 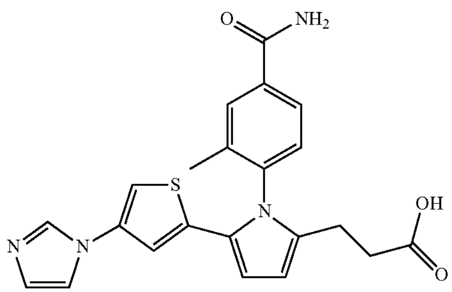 [SMILES: Cc1cc(C(N)=O)ccc1-n1c(CCC(=O)O)ccc1-c1cc(-n2ccnc2)cs1] | 3-(5-(4-(1H-imidazol-1-yl)thiophen-2-yl)-1-(4-carbamoyl-2-methylphenyl)-1H-pyrrol-2-yl)propanoic acid | C22H20N4O3S | 420.5 | 421.1 | Scheme 9b, where SM is compound #103 (before hydrolysis) instead of 9b-A, Ar = 1H-imidazol-1-yl |
| 121 | 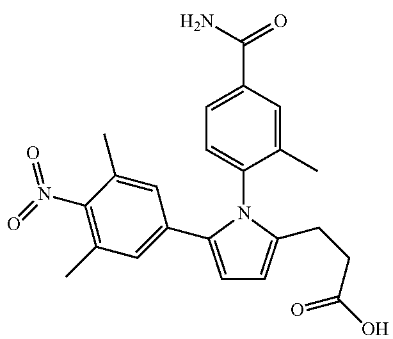 [SMILES: Cc1cc(C(N)=O)ccc1-n1c(CCC(=O)O)ccc1-c1cc(C)c([N+](=O)[O-])c(C)c1] | 3-(1-(4-carbamoyl-2-methylphenyl)-5-(3,5-dimethyl-4-nitrophenyl)-1H-pyrrol-2-yl)propanoic acid | C23H23N3O5 | 421.4 | (M − H+)− 420.1 | Scheme 19, Ar2 = 3,5-dimethyl-4-nitrophenyl |

TABLE 1-continued

| # | Structure | Compound name | Chemical formula | Molecular weight | Mass Spec | Scheme #/Method # |
|---|---|---|---|---|---|---|
| 122 | 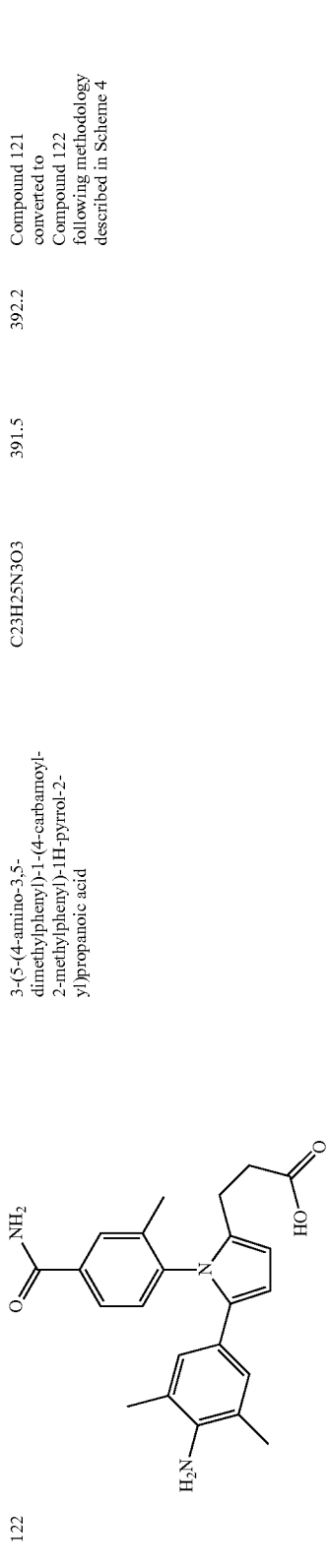 | 3-(5-(4-amino-3,5-dimethylphenyl)-1-(4-carbamoyl-2-methylphenyl)-1H-pyrrol-2-yl)propanoic acid | C23H25N3O3 | 391.5 | 392.2 | Compound 121 converted to Compound 122 following methodology described in Scheme 4 |
| 123 | 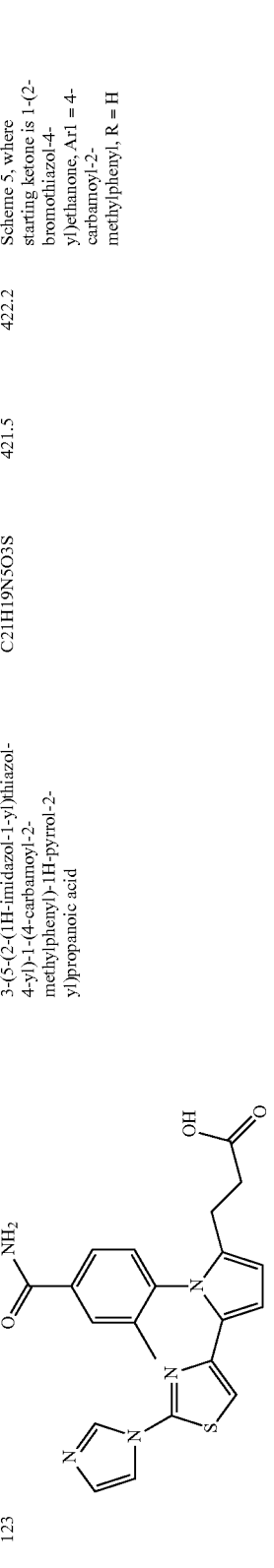 | 3-(5-(2-(1H-imidazol-1-yl)thiazol-4-yl)-1-(4-carbamoyl-2-methylphenyl)-1H-pyrrol-2-yl)propanoic acid | C21H19N5O3S | 421.5 | 422.2 | Scheme 5, where starting ketone is 1-(2-bromothiazol-4-yl)ethanone, Ar1 = 4-carbamoyl-2-methylphenyl, R = H |
| 124 | 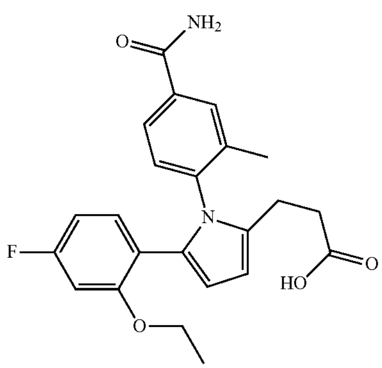 [SMILES: CCOc1cc(F)ccc1-c1ccc(CCC(=O)O)n1-c1ccc(C(N)=O)cc1C] | 3-(1-(4-carbamoyl-2-methylphenyl)-5-(2-ethoxy-4-fluorophenyl)-1H-pyrrol-2-yl)propanoic acid | C23H23FN2O4 | 410.4 | 411.2 | Scheme 6, Ar2 = 2-ethoxy-4-fluorophenyl |

TABLE 1-continued

| # | Structure | Compound name | Chemical formula | Molecular weight | Mass Spec | Scheme #/Method # |
|---|---|---|---|---|---|---|
| 125 | 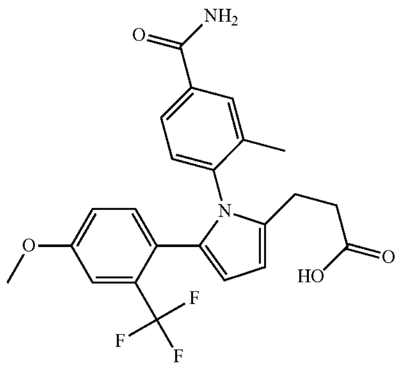 [SMILES: COc1ccc(-c2ccc(CCC(=O)O)n2-c2ccc(C(N)=O)cc2C)c(C(F)(F)F)c1] | 3-(1-(4-carbamoyl-2-methylphenyl)-5-(4-methoxy-2-(trifluoromethyl)phenyl)-1H-pyrrol-2-yl)propanoic acid | C23H21F3N2O4 | 446.4 | 447.2 | Scheme 6, Ar2 = 4-methoxy-2-(trifluoromethyl)phenyl |
| 126 | 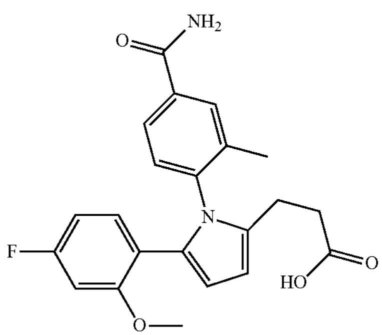 [SMILES: COc1cc(F)ccc1-c1ccc(CCC(=O)O)n1-c1ccc(C(N)=O)cc1C] | 3-(1-(4-carbamoyl-2-methylphenyl)-5-(4-fluoro-2-methoxyphenyl)-1H-pyrrol-2-yl)propanoic acid | C22H21FN2O4 | 396.4 | 397.1 | Scheme 6, Ar2 = 4-fluoro-2-methoxyphenyl |

TABLE 1-continued

| # | Structure | Compound name | Chemical formula | Molecular weight | Mass Spec | Scheme #/Method # |
|---|---|---|---|---|---|---|
| 127 | 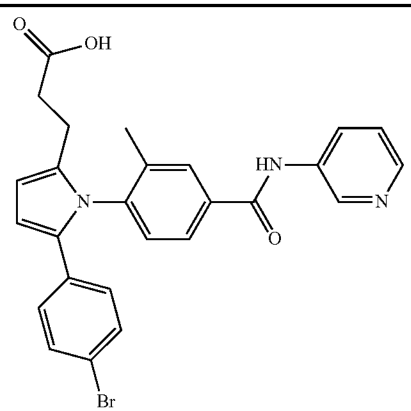 | 3-(5-(4-bromophenyl)-1-(2-methyl-4-(pyridin-3-ylcarbamoyl)phenyl)-1H-pyrrol-2-yl)propanoic acid | C26H22BrN3O3 | 504.4 | 504.1, 506.1 | Scheme 27, starting with 5B (from scheme 5) instead of 25C, Y = CH3, X1 = H, and X2 = pyridin-3-yl |
| 128 | 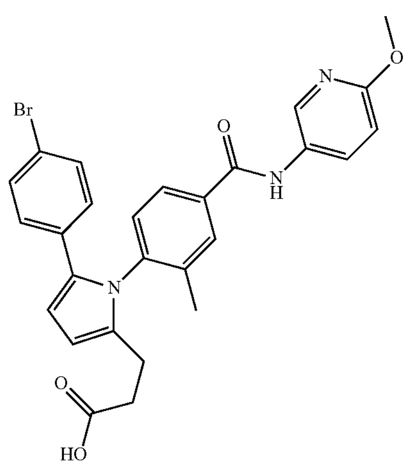 [SMILES: COc1ccc(NC(=O)c2ccc(-n3c(CCC(=O)O)ccc3-c3ccc(Br)cc3)c(C)c2)cn1] | 3-(5-(4-bromophenyl)-1-(4-(6-methoxypyridin-3-ylcarbamoyl)-2-methylphenyl)-1H-pyrrol-2-yl)propanoic acid | C27H24BrN3O4 | 534.4 | 534.0 | Scheme 27, starting with 5B (from scheme 5) instead of 25C, Y = CH3, X1 = H, and X2 = 6-methoxypyridin-3-yl |

TABLE 1-continued

| # | Structure | Compound name | Chemical formula | Molecular weight | Mass Spec | Scheme #/Method # |
|---|---|---|---|---|---|---|
| 129 | 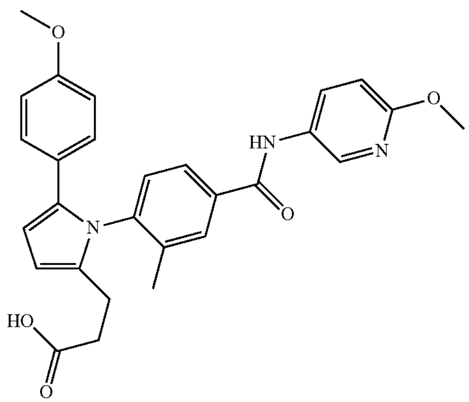 [SMILES: COc1ccc(-c2ccc(CCC(=O)O)n2-c2ccc(C(=O)Nc3ccc(OC)nc3)cc2C)cc1] | 3-(5-(4-methoxyphenyl)-1-(4-(6-methoxypyridin-3-ylcarbamoyl)-2-methylphenyl)-1H-pyrrol-2-yl)propanoic acid | C28H27N3O5 | 485.5 | 486.0 | Scheme 27, Y = CH3, X1 = H, and X2 = 6-methoxypyridin-3-yl |
| 130 | 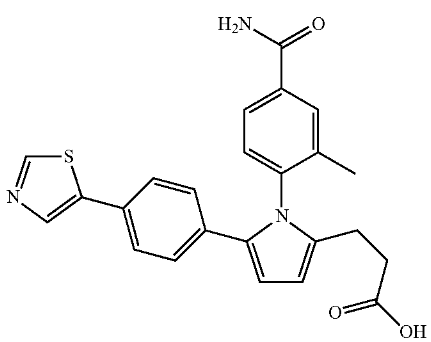 [SMILES: Cc1cc(C(N)=O)ccc1-n1c(CCC(=O)O)ccc1-c1ccc(-c2cncs2)cc1] | 3-(1-(4-carbamoyl-2-methylphenyl)-5-(4-(thiazol-5-yl)phenyl)-1H-pyrrol-2-yl)propanoic acid | C24H21N3O3S | 431.5 | 432.2 | Scheme 41 |

TABLE 1-continued

| # | Structure | Compound name | Chemical formula | Molecular weight | Mass Spec | Scheme #/Method # |
|---|---|---|---|---|---|---|
| 131 | 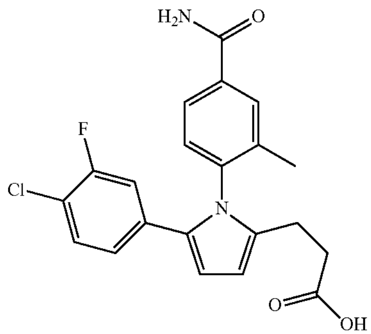 [SMILES: Cc1cc(C(N)=O)ccc1-n1c(CCC(=O)O)ccc1-c1ccc(Cl)c(F)c1] | 3-(1-(4-carbamoyl-2-methylphenyl)-5-(4-chloro-3-fluorophenyl)-1H-pyrrol-2-yl)propanoic acid | C21H18ClFN2O3 | 400.8 | 401.1 | Scheme 6, Ar2 = 4-chloro-3-fluorophenyl |
| 132 | 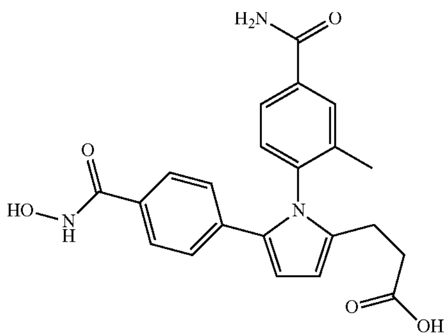 [SMILES: Cc1cc(C(N)=O)ccc1-n1c(CCC(=O)O)ccc1-c1ccc(C(=O)NO)cc1] | 3-(1-(4-carbamoyl-2-methylphenyl)-5-(4-(hydroxycarbamoyl)phenyl)-1H-pyrrol-2-yl)propanoic acid | C22H21N3O5 | 407.4 | 408.0 | Scheme 35, compound 35-7 |
| 133 | 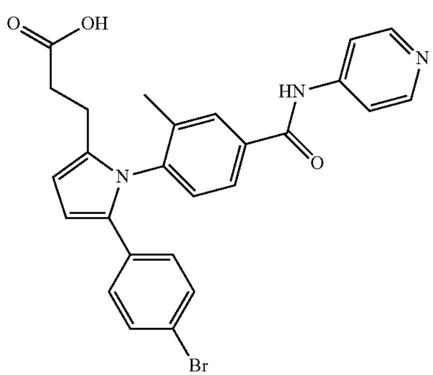 [SMILES: Cc1cc(C(=O)Nc2ccncc2)ccc1-n1c(CCC(=O)O)ccc1-c1ccc(Br)cc1] | 3-(5-(4-bromophenyl)-1-(2-methyl-4-(pyridin-4-ylcarbamoyl)phenyl)-1H-pyrrol-2-yl)propanoic acid | C26H22BrN3O3 | 504.4 | 504.2, 506.2 | Scheme 27, starting with 5B (from scheme 5) instead of 25C, Y = CH3, X1 = H, and X2 = pyridin-4-yl |

TABLE 1-continued

| # | Structure | Compound name | Chemical formula | Molecular weight | Mass Spec | Scheme #/Method # |
|---|---|---|---|---|---|---|
| 134 | 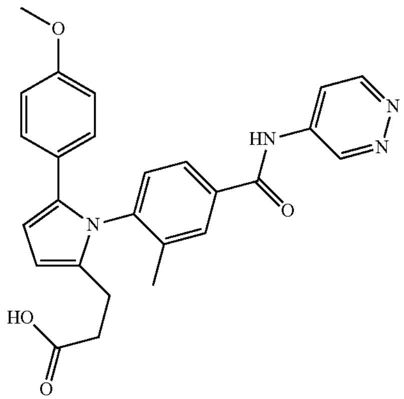 [SMILES: COc1ccc(-c2ccc(CCC(=O)O)n2-c2ccc(C(=O)Nc3ccnnc3)cc2C)cc1] | 3-(5-(4-methoxyphenyl)-1-(2-methyl-4-(pyridazin-4-ylcarbamoyl)phenyl)-1H-pyrrol-2-yl)propanoic acid | C26H24N4O4 | 456.5 | 457.2 | Scheme 32 |
| 135 | 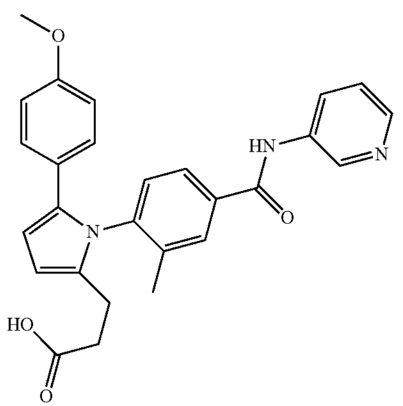 [SMILES: COc1ccc(-c2ccc(CCC(=O)O)n2-c2ccc(C(=O)Nc3cccnc3)cc2C)cc1] | 3-(5-(4-methoxyphenyl)-1-(2-methyl-4-(pyridin-3-ylcarbamoyl)phenyl)-1H-pyrrol-2-yl)propanoic acid | C27H25N3O4 | 455.5 | 456.2 | Scheme 27, Y = CH3, X1 = H, and X2 = pyridin-3-yl |

TABLE 1-continued

| # | Structure | Compound name | Chemical formula | Molecular weight | Mass Spec | Scheme #/Method # |
|---|---|---|---|---|---|---|
| 136 | 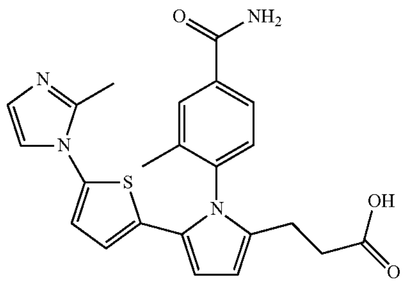 | 3-(1-(4-carbamoyl-2-methylphenyl)-5-(5-(2-methyl-1H-imidazol-1-yl)thiophen-2-yl)-1H-pyrrol-2-yl)propanoic acid | C23H22N4O3S | 434.5 | 435.0 | Scheme 9b, Ar = 2-methyl-1H-imidazol-1-yl |
| 137 | 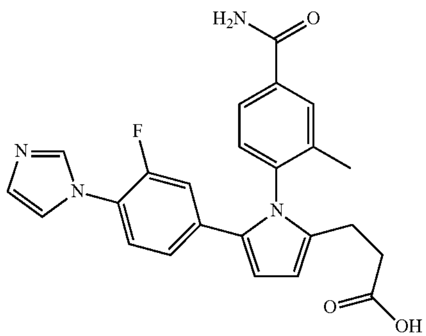 [SMILES: Cc1cc(C(N)=O)ccc1-n1c(CCC(=O)O)ccc1-c1ccc(-n2ccnc2)c(F)c1] | 3-(1-(4-carbamoyl-2-methylphenyl)-5-(3-fluoro-4-(1H-imidazol-1-yl)phenyl)-1H-pyrrol-2-yl)propanoic acid | C24H21FN4O3 | 432.4 | 433.1 | Scheme 36, R1 = 4-carbamoyl-2-methylphenyl, where 1st step was prepared according to Scheme 36A, R = H |
| 138 | 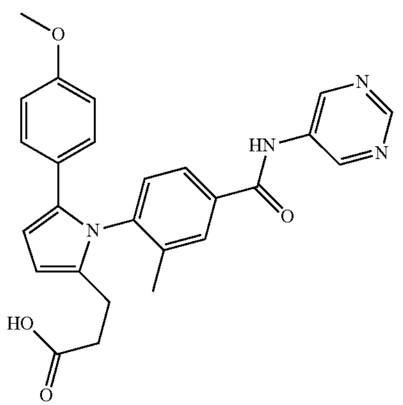 [SMILES: COc1ccc(-c2ccc(CCC(=O)O)n2-c2ccc(C(=O)Nc3cncnc3)cc2C)cc1] | 3-(5-(4-methoxyphenyl)-1-(2-methyl-4-(pyrimidin-5-ylcarbamoyl)phenyl)-1H-pyrrol-2-yl)propanoic acid | C26H24N4O4 | 456.5 | 457.2 | Scheme 32, where amine is pyrimidin-5-amine instead of 32B |

TABLE 1-continued

| # | Structure | Compound name | Chemical formula | Molecular weight | Mass Spec | Scheme #/Method # |
|---|---|---|---|---|---|---|
| 139 | 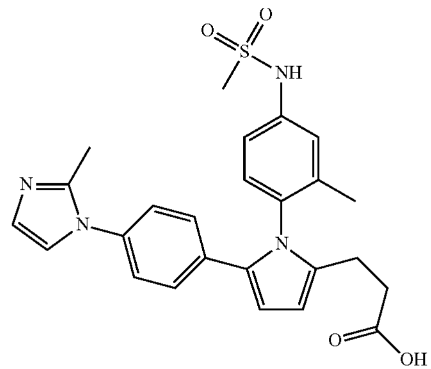 [SMILES: Cc1cc(NS(C)(=O)=O)ccc1-n1c(CCC(=O)O)ccc1-c1ccc(-n2ccnc2C)cc1] | 3-(5-(4-(2-methyl-1H-imidazol-1-yl)phenyl)-1-(2-methyl-4-(methylsulfonamido)phenyl)-1H-pyrrol-2-yl)propanoic acid | C25H26N4O4S | 478.6 | 479.2 | Scheme 20, Ar2 = 4-(2-methyl-1H-imidazol-1-yl)phenyl/where 20A is compound #3 in this table |
| 140 | 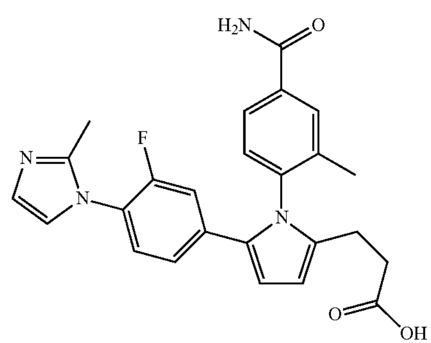 [SMILES: Cc1cc(C(N)=O)ccc1-n1c(CCC(=O)O)ccc1-c1ccc(-n2ccnc2C)c(F)c1] | 3-(1-(4-carbamoyl-2-methylphenyl)-5-(3-fluoro-4-(2-methyl-1H-imidazol-1-yl)phenyl)-1H-pyrrol-2-yl)propanoic acid | C25H23FN4O3 | 446.5 | 447.1 | Scheme 36, R1 = 4-carbamoyl-2-methylphenyl, where 1st step was prepared according to Scheme 36A, R = Me |

TABLE 1-continued

| # | Compound name | Structure | Chemical formula | Molecular weight | Mass Spec | Scheme #/Method # |
|---|---|---|---|---|---|---|
| 141 | 3-(1-(4-carbamoyl-2-methylphenyl)-5-(4-chloro-2-ethoxyphenyl)-1H-pyrrol-2-yl)propanoic acid | 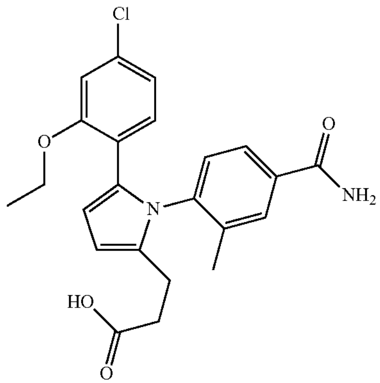 [SMILES: CCOc1cc(Cl)ccc1-c1ccc(CCC(=O)O)n1-c1ccc(C(N)=O)cc1C] | C23H23ClN2O4 | 426.9 | 427.1 | Scheme 33, R1 = 4-carbamoyl-2-methylphenyl, R2 = 4-chloro, R3 = ethyl |
| 142 | 3-(5-(5-bromo-2-methoxyphenyl)-1-(4-carbamoyl-2-methylphenyl)-1H-pyrrol-2-yl)propanoic acid | 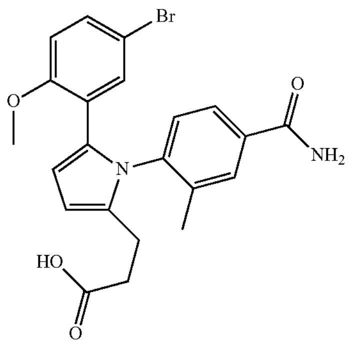 [SMILES: COc1ccc(Br)cc1-c1ccc(CCC(=O)O)n1-c1ccc(C(N)=O)cc1C] | C22H21BrN2O4 | 457.3 | 459.0 | Scheme 33, R1 = 4-carbamoyl-2-methylphenyl, R2 = 5-bromo, R3 = methyl |
| 143 | 3-(1-(4-carbamoyl-2-methylphenyl)-5-(4-(2-cyclopropyl-1H-imidazol-1-yl)phenyl)-1H-pyrrol-2-yl)propanoic acid | 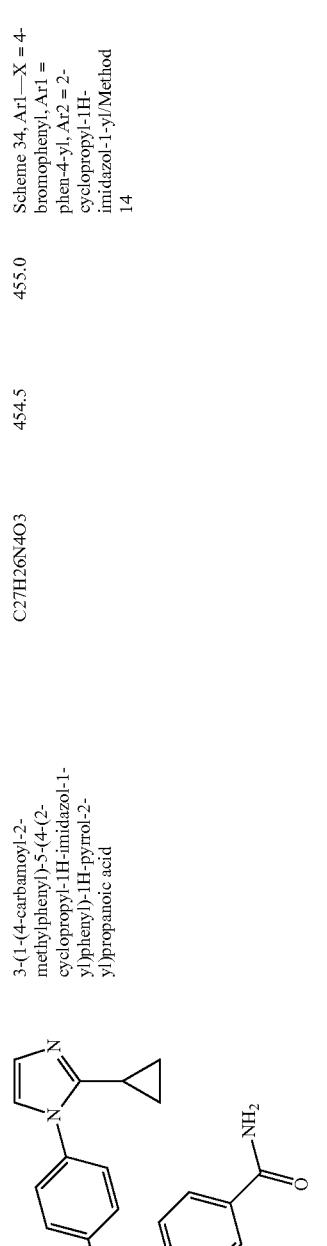 | C27H26N4O3 | 454.5 | 455.0 | Scheme 34, Ar1—X = 4-bromophenyl, Ar1 = phen-4-yl, Ar2 = 2-cyclopropyl-1H-imidazol-1-yl/Method 14 |

TABLE 1-continued

| # | Structure | Compound name | Chemical formula | Molecular weight | Mass Spec | Scheme #/Method # |
|---|---|---|---|---|---|---|
| 144 | 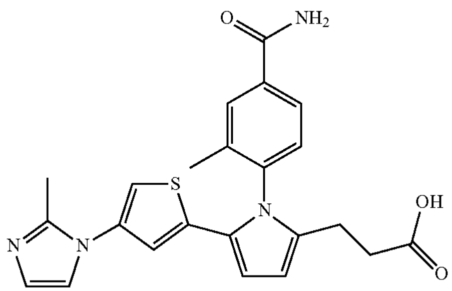 [SMILES: Cc1cc(C(N)=O)ccc1-n1c(CCC(=O)O)ccc1-c1cc(-n2ccnc2C)cs1] | 3-(1-(4-carbamoyl-2-methylphenyl)-5-(4-(2-methyl-1H-imidazol-1-yl)thiophen-2-yl)-1H-pyrrol-2-yl)propanoic acid | C23H22N4O3S | 434.5 | 435.2 | Scheme 9b, where SM was compound #103 (before hydrolysis) instead of 9b-A. Ar = 2-methyl-1H-imidazol-1-yl |
| 145 | 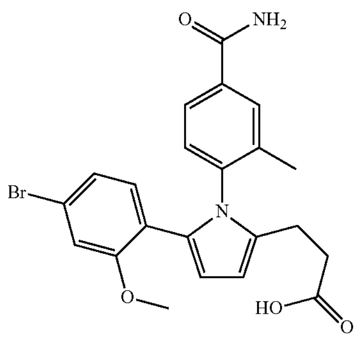 | 3-(5-(4-bromo-2-methoxyphenyl)-1-(4-carbamoyl-2-methylphenyl)-1H-pyrrol-2-yl)propanoic acid | C22H21BrN2O4 | 457.3 | 459.1 | Scheme 1, R2 = 4-bromo-2-methoxyphenyl, R1 = 4-carbamoyl-2-methylphenyl/Method 15 |
| 146 | 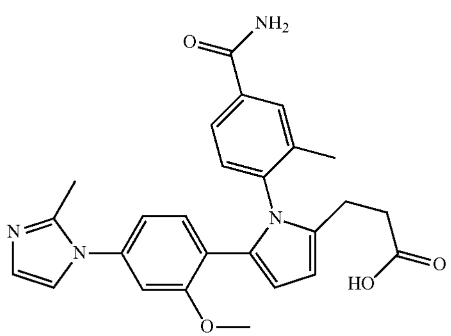 | 3-(1-(4-carbamoyl-2-methylphenyl)-5-(2-methoxy-4-(2-methyl-1H-imidazol-1-yl)phenyl)-1H-pyrrol-2-yl)propanoic acid | C26H26N4O4 | 458.5 | 459.1 | Scheme 34, Ar1—X = 4-bromo-2-methoxyphenyl, Ar2 = 2-methyl-1H-imidazol-1-yl/see previous compound for synthesis of 34A |

TABLE 1-continued

| # | Structure | Compound name | Chemical formula | Molecular weight | Mass Spec | Scheme #/Method # |
|---|---|---|---|---|---|---|
| 147 | 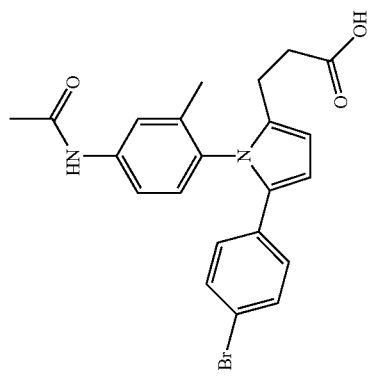 | 3-(1-(4-acetamido-2-methylphenyl)-5-(4-bromophenyl)-1H-pyrrol-2-yl)propanoic acid | C22H21BrN2O3 | 441.3 | 441.0, 442.9 | Scheme 31, R1 = methyl (acetic anhydride as acylating agent), * methyl ester was prepared (see asterik definition in scheme 31) |
| 148 | 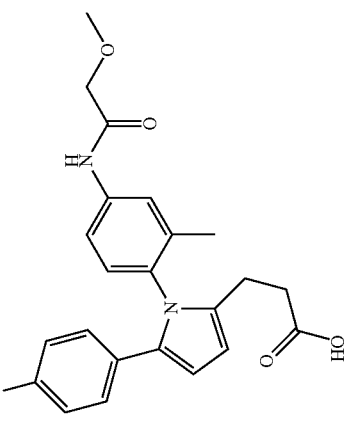 | 3-(5-(4-bromophenyl)-1-(4-(2-methoxyacetamido)-2-methylphenyl)-1H-pyrrol-2-yl)propanoic acid | C23H23BrN2O4 | 471.3 | 4714.0, 472.9 | Scheme 31, R1 = methoxy methyl, * methyl ester was prepared (see asterik definition in scheme 31) |

TABLE 1-continued

| # | Structure | Compound name | Chemical formula | Molecular weight | Mass Spec | Scheme #/Method # |
|---|---|---|---|---|---|---|
| 149 | 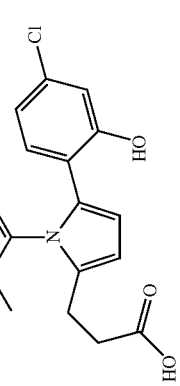 | 3-(1-(4-carbamoyl-2-methylphenyl)-5-(4-chloro-2-hydroxyphenyl)-1H-pyrrol-2-yl)propanoic acid | C21H19ClN2O4 | 398.8 | 399.0 | Scheme 1, R1 = 4-carbamoyl-2-methylphenyl, R2 = 4-chloro-2-hydroxyphenyl |
| 150 | 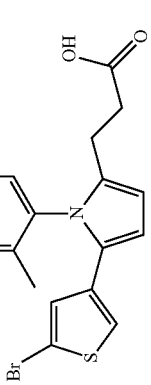 | 3-(5-(5-bromothiophen-3-yl)-1-(4-carbamoyl-2-methylphenyl)-1H-pyrrol-2-yl)propanoic acid | C19H17BrN2O3S | 433.3 | 434.9 | Scheme 1, R2 = 5-bromothiophen-3-yl, R1 = 4-carbamoyl-2-methylphenyl/Method 19 |
| 151 | 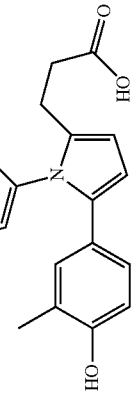 | 3-(1-(4-carbamoyl-2-methylphenyl)-5-(4-hydroxy-3-methylphenyl)-1H-pyrrol-2-yl)propanoic acid | C22H22N2O4 | 378.4 | 379.1 | Scheme 1, R2 = 4-hydroxy-3-methylphenyl, R1 = 4-carbamoyl-2-methylphenyl |

TABLE 1-continued

| # | Structure | Compound name | Chemical formula | Molecular weight | Mass Spec | Scheme #/Method # |
|---|---|---|---|---|---|---|
| 152 | 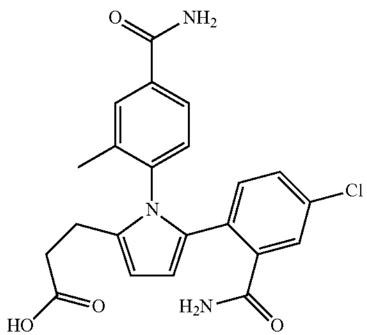 [SMILES: Cc1cc(C(N)=O)ccc1-n1c(CCC(=O)O)ccc1-c1ccc(Cl)cc1C(N)=O] | 3-(1-(4-carbamoyl-2-methylphenyl)-5-(2-carbamoyl-4-chlorophenyl)-1H-pyrrol-2-yl)propanoic acid | C22H20ClN3O4 | 425.9 | 426.1 | Scheme 6, Ar2 = 2-carbamoyl-4-chlorophenyl, using 4-chloro-2-cyanophenylboronic acid in step 6E to 6F |
| 153 | 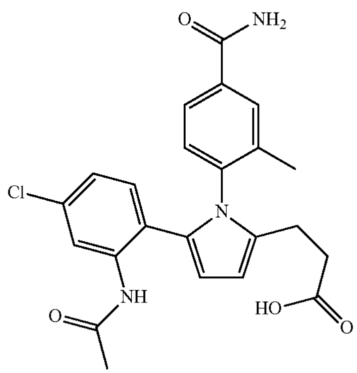 [SMILES: CC(=O)Nc1cc(Cl)ccc1-c1ccc(CCC(=O)O)n1-c1ccc(C(N)=O)cc1C] | 3-(5-(2-acetamido-4-chlorophenyl)-1-(4-carbamoyl-2-methylphenyl)-1H-pyrrol-2-yl)propanoic acid | C23H22ClN3O4 | 439.9 | 440.1 | Scheme 40, R = CH3 |
| 154 | 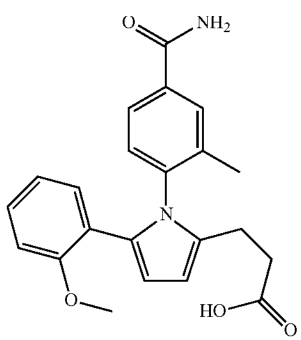 [SMILES: COc1ccccc1-c1ccc(CCC(=O)O)n1-c1ccc(C(N)=O)cc1C] | 3-(1-(4-carbamoyl-2-methylphenyl)-5-(2-methoxyphenyl)-1H-pyrrol-2-yl)propanoic acid | C22H22N2O4 | 378.4 | 379.1 | Scheme 6, Ar2 = 2-methoxyphenyl |

TABLE 1-continued

| # | Structure | Compound name | Chemical formula | Molecular weight | Mass Spec | Scheme #/Method # |
|---|---|---|---|---|---|---|
| 155 | 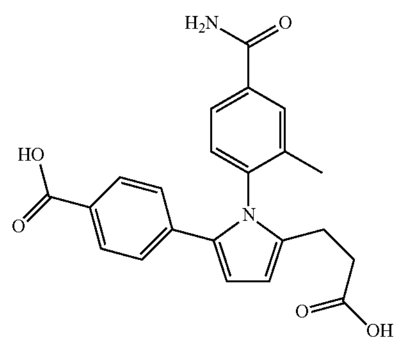 [SMILES: Cc1cc(C(N)=O)ccc1-n1c(CCC(=O)O)ccc1-c1ccc(C(=O)O)cc1] | 4-(1-(4-carbamoyl-2-methylphenyl)-5-(2-carboxyethyl)-1H-pyrrol-2-yl)benzoic acid | C22H20N2O5 | 392.4 | 393.1 | Scheme 35, compound 35-5 |
| 156 | 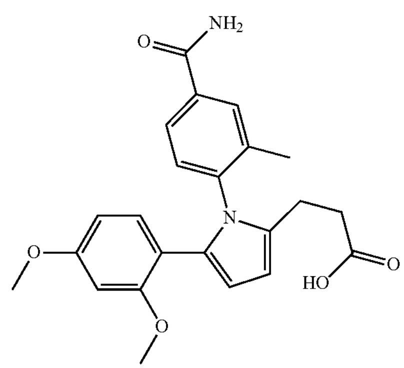 [SMILES: COc1ccc(-c2ccc(CCC(=O)O)n2-c2ccc(C(N)=O)cc2C)c(OC)c1] | 3-(1-(4-carbamoyl-2-methylphenyl)-5-(2,4-dimethoxyphenyl)-1H-pyrrol-2-yl)propanoic acid | C23H24N2O5 | 408.4 | 409.2 | Scheme 19, Ar2 = 2,4-dimethoxyphenyl |

TABLE 1-continued

| # | Structure | Compound name | Chemical formula | Molecular weight | Mass Spec | Scheme #/Method # |
|---|---|---|---|---|---|---|
| 157 | 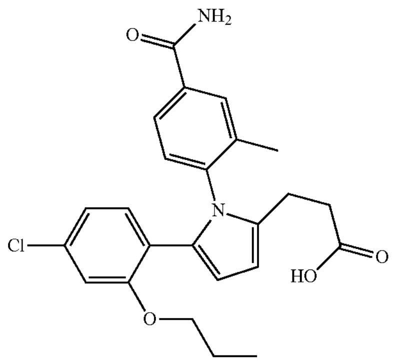 [SMILES: CCCOc1cc(Cl)ccc1-c1ccc(CCC(=O)O)n1-c1ccc(C(N)=O)cc1C] | 3-(1-(4-carbamoyl-2-methylphenyl)-5-(4-chloro-2-propoxyphenyl)-1H-pyrrol-2-yl)propanoic acid | C24H25ClN2O4 | 440.9 | 441.1 | Scheme 33, R1 = 4-carbamoyl-2-methylphenyl, R2 = 4-chloro, R3 = n-propyl |
| 158 | 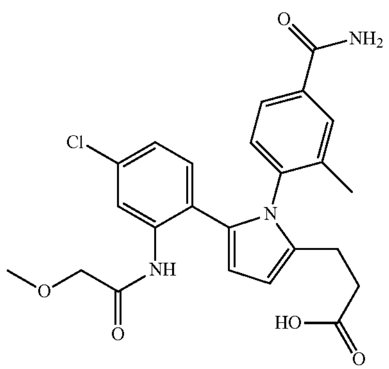 [SMILES: COCC(=O)Nc1cc(Cl)ccc1-c1ccc(CCC(=O)O)n1-c1ccc(C(N)=O)cc1C] | 3-(1-(4-carbamoyl-2-methylphenyl)-5-(4-chloro-2-(2-methoxyacetamido)phenyl)-1H-pyrrol-2-yl)propanoic acid | C24H24ClN3O5 | 469.9 | 470.1 | Scheme 40, R = methoxy methyl |

TABLE 1-continued

| # | Structure | Compound name | Chemical formula | Molecular weight | Mass Spec | Scheme #/Method # |
|---|---|---|---|---|---|---|
| 159 | 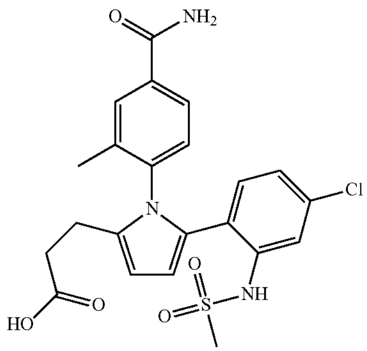 [SMILES: Cc1cc(C(N)=O)ccc1-n1c(CCC(=O)O)ccc1-c1ccc(Cl)cc1NS(C)(=O)=O] | 3-(1-(4-carbamoyl-2-methylphenyl)-5-(4-chloro-2-(methylsulfonamido)phenyl)-1H-pyrrol-2-yl)propanoic acid | C22H22ClN3O5S | 475.9 | 476.0 | Intermediate 16-4 (Method 16), then sulfonylated following 1st step of Scheme 14, then final 2 steps of Scheme 6 |
| 160 | 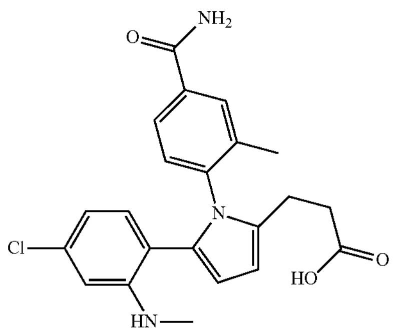 [SMILES: CNc1cc(Cl)ccc1-c1ccc(CCC(=O)O)n1-c1ccc(C(N)=O)cc1C] | 3-(1-(4-carbamoyl-2-methylphenyl)-5-(4-chloro-2-(methylamino)phenyl)-1H-pyrrol-2-yl)propanoic acid | C22H22ClN3O3 | 411.9 | 412.1 | Scheme 39 (compound 39a-B) |
| 161 | 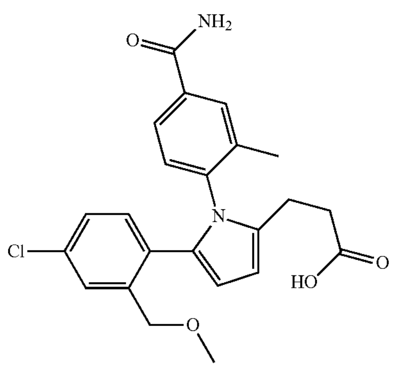 [SMILES: COCc1cc(Cl)ccc1-c1ccc(CCC(=O)O)n1-c1ccc(C(N)=O)cc1C] | 3-(1-(4-carbamoyl-2-methylphenyl)-5-(4-chloro-2-(methoxymethyl)phenyl)-1H-pyrrol-2-yl)propanoic acid | C23H23ClN2O4 | 426.9 | 427.1 | Scheme 6, R2 = 4-chloro-2-(methoxymethyl)phenyl/ Method 17 |

TABLE 1-continued

| # | Structure | Compound name | Chemical formula | Molecular weight | Mass Spec | Scheme #/Method # |
|---|---|---|---|---|---|---|
| 162 | 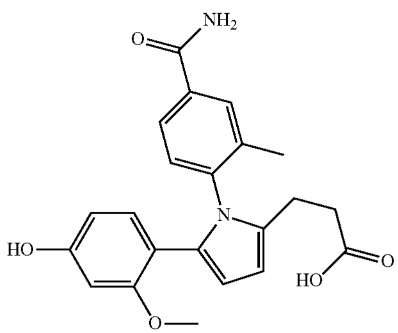 [SMILES: COc1cc(O)ccc1-c1ccc(CCC(=O)O)n1-c1ccc(C(N)=O)cc1C] | 3-(1-(4-carbamoyl-2-methylphenyl)-5-(4-hydroxy-2-methoxyphenyl)-1H-pyrrol-2-yl)propanoic acid | C22H22N2O5 | 394.4 | 395.1 | Scheme 6, R2 = 4-hydroxy-2-methoxyphenyl/Method 18 |
| 163 | 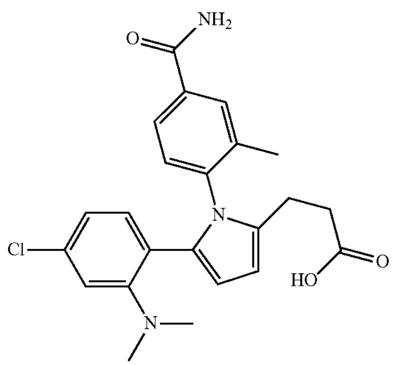 [SMILES: Cc1cc(C(N)=O)ccc1-n1c(CCC(=O)O)ccc1-c1ccc(Cl)cc1N(C)C] | 3-(1-(4-carbamoyl-2-methylphenyl)-5-(4-chloro-2-(dimethylamino)phenyl)-1H-pyrrol-2-yl)propanoic acid | C23H24ClN3O3 | 425.9 | 426.1 | Scheme 39 (compound 39b-B) |
| 164 | 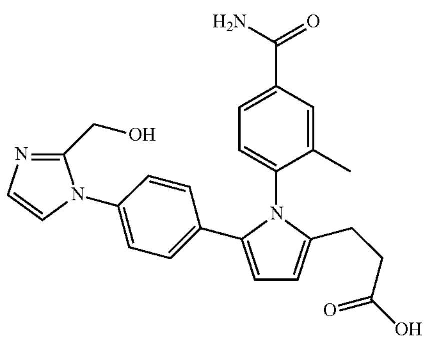 [SMILES: Cc1cc(C(N)=O)ccc1-n1c(CCC(=O)O)ccc1-c1ccc(-n2ccnc2CO)cc1] | 3-(1-(4-carbamoyl-2-methylphenyl)-5-(4-(2-(hydroxymethyl)-1H-imidazol-1-yl)phenyl)-1H-pyrrol-2-yl)propanoic acid | C25H24N4O4 | 444.5 | 445.1 | Scheme 34, Ar2—X = 4-bromophenyl, Ar2 = 2-(hydroxymethyl)-1H-imidazol-1-yl, and R1 = 4-carbamoyl-2-methylphenyl/Method 26 |

TABLE 1-continued

| # | Structure | Compound name | Chemical formula | Molecular weight | Mass Spec | Scheme #/Method # |
|---|---|---|---|---|---|---|
| 165 | 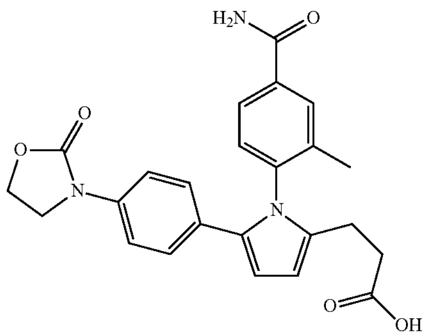 [SMILES: Cc1cc(C(N)=O)ccc1-n1c(CCC(=O)O)ccc1-c1ccc(N2CCOC2=O)cc1] | 3-(1-(4-carbamoyl-2-methylphenyl)-5-(4-(2-oxooxazolidin-3-yl)phenyl)-1H-pyrrol-2-yl)propanoic acid | C24H23N3O5 | 433.5 | 434.1 | Scheme 36, R1 = 2-oxooxazolidin-3-yl, R2 = 4-carbamoyl-2-methylphenyl, and R3 = H |
| 166 | 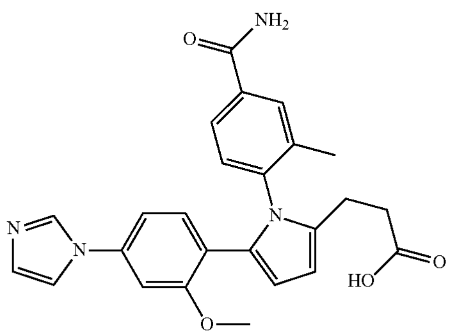 [SMILES: COc1cc(-n2ccnc2)ccc1-c1ccc(CCC(=O)O)n1-c1ccc(C(N)=O)cc1C] | 3-(5-(4-(1H-imidazol-1-yl)-2-methoxyphenyl)-1-(4-carbamoyl-2-methylphenyl)-1H-pyrrol-2-yl)propanoic acid | C25H24N4O4 | 444.5 | 445.2 | Scheme 36, R1 = 1H-imidazol-1-yl, R2 = 4-carbamoyl-2-methylphenyl, and R3 = 2-methoxy/method 15 |
| 167 | 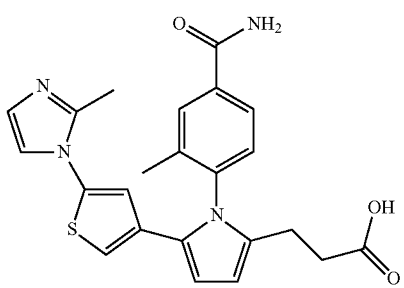 [SMILES: Cc1cc(C(N)=O)ccc1-n1c(CCC(=O)O)ccc1-c1csc(-n2ccnc2C)c1] | 3-(1-(4-carbamoyl-2-methylphenyl)-5-(2-methyl-1H-imidazol-1-yl)thiophen-3-yl)-1H-pyrrol-2-yl)propanoic acid | C23H22N4O3S | 434.5 | 435.1 | Scheme 34, Ar1—X = 5-bromothiophen-3-yl, Ar2 = 2-methyl-1H-imidazol-1-yl, R1 = 4-carbamoyl-2-methylphenyl |

TABLE 1-continued

| # | Structure | Compound name | Chemical formula | Molecular weight | Mass Spec | Scheme #/Method # |
|---|---|---|---|---|---|---|
| 168 | 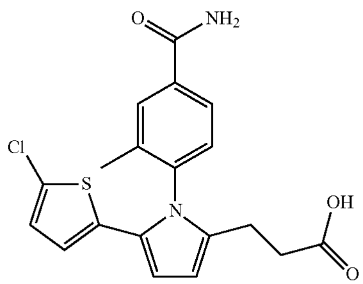 [SMILES: Cc1cc(C(N)=O)ccc1-n1c(CCC(=O)O)ccc1-c1ccc(Cl)s1] | 3-(1-(4-carbamoyl-2-methylphenyl)-5-(5-chlorothiophen-2-yl)-1H-pyrrol-2-yl)propanoic acid | C19H17ClN2O3S | 388.9 | 389.0 | Scheme 1, R2 = 5-chlorothiophen-2-yl, R1 = 4-carbamoyl-2-methylphenyl |
| 169 | 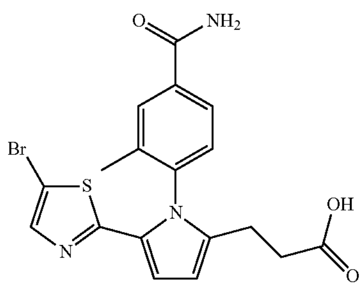 | 3-(5-(5-bromothiazol-2-yl)-1-(4-carbamoyl-2-methylphenyl)-1H-pyrrol-2-yl)propanoic acid | C18H16BrN3O3S | 434.3 | 434.0 | Scheme 1, R2 = 5-bromothiazol-2-yl, R1 = 4-carbamoyl-2-methylphenyl |
| 170 | 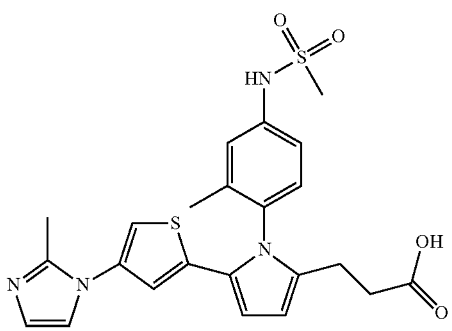 [SMILES: Cc1cc(NS(C)(=O)=O)ccc1-n1c(CCC(=O)O)ccc1-c1cc(-n2ccnc2C)cs1] | 3-(5-(4-(2-methyl-1H-imidazol-1-yl)thiophen-2-yl)-1-(2-methyl-4-(methylsulfonamido)phenyl)-1H-pyrrol-2-yl)propanoic acid | C23H24N4O4S2 | 484.6 | 485.1 | Scheme 34, Ar1—X = 4-bromothiophen-2-yl, Ar2 = 2-methyl-1H-imidazol-1-yl, R1 = 2-methyl-4-(methylsulfonamido)phenyl |

TABLE 1-continued

| # | Structure | Compound name | Chemical formula | Molecular weight | Mass Spec | Scheme #/Method # |
|---|---|---|---|---|---|---|
| 171 | 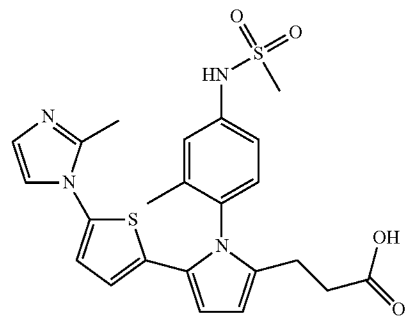 [SMILES: Cc1cc(NS(C)(=O)=O)ccc1-n1c(CCC(=O)O)ccc1-c1ccc(-n2ccnc2C)s1] | 3-(5-(5-(2-methyl-1H-imidazol-1-yl)thiophen-2-yl)-1-(2-methyl-4-(methylsulfonamido)phenyl)-1H-pyrrol-2-yl)propanoic acid | C23H24N4O4S2 | 484.6 | 485.0 | Scheme 34, Ar1—X = 5-bromothiophen-2-yl, Ar2 = 2-methyl-1H-imidazol-1-yl, R1 = 2-methyl-4-(methylsulfonamido)phenyl/Method 23 |
| 172 | 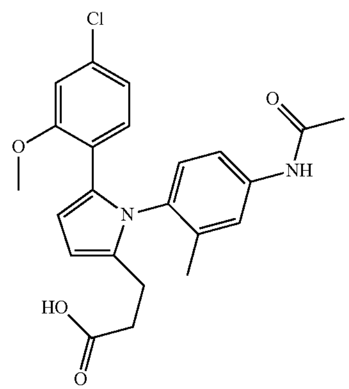 [SMILES: COc1cc(Cl)ccc1-c1ccc(CCC(=O)O)n1-c1ccc(NC(C)=O)cc1C] | 3-(1-(4-acetamido-2-methylphenyl)-5-(4-chloro-2-methoxyphenyl)-1H-pyrrol-2-yl)propanoic acid | C23H23ClN2O4 | 426.9 | 427.0 | Scheme 33, R1 = 4-carbamoyl-2-methylphenyl, R2 = 4-chloro, R3 = methyl |
| 173 | 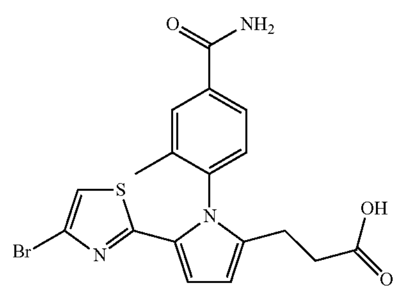 | 3-(5-(4-bromothiazol-2-yl)-1-(4-carbamoyl-2-methylphenyl)-1H-pyrrol-2-yl)propanoic acid | C18H16BrN3O3S | 434.3 | 434.1, 436.0 | Scheme 1, R1 = 4-carbamoyl-2-methylphenyl, R2 = 4-bromothiazol-2-yl/method 22 |

TABLE 1-continued

| # | Structure | Compound name | Chemical formula | Molecular weight | Mass Spec | Scheme #/Method # |
|---|---|---|---|---|---|---|
| 174 | 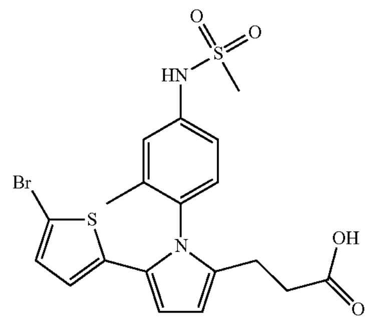 [SMILES: Cc1cc(NS(C)(=O)=O)ccc1-n1c(CCC(=O)O)ccc1-c1ccc(Br)s1] | 3-(5-(5-bromothiophen-2-yl)-1-(2-methyl-4-(methylsulfonamido)phenyl)-1H-pyrrol-2-yl)propanoic acid | C19H19BrN2O4S2 | 483.4 | 482.9 | Scheme 1, R1 = 2-methyl-4-(methylsulfonamido)phenyl, R2 = 5-bromothiophen-2-yl/method 23 |
| 175 | 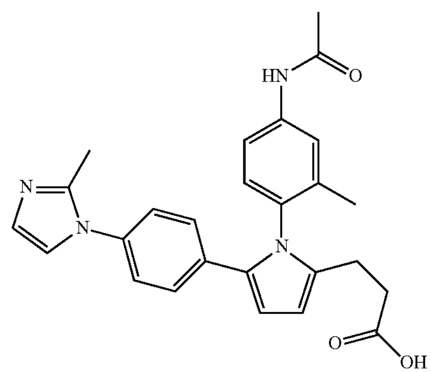 [SMILES: CC(=O)Nc1ccc(-n2c(CCC(=O)O)ccc2-c2ccc(-n3ccnc3C)cc2)c(C)c1] | 3-(1-(4-acetamido-2-methylphenyl)-5-(4-(2-methyl-1H-imidazol-1-yl)phenyl)-1H-pyrrol-2-yl)propanoic acid | C26H26N4O3 | 442.5 | 443.0 | Compound 3, then reduction according to Scheme 20 step 1, then acylation according to Scheme 31, R1 = methyl |
| 176 | 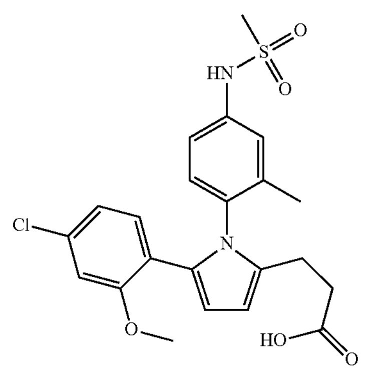 [SMILES: COc1cc(Cl)ccc1-c1ccc(CCC(=O)O)n1-c1ccc(NS(C)(=O)=O)cc1C] | 3-(5-(4-chloro-2-methoxyphenyl)-1-(2-methyl-4-(methylsulfonamido)phenyl)-1H-pyrrol-2-yl)propanoic acid | C22H23ClN2O5S | 462.9 | 462.9 | Scheme 33, R1 = 2-methyl-4-(methylsulfonamido)phenyl, R2 = 4-chloro, R3 = methyl |

TABLE 1-continued

| # | Structure | Compound name | Chemical formula | Molecular weight | Mass Spec | Scheme #/Method # |
|---|---|---|---|---|---|---|
| 177 | 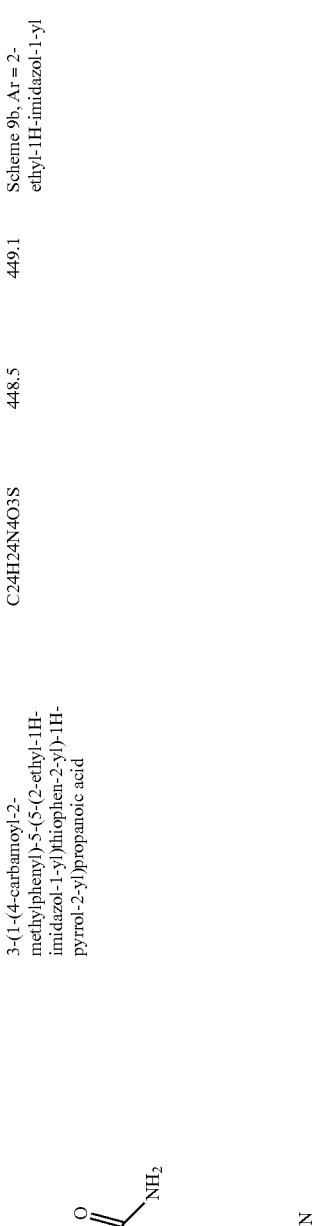 | 3-(1-(4-carbamoyl-2-methylphenyl)-5-(5-(2-ethyl-1H-imidazol-1-yl)thiophen-2-yl)-1H-pyrrol-2-yl)propanoic acid | C24H24N4O3S | 448.5 | 449.1 | Scheme 9b, Ar = 2-ethyl-1H-imidazol-1-yl |
| 178 | 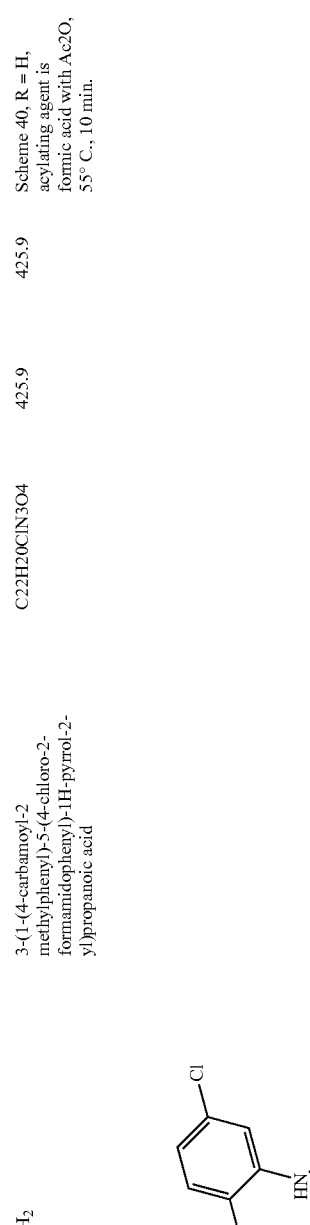 | 3-(1-(4-carbamoyl-2-methylphenyl)-5-(4-chloro-2-formamidophenyl)-1H-pyrrol-2-yl)propanoic acid | C22H20ClN3O4 | 425.9 | 425.9 | Scheme 40, R = H, acylating agent is formic acid with Ac2O, 55° C., 10 min. |
| 179 | 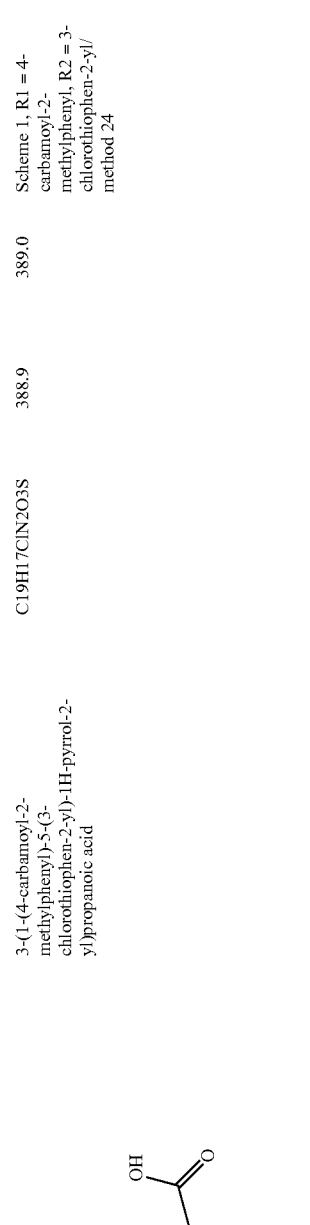 | 3-(1-(4-carbamoyl-2-methylphenyl)-5-(3-chlorothiophen-2-yl)-1H-pyrrol-2-yl)propanoic acid | C19H17ClN2O3S | 388.9 | 389.0 | Scheme 1, R1 = 4-carbamoyl-2-methylphenyl, R2 = 3-chlorothiophen-2-yl/method 24 |

TABLE 1-continued

| # | Structure | Compound name | Chemical formula | Molecular weight | Mass Spec | Scheme #/Method # |
|---|---|---|---|---|---|---|
| 180 | 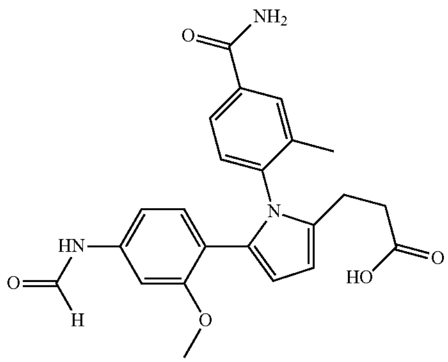 [SMILES: COc1cc(NC=O)ccc1-c1ccc(CCC(=O)O)n1-c1ccc(C(N)=O)cc1C] | 3-(1-(4-carbamoyl-2-methylphenyl)-5-(4-formamido-2-methoxyphenyl)-1H-pyrrol-2-yl)propanoic acid | C23H23N3O5 | 421.4 | 422.0 | Scheme 6, 4-formamido-2-methoxyphenyl/ Method 33 |
| 181 | 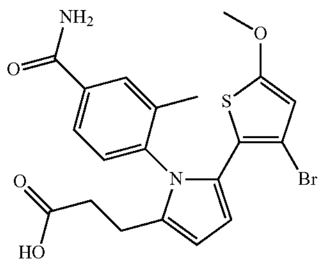 [SMILES: COc1cc(Br)c(-c2ccc(CCC(=O)O)n2-c2ccc(C(N)=O)cc2C)s1] | 3-(5-(3-bromo-5-methoxythiophen-2-yl)-1-(4-carbamoyl-2-methylphenyl)-1H-pyrrol-2-yl)propanoic acid | C20H19BrN2O4S | 463.3 | 464.6 | Scheme 1, R1 = 4-carbamoyl-2-methylphenyl, R2 = 3-bromo-5-methoxythiophen-2-yl/ method 25 |
| 182 | 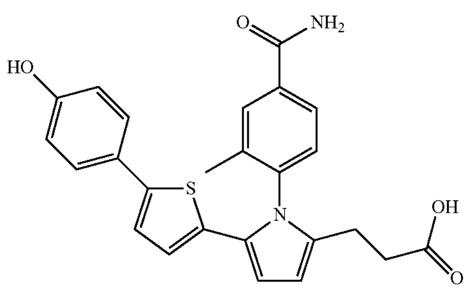 [SMILES: Cc1cc(C(N)=O)ccc1-n1c(CCC(=O)O)ccc1-c1ccc(-c2ccc(O)cc2)s1] | 3-(1-(4-carbamoyl-2-methylphenyl)-5-(5-(4-hydroxyphenyl)thiophen-2-yl)-1H-pyrrol-2-yl)propanoic acid | C25H22N2O4S | 446.5 | 447.1 | see compound 6 before hydrolysis, then followed Scheme 6, step 6 with 4-hydroxyphenylboronic acid (see 6E to 6F), then last step of Scheme 6 |

TABLE 1-continued

| # | Structure | Compound name | Chemical formula | Molecular weight | Mass Spec | Scheme #/Method # |
|---|---|---|---|---|---|---|
| 183 | 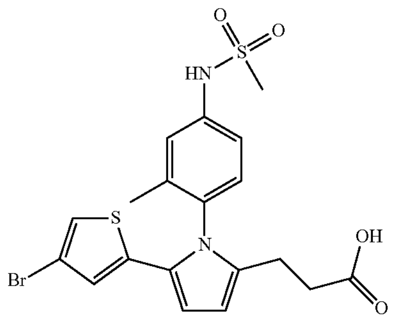 [SMILES: Cc1cc(NS(C)(=O)=O)ccc1-n1c(CCC(=O)O)ccc1-c1cc(Br)cs1] | 3-(5-(4-bromothiophen-2-yl)-1-(2-methyl-4-(methylsulfonamido)phenyl)-1H-pyrrol-2-yl)propanoic acid | C19H19BrN2O4S2 | 483.4 | 482.6 | Scheme 1, R1 = 2-methyl-4-(methylsulfonamido)phenyl, R2 = 4-bromothiophen-2-yl/method 23 (R = CH3) |
| 184 | 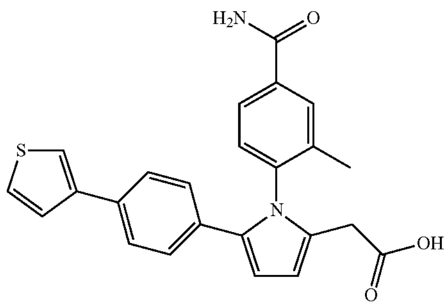 [SMILES: Cc1cc(C(N)=O)ccc1-n1c(CC(=O)O)ccc1-c1ccc(-c2ccsc2)cc1] | 2-(1-(4-carbamoyl-2-methylphenyl)-5-(thiophen-3-yl)phenyl)-1H-pyrrol-2-yl)acetic acid | C24H20N2O3S | 416.5 | 416.8 | Scheme 37 |
| 185 | 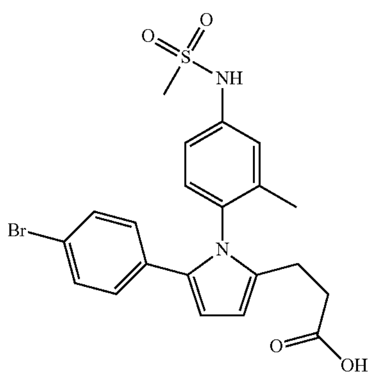 [SMILES: Cc1cc(NS(C)(=O)=O)ccc1-n1c(CCC(=O)O)ccc1-c1ccc(Br)cc1] | 3-(5-(4-bromophenyl)-1-(2-methyl-4-(methylsulfonamido)phenyl)-1H-pyrrol-2-yl)propanoic acid | C21H21BrN2O4S | 477.4 | 476.7 | Scheme 1, R1 = 2-methyl-4-(methylsulfonamido)phenyl, R2 = 4-bromophenyl/method 23 (R = CH3) |

TABLE 1-continued

| # | Structure | Compound name | Chemical formula | Molecular weight | Mass Spec | Scheme #/Method # |
|---|---|---|---|---|---|---|
| 186 | 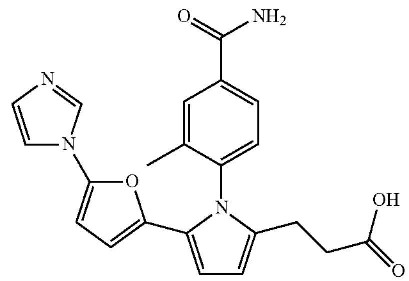 [SMILES: Cc1cc(C(N)=O)ccc1-n1c(CCC(=O)O)ccc1-c1ccc(-n2ccnc2)o1] | 3-(5-(5-(1H-imidazol-1-yl)furan-2-yl)-1-(4-carbamoyl-2-methylphenyl)-1H-pyrrol-2-yl)propanoic acid | C22H20N4O4 | 404.4 | 404.9 | Scheme 34, Ar1—X = 5-bromofuran-2-yl, Ar2 = 1H-imidazol-1-yl, R = 4-carbamoyl-2-methylphenyl/(34A synthesis, see compound 193) |
| 187 | 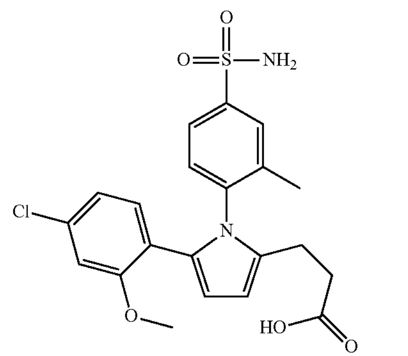 [SMILES: COc1cc(Cl)ccc1-c1ccc(CCC(=O)O)n1-c1ccc(S(N)(=O)=O)cc1C] | 3-(5-(4-chloro-2-methoxyphenyl)-1-(2-methyl-4-sulfamoylphenyl)-1H-pyrrol-2-yl)propanoic acid | C21H21ClN2O5S | 448.9 | 449.0 | Scheme 1, R1 = 2-methyl-4-sulfamoylphenyl, R2 = 4-chloro-2-methoxyphenyl, Method 21 and Method 27 |
| 188 | 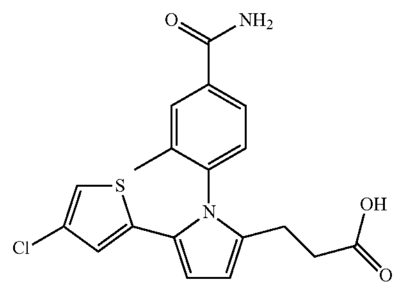 [SMILES: Cc1cc(C(N)=O)ccc1-n1c(CCC(=O)O)ccc1-c1cc(Cl)cs1] | 3-(1-(4-carbamoyl-2-methylphenyl)-5-(4-chlorothiophen-2-yl)-1H-pyrrol-2-yl)propanoic acid | C19H17ClN2O3S | 388.9 | 388.9 | Scheme 1, R1 = 4-carbamoyl-2-methylphenyl, R2 = 4-chlorothiophen-2-yl/Method 28 (28-3) |

TABLE 1-continued

| # | Structure | Compound name | Chemical formula | Molecular weight | Mass Spec | Scheme #/Method # |
|---|---|---|---|---|---|---|
| 189 | 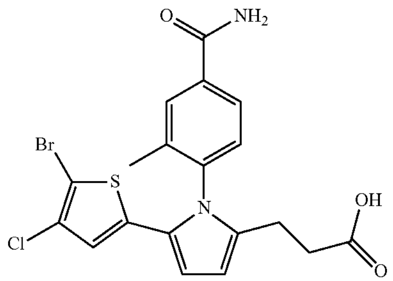 [SMILES: Cc1cc(C(N)=O)ccc1-n1c(CCC(=O)O)ccc1-c1cc(Cl)c(Br)s1] | 3-(5-(5-bromo-4-chlorothiophen-2-yl)-1-(4-carbamoyl-2-methylphenyl)-1H-pyrrol-2-yl)propanoic acid | C19H16BrClN2O3S | 467.8 | 466.9, 468.8 | Scheme 1, R1 = 4-carbamoyl-2-methylphenyl, R2 = 4-chlorothiophen-2-yl/ Method 28 (28-2) |
| 190 | 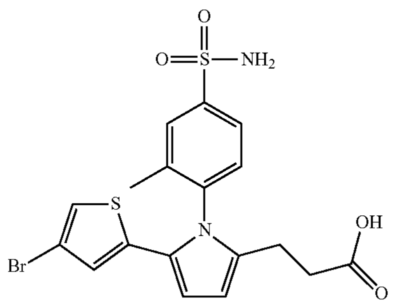 [SMILES: Cc1cc(S(N)(=O)=O)ccc1-n1c(CCC(=O)O)ccc1-c1cc(Br)cs1] | 3-(5-(4-bromothiophen-2-yl)-1-(2-methyl-4-sulfamoylphenyl)-1H-pyrrol-2-yl)propanoic acid | C18H17BrN2O4S2 | 469.4 | 470.9 | Scheme 1, R1 = 2-methyl-4-(methylsulfonamido)phenyl, R2 = 4-bromothiophen-2-yl/ method 27 |
| 191 | 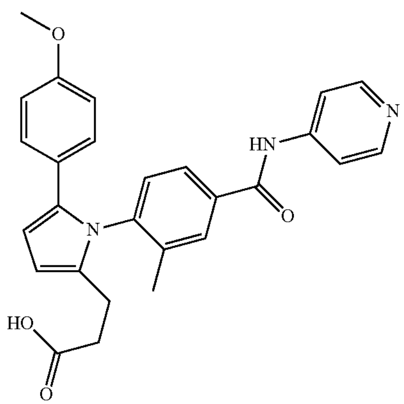 [SMILES: COc1ccc(-c2ccc(CCC(=O)O)n2-c2ccc(C(=O)Nc3ccncc3)cc2C)cc1] | 3-(5-(4-methoxyphenyl)-1-(2-methyl-4-(pyridin-4-ylcarbamoyl)phenyl)-1H-pyrrol-2-yl)propanoic acid | C27H25N3O4 | 455.5 | | Scheme 43 |

TABLE 1-continued

| # | Compound name | Chemical formula | Molecular weight | Mass Spec | Scheme #/Method # |
|---|---|---|---|---|---|
| 192 | 3-(1-(4-carbamoyl-2-methylphenyl)-5-(5-(2-methyl-1H-imidazol-1-yl)furan-2-yl)-1H-pyrrol-2-yl)propanoic acid | C23H22N4O4 | 418.4 | 419.1 | Scheme 34, Ar1—X = 5-bromofuran-2-yl, Ar2 = 2-methyl-1H-imidazol-1-yl, R = 4-carbamoyl-2-methylphenyl/(34A synthesis, see compound 193) |
| 193 | 3-(5-(5-bromofuran-2-yl)-1-(4-carbamoyl-2-methylphenyl)-1H-pyrrol-2-yl)propanoic acid | C19H17BrN2O4 | 417.3 | 418.9 | Scheme 38 |
| 194 | 3-(5-(5-(2-methyl-1H-imidazol-1-yl)thiophen-2-yl)-1-(2-methyl-4-sulfamoylphenyl)-1H-pyrrol-2-yl)propanoic acid | C22H22N4O4S2 | 470.6 | 471.0 | Scheme 36, Ar1—Br = 5-bromo-thiophen-2-yl, Ar2 = 2-methyl-1H-imidazol-1-yl, R1 = 2-methyl-4-sulfamoylphenyl/Method 27 |

TABLE 1-continued

| # | Structure | Compound name | Chemical formula | Molecular weight | Mass Spec | Scheme #/Method # |
|---|---|---|---|---|---|---|
| 195 | 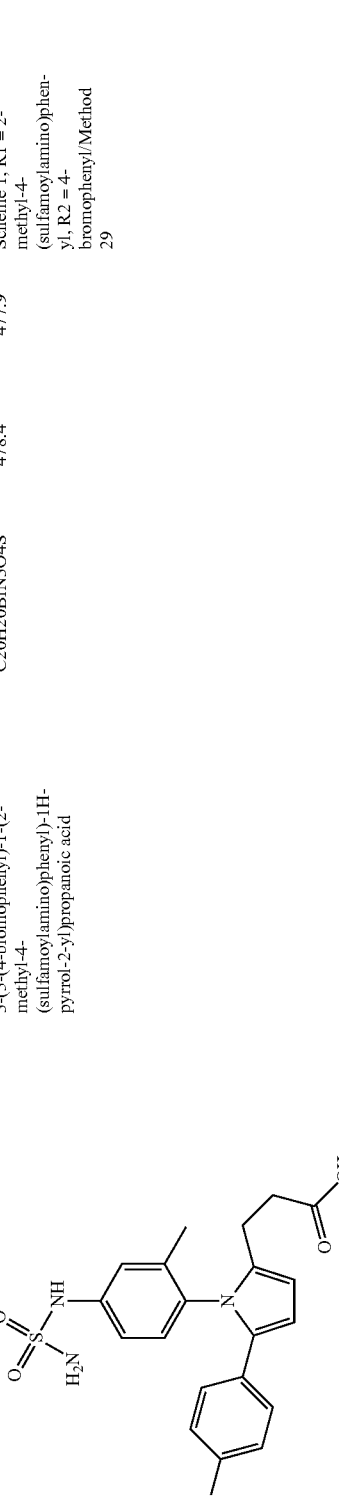 | 3-(5-(4-bromophenyl)-1-(2-methyl-4-(sulfamoylamino)phenyl)-1H-pyrrol-2-yl)propanoic acid | C20H20BrN3O4S | 478.4 | 477.9 | Scheme 1, R1 = 2-methyl-4-(sulfamoylamino)phenyl, R2 = 4-bromophenyl/Method 29 |
| 196 | 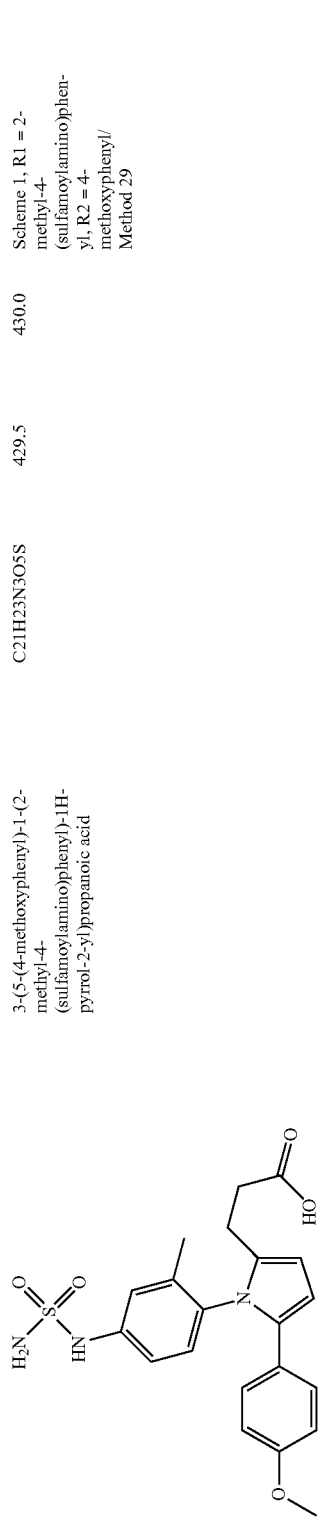 | 3-(5-(4-methoxyphenyl)-1-(2-methyl-4-(sulfamoylamino)phenyl)-1H-pyrrol-2-yl)propanoic acid | C21H23N3O5S | 429.5 | 430.0 | Scheme 1, R1 = 2-methyl-4-(sulfamoylamino)phenyl, R2 = 4-methoxyphenyl/Method 29 |
| 197 | 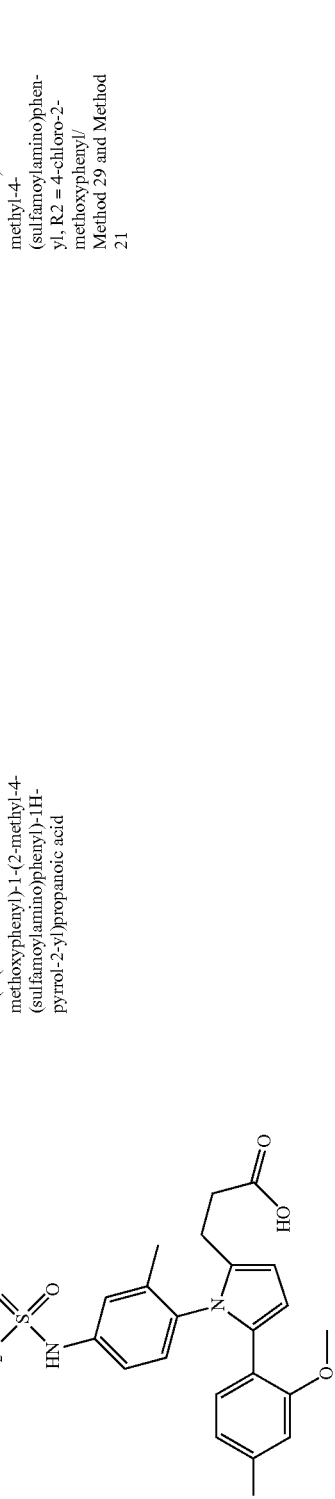 | 3-(5-(4-chloro-2-methoxyphenyl)-1-(2-methyl-4-(sulfamoylamino)phenyl)-1H-pyrrol-2-yl)propanoic acid | C21H22ClN3O5S | 463.9 | 464.0 | Scheme 1, R1 = 2-methyl-4-(sulfamoylamino)phenyl, R2 = 4-chloro-2-methoxyphenyl/Method 29 and Method 21 |

TABLE 1-continued

| # | Structure | Compound name | Chemical formula | Molecular weight | Mass Spec | Scheme #/Method # |
|---|---|---|---|---|---|---|
| 198 | 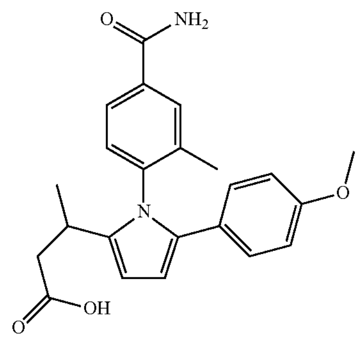 [SMILES: COc1ccc(-c2ccc(C(C)CC(=O)O)n2-c2ccc(C(N)=O)cc2C)cc1] | 3-(1-(4-carbamoyl-2-methylphenyl)-5-(4-methoxyphenyl)-1H-pyrrol-2-yl)butanoic acid | C23H24N2O4 | 392.4 | 393.2 | Scheme 50 |

Table 2 below lists representative novel pyrrole analogs of Formula II useful as GSNOR inhibitors of the invention. The synthetic methods that can be used to prepare each compound, identified in Table 2 (i.e. Scheme 1, Scheme 2, etc.) are detailed below. In some cases, if the starting material or intermediate of a scheme is not commercially available, then a corresponding method (called Method 1, Method 2, etc.) describes the synthesis of that starting material or intermediate. Table 2 provides Scheme number, defines starting materials shown in Schemes, and where necessary provides the method number which corresponds to synthesis of an intermediate or starting materials. Supporting mass spectrometry data for each compound is also included in Table 2. GSNOR inhibitor activity was determined by the assay described in Example 2 and $IC_{50}$ values were obtained. GSNOR inhibitor compounds 199-236 of Table 2 had an $IC_{50}$ of about <100 µM. GSNOR inhibitor compounds 199-212, 216, 219, 221, 223, 226, 229, 231, 232, 235, and 236 of Table 2 had an $IC_{50}$ of less than 5.0 µM. GSNOR inhibitor compounds 199-202, 216, 219, 221, 231, and 235 of Table 2 had an $IC_{50}$ of less than 1.0 µM.

TABLE 2

| # | Structure | Compound name | Formula | Molecular weight | mass spec | Synthesis |
|---|---|---|---|---|---|---|
| 199 | 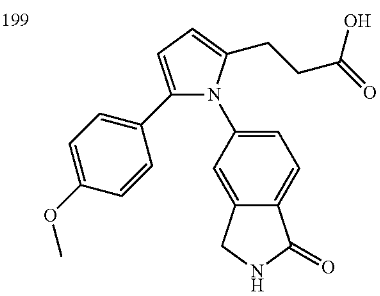 | 3-(5-(4-methoxyphenyl)-1-(1-oxoisoindolin-5-yl)-1H-pyrrol-2-yl)propanoic acid | $C_{22}H_{20}N_2O_4$ | 376.4 | 377.1 | Scheme 1A, R2 = 4-methoxyphenyl, R1 = 1-oxoisoindolin-5-yl/ Method 5 |
| 200 | 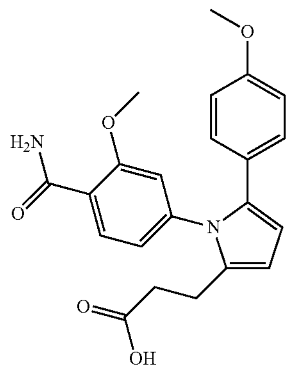 [SMILES: COc1ccc(-c2ccc(CCC(=O)O)n2-c2ccc(C(N)=O)c(OC)c2)cc1] | 3-(1-(4-carbamoyl-3-methoxyphenyl)-5-(4-methoxyphenyl)-1H-pyrrol-2-yl)propanoic acid | $C_{22}H_{22}N_2O_5$ | 394.4 | 395.1 | Scheme 1, R2 = 4-methoxyphenyl, R1 = 4-carbamoyl-3-methoxyphenyl |
| 201 | 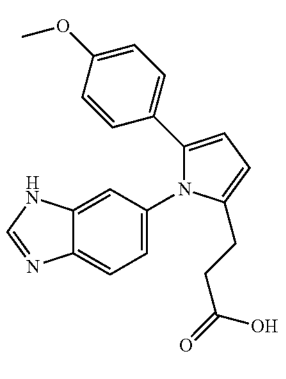 [SMILES: COc1ccc(-c2ccc(CCC(=O)O)n2-c2ccc3nc[nH]c3c2)cc1] | 3-(1-(1H-benzo[d]imidazol-6-yl)-5-(4-methoxyphenyl)-1H-pyrrol-2-yl)propanoic acid | $C_{21}H_{19}N_3O_3$ | 361.4 | 362.1 | Scheme 1, R2 = 4-methoxyphenyl, R1 = 1H-benzo[d]imidazol-6-yl |

TABLE 2-continued

| # | Structure | Compound name | Formula | Molecular weight | mass spec | Synthesis |
|---|---|---|---|---|---|---|
| 202 | 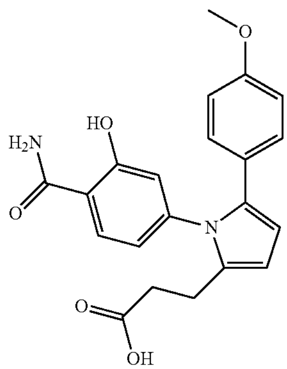 [SMILES: COc1ccc(-c2ccc(CCC(=O)O)n2-c2ccc(C(N)=O)c(O)c2)cc1] | 3-(1-(4-carbamoyl-3-hydroxyphenyl)-5-(4-methoxyphenyl)-1H-pyrrol-2-yl)propanoic acid | $C_{21}H_{20}N_2O_5$ | 380.4 | 381.1 | Scheme 1A, R2 = 4-methoxyphenyl, R1 = 4-carbamoyl-3-hydroxyphenyl |
| 203 | 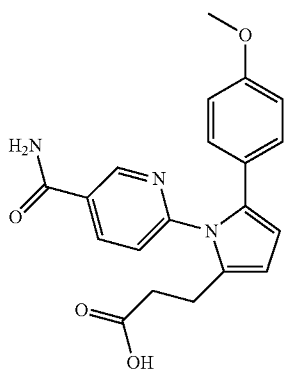 [SMILES: COc1ccc(-c2ccc(CCC(=O)O)n2-c2ccc(C(N)=O)cn2)cc1] | 3-(1-(5-carbamoylpyridin-2-yl)-5-(4-methoxyphenyl)-1H-pyrrol-2-yl)propanoic acid | $C_{20}H_{19}N_3O_4$ | 365.4 | 366.0 | Scheme 1A, R2 = 4-methoxyphenyl, R1 = 5-carbamoylpyridin-2-yl |
| 204 | 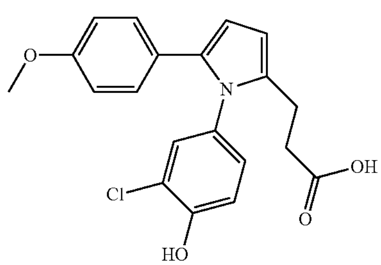 [SMILES: COc1ccc(-c2ccc(CCC(=O)O)n2-c2ccc(O)c(Cl)c2)cc1] | 3-(1-(3-chloro-4-hydroxyphenyl)-5-(4-methoxyphenyl)-1H-pyrrol-2-yl)propanoic acid | $C_{20}H_{18}ClNO_4$ | 371.8 | 372.1 | Scheme 1A, R2 = 4-methoxyphenyl, R1 = 3-chloro-4-hydroxyphenyl |
| 205 | 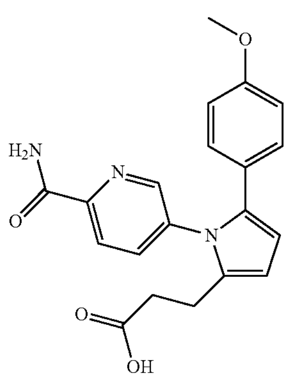 [SMILES: COc1ccc(-c2ccc(CCC(=O)O)n2-c2ccc(C(N)=O)nc2)cc1] | 3-(1-(6-carbamoylpyridin-3-yl)-5-(4-methoxyphenyl)-1H-pyrrol-2-yl)propanoic acid | $C_{20}H_{19}N_3O_4$ | 365.4 | 366.0 | Scheme 1A, R2 = 4-methoxyphenyl, R1 = 6-carbamoylpyridin-3-yl/ Method 6 |

TABLE 2-continued

| # | Structure | Compound name | Formula | Molecular weight | mass spec | Synthesis |
|---|---|---|---|---|---|---|
| 206 | 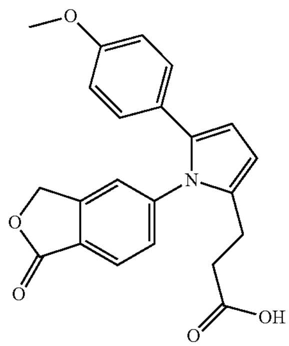 [SMILES: COc1ccc(-c2ccc(CCC(=O)O)n2-c2ccc3c(c2)COC3=O)cc1] | 3-(5-(4-methoxyphenyl)-1-(1-oxo-1,3-dihydroisobenzofuran-5-yl)-1H-pyrrol-2-yl)propanoic acid | $C_{22}H_{19}NO_5$ | 377.4 | 378.1 | Scheme 1A, R2 = 4-methoxyphenyl, R1 = 1-oxo-1,3-dihydroisobenzofuran-5-yl |
| 207 | 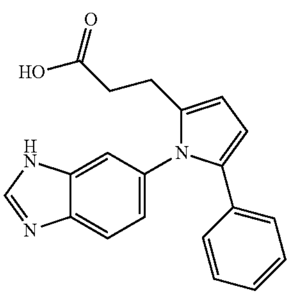 [SMILES: O=C(O)CCc1ccc(-c2ccccc2)n1-c1ccc2nc[nH]c2c1] | 3-(1-(1H-benzo[d]imidazol-6-yl)-5-phenyl-1H-pyrrol-2-yl)propanoic acid | $C_{20}H_{17}N_3O_2$ | 331.4 | 332.1 | Scheme 1, R2 = phenyl, R1 = 1H-benzo[d]imidazol-6-yl |
| 208 | 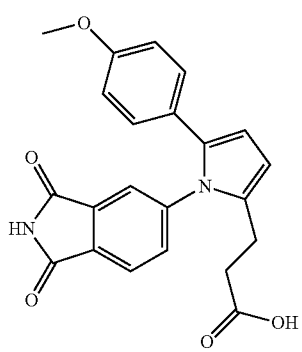 [SMILES: COc1ccc(-c2ccc(CCC(=O)O)n2-c2ccc3c(c2)C(=O)NC3=O)cc1] | 3-(1-(1,3-dioxoisoindolin-5-yl)-5-(4-methoxyphenyl)-1H-pyrrol-2-yl)propanoic acid | $C_{22}H_{18}N_2O_5$ | 390.4 | 391.1 | Scheme 1A, R2 = 4-methoxyphenyl, R1 = 1,3-dioxoisoindolin-5-yl |
| 209 | 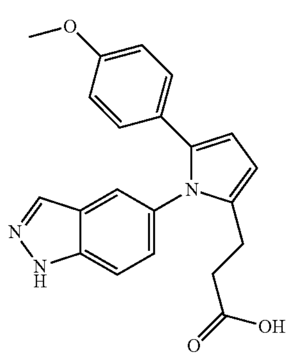 [SMILES: COc1ccc(-c2ccc(CCC(=O)O)n2-c2ccc3[nH]ncc3c2)cc1] | 3-(1-(1H-indazol-5-yl)-5-(4-methoxyphenyl)-1H-pyrrol-2-yl)propanoic acid | $C_{21}H_{19}N_3O_3$ | 361.4 | 362.1 | Scheme 1, R2 = 4-methoxyphenyl, R1 = 1H-indazol-5-yl |

TABLE 2-continued

| # | Structure | Compound name | Formula | Molecular weight | mass spec | Synthesis |
|---|---|---|---|---|---|---|
| 210 | 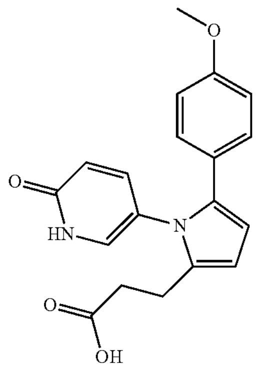 [SMILES: COc1ccc(-c2ccc(CCC(=O)O)n2-c2ccc(=O)[nH]c2)cc1] | 3-(5-(4-methoxyphenyl)-1-(6-oxo-1,6-dihydropyridin-3-yl)-1H-pyrrol-2-yl)propanoic acid | $C_{19}H_{18}N_2O_4$ | 338.4 | 339.1 | Scheme 1, R2 = 4-methoxyphenyl, R1 = 6-oxo-1,6-dihydropyridin-3-yl |
| 211 | 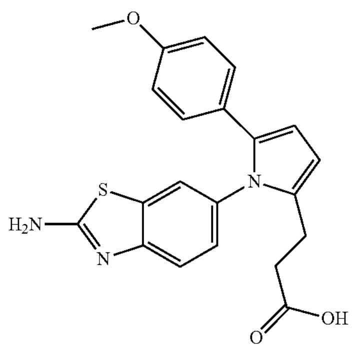 [SMILES: COc1ccc(-c2ccc(CCC(=O)O)n2-c2ccc3nc(N)sc3c2)cc1] | 3-(1-(2-aminobenzo[d]thiazol-6-yl)-5-(4-methoxyphenyl)-1H-pyrrol-2-yl)propanoic acid | $C_{21}H_{19}N_3O_3S$ | 393.5 | 394.0 | Scheme 1A, R2 = 4-methoxyphenyl, R1 = 2-aminobenzo[d]thiazol-6-yl/Method 7 |
| 212 | 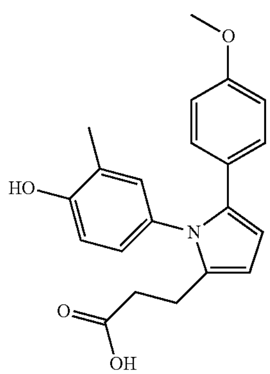 [SMILES: COc1ccc(-c2ccc(CCC(=O)O)n2-c2ccc(O)c(C)c2)cc1] | 3-(1-(4-hydroxy-3-methylphenyl)-5-(4-methoxyphenyl)-1H-pyrrol-2-yl)propanoic acid | $C_{21}H_{21}NO_4$ | 351.4 | 352.1 | Scheme 1A, R2 = 4-methoxyphenyl, R1 = 4-hydroxy-3-methylphenyl |
| 213 | 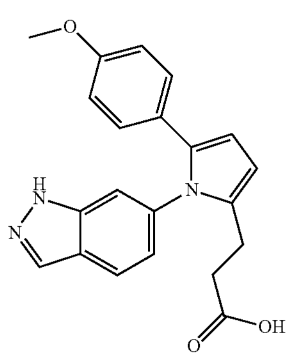 [SMILES: COc1ccc(-c2ccc(CCC(=O)O)n2-c2ccc3cn[nH]c3c2)cc1] | 3-(1-(1H-indazol-6-yl)-5-(4-methoxyphenyl)-1H-pyrrol-2-yl)propanoic acid | $C_{21}H_{19}N_3O_3$ | 361.4 | 362.1 | Scheme 1, R2 = 4-methoxyphenyl, R1 = 1H-indazol-6-yl |

TABLE 2-continued

| # | Structure | Compound name | Formula | Molecular weight | mass spec | Synthesis |
|---|---|---|---|---|---|---|
| 214 | 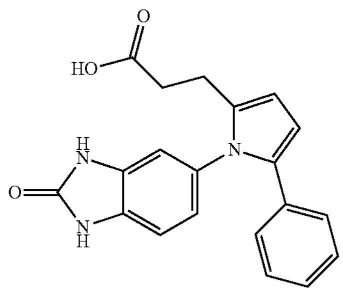 [SMILES: O=C(O)CCc1ccc(-c2ccccc2)n1-c1ccc2[nH]c(=O)[nH]c2c1] | 3-(1-(2-oxo-2,3-dihydro-1H-benzo[d]imidazol-5-yl)-5-phenyl-1H-pyrrol-2-yl)propanoic acid | $C_{20}H_{17}N_3O_3$ | 347.4 | 348.1 | Scheme 1, R2 = phenyl, R1 = 2-oxo-2,3-dihydro-1H-benzo[d]imidazol-5-yl |
| 215 | 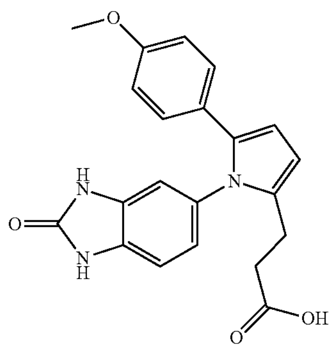 [SMILES: COc1ccc(-c2ccc(CCC(=O)O)n2-c2ccc3[nH]c(=O)[nH]c3c2)cc1] | 3-(5-(4-methoxyphenyl)-1-(2-oxo-2,3-dihydro-1H-benzo[d]imidazol-5-yl)-1H-pyrrol-2-yl)propanoic acid | $C_{21}H_{19}N_3O_4$ | 377.4 | 378.1 | Scheme 1, R2 = 4-methoxyphenyl, R1 = 2-oxo-2,3-dihydro-1H-benzo[d]imidazol-5-yl |
| 216 | 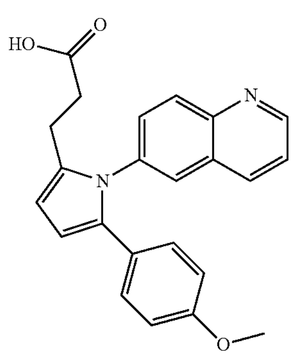 [SMILES: COc1ccc(-c2ccc(CCC(=O)O)n2-c2ccc3ncccc3c2)cc1] | 3-(5-(4-methoxyphenyl)-1-(quinolin-6-yl)-1H-pyrrol-2-yl)propanoic acid | $C_{23}H_{20}N_2O_3$ | 372.4 | 373.1 | Scheme 25, Ar1 = quinolin-6-yl |
| 217 | 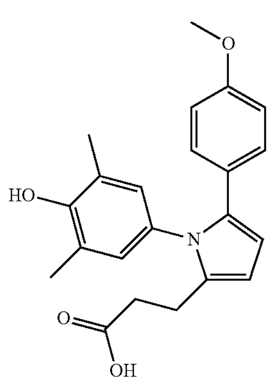 [SMILES: COc1ccc(-c2ccc(CCC(=O)O)n2-c2cc(C)c(O)c(C)c2)cc1] | 3-(1-(4-hydroxy-3,5-dimethylphenyl)-5-(4-methoxyphenyl)-1H-pyrrol-2-yl)propanoic acid | $C_{22}H_{23}NO_4$ | 365.4 | 366.1 | Scheme 1, R2 = 4-methoxyphenyl, R1 = 4-hydroxy-3,5-dimethylphenyl |

TABLE 2-continued

| # | Structure | Compound name | Formula | Molecular weight | mass spec | Synthesis |
|---|---|---|---|---|---|---|
| 218 | 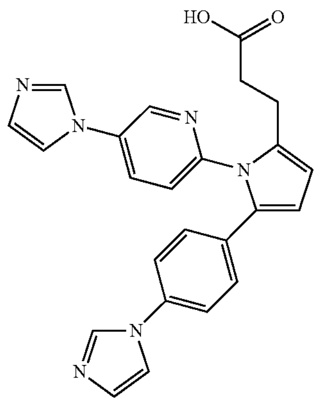 [SMILES: O=C(O)CCc1ccc(-c2ccc(-n3ccnc3)cc2)n1-c1ccc(-n2ccnc2)cn1] | 3-(5-(4-(1H-imidazol-1-yl)phenyl)-1-(5-(1H-imidazol-1-yl)pyridin-2-yl)-1H-pyrrol-2-yl)propanoic acid | $C_{24}H_{20}N_6O_2$ | 424.5 | 425.0 | Scheme 29, R1 = 5-(1H-imidazol-1-yl)pyridin-2-yl) |
| 219 | 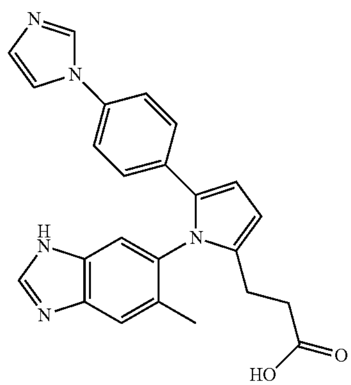 [SMILES: Cc1cc2nc[nH]c2cc1-n1c(CCC(=O)O)ccc1-c1ccc(-n2ccnc2)cc1] | 3-(5-(4-(1H-imidazol-1-yl)phenyl)-1-(5-methyl-1H-benzo[d]imidazol-6-yl)-1H-pyrrol-2-yl)propanoic acid | $C_{24}H_{21}N_5O_2$ | 411.5 | 412.0 | Scheme 29, R1 = 5-methyl-1H-benzo[d]imidazol-6-yl/ Method 30 (30-3A) |
| 220 | 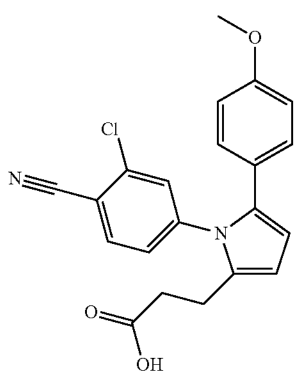 [SMILES: COc1ccc(-c2ccc(CCC(=O)O)n2-c2ccc(C#N)c(Cl)c2)cc1] | 3-(1-(3-chloro-4-cyanophenyl)-5-(4-methoxyphenyl)-1H-pyrrol-2-yl)propanoic acid | $C_{21}H_{17}ClN_2O_3$ | 380.8 | 381.1 | Scheme 1A, R1 = 3-chloro-4-cyanophenyl, R2 = 4-methoxyphenyl |
| 221 | 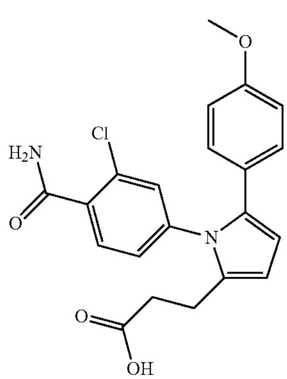 [SMILES: COc1ccc(-c2ccc(CCC(=O)O)n2-c2ccc(C(N)=O)c(Cl)c2)cc1] | 3-(1-(4-carbamoyl-3-chlorophenyl)-5-(4-methoxyphenyl)-1H-pyrrol-2-yl)propanoic acid | $C_{21}H_{19}ClN_2O_4$ | 398.8 | 399.1 | Scheme 44 |

TABLE 2-continued

| # | Structure | Compound name | Formula | Molecular weight | mass spec | Synthesis |
|---|---|---|---|---|---|---|
| 222 | 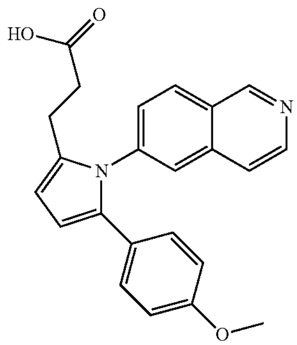 [SMILES: COc1ccc(-c2ccc(CCC(=O)O)n2-c2ccc3cnccc3c2)cc1] | 3-(1-(isoquinolin-6-yl)-5-(4-methoxyphenyl)-1H-pyrrol-2-yl)propanoic acid | $C_{23}H_{20}N_2O_3$ | 372.4 | 373.0 | Scheme 36, steps 2 and 3, Ar2 = null, Ar1 = 4-methoxyphenyl, R1 = isoquinolin-6-yl/Method 32 |
| 223 | 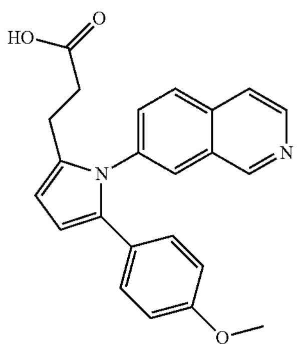 [SMILES: COc1ccc(-c2ccc(CCC(=O)O)n2-c2ccc3ccncc3c2)cc1] | 3-(1-(isoquinolin-7-yl)-5-(4-methoxyphenyl)-1H-pyrrol-2-yl)propanoic acid | $C_{23}H_{20}N_2O_3$ | 372.4 | 373.2 | Scheme 36, steps 2 and 3, Ar2 = null, Ar1 = 4-methoxyphenyl, R1 = isoquinolin-6-yl/Method 31 |
| 224 | 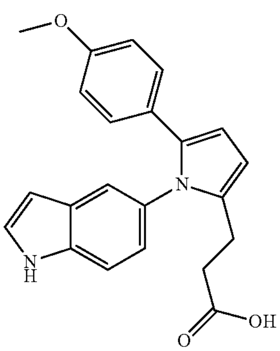 [SMILES: COc1ccc(-c2ccc(CCC(=O)O)n2-c2ccc3[nH]ccc3c2)cc1] | 3-(1-(1H-indol-5-yl)-5-(4-methoxyphenyl)-1H-pyrrol-2-yl)propanoic acid | $C_{22}H_{20}N_2O_3$ | 360.4 | 361.5 | Scheme 1A, R2 = 4-methoxyphenyl, R1 = 1H-indol-5-yl |
| 225 | 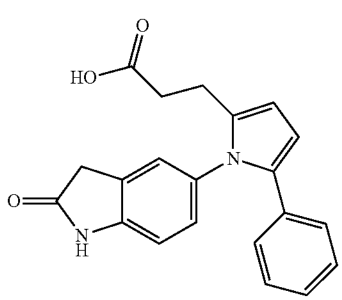 [SMILES: O=C(O)CCc1ccc(-c2ccccc2)n1-c1ccc2c(c1)CC(=O)N2] | 3-(1-(2-oxoindolin-5-yl)-5-phenyl-1H-pyrrol-2-yl)propanoic acid | $C_{21}H_{18}N_2O_3$ | 346.4 | 347.1 | Scheme 1A, R2 = phenyl, R1 = 2-oxoindolin-5-yl |

TABLE 2-continued

| # | Structure | Compound name | Formula | Molecular weight | mass spec | Synthesis |
|---|---|---|---|---|---|---|
| 226 | 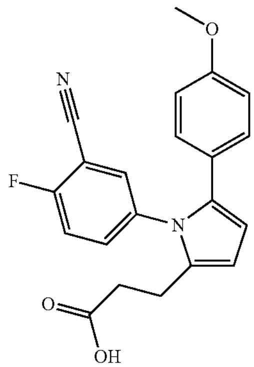 [SMILES: COc1ccc(-c2ccc(CCC(=O)O)n2-c2ccc(F)c(C#N)c2)cc1] | 3-(1-(3-cyano-4-fluorophenyl)-5-(4-methoxyphenyl)-1H-pyrrol-2-yl)propanoic acid | $C_{21}H_{17}FN_2O_3$ | 364.4 | 363.1 (M − H)− | Scheme 1A, R2 = 4-methoxyphenyl, R1 = 3-cyano-4-fluorophenyl |
| 227 | 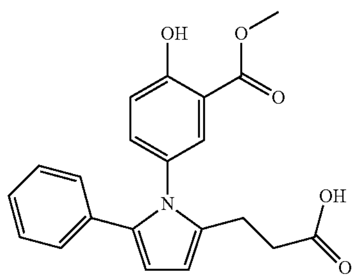 [SMILES: COC(=O)c1cc(-n2c(CCC(=O)O)ccc2-c2ccccc2)ccc1O] | 3-(1-(4-hydroxy-3-(methoxycarbonyl)phenyl)-5-phenyl-1H-pyrrol-2-yl)propanoic acid | $C_{21}H_{19}NO_5$ | 365.4 | 366.1 | Scheme 45, R2 = H, R1 = 4-hydroxy-3-(methoxycarbonyl)phenyl |
| 228 | 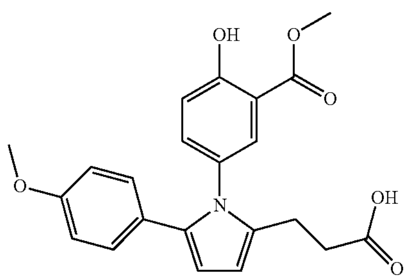 [SMILES: COC(=O)c1cc(-n2c(CCC(=O)O)ccc2-c2ccc(OC)cc2)ccc1O] | 3-(1-(4-hydroxy-3-(methoxycarbonyl)phenyl)-5-(4-methoxyphenyl)-1H-pyrrol-2-yl)propanoic acid | $C_{22}H_{21}NO_6$ | 395.4 | 396.1 | Scheme 45, R2 = OMe, R1 = 4-hydroxy-3-(methoxycarbonyl)phenyl |
| 229 | 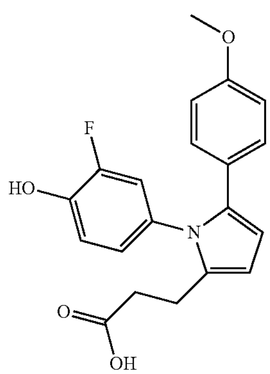 | 3-(1-(3-fluoro-4-hydroxyphenyl)-5-(4-methoxyphenyl)-1H-pyrrol-2-yl)propanoic acid | $C_{20}H_{18}FNO_4$ | 355.4 | 356.1 | Scheme 45, R2 = OMe, R1 = 3-fluoro-4-hydroxyphenyl |
| 230 | 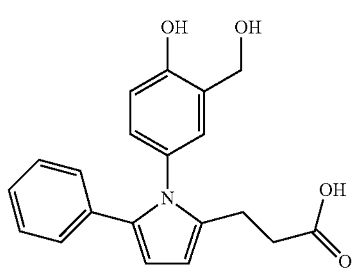 [SMILES: O=C(O)CCc1ccc(-c2ccccc2)n1-c1ccc(O)c(CO)c1] | 3-(1-(4-hydroxy-3-(hydroxymethyl)phenyl)-5-phenyl-1H-pyrrol-2-yl)propanoic acid | $C_{20}H_{19}NO_4$ | 337.4 | 337.8 | Scheme 46 |

TABLE 2-continued

| # | Structure | Compound name | Formula | Molecular weight | mass spec | Synthesis |
|---|---|---|---|---|---|---|
| 231 | 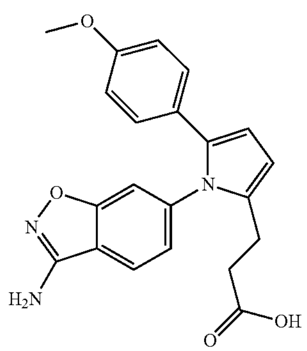 [SMILES: COc1ccc(-c2ccc(CCC(=O)O)n2-c2ccc3c(N)noc3c2)cc1] | 3-(1-(3-aminobenzo[d]isoxazol-6-yl)-5-(4-methoxyphenyl)-1H-pyrrol-2-yl)propanoic acid | $C_{21}H_{19}N_3O_4$ | 377.4 | 377.7 | Scheme 47 |
| 232 | 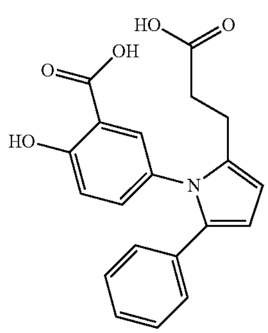 [SMILES: O=C(O)CCc1ccc(-c2ccccc2)n1-c1ccc(O)c(C(=O)O)c1] | 5-(2-(2-carboxyethyl)-5-phenyl-1H-pyrrol-1-yl)-2-hydroxybenzoic acid | $C_{20}H_{17}NO_5$ | 351.4 | 352.1 | Hydrolysis of compound 227 following procedure described in final step of Scheme 1 |
| 233 | 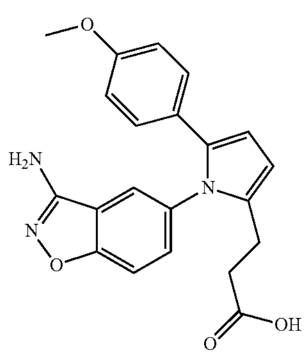 [SMILES: COc1ccc(-c2ccc(CCC(=O)O)n2-c2ccc3onc(N)c3c2)cc1] | 3-(1-(3-aminobenzo[d]isoxazol-5-yl)-5-(4-methoxyphenyl)-1H-pyrrol-2-yl)propanoic acid | $C_{21}H_{19}N_3O_4$ | 377.4 | 378.1 | Compound 226 is cyclized following same procedure described in step 2 of Scheme 47, with purification by prep TLC |
| 234 | 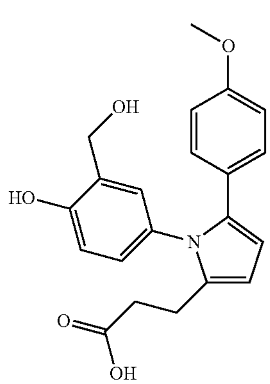 [SMILES: COc1ccc(-c2ccc(CCC(=O)O)n2-c2ccc(O)c(CO)c2)cc1] | 3-(1-(4-hydroxy-3-(hydroxymethyl)phenyl)-5-(4-methoxyphenyl)-1H-pyrrol-2-yl)propanoic acid | $C_{21}H_{21}NO_5$ | 367.4 | 368.1 | Compound 228 is reduced following the same procedure described in Scheme 46 |

TABLE 2-continued

| # | Structure | Compound name | Formula | Molecular weight | mass spec | Synthesis |
|---|---|---|---|---|---|---|
| 235 | 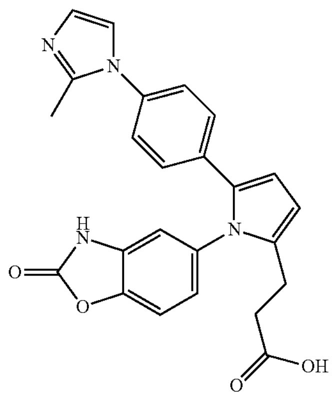 [SMILES: Cc1nccn1-c1ccc(-c2ccc(CCC(=O)O)n2-c2ccc3oc(=O)[nH]c3c2)cc1] | 3-(5-(4-(2-methyl-1H-imidazol-1-yl)phenyl)-1-(2-oxo-2,3-dihydrobenzo[d]oxazol-5-yl)-1H-pyrrol-2-yl)propanoic acid | $C_{24}H_{20}N_4O_4$ | 428.4 | 428.9 | Scheme 36, Ar2 = 2-methyl-1H-imidazol-1-yl, Ar1 = phen-4-yl, R1 = 2-oxo-2,3-dihydrobenzo[d]oxazol-6-yl/Method 39 |
| 236 | 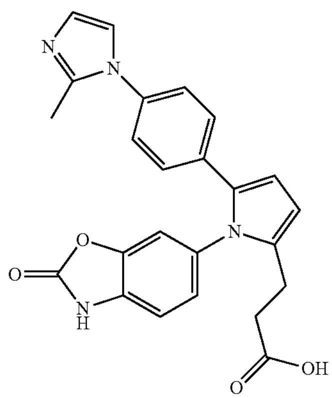 [SMILES: Cc1nccn1-c1ccc(-c2ccc(CCC(=O)O)n2-c2ccc3[nH]c(=O)oc3c2)cc1] | 3-(5-(4-(2-methyl-1H-imidazol-1-yl)phenyl)-1-(2-oxo-2,3-dihydrobenzo[d]oxazol-6-yl)-1H-pyrrol-2-yl)propanoic acid | $C_{24}H_{20}N_4O_4$ | 428.4 | 428.9 | Scheme 36, Ar2 = 2-methyl-1H-imidazol-1-yl, Ar1 = phen-4-yl, R1 = 2-oxo-2,3-dihydrobenzo[d]oxazol-6-yl/Method 40 |

Table 3 below lists representative novel pyrrole analogs of Formula III useful as GSNOR inhibitors of the invention. The synthetic methods that can be used to prepare each compound, identified in Table 2 (i.e. Scheme 1, Scheme 2, etc.) are detailed below. In some cases, if the starting material or intermediate of a scheme is not commercially available, then a corresponding method (called Method 1, Method 2, etc.) describes the synthesis of that starting material or intermediate. Table 3 provides Scheme number, defines starting materials shown in Schemes, and where necessary provides the method number which corresponds to synthesis of an intermediate or starting materials. Supporting mass spectrometry data for each compound is also included in Table 3. GSNOR inhibitor activity was determined by the assay described in Example 2 and $IC_{50}$ values were obtained. GSNOR inhibitor compounds 237-242 of Table 3 had an $IC_{50}$ of about <100 µM. GSNOR inhibitor compounds 237 and 238 of Table 3 had an $IC_{50}$ of about less than 5.0 µM.

TABLE 3

| # | STRUCTURE | Name | Chemical formula | Molecular weight | Mass Spec | Synthesis |
|---|---|---|---|---|---|---|
| 237 | 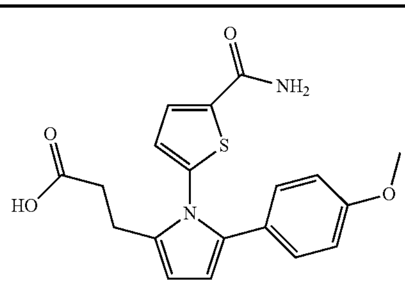 | 3-(1-(5-carbamoylthiophen-2-yl)-5-(4-methoxyphenyl)-1H-pyrrol-2-yl)propanoic acid | C19H18N2O4S | 370.4 | 371.1 | Scheme 1, R2 = 4-methoxyphenyl, R1 = 5-carbamoylthiophen-2-yl,/Method 8 |

TABLE 3-continued

| # | STRUCTURE | Name | Chemical formula | Molecular weight | Mass Spec | Synthesis |
|---|---|---|---|---|---|---|
| 238 | 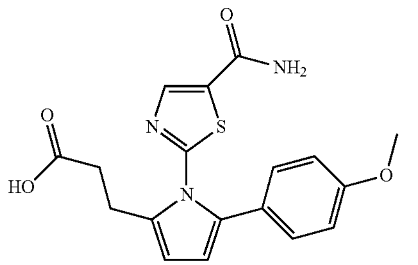 [SMILES: COc1ccc(-c2ccc(CCC(=O)O)n2-c2ncc(C(N)=O)s2)cc1] | 3-(1-(5-carbamoylthiazol-2-yl)-5-(4-methoxyphenyl)-1H-pyrrol-2-yl)propanoic acid | C18H17N3O4S | 371.4 | 371.9 | Scheme 1, R2 = 4-methoxyphenyl, R1 = 5-carbamoylthiazol-2-yl |
| 239 | 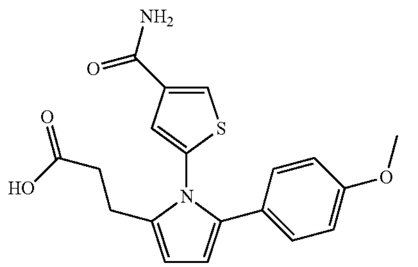 [SMILES: COc1ccc(-c2ccc(CCC(=O)O)n2-c2cc(C(N)=O)cs2)cc1] | 3-(1-(4-carbamoylthiophen-2-yl)-5-(4-methoxyphenyl)-1H-pyrrol-2-yl)propanoic acid | C19H18N2O4S | 370.4 | 371.1 | Scheme 1, R2 = 4-methoxyphenyl, R1 = 4-carbamoylthiophen-2-yl |
| 240 | 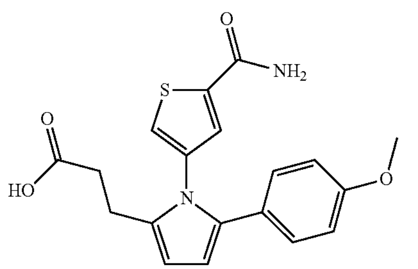 [SMILES: COc1ccc(-c2ccc(CCC(=O)O)n2-c2csc(C(N)=O)c2)cc1] | 3-(1-(5-carbamoylthiophen-3-yl)-5-(4-methoxyphenyl)-1H-pyrrol-2-yl)propanoic acid | C19H18N2O4S | 370.4 | 371.1 | Scheme 1, R2 = 4-methoxyphenyl, R1 = 5-carbamoylthiophen-3-yl/Method 9 |
| 241 | 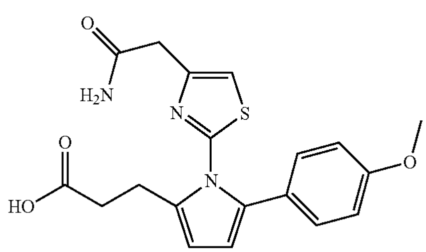 [SMILES: COc1ccc(-c2ccc(CCC(=O)O)n2-c2nc(CC(N)=O)cs2)cc1] | 3-(1-(4-(2-amino-2-oxoethyl)thiazol-2-yl)-5-(4-methoxyphenyl)-1H-pyrrol-2-yl)propanoic acid | C19H19N3O4S | 385.4 | 386.1 | Scheme 1, R2 = 4-methoxyphenyl, R1 = 2-amino-2-oxoethyl)thiazol-2-yl,/Method 10 |
| 242 | 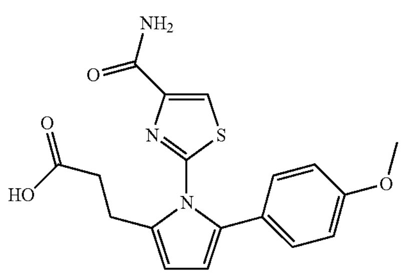 | 3-(1-(4-carbamoylthiazol-2-yl)-5-(4-methoxyphenyl)-1H-pyrrol-2-yl)propanoic acid | C18H17N3O4S | 371.4 | 372.1 | Scheme 1, R2 = 4-methoxyphenyl, R1 = 4-carbamoylthiazol-2-yl |

Table 4 below lists representative novel pyrrole analogs of Formula IV useful as GSNOR inhibitors of the invention. The synthetic methods that can be used to prepare each compound, identified in Table 4 (i.e. Scheme 1, Scheme 2, etc.) are detailed below. In some cases, if the starting material or intermediate of a scheme is not commercially available, then a corresponding method (called Method 1, Method 2, etc.) describes the synthesis of that starting material or intermediate. Table 4 provides Scheme number, defines starting materials shown in Schemes, and where necessary provides the method number which corresponds to synthesis of an intermediate or starting materials. Supporting mass spectrometry data for each compound is also included in Table 4. GSNOR inhibitor activity was determined by the assay described in Example 2 and $IC_{50}$ values were obtained. GSNOR inhibitor compounds 243-273 of Table 4 had an $IC_{50}$ of about <100 µM. GSNOR inhibitor compounds 243-244, 248-249, 251-253, 255, 262, 264-271, and 273 of Table 4 had an IC$_{50}$ of less than 5.0 μM. GSNOR inhibitor compounds 249, 251-253, 255, 262, 264, 267, 269-270, and 273 of Table 4 had an IC$_{50}$ of less than 1.0 μM.

TABLE 4

| # | Structure | Compound Name | Chemical formula | Molecular weight | Mass Spec | Synthesis |
|---|---|---|---|---|---|---|
| 243 | 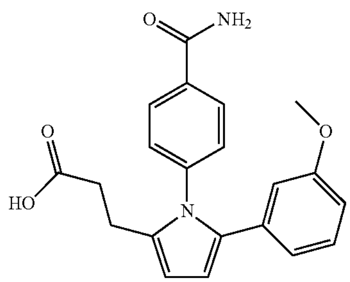 [SMILES: COc1cccc(-c2ccc(CCC(=O)O)n2-c2ccc(C(N)=O)cc2)c1] | 3-(1-(4-carbamoylphenyl)-5-(3-methoxyphenyl)-1H-pyrrol-2-yl)propanoic acid | C21H20N2O4 | 364.4 | 365.1 | Scheme 1, R2 = 3-methoxyphenyl, R1 = 4-carbamoylphenyl |
| 244 | 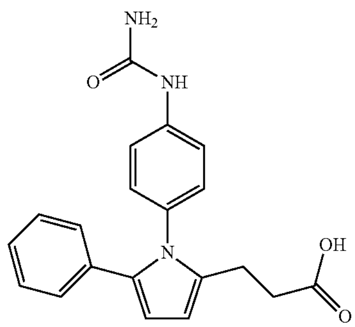 [SMILES: NC(=O)Nc1ccc(-n2c(CCC(=O)O)ccc2-c2ccccc2)cc1] | 3-(5-phenyl-1-(4-ureidophenyl)-1H-pyrrol-2-yl)propanoic acid | C20H19N3O3 | 349.4 | 350.1 | Scheme 1, R2 = phenyl, R1 = 4-ureidophenyl |
| 245 | 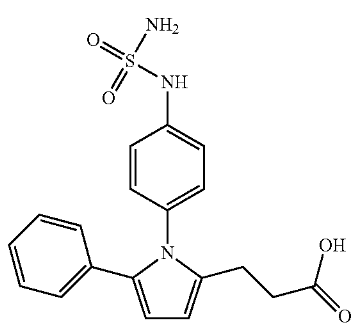 [SMILES: NS(=O)(=O)Nc1ccc(-n2c(CCC(=O)O)ccc2-c2ccccc2)cc1] | 3-(5-phenyl-1-(4-(sulfamoylamino)phenyl)-1H-pyrrol-2-yl)propanoic acid | C19H19N3O4S | 385.4 | 386.1 | Scheme 1, R2 = phenyl, R1 = 4-(sulfamoylamino)phenyl |
| 246 | 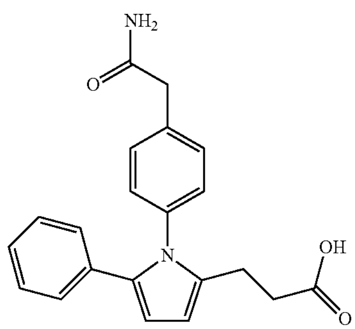 [SMILES: NC(=O)Cc1ccc(-n2c(CCC(=O)O)ccc2-c2ccccc2)cc1] | 3-(1-(4-(2-amino-2-oxoethyl)phenyl)-5-phenyl-1H-pyrrol-2-yl)propanoic acid | C21H20N2O3 | 348.4 | 349.1 | Scheme 1, R2 = phenyl, R1 = 4-(2-amino-2-oxoethyl)phenyl |

TABLE 4-continued

| # | Structure | Compound Name | Chemical formula | Molecular weight | Mass Spec | Synthesis |
|---|---|---|---|---|---|---|
| 247 | 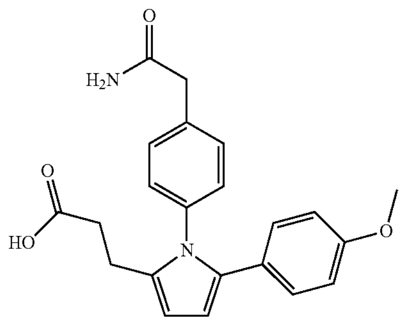 [SMILES: COc1ccc(-c2ccc(CCC(=O)O)n2-c2ccc(CC(N)=O)cc2)cc1] | 3-(1-(4-(2-amino-2-oxoethyl)phenyl)-5-(4-methoxyphenyl)-1H-pyrrol-2-yl)propanoic acid | C22H22N2O4 | 378.4 | 379.1 | Scheme 1, R2 = 4-methoxyphenyl, R1 = 4-(2-amino-2-oxoethyl)phenyl |
| 248 | 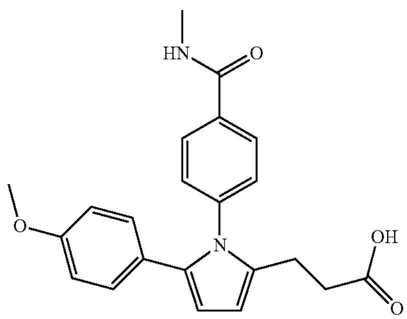 [SMILES: CNC(=O)c1ccc(-n2c(CCC(=O)O)ccc2-c2ccc(OC)cc2)cc1] | (3-(5-(4-methoxyphenyl)-1-(4-(methylcarbamoyl)phenyl)-1H-pyrrol-2-yl)propanoic acid | C22H22N2O4 | 378.4 | 379.1 | Scheme 1A, R2 = 4-methoxyphenyl, R1 = 4-(methylcarbamoyl)phenyl |
| 249 | 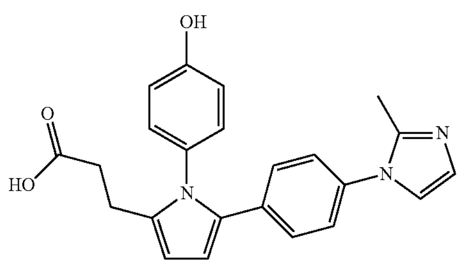 [SMILES: Cc1nccn1-c1ccc(-c2ccc(CCC(=O)O)n2-c2ccc(O)cc2)cc1] | 3-(1-(4-hydroxyphenyl)-5-(4-(2-methyl-1H-imidazol-1-yl)phenyl)-1H-pyrrol-2-yl)propanoic acid | C23H21N3O3 | 387.4 | 388.0 | Scheme 5, Ar1 = 4-hydroxyphenyl, R = CH3 |
| 250 | 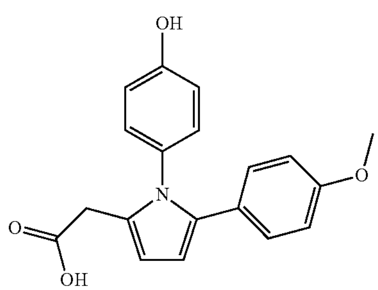 [SMILES: COc1ccc(-c2ccc(CC(=O)O)n2-c2ccc(O)cc2)cc1] | 2-(1-(4-hydroxyphenyl)-5-(4-methoxyphenyl)-1H-pyrrol-2-yl)acetic acid | C19H17NO4 | 323.3 | 324.1 | Followed Scheme 37, R = methoxy, Steps 1-3, followed by step 3 of Scheme 1 with 4-aminophenol, then hydrolysis by Scheme 5 step 5 |
| 251 | 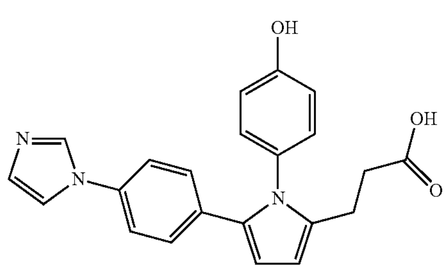 [SMILES: O=C(O)CCc1ccc(-c2ccc(-n3ccnc3)cc2)n1-c1ccc(O)cc1] | 3-(5-(4-(1H-imidazol-1-yl)phenyl)-1-(4-hydroxyphenyl)-1H-pyrrol-2-yl)propanoic acid | C22H19N3O3 | 373.4 | 374.2 | Scheme 5, Ar1 = 4-hydroxyphenyl, R = H |

TABLE 4-continued

| # | Structure | Compound Name | Chemical formula | Molecular weight | Mass Spec | Synthesis |
|---|---|---|---|---|---|---|
| 252 | 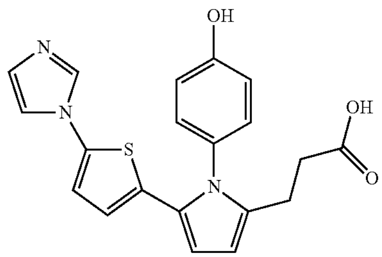 [SMILES: O=C(O)CCc1ccc(-c2ccc(-n3ccnc3)s2)n1-c1ccc(O)cc1] | 3-(5-(5-(1H-imidazol-1-yl)thiophen-2-yl)-1-(4-hydroxyphenyl)-1H-pyrrol-2-yl)propanoic acid | C20H17N3O3S | 379.4 | 379.9 | 1st 3 Steps of Scheme 1, R1 = 4-hydroxyphenyl, R2 = 5-bromothiophen-2-yl, then Scheme 5, Steps 4 and 5 (Ar1 = 4-hydroxyphenyl, R = H) |
| 253 | 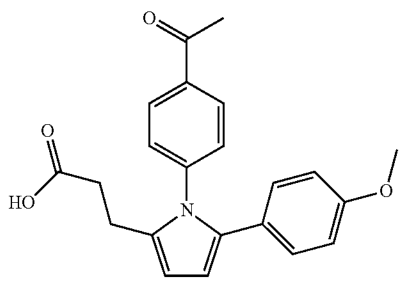 [SMILES: COc1ccc(-c2ccc(CCC(=O)O)n2-c2ccc(C(C)=O)cc2)cc1] | 3-(1-(4-acetylphenyl)-5-(4-methoxyphenyl)-1H-pyrrol-2-yl)propanoic acid | C22H21NO4 | 363.4 | 364.1 | Scheme 45, R2 = methoxy, R1 = 4-acetylphenyl |
| 254 | 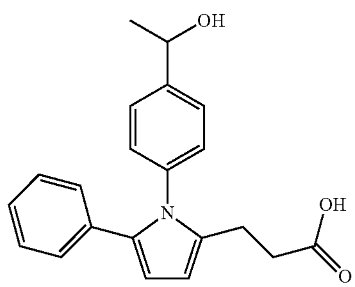 [SMILES: CC(O)c1ccc(-n2c(CCC(=O)O)ccc2-c2ccccc2)cc1] | 3-(1-(4-(1-hydroxyethyl)phenyl)-5-phenyl-1H-pyrrol-2-yl)propanoic acid | C21H21NO3 | 335.4 | 336.2 | Reduction of compound 253 following synthesis described in Scheme 46 with NaBH4 |
| 255 | 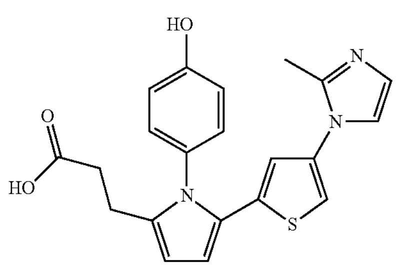 [SMILES: Cc1nccn1-c1csc(-c2ccc(CCC(=O)O)n2-c2ccc(O)cc2)c1] | 3-(1-(4-hydroxyphenyl)-5-(4-(2-methyl-1H-imidazol-1-yl)thiophen-2-yl)-1H-pyrrol-2-yl)propanoic acid | C21H19N3O3S | 393.5 | 394.2 | 1st 3 Steps of Scheme 1, R1 = 4-hydroxyphenyl, R2 = 4-bromothiophen-2-yl, then Scheme 5, Steps 4 and 5 (Ar1 = 4-hydroxyphenyl, R = H) |
| 256 | 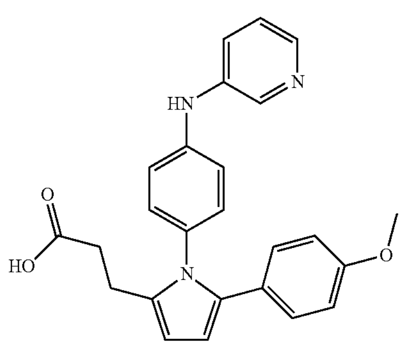 [SMILES: COc1ccc(-c2ccc(CCC(=O)O)n2-c2ccc(Nc3cccnc3)cc2)cc1] | 3-(5-(4-methoxyphenyl)-1-(4-(pyridin-3-ylamino)phenyl)-1H-pyrrol-2-yl)propanoic acid | C25H23N3O3 | 413.5 | 414.2 | Scheme 48, R = pyridin-3-yl |

TABLE 4-continued

| # | Structure | Compound Name | Chemical formula | Molecular weight | Mass Spec | Synthesis |
|---|---|---|---|---|---|---|
| 257 | 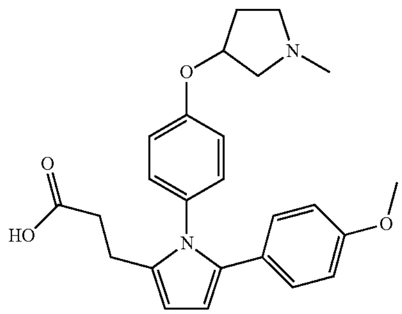 [SMILES: COc1ccc(-c2ccc(CCC(=O)O)n2-c2ccc(OC3CCN(C)C3)cc2)cc1] | 3-(5-(4-methoxyphenyl)-1-(4-(1-methylpyrrolidin-3-yloxy)phenyl)-1H-pyrrol-2-yl)propanoic acid | C25H28N2O4 | 420.5 | 421.1 | Scheme 25, Ar1 = 4-(1-methylpyrrolidin-3-yloxy)phenyl/ Method 37 |
| 258 | 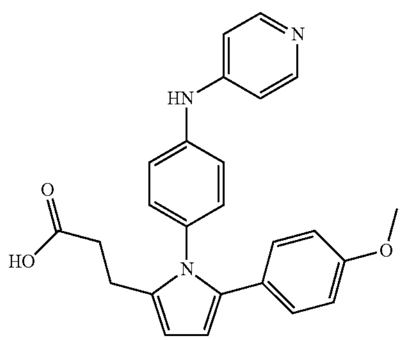 [SMILES: COc1ccc(-c2ccc(CCC(=O)O)n2-c2ccc(Nc3ccncc3)cc2)cc1] | 3-(5-(4-methoxyphenyl)-1-(4-(pyridin-4-ylamino)phenyl)-1H-pyrrol-2-yl)propanoic acid | C25H23N3O3 | 413.5 | 414.0 | Scheme 48, R = pyridin-4-yl |
| 259 | 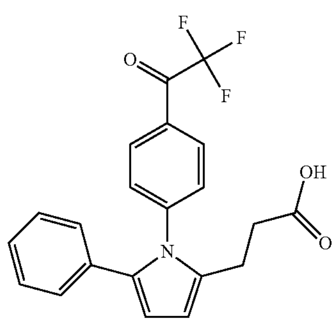 [SMILES: O=C(O)CCc1ccc(-c2ccccc2)n1-c1ccc(C(=O)C(F)(F)F)cc1] | 3-(5-phenyl-1-(4-(2,2,2-trifluoroacetyl)phenyl)-1H-pyrrol-2-yl)propanoic acid | C21H16F3NO3 | 387.4 | 388.1 | Scheme 45, R1 = 2,2,2-trifluoroacetyl)phenyl, R2 = H |
| 260 | 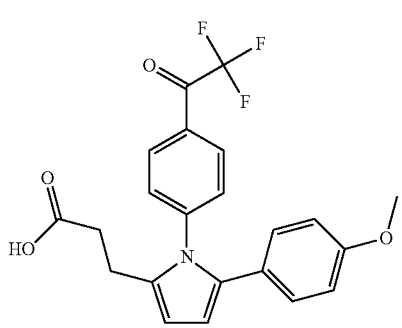 [SMILES: COc1ccc(-c2ccc(CCC(=O)O)n2-c2ccc(C(=O)C(F)(F)F)cc2)cc1] | 3-(5-(4-methoxyphenyl)-1-(4-(2,2,2-trifluoroacetyl)phenyl)-1H-pyrrol-2-yl)propanoic acid | C22H18F3NO4 | 417.4 | 417.7 | Scheme 45, R1 = 2,2,2-trifluoroacetyl)phenyl, R2 = methoxy |

TABLE 4-continued

| # | Structure | Compound Name | Chemical formula | Molecular weight | Mass Spec | Synthesis |
|---|---|---|---|---|---|---|
| 261 | 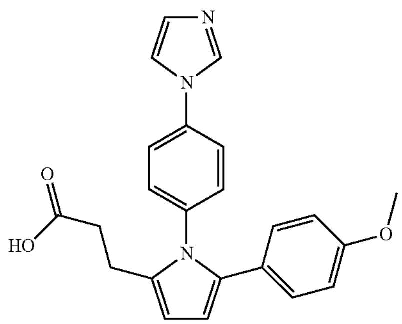 [SMILES: COc1ccc(-c2ccc(CCC(=O)O)n2-c2ccc(-n3ccnc3)cc2)cc1] | 3-(1-(4-(1H-imidazol-1-yl)phenyl)-5-(4-methoxyphenyl)-1H-pyrrol-2-yl)propanoic acid | C23H21N3O3 | 387.4 | 388.2 | Scheme 1 using 1A conditions/R1 = 4-(1H-imidazol-1-yl)phenyl and R2 = 4-methoxyphenyl |
| 262 | 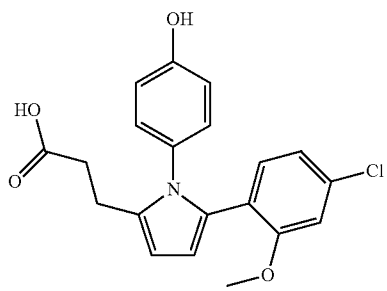 [SMILES: COc1cc(Cl)ccc1-c1ccc(CCC(=O)O)n1-c1ccc(O)cc1] | 3-(5-(4-chloro-2-methoxyphenyl)-1-(4-hydroxyphenyl)-1H-pyrrol-2-yl)propanoic acid | C20H18ClNO4 | 371.8 | 372.1 | Scheme 33, R1 = 4-hydroxyphenyl, R2 = 4-chloro, R3 = methyl |
| 263 | 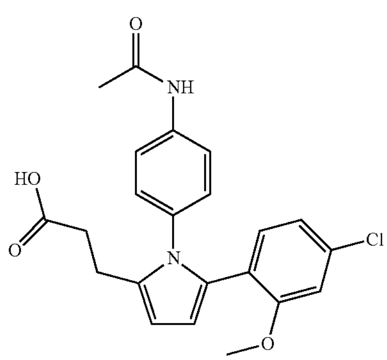 [SMILES: COc1cc(Cl)ccc1-c1ccc(CCC(=O)O)n1-c1ccc(NC(C)=O)cc1] | 3-(1-(4-acetamidophenyl)-5-(4-chloro-2-methoxyphenyl)-1H-pyrrol-2-yl)propanoic acid | C22H21ClN2O4 | 412.9 | 413.1 | Scheme 33, R1 = 4-acetamidophenyl, R2 = 4-chloro, R3 = methyl/Method 36 |
| 264 | 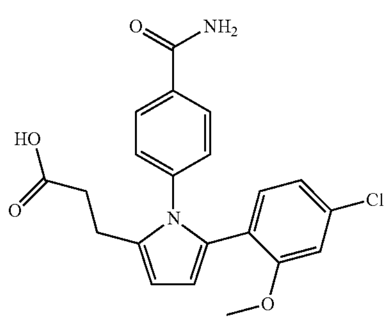 [SMILES: COc1cc(Cl)ccc1-c1ccc(CCC(=O)O)n1-c1ccc(C(N)=O)cc1] | 3-(1-(4-carbamoylphenyl)-5-(4-chloro-2-methoxyphenyl)-1H-pyrrol-2-yl)propanoic acid | C21H19ClN2O4 | 398.8 | 399.0 | Scheme 33, R1 = 4-carbamoylphenyl, R2 = 4-chloro, R3 = methyl |

TABLE 4-continued

| # | Structure | Compound Name | Chemical formula | Molecular weight | Mass Spec | Synthesis |
|---|---|---|---|---|---|---|
| 265 | 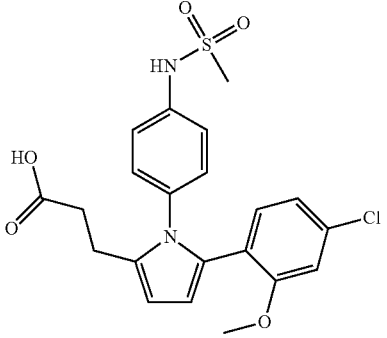 [SMILES: COc1cc(Cl)ccc1-c1ccc(CCC(=O)O)n1-c1ccc(NS(C)(=O)=O)cc1] | 3-(5-(4-chloro-2-methoxyphenyl)-1-(4-(methylsulfonamido)phenyl)-1H-pyrrol-2-yl)propanoic acid | C21H21ClN2O5S | 448.9 | 449.1 | Scheme 33, R1 = 4-(methylsulfonamido)phenyl, R2 = 4-chloro, R3 = methyl/Method 23, R = H |
| 266 | 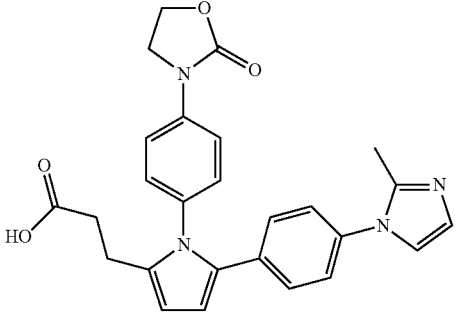 [SMILES: Cc1nccn1-c1ccc(-c2ccc(CCC(=O)O)n2-c2ccc(N3CCOC3=O)cc2)cc1] | 3-(5-(4-(2-methyl-1H-imidazol-1-yl)phenyl)-1-(4-(2-oxooxazolidin-3-yl)phenyl)-1H-pyrrol-2-yl)propanoic acid | C26H24N4O4 | 456.5 | 457.2 | Scheme 36 (36B conditions for Step 1) Ar1 = 4-phenyl, Ar2 = 2-methyl-1H-imidazol-1-yl and R1 = 4-(2-oxooxazolidin-3-yl)phenyl/Method 38 |
| 267 | 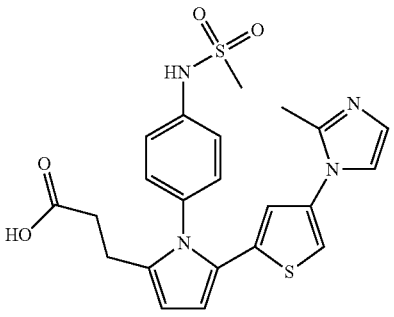 [SMILES: Cc1nccn1-c1csc(-c2ccc(CCC(=O)O)n2-c2ccc(NS(C)(=O)=O)cc2)c1] | 3-(5-(4-(2-methyl-1H-imidazol-1-yl)thiophen-2-yl)-1-(4-(methylsulfonamido)phenyl)-1H-pyrrol-2-yl)propanoic acid | C22H22N4O4S2 | 470.6 | 470.9 | Scheme 34, Ar1—X = 4-bromothiophen-2-yl, Ar2 = 2-methyl-1H-imidazol-1-yl, R1 = 4-(methylsulfonamido)phenyl/Method 23 |
| 268 | 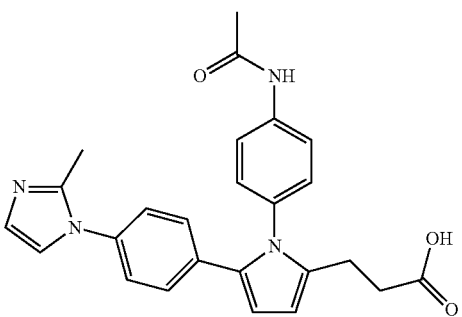 [SMILES: CC(=O)Nc1ccc(-n2c(CCC(=O)O)ccc2-c2ccc(-n3ccnc3C)cc2)cc1] | 3-(1-(4-acetamidophenyl)-5-(4-(2-methyl-1H-imidazol-1-yl)phenyl)-1H-pyrrol-2-yl)propanoic acid | C25H24N4O3 | 428.5 | 429.1 | Scheme 29, R1 = 4-acetamidophenyl, R2 = methyl/Method 36 |

TABLE 4-continued

| # | Structure | Compound Name | Chemical formula | Molecular weight | Mass Spec | Synthesis |
|---|---|---|---|---|---|---|
| 269 | 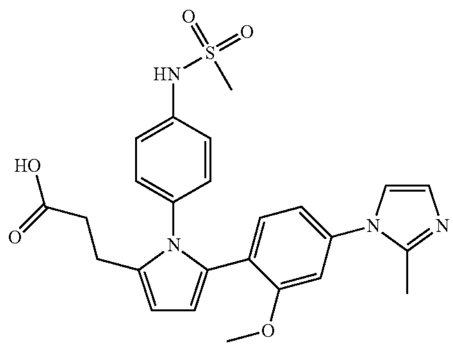 [SMILES: COc1cc(-n2ccnc2C)ccc1-c1ccc(CCC(=O)O)n1-c1ccc(NS(C)(=O)=O)cc1] | 3-(5-(2-methoxy-4-(2-methyl-1H-imidazol-1-yl)phenyl)-1-(4-(methylsulfonamido)phenyl)-1H-pyrrol-2-yl)propanoic acid | C25H26N4O5S | 494.6 | 495.1 | Scheme 34, Ar1—X = 2-methoxy-4-bromophenyl, Ar2 = 2-methyl-1H-imidazol-1-yl, R1 = 4-(methylsulfonamido)phenyl/Method 23 and Method 15 |
| 270 | 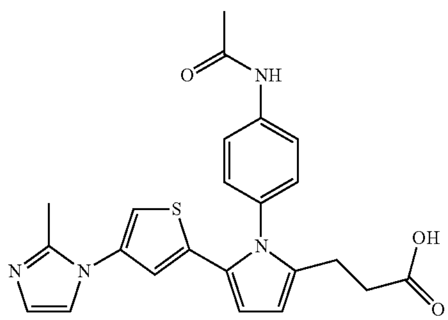 [SMILES: CC(=O)Nc1ccc(-n2c(CCC(=O)O)ccc2-c2cc(-n3ccnc3C)cs2)cc1] | 3-(1-(4-acetamidophenyl)-5-(4-(2-methyl-1H-imidazol-1-yl)thiophen-2-yl)-1H-pyrrol-2-yl)propanoic acid | C23H22N4O3S | 434.5 | 435.1 | Scheme 1 steps 1-3 to prepare 1C (R1 = 4-acetamidophenyl, R2 = 4-bromothiophen-2-yl) followed by the last 2 steps of scheme 5, R = CH3 |
| 271 | 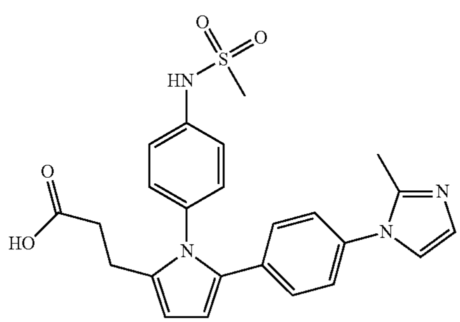 [SMILES: Cc1nccn1-c1ccc(-c2ccc(CCC(=O)O)n2-c2ccc(NS(C)(=O)=O)cc2)cc1] | 3-(5-(4-(2-methyl-1H-imidazol-1-yl)phenyl)-1-(4-(methylsulfonamido)phenyl)-1H-pyrrol-2-yl)propanoic acid | C24H24N4O4S | 464.5 | 464.9 | Scheme 34, Ar1—X = 4-bromophenyl, Ar2 = 2-methyl-1H-imidazol-1-yl, R1 = 4-(methylsulfonamido)phenyl/Method 23 |
| 272 | 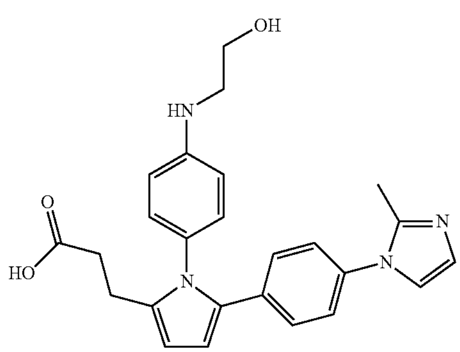 [SMILES: Cc1nccn1-c1ccc(-c2ccc(CCC(=O)O)n2-c2ccc(NCCO)cc2)cc1] | 3-(1-(4-(2-hydroxyethylamino)phenyl)-5-(4-(2-methyl-1H-imidazol-1-yl)phenyl)-1H-pyrrol-2-yl)propanoic acid | C25H26N4O3 | 430.5 | 431.2 | Scheme 49 |

TABLE 4-continued

| # | Structure | Compound Name | Chemical formula | Molecular weight | Mass Spec | Synthesis |
|---|---|---|---|---|---|---|
| 273 | 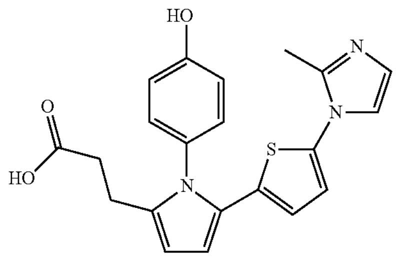 [SMILES: Cc1nccn1-c1ccc(-c2ccc(CCC(=O)O)n2-c2ccc(O)cc2)s1] | 3-(1-(4-hydroxyphenyl)-5-(5-(2-methyl-1H-imidazol-1-yl)thiophen-2-yl)-1H-pyrrol-2-yl)propanoic acid | C21H19N3O3S | 393.5 | 394.0 | Scheme 1 steps 1-3 to prepare 1C (R1 = 4-hydroxyphenyl, R2 = 5-bromothiophen-2-yl) followed by the last 2 steps of scheme 5, R = CH3 |

D. Pharmaceutical Compositions Comprising a GSNOR Inhibitor

The invention encompasses pharmaceutical compositions comprising at least one GSNOR inhibitor described herein and at least one pharmaceutically acceptable carrier. Suitable carriers are described in "Remington: The Science and Practice, Twentieth Edition," published by Lippincott Williams & Wilkins, which is incorporated herein by reference. Pharmaceutical compositions according to the invention may also comprise one or more non-GSNOR inhibitor active agents.

The pharmaceutical compositions of the invention can comprise novel GSNOR inhibitors described herein, the pharmaceutical compositions can comprise known compounds which previously were not know to have GSNOR inhibitor activity, or a combination thereof.

The GSNOR inhibitors can be utilized in any pharmaceutically acceptable dosage form, including but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the GSNOR inhibitors described herein can be formulated: (a) for administration selected from the group consisting of oral, pulmonary, intravenous, intra-arterial, intrathecal, intra-articular, rectal, ophthalmic, colonic, parenteral, intracisternal, intravaginal, intraperitoneal, local, buccal, nasal, and topical administration; (b) into a dosage form selected from the group consisting of liquid dispersions, gels, aerosols, ointments, creams, tablets, sachets and capsules; (c) into a dosage form selected from the group consisting of lyophilized formulations, dry powders, fast melt formulations, controlled release formulations, delayed release formulations, extended release formulations, pulsatile release formulations, and mixed immediate release and controlled release formulations; or (d) any combination thereof.

For respiratory infections, an inhalation formulation can be used to achieve high local concentrations. Formulations suitable for inhalation include dry powder or aerosolized or vaporized solutions, dispersions, or suspensions capable of being dispensed by an inhaler or nebulizer into the endobronchial or nasal cavity of infected patients to treat upper and lower respiratory bacterial infections.

Solutions or suspensions used for parenteral, intradermal, or subcutaneous application can comprise one or more of the following components: (1) a sterile diluent such as water for injection, saline solution, fixed oils, polyethylene glycols, glycerine, propylene glycol or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates or phosphates; and (5) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use may comprise sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringability exists. The pharmaceutical composition should be stable under the conditions of manufacture and storage and should be preserved against the contaminating action of microorganisms such as bacteria and fungi.

The carrier can be a solvent or dispersion medium comprising, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent (e.g., GSNOR inhibitor) in the required amount in an appropriate solvent with one or a combination of ingredients enumerated above, as required, followed by filtered sterilization. Generally, dispersions are prepared by incorporating at least one GSNOR inhibitor into a sterile vehicle that contains a basic dispersion medium and any other required ingredients. In the case of sterile powders for the preparation of sterile injectable solutions, exemplary methods of preparation include vacuum drying and freeze-drying, both of which yield a powder of the GSNOR inhibitor plus any additional desired ingredient from a previously sterile-filtered solution thereof.

Oral compositions generally include an inert diluent or an edible carrier. They can be enclosed, for example, in gelatin capsules or compressed into tablets. For the purpose of oral therapeutic administration, the GSNOR inhibitor can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from pressured container or dispenser that contains a suitable propellant, e.g., a gas such as carbon dioxide, a nebulized liquid, a vaporized solution, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In one embodiment, the GSNOR inhibitors are prepared with carriers that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of the GSNOR inhibitors may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of GSNOR inhibitor calculated to produce the desired therapeutic effect in association with the required pharmaceutical carrier. The specification for the dosage unit forms of the invention are dictated by and directly dependent on the unique characteristics of the GSNOR inhibitor and the particular therapeutic effect to be achieved, and the limitations inherent in the art of compounding such an active agent for the treatment of individuals.

Pharmaceutical compositions according to the invention comprising at least one GSNOR inhibitor can comprise one or more pharmaceutical excipients. Examples of such excipients include, but are not limited to binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and crosslinked polyvinylpyrrolidone, microcrystalline cellulose, such as Avicel® PH101 and Avicel® PH102, silicified microcrystalline cellulose (ProSolv SMCC™), gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, cross-povidone, sodium starch glycolate, and mixtures thereof; (4) lubricants, including agents that act on the flowability of a powder to be compressed, include magnesium stearate, colloidal silicon dioxide, such as Aerosil® 200, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, Magnasweet® (trademark of MAFCO), bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

E. Kits Comprising the Compositions of the Invention

The present invention also encompasses kits comprising the compositions of the invention. Such kits can comprise, for example, (1) at least one GSNOR inhibitor; and (2) at least one pharmaceutically acceptable carrier, such as a solvent or solution. Additional kit components can optionally include, for example: (1) any of the pharmaceutically acceptable excipients identified herein, such as stabilizers, buffers, etc., (2) at least one container, vial or similar apparatus for holding and/or mixing the kit components; and (3) delivery apparatus, such as an inhaler, nebulizer, syringe, etc.

F. Methods of Preparing GSNOR Inhibitors

The GSNOR inhibitors of the invention can readily be synthesized using known synthetic methodologies or via a modification of known synthetic methodologies. As would be readily recognized by a skilled artisan, the methodologies described below allow the synthesis of pyrroles having a variety of substituents. Exemplary synthetic methods are described in the examples below.

According to one synthetic protocol, reaction of 2-furaldehyde with an appropriately substituted acetophenone followed by treatment with a strong acid gives the appropriately substituted 1,4,7-trione. Cyclization of the trione to the corresponding 1,2,5-trisubstituted pyrrole is readily achieved by reacting the trione with a primary amine in the presence of p-toluenesulfonic acid. In one embodiment of the present invention, further derivatization of the phenyl ring at C5 of the pyrrole is readily achieved, for example, by various cross-coupling reactions. For example, synthesis of the trisubstituted pyrroles by reacting 1-(4-chlorophenyl)ethanone and 2-furaldehyde will give the target pyrrole with 4-chlorophenyl group at C5. The aryl chloride can be derivatized by reaction with a boronic acid under Suzuki coupling conditions. Such routine derivatization methodologies allow the rapid generation of compound libraries for in vitro GSNOR inhibition studies. A variety of additional methods are described in Example 1 of this document.

If needed, further purification and separation of enantiomers and diastereomers can be achieved by routine procedures known in the art. Thus, for example, the separation of enantiomers of a compound can be achieved by the use of chiral HPLC and related chromatographic techniques. Diastereomers can be similarly separated. In some instances, however, diastereomers can simply be separated physically, such as, for example, by controlled precipitation or crystallization.

The process of the invention, when carried out as prescribed herein, can be conveniently performed at temperatures that are routinely accessible in the art. In one embodiment, the process is performed at a temperature in the range of about 25° C. to about 110° C. In another embodiment, the temperature is in the range of about 40° C. to about 100° C. In yet another embodiment, the temperature is in the range of about 50° C. to about 95° C.

Synthetic steps that require a base are carried out using any convenient organic or inorganic base. Typically, the base is not nucleophilic. Thus, in one embodiment, the base is selected from carbonates, phosphates, hydroxides, alkoxides, salts of disilazanes, and tertiary amines.

The process of the invention, when performed as described herein, can be substantially complete after several minutes to after several hours depending upon the nature and quantity of reactants and reaction temperature. The determination of when the reaction is substantially complete can be conveniently evaluated by ordinary techniques known in the art such as, for example, HPLC, LCMS, TLC, and $^1$H NMR.

G. Method of Treatment

The invention encompasses methods of preventing or treating (e.g., alleviating one or more symptoms of) medical conditions through use of one or more of the disclosed compounds. The methods comprise administering a therapeutically effective amount of a GSNOR inhibitor to a patient in need. The compositions of the invention can also be used for prophylactic therapy.

The GSNOR inhibitor used in the methods of treatment according to the invention can be: (1) a novel GSNOR inhibitor described herein, or a pharmaceutically acceptable salt thereof, a prodrug thereof, or a metabolite thereof; (2) a compound which was known prior to the present invention, but wherein it was not known that the compound is a GSNOR inhibitor, or a pharmaceutically acceptable salt thereof, a prodrug thereof, or a metabolite thereof; or (3) a compound which was known prior to the present invention, and wherein it was known that the compound is a GSNOR inhibitor, but wherein it was not known that the compound is useful for the methods of treatment described herein, or a pharmaceutically acceptable salt thereof, a prodrug thereof, or a metabolite thereof.

The patient can be any animal, domestic, livestock or wild, including, but not limited to cats, dogs, horses, pigs and cattle, and preferably human patients. As used herein, the terms patient and subject may be used interchangeably.

In subjects with deleteriously high levels of GSNOR or GSNOR activity, modulation may be achieved, for example, by administering one or more of the disclosed compounds that disrupts or down-regulates GSNOR function, or decreases GSNOR levels. These compounds may be administered with other GSNOR inhibitor agents, such as anti-GSNOR antibodies or antibody fragments, GSNOR antisense, iRNA, or small molecules, or other inhibitors, alone or in combination with other agents as described in detail herein.

The present invention provides a method of treating a subject afflicted with a disorder ameliorated by NO donor therapy. Such a method comprises administering to a subject a therapeutically effective amount of a GSNOR inhibitor.

As used herein, "treating" describes the management and care of a patient for the purpose of combating a disease, condition, or disorder and includes the administration of a compound of the present invention to prevent the onset of the symptoms or complications, alleviating the symptoms or complications, or eliminating the disease, condition or disorder. More specifically, "treating" includes reversing, attenuating, alleviating, minimizing, suppressing or halting at least one deleterious symptom or effect of a disease (disorder) state, disease progression, disease causative agent (e.g., bacteria or viruses), or other abnormal condition. Treatment is continued as long as symptoms and/or pathology ameliorate.

The disorders can include pulmonary disorders associated with hypoxemia and/or smooth muscle constriction in the lungs and/or lung infection and/or lung injury (e.g., pulmonary hypertension, ARDS, asthma, pneumonia, pulmonary fibrosis/interstitial lung diseases, cystic fibrosis, COPD) cardiovascular disease and heart disease, including conditions such as hypertension, ischemic coronary syndromes, atherosclerosis, heart failure, glaucoma, diseases characterized by angiogenesis (e.g., coronary artery disease), disorders where there is risk of thrombosis occurring, disorders where there is risk of restenosis occurring, chronic inflammatory diseases (e.g., AID dementia and psoriasis), diseases where there is risk of apoptosis occurring (e.g., heart failure, atherosclerosis, degenerative neurologic disorders, arthritis and liver injury (ischemic or alcoholic)), impotence, obesity caused by eating in response to craving for food, stroke, reperfusion injury (e.g., traumatic muscle injury in heart or lung or crush injury), and disorders where preconditioning of heart or brain for NO protection against subsequent ischemic events is beneficial.

In one embodiment, the compounds of the present invention or a pharmaceutically acceptable salt thereof, or a prodrug or metabolite thereof, can be administered in combination with an NO donor. An NO donor donates nitric oxide or a related redox species and more generally provides nitric oxide bioactivity, that is activity which is identified with nitric oxide, e.g., vasorelaxation or stimulation or inhibition of a receptor protein, e.g., ras protein, adrenergic receptor, NFκB. NO donors including S-nitroso, O-nitroso, C-nitroso and N-nitroso compounds and nitro derivatives thereof and metal NO complexes, but not excluding other NO bioactivity generating compounds, useful herein are described in "Methods in Nitric Oxide Research," Feelisch et al. eds., pages 71-115 (J. S., John Wiley & Sons, New York, 1996), which is incorporated herein by reference. NO donors which are C-nitroso compounds where nitroso is attached to a tertiary carbon which are useful herein include those described in U.S. Pat. No. 6,359,182 and in WO 02/34705. Examples of S-nitroso compounds, including S-nitrosothiols useful herein, include, for example, S-nitrosoglutathione, S-nitroso-N-acetylpenicillamine, S-nitroso-cysteine and ethyl ester thereof, S-nitroso cysteinyl glycine, S-nitroso-gamma-methyl-L-homocysteine, S-nitroso-L-homocysteine, S-nitroso-gamma-thio-L-leucine, S-nitroso-delta-thio-L-leucine, and S-nitrosoalbumin. Examples of other NO donors useful herein are sodium nitroprusside (nipride), ethyl nitrite, isosorbide, nitroglycerin, SIN 1 which is molsidomine, furoxamines, N-hydroxy (N-nitrosamine) and perfluorocarbons that have been saturated with NO or a hydrophobic NO donor.

The combination of a GSNOR inhibitor with R(+) enantiomer of amlodipine, a known NO releaser (Zhang X. P at al. 2002 J. Cardiovascular Pharmacology 39, 208-214) is also an embodiment of the present invention.

The present invention also provides a method of treating a subject afflicted with pathologically proliferating cells where the method comprises administering to said subject a therapeutically effective amount of an inhibitor of GSNOR. The inhibitors of GSNOR are the compounds as defined above, or a pharmaceutically acceptable salt thereof, or a prodrug or metabolite thereof, in combination with a pharmaceutically acceptable carrier. Treatment is continued as long as symptoms and/or pathology ameliorate.

In another embodiment, the pathologically proliferating cells can be pathologically proliferating microbes. The microbes involved can be those where GSNOR is expressed to protect the microbe from nitrosative stress or where a host cell infected with the microbe expresses the enzyme, thereby protecting the microbe from nitrosative stress. The term "pathologically proliferating microbes" is used herein to mean pathologic microorganisms including but not limited to pathologic bacteria, pathologic viruses, pathologic *Chlamydia*, pathologic protozoa, pathologic *Rickettsia*, pathologic fungi, and pathologic mycoplasmata. More detail on the applicable microbes is set forth at columns 11 and 12 of U.S. Pat. No. 6,057,367. The term "host cells infected with pathologic microbes" includes not only mammalian cells infected with pathologic viruses but also mammalian cells containing intracellular bacteria or protozoa, e.g., macrophages containing *Mycobacterium tuberculosis, Mycobacterium leper* (leprosy), or *Salmonella typhi* (typhoid fever).

In another embodiment, the pathologically proliferating cells can be pathologic helminths. The term "pathologic helminths" is used herein to refer to pathologic nematodes, pathologic trematodes and pathologic cestodes. More detail on the applicable helminths is set forth at column 12 of U.S. Pat. No. 6,057,367.

In another embodiment, the pathologically proliferating cells can be pathologically proliferating mammalian cells. The term "pathologically proliferating mammalian cells" as used herein means cells of the mammal that grow in size or number in said mammal so as to cause a deleterious effect in the mammal or its organs. The term includes, for example, the pathologically proliferating or enlarging cells causing restenosis, the pathologically proliferating or enlarging cells causing benign prostatic hypertrophy, the pathologically proliferating cells causing myocardial hypertrophy and proliferating cells at inflammatory sites such as synovial cells in arthritis or cells associated with a cell proliferation disorder.

As used herein, the term "cell proliferative disorder" refers to conditions in which the unregulated and/or abnormal growth of cells can lead to the development of an unwanted condition or disease, which can be cancerous or non-cancerous, for example a psoriatic condition. As used herein, the term "psoriatic condition" refers to disorders involving keratinocyte hyperproliferation, inflammatory cell infiltration, and cytokine alteration. The cell proliferative disorder can be a precancerous condition or cancer. The cancer can be primary cancer or metastatic cancer, or both.

As used herein, the term "cancer" includes solid tumors, such as lung, breast, colon, ovarian, pancreas, prostate, adenocarcinoma, squamous carcinoma, sarcoma, malignant glioma, leiomyosarcoma, hepatoma, head and neck cancer, malignant melanoma, non-melanoma skin cancers, as well as hematologic tumors and/or malignancies, such as leukemia, childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS.

In addition to psoriatic conditions, the types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses and the like. In one embodiment, proliferative diseases include dysplasias and disorders of the like.

In one embodiment, the treating cancer comprises a reduction in tumor size, decrease in tumor number, a delay of tumor growth, decrease in metastaic lesions in other tissues or organs distant from the primary tumor site, an improvement in the survival of patients, or an improvement in the quality of patient life, or at least two of the above.

In another embodiment, the treating a cell proliferative disorder comprises a reduction in the rate of cellular proliferation, reduction in the proportion of proliferating cells, a decrease in size of an area or zone of cellular proliferation, or a decrease in the number or proportion of cells having an abnormal appearance or morphology, or at least two of the above.

In yet another embodiment, the compounds of the present invention or a pharmaceutically acceptable salt thereof, a prodrug thereof, or metabolite thereof, can be administered in combination with a second chemotherapeutic agent. In a further embodiment, the second chemotherapeutic agent is selected from the group consisting of tamoxifen, raloxifene, anastrozole, exemestane, letrozole, cisplatin, carboplatin, paclitaxel, cyclophosphamide, lovastatin, minosine, gemcitabine, ara C, 5-fluorouracil, methotrexate, docetaxel, goserelin, vincristin, vinblastin, nocodazole, teniposide, etoposide, epothilone, navelbine, camptothecin, daunonibicin, dactinomycin, mitoxantrone, amsacrine, doxorubicin, epirubicin, idarubicin imatanib, gefitinib, erlotinib, sorafenib, sunitinib malate, trastuzumab, rituximab, cetuximab, and bevacizumab.

In one embodiment, the compounds of the present invention or a pharmaceutically acceptable salt thereof, a prodrug thereof, or metabolite thereof, can be administered in combination with an agent that imposes nitrosative or oxidative stress. Agents for selectively imposing nitrosative stress to inhibit proliferation of pathologically proliferating cells in combination therapy with GSNOR inhibitors herein and dosages and routes of administration therefor include those disclosed in U.S. Pat. No. 6,057,367, which is incorporated herein. Supplemental agents for imposing oxidative stress (i.e., agents that increase GSSG (oxidized glutathione) over GSH (glutathione) ratio or NAD(P) over NAD(P)H ratio or increase thiobarbituric acid derivatives) in combination therapy with GS-FDH inhibitors herein include, for example, L-buthionine-5-sulfoximine (BSO), glutathione reductase inhibitors (e.g., BCNU), inhibitors or uncouplers of mitochondrial respiration and drugs that increase reactive oxygen species (ROS), e.g., adriamycin, in standard dosages with standard routes of administration.

GSNOR inhibitors may also be co-administered with a phosphodiesterase inhibitor (e.g., rolipram, cilomilast, roflumilast, Viagra® (sildenifil citrate), Cialis® (tadalafil), Levitra® (vardenifil), etc.) a β-agonist, a steroid, or a leukotriene antagonist (LTD4). Those skilled in the art can readily determine the appropriate therapeutically effective amount depending on the disorder to be ameliorated.

GSNOR inhibitors may be used as a means to improve β-adrenergic signaling. In particular, inhibitors of GSNOR alone or in combination with β-agonists could be used to treat or protect against heart failure, or other vascular disorders such as hypertension and asthma. GSNOR inhibitors can also be used to modulate G protein coupled receptors (GPCRs) by potentiating Gs G-protein, leading to smooth muscle relaxation (e.g., airway and blood vessels), and by attenuating Gq G-protein, and thereby preventing smooth muscle contraction (e.g., in airway and blood vessels).

The therapeutically effective amount for the treatment of a subject afflicted with a disorder ameliorated by NO donor therapy is the GSNOR inhibiting amount in vivo that causes amelioration of the disorder being treated or protects against a risk associated with the disorder. For example, for asthma, a therapeutically effective amount is a bronchodilating effective amount; for cystic fibrosis, a therapeutically effective amount is an airway obstruction ameliorating effective amount; for ARDS, a therapeutically effective amount is a hypoxemia ameliorating effective amount; for heart disease, a therapeutically effective amount is an angina relieving or angiogenesis inducing effective amount; for hypertension, a therapeutically effective amount is a blood pressure reducing effective amount; for ischemic coronary disorders, a therapeutic amount is a blood flow increasing effective amount; for atherosclerosis, a therapeutically effective amount is an endothelial dysfunction reversing effective amount; for glaucoma, a therapeutic amount is an intraocular pressure reducing effective amount; for diseases characterized by angiogenesis, a therapeutically effective amount is an angiogenesis inhibiting effective amount; for disorders where there is risk of thrombosis occurring, a therapeutically effective amount is a thrombosis preventing effective amount; for disorders where there is risk of restenosis occurring, a therapeutically effective amount is a restenosis inhibiting effective amount; for chronic inflammatory diseases, a therapeutically effective amount is an inflammation reducing effective amount; for disorders where there is risk of apoptosis occurring, a therapeutically effective amount is an apoptosis preventing effective amount; for impotence, a therapeutically effective is an erection attaining or sustaining effective amount; for obesity, a therapeutically effective amount is a satiety causing effective amount; for stroke, a therapeutically effective amount is a blood flow increasing or a TIA protecting effective amount; for reperfusion injury, a therapeutically effective amount is a function increasing effective amount; and for preconditioning of heart and brain, a therapeutically effective amount is a cell protective effective amount, e.g., as measured by triponin or CPK.

The therapeutically effective amount for the treatment of a subject afflicted with pathologically proliferating cells means a GSNOR inhibiting amount in vivo which is an antiproliferative effective amount. Such antiproliferative effective amount as used herein means an amount causing reduction in rate of proliferation of at least about 20%, at least about 10%, at least about 5%, or at least about 1%.

In general, the dosage, i.e., the therapeutically effective amount, ranges from 1 μg to 10 g/kg and often ranges from 10 μg to 1 g/kg or 10 μg to 100 mg/kg body weight of the subject being treated, per day.

H. Other Uses

The compounds of the present invention or a pharmaceutically acceptable salt thereof, or a prodrug or metabolite thereof, can be applied to various apparatus in circumstances when the presence of such compounds would be beneficial. Such apparatus can be any device or container, for example, implantable devices in which a GSNOR inhibitor can be used to coat a surgical mesh or cardiovascular stent prior to implantation in a patient. The GSNOR inhibitors of the present invention can also be applied to various apparatus for in vitro assay purposes or for culturing cells.

The compounds of the present invention or a pharmaceutically acceptable salt thereof, or a prodrug or metabolite thereof, can also be used as an agent for the development, isolation or purification of binding partners to GSNOR inhibitor compounds, such as antibodies, natural ligands, and the like. Those skilled in the art can readily determine related uses for the compounds of the present invention.

EXAMPLES

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

Example 1

General and Specific Methods of Preparing Novel GSNOR Pyrrole Inhibitors

This example describes Schemes for preparing the GSNOR inhibitors depicted in Tables 1-4. Some schemes are specific to a particular compound, while others are general schemes that include an exemplary method for preparing a representative compound. Following the schemes are Methods which describe the preparation of intermediates or starting materials that were used in select schemes.

Scheme 1: A general scheme for preparing GSNOR inhibitors with structure 1D

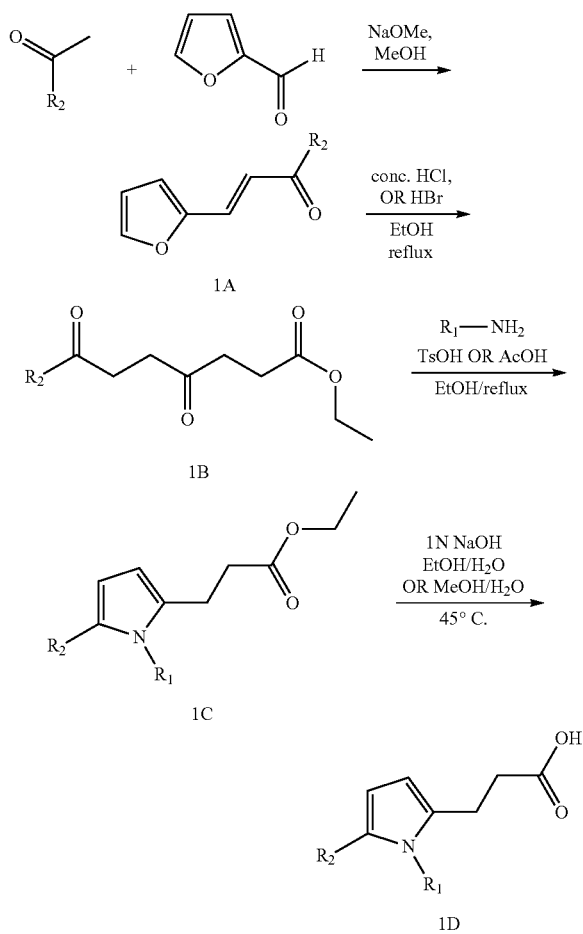

Representative Procedure for Scheme 1: Synthesis of 3-[1-(4-Carbamoyl-2-methyl-phenyl)-5-(4-methoxy-phenyl]-1H-pyrrol-2-yl]-propanoic acid Step 1: Synthesis of (E)-3-Furan-2-yl-1-(4-methoxy-phenyl)-propenone A solution of 2-furaldehyde (5.85 g, 60.92 mmol) was added to a methanol solution (120 mL) of 4-methoxy acetophenone (8.5 g, 56.6 mmol), followed by the addition of sodium methoxide (3.1 g, 56.6 mmol). The reaction mixture was stirred at room temperature for 16 h, followed by removal of the solvent in vacuo. The resultant mixture was diluted with water (130 mL) and extracted with ethyl acetate (350 mL). The aqueous layer was re-extracted with ethyl acetate (100 mL). The combined organic layers were dried over anhydrous $Na_2SO_4$ and the solvent was removed in vacuo to obtain the product (E)-3-Furan-2-yl-1-(4-methoxy-phenyl)-propenone as an orange solid (12.6 g, 97%).

Step 2: Synthesis of 1-(4-Methoxy-phenyl)-decane-1,4,7-trione

Conc. HCl (59 mL) was added to a solution of (E)-3-Furan-2-yl-1-(4-methoxy-phenyl)-propenone (12.6 g, 55.2 mmol) in ethanol (237 mL). The reaction mixture was heated under reflux for 16 h, concentrated, and diluted with dichloromethane (250 mL), and the resultant organic layer was washed with water (25 mL). After phase separation, the organic layer was dried over anhydrous $Na_2SO_4$ and the solvent removed in vacuo to obtain the crude mixture, which was purified by silica gel flash chromatography to obtain 1-(4-methoxy-phenyl)-decane-1,4,7-trione (6.89 g, 43%).

Step 3: Synthesis of 3-[1-(4-Carbamoyl-2-methyl-phenyl)-5-(4-methoxy-phenyl)-1H-pyrrol-2-yl]propanoic acid ethyl ester 4-amino-3-methylbenzamide (180 mg, 1.2 mmol) was added to a solution 1-(4-methoxy-phenyl)-decane-1,4,7-trione (350 mg, 1.2 mmol) in ethanol (6 mL), followed by the addition of p-toluenesulfonic acid monohydrate (23 mg, 0.12 mmol). The reaction mixture was heated under reflux for 16 h, and the solvent removed in vacuo to obtain a crude product which upon purification by silica gel flash chromatography, gives 3-[1-(4-carbamoyl-2-methyl-phenyl)-5-(4-methoxy-phenyl)-1H-pyrrol-2-yl]propanoic acid ethyl ester (147 mg, 30%).

Step 4: Synthesis of 3-[1-(4-Carbamoyl-2-methyl-phenyl)-5-(4-methoxy-phenyl)-1H-pyrrol-2-yl]-propanoic acid 3-[1-(4-carbamoyl-2-methyl-phenyl)-5-(4-methoxy-phenyl)-1H-pyrrol-2-yl]propanoic acid ethyl ester (86 mg, 0.216 mmol) was dissolved in ethanol (4 mL). Water (0.5 mL) was added to the ethanolic solution followed by the addition of 1N NaOH (0.51 mL, 0.51 mmol). The reaction mixture was stirred at room temperature for 1 h and then at 45° C. for an additional hour. After removal of the solvent in vacuo, the residue was diluted with water (6 mL) and extracted with ethyl acetate (2×6 mL). The pH of the aqueous layer was adjusted to 2 with 1N HCl and then extracted with ethyl acetate (6 mL). The combined organic layer was dried over anhydrous $Na_2SO_4$ and the solvent removed in vacuo to obtain 3-[1-(4-Carbamoyl-2-methyl-phenyl)-5-(4-methoxy-phenyl)-1H-pyrrol-2-yl]-propanoic acid as the product (68 mg, 85%).

Scheme 1A: Alternate conditions

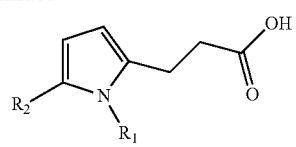

1D

Representative procedure for Scheme 1A, alternate conditions: Synthesis of 3-[1-(4-Carbamoyl-thiazol-2-yl)-5-(4-methoxy-phenyl)-1H-pyrrol-2-yl]-propionic acid Step 3: Synthesis of 3-[1-(4-Carbamoyl-thiazol-2-yl)-5-(4-methoxy-phenyl)-1H-pyrrol-2-yl]-propionic acid ethyl ester (1C, R1=4-carbamoyl-thiazol-2-yl, R2=4-methoxy-phenyl)

To a solution of 7-(4-methoxy-phenyl)-4,7-dioxo-heptanoic acid ethyl ester (0.5 mmol), see scheme 1, in ethanol (2 mL) were added the amine (1.5 equivalents) and p-toluenesulfonic acid monohydrate (0.5 eq.). The reaction was run using the Biotage Microwave Initiator for 1 to 3 hours at 150° C. The solvent was removed in vacuo to obtain the crude mixture which was purified by prep silica gel plate to obtain the final product (70 mg, 38%).

Step 4: Synthesis of 3-[1-(4-Carbamoyl-thiazol-2-yl)-5-(4-methoxy-phenyl)-1H-pyrrol-2-yl]-propionic acid (1D, R1=4-carbamoyl-thiazol-2-yl, R2=4-methoxy-phenyl)

To 3-[1-(4-Carbamoyl-thiazol-2-yl)-5-(4-methoxy-phenyl)-1H-pyrrol-2-yl]-propionic acid ethyl ester (0.15 mmol) in a 2:1 mixture of methanol/THF was added 2M LiOH (0.30 mmol). The reaction mixture was stirred for 24 hours. The solvent was removed in vacuo. The residue was diluted with water (2 mL) and extracted with ethyl ether. The pH of the aqueous layer was adjusted to 2 with 1N HCl. The resulting suspension was filtered off; the solid was washed with water and dried to give the final compound. Yield: 36 mg, 69%.

Scheme 2: A general scheme for preparing GSNOR inhibitors with structure 2F

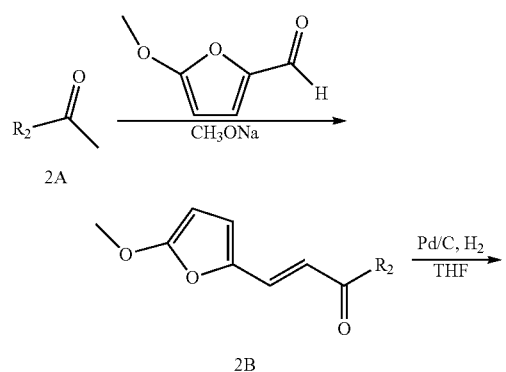

2A

2B

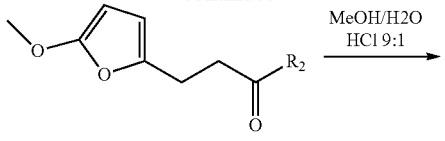

2C

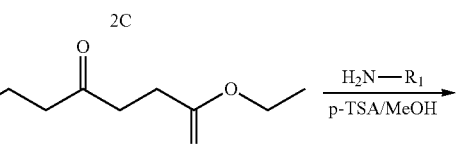

2D

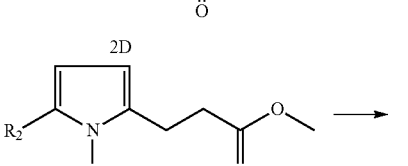

2E

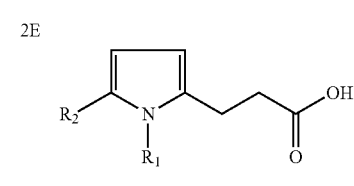

2F

Representative procedure for Scheme 2: Synthesis of 3-(1-(4-carbamoyl-2-methylphenyl)-5-(4-carbamoylphenyl)-1H-pyrrol-2-yl)propanoic acid Synthesis of 4-[(E)-3-(5-methoxy-furan-2-yl)-acryloyl]-benzamide Sodium methoxide (in portions) was added, over a time interval of about three minutes, to 4-acetyl-benzamide (1.38 g, 8.5 mmol) and 5-methoxy-furan-2-carbaldehyde (1.31 g, 10.6 mmol) in a 1:1 mixture of methanol and dimethylformamide (16 mL). The resulting solution was placed under $N_2$ and stirred overnight at 45° C. The reaction mixture was then evaporated to dryness under vacuum, followed by the addition of water and brine (100 mL) to the resulting residue. The aqueous solution was extracted with ethyl acetate (125 mL×3) and the combined organic layers were washed with brine (100 mL) and dried over $MgSO_4$. The crude reaction mixture of 4-[(E)-3-(5-methoxy-furan-2-yl)-acryloyl]-benzamide and unreacted 4-acetyl acetamide is used without purification.

Synthesis of 4-[3-(5-methoxy-furan-2-yl-propionyl]-benzamide

10% Pd/C (60 mg) was added to crude 4-[(E)-3-(5-methoxy-furan-2-yl)-acryloyl]-benzamide (180 mg) in THF (4 mL). The mixture was subjected to hydrogenation at 45 psi for 4 hours. After removal of the catalyst by filtration through celite, the mixture was concentrated and carried forward without any purification.

Synthesis of 7-(4-carbamoyl-phenyl)-4,7-dioxo-heptanoic acid

Crude 4-[3-(5-methoxy-furan-2-yl-propionyl]-benzamide (175 mg) was dissolved in 10% aqueous methanol (3 mL) to which was added 0.2 N HCl (0.2 mL) so as to obtain a solution having a final pH=3. The resulting solution was stirred for 30 minutes, evaporated to dryness and subjected to chromatographic purification using dichloromethane as the solvent (53 mg) of material with 67% purity.

Synthesis of 3-[1-carbamoyl-2-methyl-phenyl)-5-(4-carbamoyl-phenyl)-1H-pyrrole-2-yl]-propanoic acid methyl ester 4-amino-3-methyl benzamide (20 mg, 0.13 mmol) was added to 7-(4-carbamoyl-phenyl)-4,7-dioxo-heptanoic acid ethyl ester mixture (~0.11 mmol) in EtOH, followed by the addition of p-toluenesulfonic acid (2 mg, 0.01 mmol). The resultant mixture was heated at 80° C. for 12 hours. The residue of the crude reaction mixture was dissolved in dichloromethane and then purified by silica-gel chromatography using 5% methanol in chloroform as the solvent system (5 mg; product: 3-[1-carbamoyl-2-methyl-phenyl)-5-(4-carbamoyl-phenyl)-1H-pyrrole-2-yl]-propanoic acid methyl ester).

Synthesis of 3-(1-(4-carbamoyl-2-methylphenyl)-5-(4-carbamoylphenyl)-1H-pyrrol-2-yl)propanoic acid 3-[1-carbamoyl-2-methyl-phenyl)-5-(4-carbamoyl-phenyl)-1H-pyrrole-2-yl]-acid methyl ester was hydrolyzed using the procedure described above in the final step of scheme 1 (product: 4.8 mg).

Representative procedure for Scheme 3: Synthesis of 3-(5-(4-(1H-pyrazol-4-yl)phenyl)-1-(4-carbamoyl-2-methylphenyl)-1H-pyrrol-2-yl)propanoic acid Synthesis of 3-[1-(4-Carbamoyl-2-methyl-phenyl)-5-(4-iodo-phenyl)-1H-pyrrol-2-yl]-propanoic acid ethyl ester The titled compound was prepared according to the first 3 steps of Scheme 1, (where $R_2$=4-iodo-phenyl, and $R_1$=4-carbamoyl-2-methylphenyl).

Synthesis of ethyl 3-(5-(4-(1H-pyrazol-4-yl)phenyl)-1-(4-carbamoyl-2-methylphenyl)-1H-pyrrol-2-yl) propanoate A mixture of 3-[1-(4-Carbamoyl-2-methyl-phenyl)-5-(4-iodo-phenyl)-1H-pyrrol-2-yl]-propanoic acid ethyl ester (127 mg, 0.252 mmol), 1H-pyrazole boronic acid pinacol ester (147 mg, 0.75 mmol), potassium acetate (222 mg, 2.3 mmol), and [1,1'-bis(diphenylphosphino)ferrocene]dichloropalladium(II) (60.0 mg, 0.074 mmol) in anhydrous DMF (4 mL) was degassed with nitrogen and then heated at 100° C. for 16 h. The mixture was then diluted with ethyl acetate (50 mL) and washed with water (30 mL). After drying the organic layer over anhydrous $Na_2SO_4$, the solvent was removed to obtain a crude product which is purified by silica gel flash chromatography (33 mg, 28%).

Synthesis of 3-(5-(4-(1H-pyrazol-4-yl)phenyl)-1-(4-carbamoyl-2-methylphenyl)-1H-pyrrol-2-yl)propanoic acid To the product from step 1 (33 mg, 0.074 mmol) in ethanol (0.5 mL) was added 1N NaOH (88 µL, 0.089 mmol). The reaction mixture was stirred at room temperature for 16 h, followed by removal of the solvent in vacuo. The resultant residue was diluted with water (4 mL) and extracted with ethyl acetate (5 mL). The pH of the aqueous layer was then adjusted to 4 pH units using 1N HCl. This results in the precipitation of a solid which was filtered and dried to give the product 3-(5-(4-(1H-pyrazol-4-yl)phenyl)-1-(4-carbamoyl-2-methylphenyl)-1H-pyrrol-2-yl)propanoic acid (12 mg, 38%).

Scheme 3: A general scheme for preparing GSNOR inhibitors with structure 3C

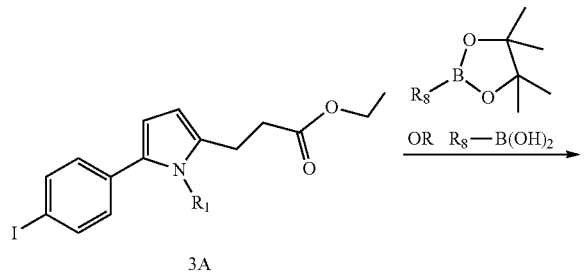

Scheme 4: A general scheme for preparing GSNOR inhibitors with structure 4C

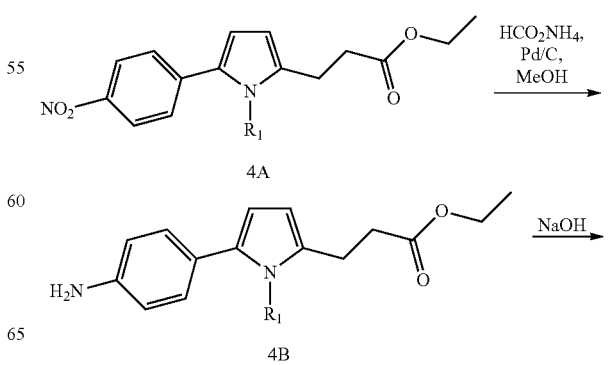

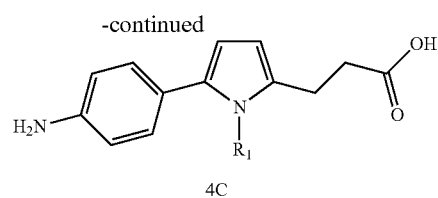

4C

Representative procedure for Scheme 4: Synthesis of 3-[5-(4-aminophenyl)-1-(4-carbamoyl-2-methylphenyl)-1H-pyrrol-2-yl]-propanoic acid Synthesis of 3-[1-(4-carbamoyl-2-methyl-phenyl)-5-(4-nitro-phenyl)-1H-pyrrole-2-yl]-propanoic acid ethyl ester The titled compound was prepared according to the first 3 steps of Scheme 1, $R_2$=4-nitro-phenyl, and $R_1$=4-carbamoyl-2-methylphenyl).

Synthesis of 3-[5-(4-aminophenyl)-1-(4-carbamoyl-2-methylphenyl)-1H-pyrrol-2-yl]-propanoic acid ethyl ester 3-[1-(4-carbamoyl-2-methyl-phenyl)-5-(nitro-phenyl)-1H-pyrrole-2-yl]-propanoic acid ethyl ester (83 mg, 0.2 mmol) was dissolved in 2 mL methanol under an inert atmosphere of nitrogen. To this solution was added ammonium formate (117 mg, 1.8 mmol) and 10% Pd/C (10 mg). After 24 hrs, the reaction mixture was filtered using celite, rinsed with MeOH and concentrated in vacuo. The residue was diluted with acetone, filtered and the filtrate concentrated in vacuo to give the crude product, which was purified using preparative TLC (solvent: 5% IPA/CH$_2$Cl$_2$). The band corresponding to 3-[5-(4-aminophenyl)-1-(4-carbamoyl-2-methylphenyl)-1H-pyrrol-2-yl]-propanoic acid ethyl ester ($R_f$=0.6) was isolated and dried under high vacuum (36 mg, 77%, light orange hydroscopic powder).

Synthesis of 3-[5-(4-aminophenyl)-1-(4-carbamoyl-2-methylphenyl)-1H-pyrrol-2-yl]-propanoic acid 3-[5-(4-aminophenyl)-1-(4-carbamoyl-2-methylphenyl)-1H-pyrrol-2-yl]-propanoic acid ethyl ester (36 mg, 0.09 mmol) was dissolved in 1 mL methanol. 1 N NaOH (0.18 mL, 0.18 mmoL) was added. After 18 hrs, the reaction was concentrated in vacuo and diluted with water. The pH was adjusted to 1 with 1 M HCl and extracted with EtOAc (3×4 mL). The combined organic layers were dried over Na$_2$SO$_4$, filtered and concentrated in vacuo. The residue was triturated with hexanes and dried under high vacuum to yield 3-[5-(4-aminophenyl)-1-(4-carbamoyl-2-methylphenyl)-1H-pyrrol-2-yl]-propanoic acid (16 mg, 50%, light orange powder).

Scheme 5: A general scheme for preparing GSNOR inhibitors with structure 5E

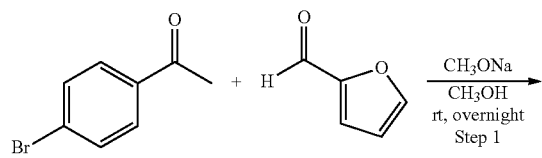

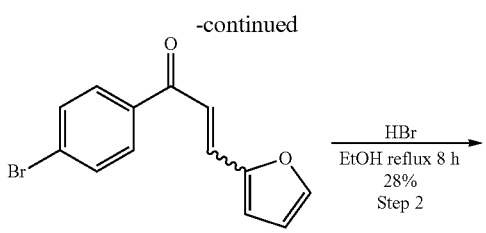

5A

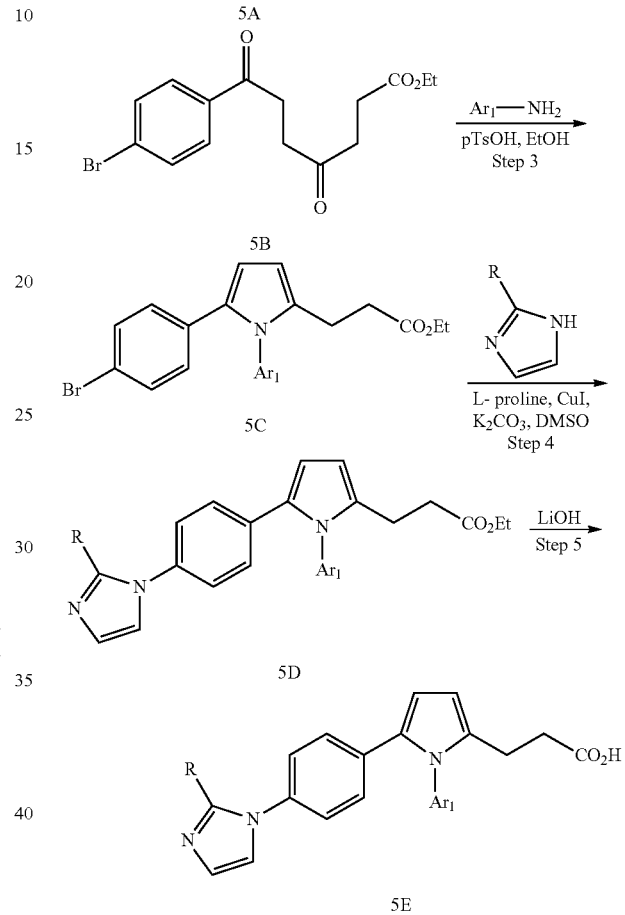

Representative procedure for Scheme 5: Synthesis of 3-(5-(4-(1H-imidazol-1-yl)phenyl)-1-(4-carbamoyl-2-methylphenyl)-1H-pyrrol-2-yl)propanoic acid Step 1: Synthesis of 1-(4-bromophenyl)-3-(furan-2-yl)prop-2-en-1-one (5A)

To a solution of 4-bromophenylethanone (112.6 g, 570 mmol) and furan-2-carbaldehyde (58.5 g, 610 mmol) in methanol (1.5 L) was added CH$_3$ONa (31 g, 570 mmol) over 10 min and the reaction solution was stirred at room temperature overnight. The reaction mixture was neutralized with conc. HCl to pH=7, and the solvent was removed under reduced pressure. To the resultant residue was added EA and water. The aqueous layer was extracted with EA for 3 times. The combined layers were washed with brine, dried over MgSO$_4$, concentrated and purified by silica gel column chromatography (PE:EA=10:1) to afford 1-(4-bromophenyl)-3-(furan-2-yl)prop-2-en-1-one (5A) as a yellow solid (90.2 g, 65%).

Step 2: Synthesis of ethyl 7-(4-bromophenyl)-4,7-dioxoheptanoate (5B)

To a solution of compound 1-(4-bromophenyl)-3-(furan-2-yl)prop-2-en-1-one (5A) (20.0 g, 72.2 mmol) in ethanol (160 mL) was added HBr (48% in water, 40 mL). The resultant mixture was stirred under reflux for 8 h, and then the reaction solution was concentrated in vacuo. To the residue was added sat. NaHCO$_3$ to PH=7 and extracted with EA. The combined organic layers were washed with brine, dried over MgSO$_4$, concentrated and purified by silica gel column chromatography (PE:EA=5:1) to afford ethyl 7-(4-bromophenyl)-4,7-dioxoheptanoate (5B) as a yellow solid (7.0 g, 28%).

Step 3: Synthesis of Ethyl 3-(5-(4-bromophenyl)-1-(4-carbamoyl-2-methylphenyl)-1H-pyrrol-2-yl)propanoate To a solution of ethyl 7-(4-bromophenyl)-4,7-dioxoheptanoate (5B) (3.41 g, 10 mmol) and 4-amino-3-methylbenzamide (1.65 g, 11 mmol) in 50 mL of ethanol was added TsOH.H$_2$O (570 mg, 3 mmol). The reaction solution was stirred under reflux overnight and then concentrated in vacuo. The resultant residue was neutralized with sat. NaHCO$_3$ and extracted with Ethyl Acetate. The organic layers were washed with brine, concentrated and purified by silica gel column chromatography (DCM:PE=1:1) to afford ethyl 7-(4-bromophenyl)-4,7-dioxoheptanoate as a pale solid (2.80 g, 61%).

Step 4: Synthesis of ethyl 3-(5-(4-(1H-imidazol-1-yl)phenyl)-1-(4-carbamoyl-2-methylphenyl)-1H-pyrrol-2-yl)propanoate To a mixture of ethyl 7-(4-bromophenyl)-4,7-dioxoheptanoate (4.54 g, 10 mmol) and imidazole (2.04 g, 30 mmol) in DMSO (50 mL) was added L-proline (0.345 g, 3 mmol), CuI (1.14 g, 6 mmol) and K$_2$CO$_3$ (2.76 g, 20 mmol). The resultant mixture was stirred under N$_2$ at 100° C. overnight, cooled to room temperature, filtered, and concentrated in vacuum. The residue was dissolved in ethyl acetate and saturated aqueous NaHCO$_3$ was added till pH=8.5. The mixture was filtered and the resultant aqueous layer was extracted with EA (5 times). The combined organic layers were washed with brine, dried over MgSO$_4$, concentrated and purified by silica gel column chromatography (DCM:MeOH=30:1-20:1) to afford 3-(5-(4-(1H-imidazol-1-yl)phenyl)-1-(4-carbamoyl-2-methylphenyl)-1H-pyrrol-2-yl)propanoate as a pale solid (1.6 g, 36%).

Step 5: Synthesis of 3-(5-(4-(1H-imidazol-1-yl)phenyl)-1-(4-carbamoyl-2-methylphenyl)-1H-pyrrol-2-yl)propanoic acid To a solution of compound 3-(5-(4-(1H-imidazol-1-yl)phenyl)-1-(4-carbamoyl-2-methylphenyl)-1H-pyrrol-2-yl)propanoate (22.0 g, 48.3 mmol) in THF/H$_2$O (v/v=1/1, 220 mL) was added LiOH.H$_2$O (4.15 g, 96.6 mmol). The reaction solution was stirred at room temperature for 5 h. The THF was removed under reduced pressure and the aqueous solution was acidified with 10% HCl to pH=5. The solid was filtered and recrystallized from THF and water [1:1 (v/v)] to afford 3-(5-(4-(1H-imidazol-1-yl)phenyl)-1-(4-carbamoyl-2-methylphenyl)-1H-pyrrol-2-yl)propanoic acid as a yellow solid (11.35 g, 55%).

Scheme 6: A general scheme for preparing GSNOR inhibitors with structure 6H

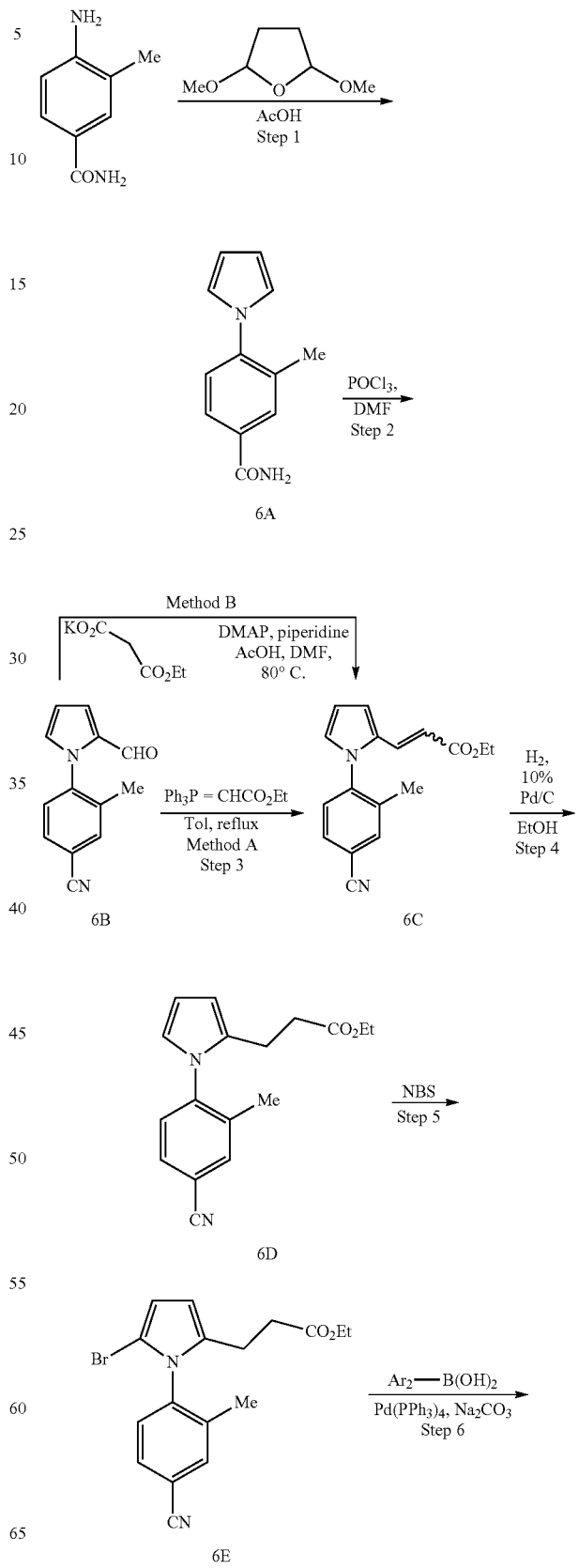

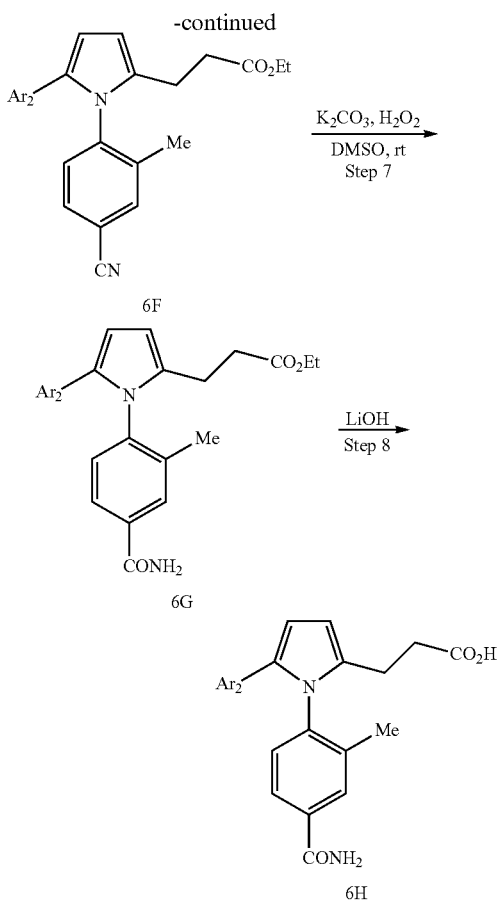

Representative procedure for Scheme 6: Synthesis of 3-(5-(benzo[d][1,3]dioxol-5-yl)-1-(4-carbamoyl-2-methylphenyl)-1H-pyrrol-2-yl)propanoic acid

Step 1: Synthesis of 3-methyl-4-(1H-pyrrol-1-yl)benzamide (6A)

The 2,5-dimethoxy-tetrahydrofuran (106 g, 80 mmol) was added to the solution of 4-amino-3-methylbenzamide (100 g, 66.7 mmol) in AcOH (300 mL). The mixture was stirred at 80° C. for about 1.5 h and then cooled to room temperature. The solution of $Na_2CO_3$ was added dropwise at 0° C. and extracted with ethyl acetate for three times. The combined organic layers were washed with brine, dried over $Na_2SO_4$, concentrated and washed with petroleum ether. The resultant solid was filtrated and dried to afford 3-methyl-4-(1H-pyrrol-1-yl)benzamide as a pale solid (89.7 g, yield 67%).

Step 2: Synthesis of 4-(2-formyl-1H-pyrrol-1-yl)-3-methylbenzonitrile (6B)

$POCl_3$ (65 g, 427 mmol) was added to DMF (34 mL) at 0° C. for 30 min. After addition, the mixture was stirred at room temperature for 1.5 h, and then cooled to 0° C. A solution of 3-methyl-4-(1H-pyrrol-1-yl)benzamide (6A) (42.7 g, 213.5 mmol) in DMF (150 mL) was added at 0° C. and the resultant mixture was stirred at room temperature for 20 min, and then heated to 80° C. for 1 h. The solution was cooled to room temperature and then sat. $Na_2CO_3$ was added at 0° C. until pH=8. The mixture was extracted with ethyl acetate three times. The combined organic layers were washed with sat. $NaHCO_3$ and brine, dried over $Na_2SO_4$, concentrated and purified by silica gel column chromatography (PE:EA=10:1) to afford 4-(2-formyl-1H-pyrrol-1-yl)-3-methylbenzonitrile as a yellow solid (30.5 g, yield 68%).

Step 3: Synthesis of ethyl 3-(1-(4-cyano-2-methylphenyl)-1H-pyrrol-2-yl)acrylate (6C)

Method A:
The mixture of 4-(2-formyl-1H-pyrrol-1-yl)-3-methylbenzonitrile (15 g, 71.4 mmol) and (carbethoxymethylene)-triphenylphosphorane (27.5 g, 78.6 mmol) in toluene was heated to 100° C. overnight. Then it was cooled to room temperature, concentrated and purified by silica gel column chromatography (PE:EA=5:1) to afford ethyl 3-(1-(4-cyano-2-methylphenyl)-1H-pyrrol-2-yl)acrylate as a yellow oil (19.8 g, 98%).

Method B:
To a mixture of 4-(2-formyl-1H-pyrrol-1-yl)-3-methylbenzonitrile (24.5 g, 116.7 mmol), DMAP (2.9 g, 23.3 mmol) and potassium monoethyl malonate (99.2 g, 583.3 mmol) in DMF (600 mL) was added AcOH (35.0 g, 583.3 mmol) and piperidine (29.8 g, 350 mmol). The resultant mixture was heated to 80° C. and stirred for 48 h. The reaction mixture was poured into cooled water and extracted with ethyl acetate (800 mL×3). The combined organic layers were washed with sat. $NaHCO_3$ and brine, dried over $Na_2SO_4$, concentrated and purified by silica gel column chromatography (PE:EA=5:1) to afford ethyl 3-(1-(4-cyano-2-methylphenyl)-1H-pyrrol-2-yl)acrylate as a yellow oil (21.8 g, 67%).

Step 4: Synthesis of ethyl 3-(1-(4-cyano-2-methylphenyl)-1H-pyrrol-2-yl)propanoate (6D)

To a solution of ethyl 3-(1-(4-cyano-2-methylphenyl)-1H-pyrrol-2-yl)acrylate (6C) (8.0 g, 28.6 mmol) in ethanol was added 10% Pd/C (0.8 g). The mixture was stirred under 1 atm of $H_2$ for 30 min at room temperature and filtrated. The resultant filtrate was concentrated to dryness affording the crude product of ethyl 3-(1-(4-cyano-2-methylphenyl)-1H-pyrrol-2-yl)propanoate (7.5 g), which was used for the next step without further purification: LC-MS m/z 283.0 [M+H]$^+$, purity 68%.

Step 5: Synthesis of ethyl 3-(5-bromo-1-(4-cyano-2-methylphenyl)-1H-pyrrol-2-yl)propanoate (6E)

NBS (4.76 g, 1 equiv) was added portionwise to a solution of ethyl 3-(1-(4-cyano-2-methylphenyl)-1H-pyrrol-2-yl)propanoate in DMF at 0° C. during 45 min. After addition, the mixture was stirred at room temperature for 30 min, then poured into water, and extracted with ethyl acetate for three times. The combined organic layers were washed with brine, dried over $Na_2SO_4$, concentrated and purified by silica gel column chromatography (PE:EA=15:1) to afford ethyl 3-(5-bromo-1-(4-cyano-2-methylphenyl)-1H-pyrrol-2-yl)propanoate as a white solid.

Step 6: Synthesis of ethyl 3-(5-(benzo[d][1,3]dioxol-5-yl)-1-(4-cyano-2-methylphenyl)-1H-pyrrol-2-yl)propanoate To a suspension of ethyl 3-(5-bromo-1-(4-cyano-2-methylphenyl)-1H-pyrrol-2-yl)propanoate (400 mg, 0.665 mmol), 3,4-methylenedioxylphenylboric acid (143 mg, 0.864 mmol), sodium bicarbonate (560 mg, 5.32 mmol) in solvent (4 mL) was added Pd(PPh$_3$)$_4$ (60 mg, 0.199 mmol). The reaction was degassed and heated to reflux for 5 h. TLC showed that the reaction was completed. Water (4 mL) was added and the mixture was extracted with ethyl acetate (5 mL×3). The combined organic layers were dried with magnesium sulfate, filtered and evaporated to obtain a brown oil, which was purified by silica gel column chromatography to afford ethyl 3-(5-(benzo[d][1,3]dioxol-5-yl)-1-(4-cyano-2-methylphenyl)-1H-pyrrol-2-yl)propanoate as a colorless oil (308 mg, 69%).

Step 7 and Step 8: Synthesis of 3-(5-(benzo[d][1,3]dioxol-5-yl)-1-(4-carbamoyl-2-methylphenyl)-1H-pyrrol-2-yl)propanoic acid To a mixture of ethyl 3-(5-(benzo[d][1,3]dioxol-5-yl)-1-(4-cyano-2-methylphenyl)-1H-pyrrol-2-yl)propanoate (100 mg, 0.249 mmol) and potassium carbonate (52 mg, 0.373 mmol) in DMSO (1 mL) was added 30% aqueous $H_2O_2$ (28.2 mg, 0.249 mmol). The resultant mixture was stirred at room temperature for 2 h. TLC showed the reaction was completed. Water (7 mL) was added and white solid precipitated. The suspension was centrifuged and the aqueous phase was discarded. The resultant solid was dried in vacuum to afford the amide intermediate as a white solid (85 mg, yield 81%). To the mixture of this intermediate in $H_2O$ (0.6 mL) and THF (0.6 mL) was added $LiOH \cdot H_2O$ (10 mg, 0.238 mmol). The reaction mixture was stirred at room temperature overnight. THF was evaporated in vacuum. The residue was acidified to pH=4 with 5% hydrochloric acid, centrifuged and dried to afford 3-(5-(benzo[d][1,3]dioxol-5-yl)-1-(4-carbamoyl-2-methylphenyl)-1H-pyrrol-2-yl)propanoic acid as a white solid (46 mg, overall yield 47%).

Scheme 7: A general scheme for preparing GSNOR inhibitors with structure 7B

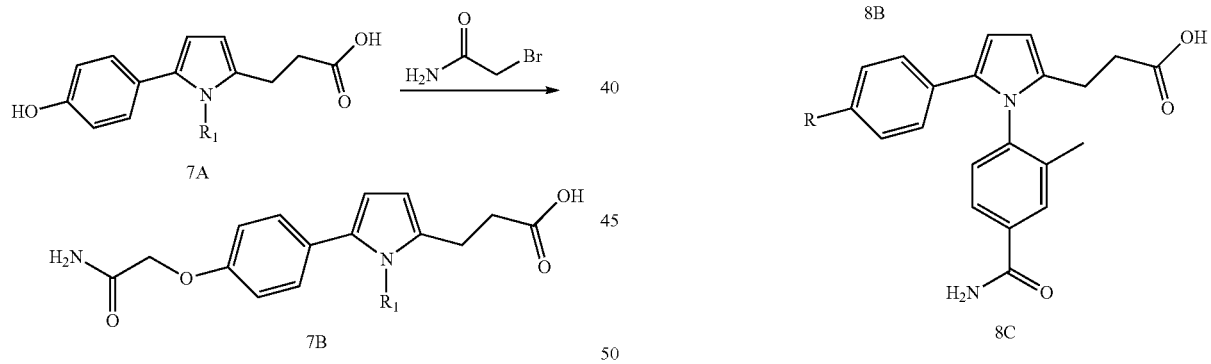

Representative procedure for Scheme 7: Synthesis of 3-(5-(4-(2-amino-2-oxoethoxy)phenyl)-1-(4-carbamoyl-2-methylphenyl)-1H-pyrrol-2-yl)propanoic acid Synthesis of 3-(5-(4-(2-amino-2-oxoethoxy)phenyl)-1-(4-carbamoyl-2-methylphenyl)-1H-pyrrol-2-yl) propanoic acid (7B)

3-(1-(4-carbamoyl-2-methylphenyl)-5-(4-hydroxyphenyl)-1H-pyrrol-2-yl)propanoic acid (7A, R1=4-carbamoyl-2-methylphenyl) was prepared according to the methodology shown in Scheme 1, R2=4-hydroxyphenyl, R1=4-carbamoyl-2-methylphenyl. A N,N-dimethylformamide solution of 3-(1-(4-carbamoyl-2-methylphenyl)-5-(4-hydroxyphenyl)-1H-pyrrol-2-yl)propanoic acid (36 mg, 0.1 mmol, 1 ml), potassium carbonate (27 mg, 0.2 mmol) and 2-bromoacetamide (18 mg, 0.12 mmol) was stirred for 18 hrs at ambient temperature, after which time the reaction was diluted with water and the pH adjusted to 2 with 1 M HCl. The aqueous layer was extracted with EtOAc (3×3 mL), dried over $N_2SO_4$, filtered and concentrated in vacuo. The residue thus obtained was triturated with hexanes and dried under high vacuum to yield the title compound as a light yellow powder (13 mg).

Scheme 8: A general scheme for preparing GSNOR inhibitors with structure 8C

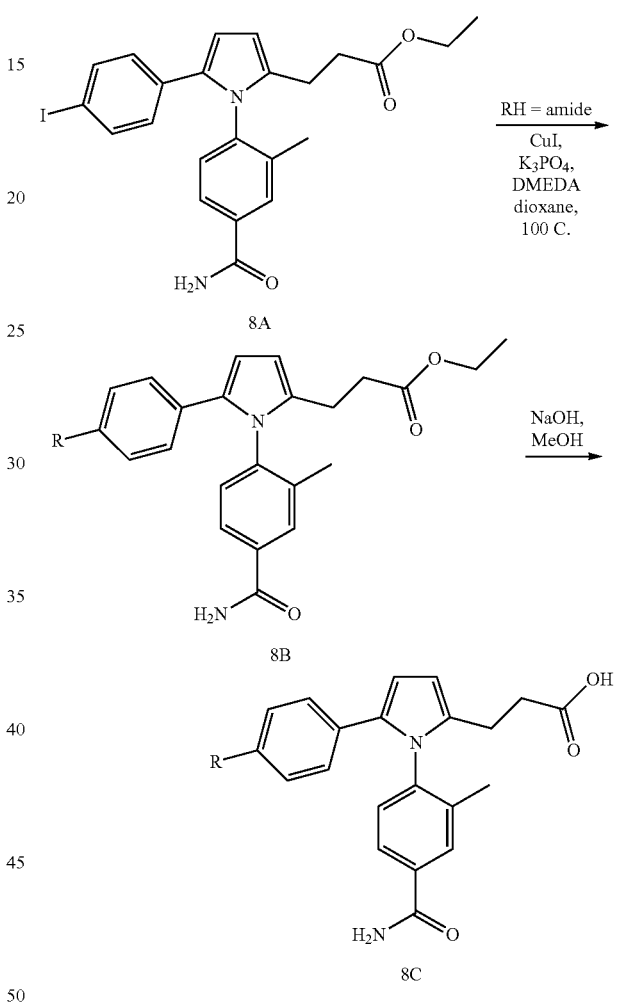

Representative procedure for Scheme 8: Synthesis of 3-[1-(4-carbamoyl-2-methylphenyl)-5-[4-(2-oxo-imidazolidin-1-yl)-phenyl]-1H-pyrrol-2-yl]-propionic acid Synthesis of 3-[1-(4-carbamoyl-2-methylphenyl)-5-[4-(2-oxo-imidazolidin-1-yl)-phenyl]-1H-pyrrol-2-yl]-propionic acid ethyl ester In a 2.5 mL microwave reaction vial, 3-[1-(4-carbamoyl-2-methyl-phenyl)-5-((4-iodo-phenyl)-1H-2-yl]-propionic acid ethyl ester 8A (which was prepared according to the first 3 steps of Scheme 1, $R_2$=4-iodo-phenyl, and $R_1$=4-carbamoyl-2-methylphenyl) (51 mg, 0.1 mmol), 2-imidazolidone (44 mg, 0.5 mmol), CuI (5 mg, 0.02 mmol), N,N' dimethylethylenediamine (DMEDA) (0.01 mL, 0.04 mmol), and potassium phosphate tribasic (44 mg, 0.2 mmol) were dissolved in 0.5 mL anhydrous N,N-dimethylformamide. The vial was purged with nitrogen, sealed and placed in microwave reactor at 120° C. for 20 min. TLC (10% IPA/CH$_2$Cl$_2$) showed reaction 50% complete. CuI (5 mg) and 2-imidazolidone (40 mg) were added; the reaction was repurged with nitrogen, sealed and placed in microwave reactor at 130° C. for 20 min. Reaction was filtered over celite, rinsed with EtOAc and concentrated in vacuo. The crude product was purified by preparative plate TLC (5% MeOH/CH$_2$Cl$_2$). Desired band (rf=0.28) was isolated and dried under high vacuum to yield intermediate 3-[1-(4-carbamoyl-2-methylphenyl)-5-[4-(2-oxo-imidazolidin-1-yl)-phenyl]-1H-pyrrol-2-yl]-propionic acid ethyl ester (43 mg, 93%, dark yellow solid).

3-[1-(4-carbamoyl-2-methylphenyl)-5-[4-(2-oxo-imidazolidin-1-yl)-phenyl]-1H-pyrrol-2-yl]-propionic acid.

3-[1-(4-carbamoyl-2-methylphenyl)-5-[4-(2-oxo-imidazolidin-1-yl)-phenyl]-1H-pyrrol-2-yl]-propionic acid ethyl ester (43 mg, 0.10 mmol) was hydrolyzed according to procedure described above in the final step of scheme 4 (52%, light orange hygroscopic solid).

Scheme 9a: A general scheme for preparing GSNOR inhibitors with structure 9a-C

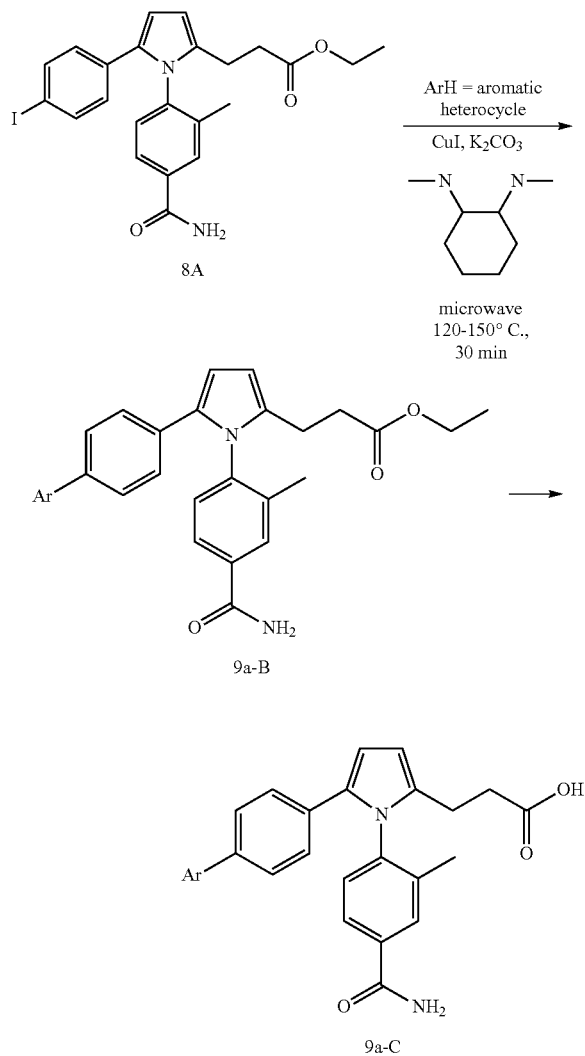

Representative procedure for Scheme 9a: Synthesis of 3-(5-(4-(1H-pyrazol-1-yl)phenyl)-1-(4-carbamoyl-2-methylphenyl)-1H-pyrrol-2-yl)propanoic acid Synthesis of 3-[1-(4-carbamoyl-2-methyl-phenyl)-5-(4-pyrazole-1-yl-phenyl)-1H-pyrrol-2-yl]-propionic acid ethyl ester (9a-B, Ar=1H-pyrazol-1-yl)

N,N-dimethyl-cyclohexane-1,2-diamine (11 mg, 0.08 mmol) was dissolved in DMSO and degassed by bubbling argon through the solution for 2 minutes. The resulting solution was then added to a mixture of 3-[1-(4-carbamoyl-2-methyl-phenyl)-5-(4-iodo-phenyl)-1H-pyrrole-2-yl]-propionic acid ethyl ester 8A (which was prepared according to the first 3 steps of Scheme 1, R$_2$=4-iodo-phenyl, and R$_1$=4-carbamoyl-2-methylphenyl) (150 mg, 0.29 mmol), pyrazole (500 mg, 7.5 mmol), copper iodide (11 mg, 0.06 mmol), and potassium carbonate (86 mg (0.61 mmole) and the resulting reaction mixture again degassed for 2 minutes by bubbling argon gas through the solution. The reaction mixture was then submitted to microwave irradiation for 30 minutes at 120° C. The reaction mixture was then added to water (10 mL), extracted into ethyl acetate (3×10 mL). The ethyl acetate extracts were combined, washed with water (5 mL) and then brine (5 mL). The organic layer was then dried over MgSO$_4$. Chromatography (5 g silica sep-pak cartridge) with dichloromethane then 1% methanol in dichloromethane yielded pure intermediate 3-[1(4-carbamoyl-2-methyl-phenyl)-5-(4-pyrazole-1-yl)-1H-pyrrol-2-yl]-propionic acid ethyl ester (26 mg, 20%).

Synthesis of 3-(5-(4-(1H-pyrazol-1-yl)phenyl)-1-(4-carbamoyl-2-methylphenyl)-1H-pyrrol-2-yl)propanoic acid (9a-C, Ar=1H-pyrazol-1-yl)

3-[1-(4-carbamoyl-2-methyl-phenyl)-5-(4-pyrazole-1-yl-phenyl)-1H-pyrrol-2-yl]-propionic acid ethyl ester (24 mg, 0.06 mmol) was hydrolyzed using the procedure described above in the final step of scheme 4 to give the title compound, 3-[1[(4-carbamoyl-2-methyl-phenyl)-5-(4-pyrazole-1-yl)-1H-pyrrol-2-yl]-propionic acid (18 mg, 75%).

A second representative procedure for Scheme 9a: Synthesis of 3-{1-(4-carbamoyl-2-methyl-phenyl)-5-[4-(2-methyl-imidazole-1-yl)phenyl-1-yl]-1H-pyrrole-2-yl}-propionic acid.

Synthesis of 3-[1-(4-carbamoyl-2-methyl-phenyl)-5-[4-(2-methyl-imidazole-1-yl)phenyl-1-yl]-1H-pyrrole-2-yl]-propionic acid ethyl ester Step one run as above on 120 mg 8A (0.24 mmol), except at 150° C. under microwave irradiation for 2×45 minutes to provide 50 mg of titled compound (45%).

Synthesis of 3-[1-(4-carbamoyl-2-methyl-phenyl)-5-[4-(2-methyl-imidazole-1-yl)phenyl-1-yl]-1H-pyrrole-2-yl]-propionic acid Step two was run on 3-{1-(4-carbamoyl-2-methyl-phenyl)-5-[4-(2-methyl-imidazole-1-yl)phenyl-1-yl]-1H-pyrrole-2-yl}-propionic acid ethyl ester (85 mg, 0.2 mmol) as above (following final step of scheme 4) with isolation as follows: The reaction mixture was concentrated to half by N$_2$ stream and washed with EtOAc. One equivalent of 1N HCl was added to the reaction mixture, which was then evaporated to dryness and taken up in 0.5 mL water. The mixture was then purified on a reverse phase C18 column to isolate product from salts. Yield: 3-{1-(4-carbamoyl-2-methyl-phenyl)-5-[4-(2-methyl-imidazole-1-yl)phenyl-1-yl]-1H-pyrrole-2-yl}-propionic acid, 36 mg, 42%.

Scheme 9b: A general scheme for preparing GSNOR inhibitors with structure 9b-C

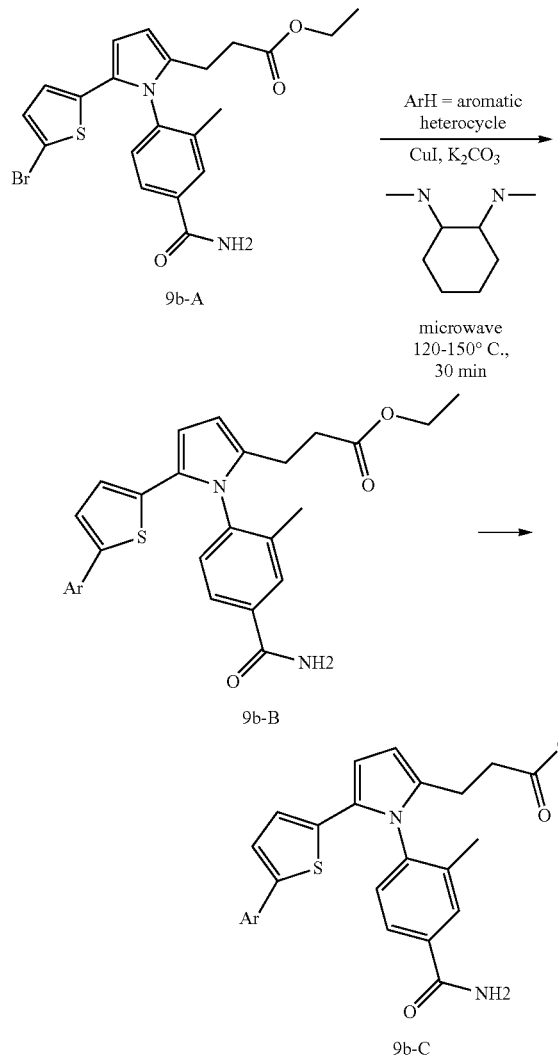

Representative procedure for Scheme 9b: Synthesis of 3-[1-(4-carbamoyl-2-methyl-phenyl)-5-(5-imidazole-1-yl-thiophene-2-yl)-1H-pyrrole-2-yl]-propionic acid Synthesis of 3-[1-(4-carbamoyl-2-methyl-phenyl)-5-(5-imidazole-1-yl-thiophene-2-yl)-1H-pyrrole-2-yl]-propionic acid ethyl ester Prepared using same protocol as Step 1 of Scheme 9a except starting with ethyl 3-(5-(5-bromothiophen-2-yl)-1-(4-carbamoyl-2-methylphenyl)-1H-pyrrol-2-yl)propanoate (which was prepared according to the first 3 steps of Scheme 1, $R_2$=5-bromothiophen-2-yl, and $R_1$=4-carbamoyl-2-methylphenyl).

Synthesis of 3-[1-(4-carbamoyl-2-methyl-phenyl)-5-(5-imidazole-1-yl-thiophene-2-yl)-1H-pyrrole-2-yl]-propionic acid 3-[1-(4-carbamoyl-2-methyl-phenyl)-5-(5-imidazole-1-yl-thiophene-2-yl)-1H-pyrrole-2-yl]-propionic acid ethyl ester was hydrolyzed according to the procedure described in the final step of scheme 4 to give the title compound 3-[1-(4-carbamoyl-2-methyl-phenyl)-5-(5-imidazole-1-yl-thiophene-2-yl)-1H-pyrrole-2-yl]-propionic acid.

Scheme 10: A general scheme for preparing GSNOR inhibitors with structure 10C

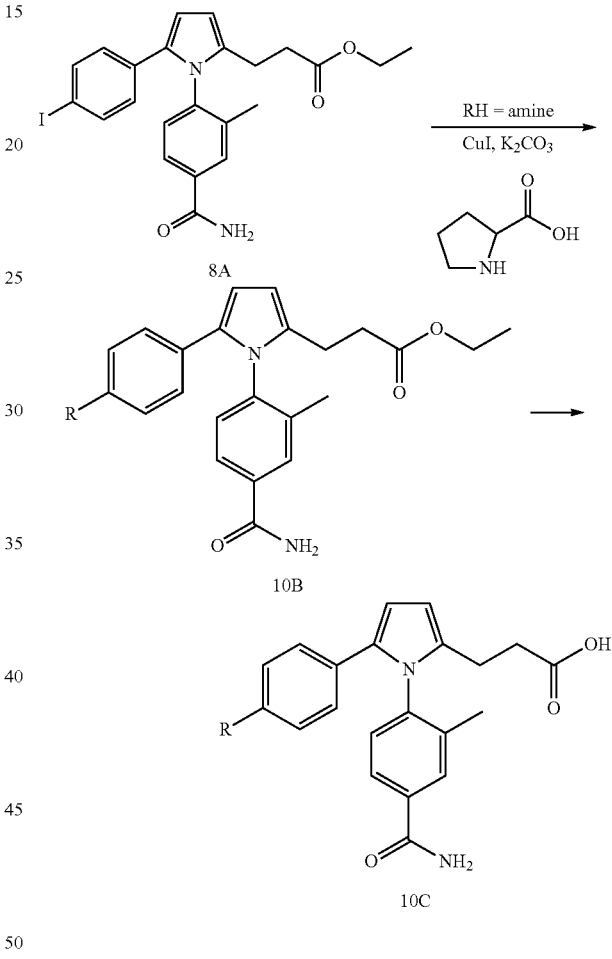

Representative procedure for Scheme 10: Synthesis of 3-[1-(4-carbamoyl-2-methyl-phenyl)-5-(4-morpholin-4-yl-phenyl-1H-pyrrole-2-yl]-propionic acid Synthesis of 3-[1-(4-carbamoyl-2-methyl-phenyl)-5-(4-morpholin-4-yl-phenyl-1H-pyrrole-2-yl]-propionic acid ethyl ester L-proline (14 mg, 0.08 mmol) was dissolved in DMSO and degassed by bubbling argon through the solution for 2 minutes. The resulting solution was then added to a mixture of 3-[1-(4-carbamoyl-2-methyl-phenyl)-5-(4-iodo-phenyl)-1H-pyrrole-2-yl]-propionic acid ethyl ester (8A) (150 mg, 0.29 mmol), morpholine (0.60 mL, 7.5 mmol), copper iodide (11 mg, 0.06 mmol), and potassium carbonate (86 mg (0.61 mmole) and the resulting reaction mixture again degassed for 2 minutes by bubbling argon gas through the solution. The reaction mixture was then submitted to microwave irradiation for 30 minutes at 120° C. The reaction mixture was then added to ethyl acetate (30 mL), washed with water (2×8 mL), saturated ammonium chloride (5×4 mL), water (5 mL) and brine (5 mL). It was then dried over MgSO$_4$. Chromatography (5 g sep-pak cartridge) 2% methanol in dichloromethane yielded 3-[1-(4-carbamoyl-2-methyl-phenyl)-5-(4-morpholin-4-yl-phenyl-1H-pyrrole-2-yl]-propionic acid ethyl ester (80 mg, 53%).

Synthesis of 3-[1-(4-carbamoyl-2-methyl-phenyl)-5-(4-morpholin-4-yl-phenyl-1H-pyrrole-2-yl]-propionic acid 3-[1-(4-carbamoyl-2-methyl-phenyl)-5-(4-morphylin-1-yl-phenyl)-1H-pyrrol-2-yl]-propionic acid ethyl ester (50 mg, 0.11 mmol) was hydrolyzed using the procedure described above in the final step of Scheme 4 to give the title compound, 3-[1-(4-carbamoyl-2-methyl-phenyl)-5-(4-morpholin-4-yl-phenyl-1H-pyrrole-2-yl]-propionic acid (37 mg, 74%).

Scheme 11: Preparation of 3-[1-(4-carbamoyl-2-methylphenyl)-5-(4-[1,2,4]triazol-4-yl-[phenyl]-1H-pyrrol-2-yl]-propionic acid (11C)

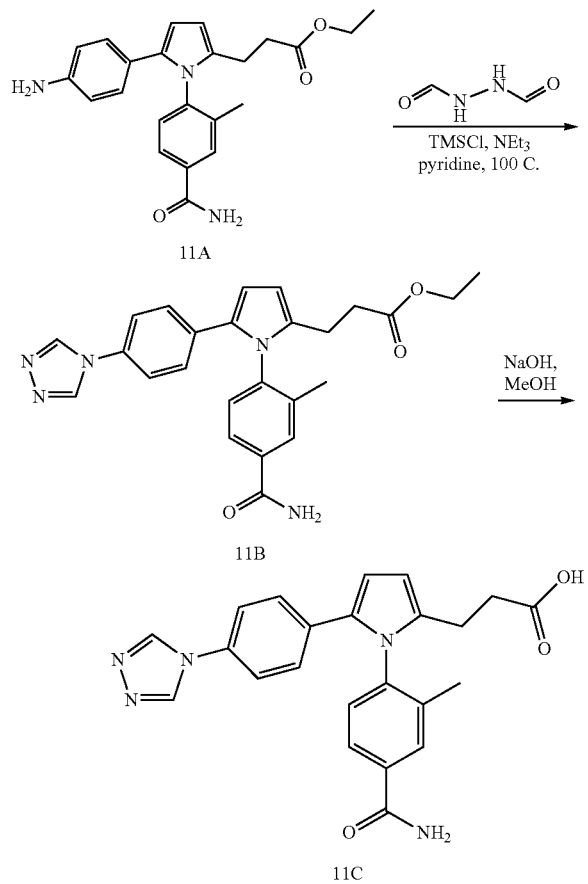

Synthesis of 3-[1-(4-carbamoyl-2-methylphenyl)-5-(4-[1,2,4]triazol-4-yl-phenyl)-1H-pyrrol-2-yl]-propionic acid ethyl ester (11B)

Under a nitrogen atmosphere, 3-[5-(4-aminophenyl)-1-(4-carbamoyl-2-methylphenyl)-1H-pyrrol-2-yl]-propionic acid ethyl ester (11A, synthesis described in Scheme 4 where R1=4-carbamoyl-2-methylphenyl) (102 mg, 0.26 mmol) was dissolved in 4 mL pyridine. 1,2-diformylhydrazine (69 mg, 0.78 mmol) was added. Chlorotrimethylsilane (0.5 mL, 3.9 mmol) was added dropwise. Triethylamine (0.25 mL, 1.82 mmol) was added dropwise. The reaction was heated to 100° C. for 24 hrs. After cooling, the reaction was diluted with water and extracted with ethyl acetate. The combined organic layers were washed with brine, dried over Na$_2$SO$_4$, filtered and concentrated in vacuo. The crude material was purified by preparative tlc plate (1500 microns, 10% IPA/CH$_2$Cl$_2$). The desired band (rf=0.3) was isolated and dried under high vacuum to yield 3-[1-(4-carbamoyl-2-methylphenyl)-5-(4-[1,2,4]triazol-4-yl-phenyl)-1H-pyrrol-2-yl]-propionic acid ethyl ester (11B) (95 mg, 82%, light tan powder).

Synthesis of 3-[1-(4-carbamoyl-2-methylphenyl)-5-(4-[1,2,4]triazol-4-yl-phenyl)-1H-pyrrol-2-yl]-propionic acid (11C)

3-[1-(4-carbamoyl-2-methylphenyl)-5-(4-[1,2,4]triazol-4-yl-phenyl)-1H-pyrrol-2-yl]-propionic acid ethyl ester (11B) (95 mg, 0.21 mmol) was hydrolyzed according to the procedure described above in the final step of Scheme 4 to give the title compound, 3-[1-(4-carbamoyl-2-methylphenyl)-5-(4-[1,2,4]triazol-4-yl-phenyl)-1H-pyrrol-2-yl]-propionic acid (11C) (43 mg, 48%, light yellow powder).

Scheme 12: Preparation of 3-[1-(4-carbamoyl-2-methylphenyl)-5-(4-tetrazol-1-yl-phenyl)-1H-pyrrol-2-yl]-propionic acid (12C)

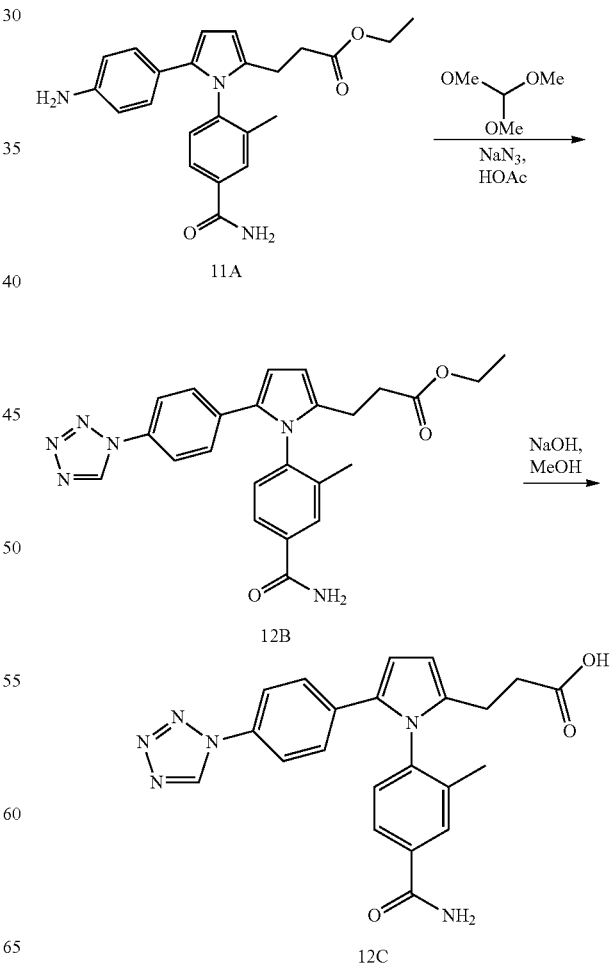

Synthesis of 3-[1-(4-carbamoyl-2-methylphenyl)-5-(4-tetrazol-1-yl-phenyl)-1H-pyrrol-2-yl]-propionic acid ethyl ester (12B)

Under a nitrogen atmosphere, 3-[5-(4-aminophenyl)-1-(4-carbamoyl-2-methylphenyl)-1H-pyrrol-2-yl]-propionic acid ethyl ester (11A, synthesis described in Scheme 4 where R1=4-carbamoyl-2-methylphenyl) (102 mg, 0.26 mmol) was dissolved in 2 mL glacial acetic acid. Trimethylorthoformate (0.1 mL, 0.78 mmol) was added. The mixture was stirred for 20 min. at room temperature. Sodium azide (25 mg, 0.39 mmol) was added and the reaction was heated to 80° C. for 2 hrs. After cooling, the reaction was diluted with water (3 mL) and extracted with ethyl acetate. The combined organic layers were washed with brine, dried over Na$_2$SO$_4$, filtered and concentrated in vacuo. The crude material was purified by preparative TLC plate (1500 microns, 10% IPA/CH$_2$Cl$_2$). The desired band (rf=0.5) was isolated and dried under high vacuum to yield 3-[1-(4-carbamoyl-2-methylphenyl)-5-(4-tetrazol-1-yl-phenyl)-1H-pyrrol-2-yl]-propionic acid ethyl ester (12B) (71 mg, 60%, light orange powder).

Synthesis of 3-[1-(4-carbamoyl-2-methylphenyl)-5-(4-tetrazol-1-yl-phenyl)-1H-pyrrol-2-yl]-propionic acid (12C)

3-[1-(4-carbamoyl-2-methylphenyl)-5-(4-tetrazol-1-yl-phenyl)-1H-pyrrol-2-yl]-propionic acid ethyl ester (12B) (71 mg, 0.16 mmol) was hydrolyzed according to the procedure described above in the final step of scheme 4 to give the title compound, 3-[1-(4-carbamoyl-2-methylphenyl)-5-(4-tetrazol-1-yl-phenyl)-1H-pyrrol-2-yl]-propionic acid (12C) (50 mg, 75%, off-white powder).

Scheme 13: Preparation of 3-[1-(4-carbamoyl-2-methylphenyl)-5-(4-ureidophenyl-1H-pyrrol-2-yl]-propionic acid (13D)

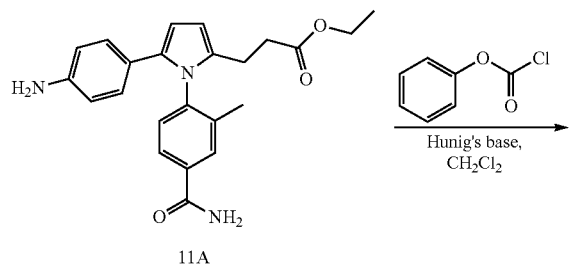

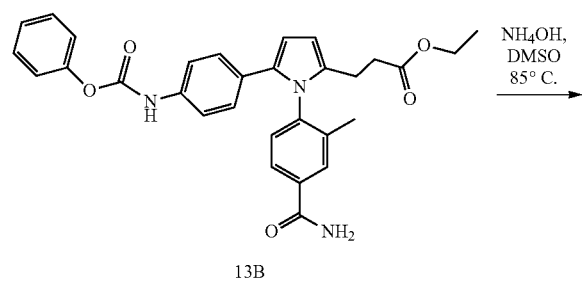

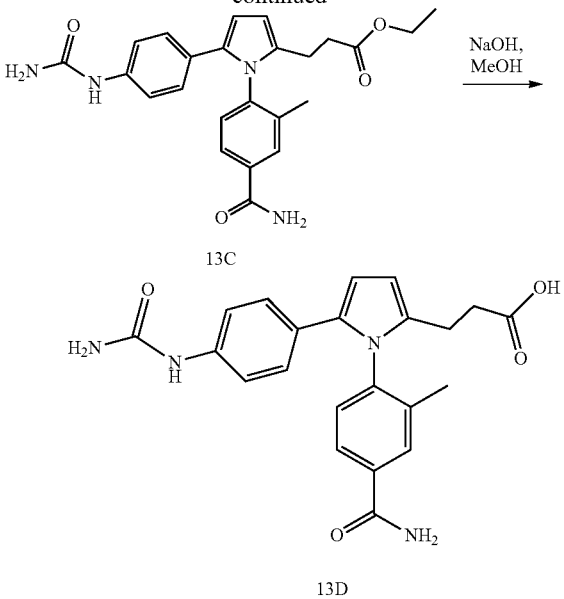

Synthesis of 3-[1-(4-carbamoyl-2-methylphenyl)-5-(4-phenoxycarbonylaminophenyl)-1H-pyrrol-2-yl]-propionic acid ethyl ester (13B)

Under a nitrogen atmosphere, 3-[5-(4-aminophenyl)-1-(4-carbamoyl-2-methylphenyl)-1H-pyrrol-2-yl]-propionic acid ethyl ester (11A, synthesis described in Scheme 4 where R1=4-carbamoyl-2-methylphenyl) (106 mg, 0.26 mmol) was dissolved in 1 mL methylene chloride. The mixture was cooled in an ice bath. Hünig's base (0.12 mL, 0.65 mmol) was added. Phenylcarbamate (0.05 mL, 0.39 mmol) was added dropwise. The reaction was stirred at 0° C. for 30 min, and then allowed to warm to room temperature. After 24 hrs, 3 mL THF/3 mL sodium bicarbonate was added and stirred for 40 min. Then ethyl acetate (3 mL) was added and the layers separated. The aqueous layer was further extracted with ethyl acetate. The combined organic layers were washed with brine, dried over Na$_2$SO$_4$, filtered and concentrated in vacuo. The crude material was purified by preparative TLC plate (1500 microns, 5% MeOH/CH$_2$Cl$_2$). The desired band (rf=0.51) was isolated and dried under high vacuum to yield 3-[1-(4-carbamoyl-2-methylphenyl)-5-(4-phenoxycarbonylaminophenyl)-1H-pyrrol-2-yl]-propionic acid ethyl ester (13B) (66 mg, 48%, hygroscopic tan powder).

Synthesis of 3-[1-(4-carbamoyl-2-methylphenyl)-5-(4-ureidophenyl)-1H-pyrrol-2-yl]-propionic acid ethyl ester (13C)

Under a nitrogen atmosphere, ammonium hydroxide (2 mL) was slowly added to 3-[1-(4-carbamoyl-2-methylphenyl)-5-(4-phenoxycarbonylaminophenyl)-1H-pyrrol-2-yl]-propionic acid ethyl ester (13B) (66 mg, 0.13 mmol). Dimethylsulfoxide (1 mL) was slowly added. The reaction was then heated to 85° C. for 24 hrs. After cooling, the reaction was diluted with water and extracted with ethyl acetate. The combined organic layers were dried over Na$_2$SO$_4$, filtered and concentrated in vacuo. The crude material was purified by preparative TLC plate (1500 microns, 10% IPA/CH$_2$Cl$_2$). The desired band (rf=0.2) was isolated and dried under high vacuum to yield 3-[1-(4-carbamoyl-2-methylphenyl)-5-(4-ureidophenyl)-1H-pyrrol-2-yl]-propionic acid ethyl ester (13C) (20 mg, 35%, light yellow powder).

Synthesis of 3-[1-(4-carbamoyl-2-methylphenyl)-5-(4-ureidophenyl)-1H-pyrrol-2-yl]-propionic acid (13D)

3-[1-(4-carbamoyl-2-methylphenyl)-5-(4-ureidophenyl)-1H-pyrrol-2-yl]-propionic acid ethyl ester (13C) (20 mg, 0.05 mmol) was hydrolyzed according to the procedure described above in the final step of scheme 4 to give the title compound, 3-[1-(4-carbamoyl-2-methylphenyl)-5-(4-ureidophenyl)-1H-pyrrol-2-yl]-propionic acid (13D) (9.0 mg, 48%, light yellow powder).

Scheme 14: Preparation of 3-[1-(4-carbamoyl-2-methylphenyl)-5-(4-methanesulfonylaminophenyl)-1H-pyrrol-2-yl]-propionic acid (14C)

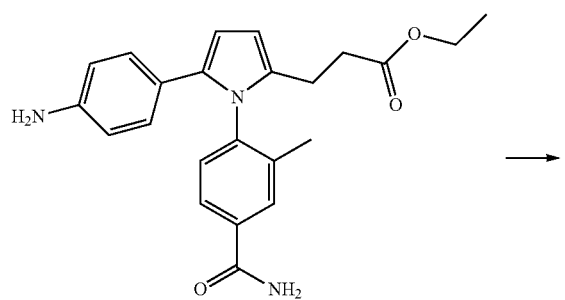

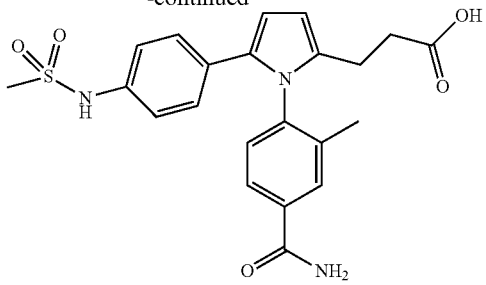

14C

Synthesis of 3-[1-(4-carbamoyl-2-methylphenyl)-5-(4-methanesulfonylaminophenyl)-1H-pyrrol-2-yl]-propionic acid

Step 1

Under nitrogen atmosphere, 3-[1-(4-carbamoyl-2-methyl-phenyl)-5-(amino-phenyl)-1H-pyrrole-2-yl]-propionic acid ethyl ester (11A, synthesis described in Scheme 4 where R1=4-carbamoyl-2-methylphenyl) (51 mg, 0.13 mmol) was dissolved in 1 mL anhydrous THF. Triethylamine (0.04 mL, 0.26 mmol) and then methane sulfonylchloride (0.01 mL, 0.13 mmol) were added. After 18 hrs, 0.01 mL methane sulfonylchloride was added to push the reaction to completion. After another 18 hrs, the reaction was diluted with water and extracted with EtOAc (3×5 mL). The combined organic layers were dried over $Na_2SO_4$, filtered and concentrated in vacuo. The crude material was purified by preparative TLC plate (5% MeOH/$CH_2Cl_2$). 14B, ethyl 3-(1-(4-carbamoyl-2-methylphenyl)-5-(4-(methylsulfonamido)phenyl)-1H-pyrrol-2-yl)propanoate was isolated, rf=0.17 (28 mg, 50%).

Step 2

Product 14B (28 mg, 0.052 mmol) was hydrolyzed according to the procedure described above in the final step of scheme 4 to give the title compound 3-[1-(4-carbamoyl-2-methylphenyl)-5-(4-methanesulfonylaminophenyl)-1H-pyrrol-2-yl]-propionic acid (14C) (19 mg, 82%, yellow powder).

Scheme 15: Preparation of 3-[1-(4-carbamoyl-2-methylphenyl)-5-(4-[1,2,3]triazol-1-yl-phenyl)-1H-pyrrol-2-yl]-propionic acid (15C)

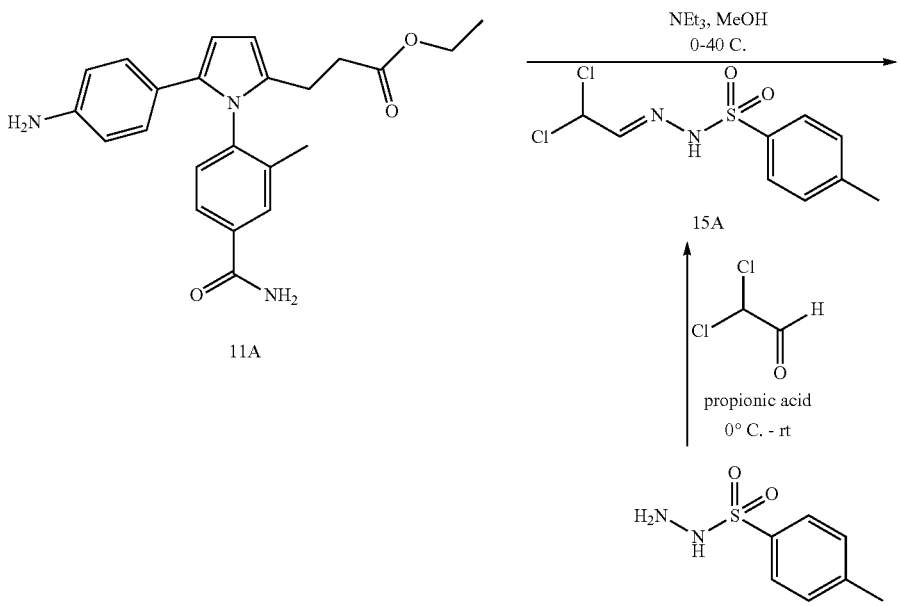

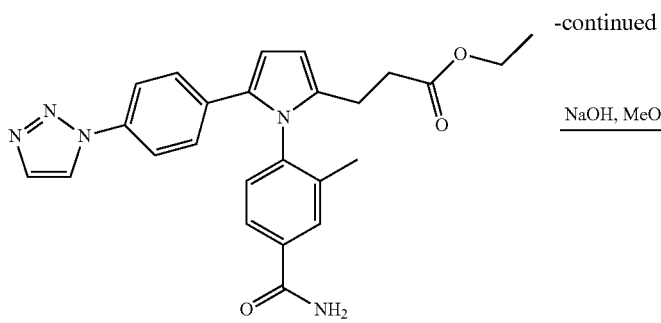

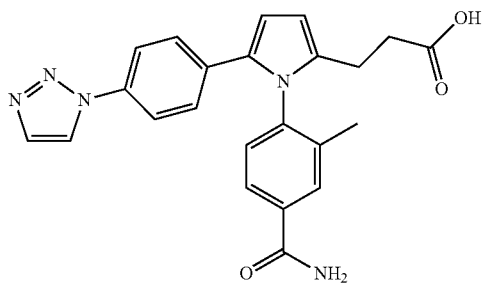

15B → 15C (NaOH, MeOH)

Synthesis of 2,2-dichloroacetaldehyde tosylhydrazone (15A)

To an Erlenmeyer flask cooled in ice water was added p-toluene sulfonylhydrazide (466 mg, 2.5 mmol) to propionic acid (4 mL). Dichloroacetaldehyde (282 mg, 2.5 mmol) was slowly added. The reaction was stirred at 0° C. for 30 min, and then warmed to room temperature. After 2 hr, the reaction was cooled to 0° C. for another 2 hr, and then the precipitate was collected by filtration and rinsed well with toluene. The product was dried in vacuo to yield 2,2-dichloroacetaldehyde tosylhydrazone (15A) (356 mg, 50%, white powder).

Synthesis of 3-[1-(4-carbamoyl-2-methylphenyl)-5-(4-[1,2,3]triazol-1-yl-phenyl)-1H-pyrrol-2-yl]-propionic acid ethyl ester (15B)

Under a nitrogen atmosphere, 3-[5-(4-aminophenyl)-1-(4-carbamoyl-2-methylphenyl)-1H-pyrrol-2-yl]-propionic acid ethyl ester (11A, see Scheme 11) (103 mg, 0.26 mmol) was dissolved in methanol (5 mL). Triethylamine (0.07 mL, 0.48 mmol) was added. The mixture was cooled to 0° C. 2,2-dichloroacetaldehyde tosylhydrazone (15A) (62 mg, 0.22 mmol), dissolved in methanol (1.5 mL) was added slowly. The reaction was stirred at 0° C. for 5 min, and then heated to 40° C. for 3 hrs, then cooled to room temperature for 16 hrs. 2,2-dichloroacetaldehyde tosylhydrazone (15A) (62 mg) was added and stirred an additional 4 hr. The reaction was diluted with water (5 mL) and extracted with ethyl acetate. The combined organic layers were washed with brine, dried over $Na_2SO_4$, filtered and concentrated in vacuo. The crude material was purified by preparative TLC plate (1500 microns, 10% IPA/$CH_2Cl_2$). The desired band (RF=0.3) was isolated and dried under high vacuum to yield 3-[1-(4-carbamoyl-2-methylphenyl)-5-(4-[1,2,3]triazol-1-yl-phenyl)-1H-pyrrol-2-yl]-propionic acid ethyl ester (15B) (50 mg, 43%, light tan powder).

Synthesis of 3-[1-(4-carbamoyl-2-methylphenyl)-5-(4-[1,2,3]triazol-1-yl-phenyl)-1H-pyrrol-2-yl]-propionic acid (15C)

3-[1-(4-carbamoyl-2-methylphenyl)-5-(4-[1,2,3]triazol-1-yl-phenyl)-1H-pyrrol-2-yl]-propionic acid ethyl ester (15B) (50 mg, 0.11 mmol) was hydrolyzed according to the procedure described above in the final step of scheme 4 to give the title compound 3-[1-(4-carbamoyl-2-methylphenyl)-5-(4-[1,2,3]triazol-1-yl-phenyl)-1H-pyrrol-2-yl]-propionic acid (15C) (12 mg, 25%, light green powder).

Scheme 16: Preparation of 3-[1-(4-Carbamoyl-2-methylphenyl)-5-(4-methoxycarbonyl-methyoxyphenyl)-1H-pyrrol-2-yl]-propionic acid (16C)

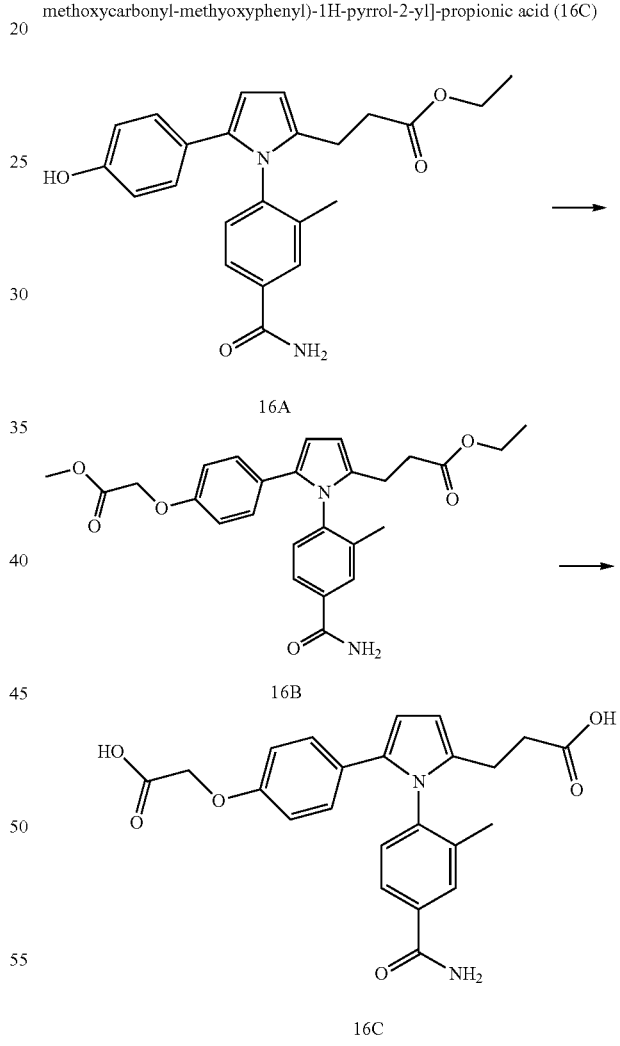

Synthesis of 3-[1-(4-Carbamoyl-2-methylphenyl)-5-(4-methoxycarbonyl-methyoxyphenyl)-1H-pyrrol-2-yl]-propionic acid ethyl ester (16B)

3-[1-(4-Carbamoyl-2-methylphenyl)-5-(4-hyroxyphenyl)-1H-pyrrol-2-yl]-propionic acid ethyl ester 16A (synthesized according to the first three steps of Scheme 1, where Ar2=4-hyroxyphenyl, and Ar1=4-carbamoyl-2-methylphenyl) (47 mg, 0.12 mmol) was dissolved in 0.5 mL N,N-dimethylformamide. Potassium carbonate (33 mg, 0.24 mmol) was added. Methyl 2-bromoacetate (0.02 mL, 0.13 mmol) was added. After 18 hrs, the reaction was poured into NH$_4$Cl (sat) and extracted with EtOAc (2×5 mL). The combined organic layers were washed with brine and dried over Na$_2$SO$_4$, filtered and concentrated in vacuo. The residue was purified by preparative TLC plate (10% IPA/CH$_2$Cl$_2$). The desired band (RF=0.57) was isolated and dried under high vacuum to yield 3-[1-(4-Carbamoyl-2-methylphenyl)-5-(4-methoxycarbonyl-methyoxyphenyl)-1H-pyrrol-2-yl]-propionic acid ethyl ester (16B) (57 mg, 98%, white powder).

Synthesis of 3-[1-(4-Carbamoyl-2-methylphenyl)-5-(4-methoxycarbonyl-methyoxyphenyl)-1H-pyrrol-2-yl]-propionic acid (16C)

3-[1-(4-Carbamoyl-2-methylphenyl)-5-(4-methoxycarbonylmethoxy-phenyl)-1H-pyrrol-2-yl]-propionic acid ethyl ester 16B (57 mg, 0.12 mmol) was dissolved in 1 mL methanol. 1 N NaOH (0.25 mL, 0.25 mmoL) was added. After 18 hrs, the reaction was concentrated in vacuo and diluted with water. The pH was adjusted to 1 with 1 M HCl and extracted with EtOAc (3×4 mL). The combined organic layers were dried over Na$_2$SO$_4$, filtered and concentrated in vacuo. The residue was triturated with hexanes and dried under high vacuum to yield 3-[1-(4-Carbamoyl-2-methylphenyl)-5-(4-methoxycarbonyl-methyoxyphenyl)-1H-pyrrol-2-yl]-propionic acid (16C) (34 mg, 65%, light yellow powder).

Scheme 17: Preparation of 3-{1-(4-carbamoyl-2-methylphenyl)-5-[4-2-methoxyacetylamino)-phenyl]-1H-pyrrol-2-yl}-propionic acid (17C)

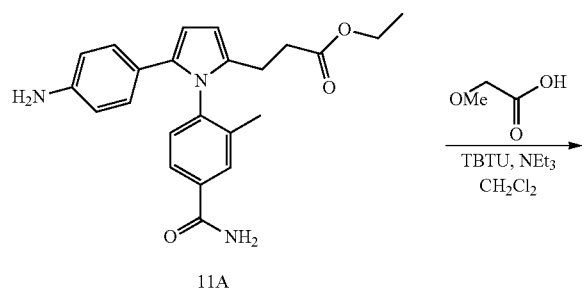

11A

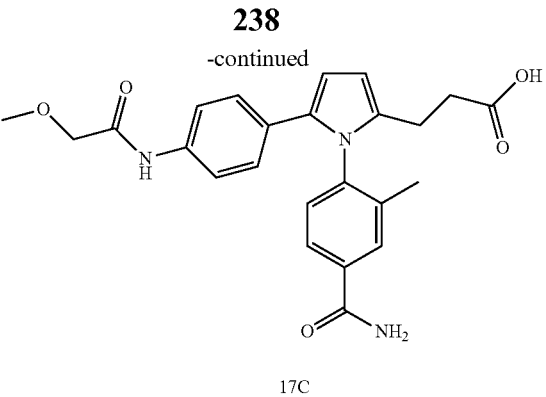

17C

Synthesis of 3-[1-(4-carbamoyl-2-methylphenyl-5-[4-(2-methoxyacetylamino)-phenyl]-1H-pyrrol-2-yl]-propionic acid ethyl ester (17B)

Under a nitrogen atmosphere, 3-[5-(4-aminophenyl)-1-(4-carbamoyl-2-methylphenyl)-1H-pyrrol-2-yl]-propionic acid ethyl ester (11A, see scheme 11) (102 mg, 0.26 mmol), methoxyacetic acid (0.02 mL, 0.31 mmol), and TBTU (167 mg, 0.52 mmol) were dissolved in 1 mL methylene chloride. Triethylamine (0.11 mL, 0.78 mmol) was added. After 24 hrs, the reaction was diluted with water/NaHCO$_3$ (sat.) (1:1) and extracted with methylene chloride. The combined organic layers were dried over Na$_2$SO$_4$, filtered and concentrated in vacuo. The crude material was purified by preparative TLC plate (1500 microns, 10% IPA/CH$_2$Cl$_2$). The desired band (rf=0.67) was isolated and dried under high vacuum to yield 3-{1-(4-carbamoyl-2-methylphenyl-5-[4-(2-methoxyacetylamino)-phenyl]-1H-pyrrol-2-yl}-propionic acid ethyl ester (17B) (80 mg, 66%, yellow solid).

Synthesis of 3-[1-(4-carbamoyl-2-methylphenyl-5-[4-(2-methoxyacetylamino)-phenyl]-1H-pyrrol-2-yl]-propionic acid (17C)

3-{1-(4-carbamoyl-2-methylphenyl-5-[4-(2-methoxyacetylamino)-phenyl]-1H-pyrrol-2-yl}-propionic acid ethyl ester (17B) (80 mg, 0.17 mmol) was hydrolyzed according to the procedure described above in the final step of scheme 4, to give the title compound 3-{1-(4-carbamoyl-2-methylphenyl-5-[4-(2-methoxyacetylamino)-phenyl]-1H-pyrrol-2-yl}-propionic acid (17C) (46 mg, 62%, light yellow powder).

Scheme 18: Preparation of 3-{1-(4-carbamoyl-2-methylphenyl)-5-[4-2-hydroxyacetylamino)-phenyl]-1H-pyrrol-2-yl]-propionic acid (18C)

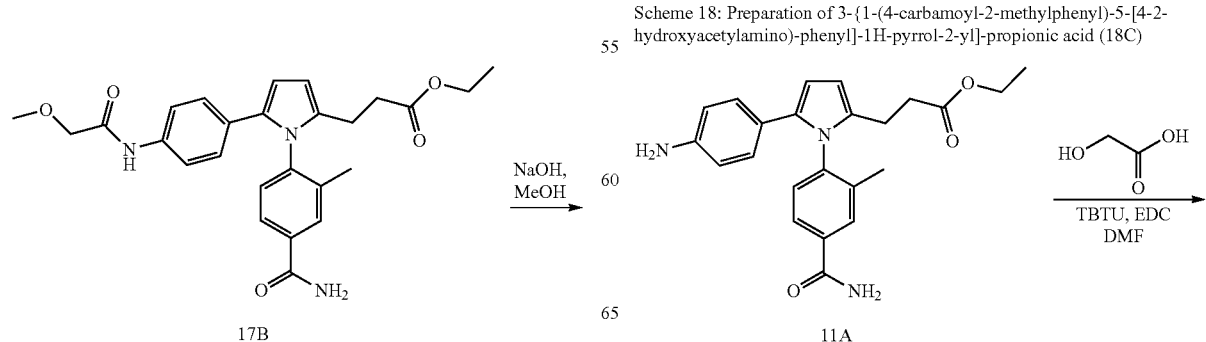

17B

11A

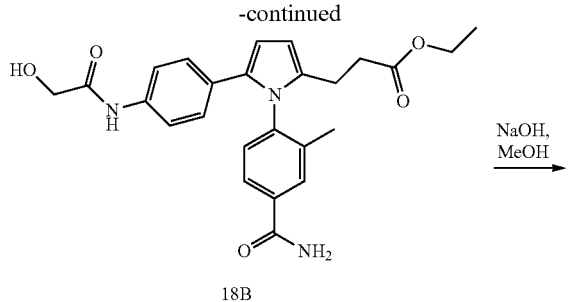

Synthesis of 3-[1-(4-carbamoyl-2-methylphenyl)-5-[4-(2-hydroxyacetylamino)-phenyl]-1H-pyrrol-2-yl]-propionic acid ethyl ester (18B)

Under a nitrogen atmosphere, 3-[5-(4-aminophenyl)-1-(4-carbamoyl-2-methylphenyl)-1H-pyrrol-2-yl]-propionic acid ethyl ester (11A, see scheme 11) (102 mg, 0.26 mmol), glycolic acid (40 mg, 0.52 mmol), TBTU (167 mg, 0.52 mmol), and EDC (101 mg, 0.65 mmol) were dissolved in 1 mL N,N-dimethylformamide. After 24 hrs, the reaction was diluted with water and extracted with ethyl acetate. The combined organic layers were dried over $Na_2SO_4$, filtered and concentrated in vacuo. The crude material was purified by preparative TLC plate (1500 microns, 10% IPA/$CH_2Cl_2$). The desired band (rf=0.25) was isolated and dried under high vacuum to yield 3-{1-(4-carbamoyl-2-methylphenyl)-5-[4-(2-hydroxyacetylamino)-phenyl]-1H-pyrrol-2-yl]-propionic acid ethyl ester (18B) (66 mg, 60%, yellow powder).

Synthesis of 3-[1-(4-carbamoyl-2-methylphenyl)-5-[4-(2-hydroxyacetylamino)-phenyl]-1H-pyrrol-2-yl]-propionic acid (18C)

3-[1-(4-carbamoyl-2-methylphenyl)-5-[4-(2-hydroxyacetylamino)-phenyl]-1H-pyrrol-2-yl]-propionic acid ethyl ester (18B) (66 mg, 0.16 mmol) was hydrolyzed according to the procedure described above in the final step of scheme 4, to give the title compound 3-{1-(4-carbamoyl-2-methylphenyl)-5-[4-(2-hydroxyacetylamino)-phenyl]-1H-pyrrol-2-yl]-propionic acid (18C) (44 mg, 72%, light yellow powder).

Scheme 19: A general scheme for preparing GSNOR inhibitors with structure 19F

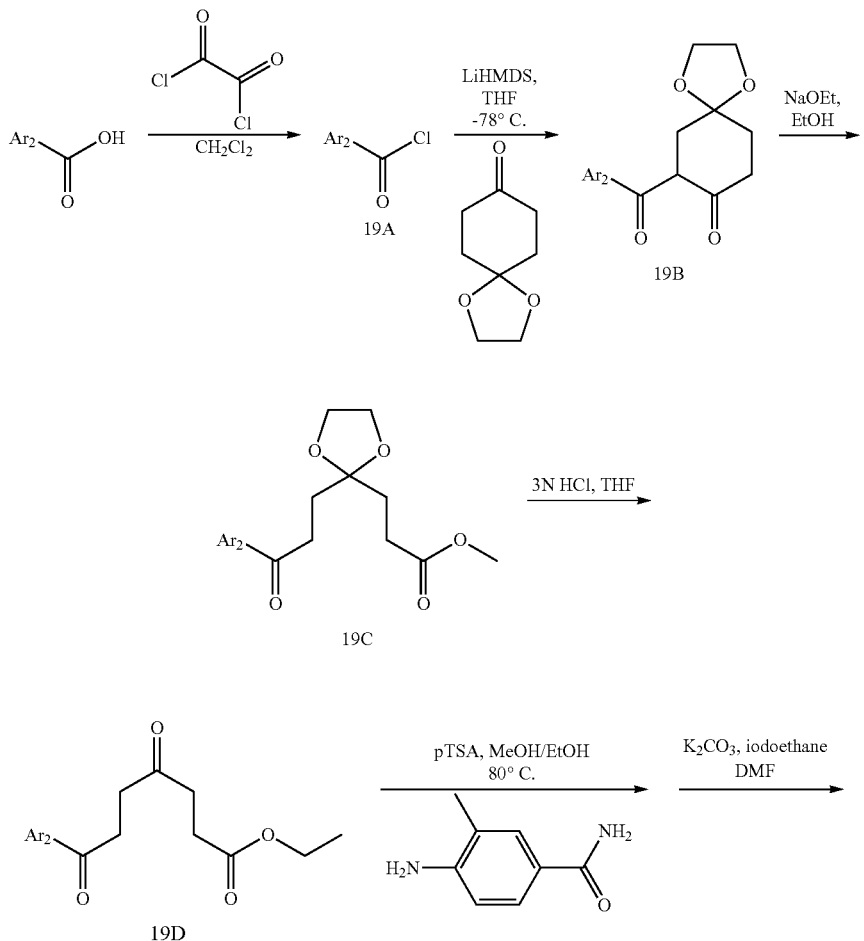

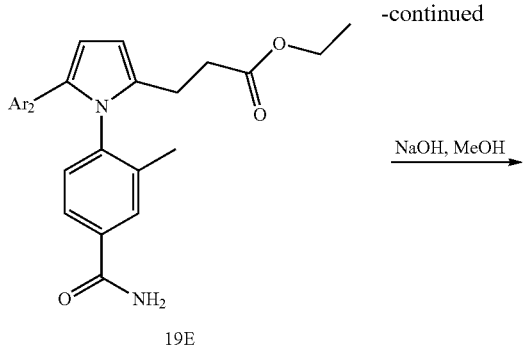 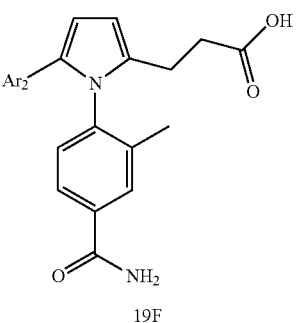

19E → 19F (NaOH, MeOH)

Representative procedure for Scheme 19: Synthesis of 3-[5-Benzothiazol-6-yl-1-(4-carbamoyl-2-methylphenyl)-1H-pyrrol-2-yl]-propionic acid (19F, Ar2=benzothiazol-6-yl)

Synthesis of Benzothiazole-6-carbonyl chloride (19A, Ar2=benzothiazol-6-yl)

Under a nitrogen atmosphere, benzothiazole-6-carboxylic acid (1.014 g, 5.6 mmol) was dissolved in methylene chloride (25 mL). Five drops of N,N-dimethylforamide was added. Oxalyl chloride (0.5 mL, 5.6 mmol) was slowly added. After 2 hrs, the reaction was heated to 30° C. for 16 hrs. The reaction was concentrated in vacuo to yield benzothiazole-6-carbonyl chloride (19A) (1.665 g, quant., light yellow powder).

Synthesis of 7-(Benzothiazole-6-carbonyl)-1,4-dioxa-spiro[4.5]decan-8-one (19B, Ar2=benzothiazol-6-yl)

Under a nitrogen atmosphere, lithium hexamethyldisilazide (2.4 mL, 2.4 mmol) was mixed with THF (5 mL). The reaction was cooled to −78° C. 1,4-cyclohexane-dione monoethylene acetal (374 mg, 2.4 mmol), dissolved in THF (2 mL) was slowly added via dropping funnel. The reaction was stirred for 20 min at −78° C. It was then cannulated to a flask, cooled at −78° C., containing benzothiazole-6-carbonyl chloride (498 mg, 2.52 mmol) dissolved in THF (5 mL). After the addition, the reaction was stirred at −78° C. for 1 hr, and then allowed to warm to room temperature. After 12 h, water (30 mL) was added and extracted with ethyl acetate (3×20 mL). The combined organic layers were washed with 10% citric acid (20 mL), water (20 mL), bicarb (20 mL), and brine (20 mL). It was then dried over Na$_2$SO$_4$, filtered and concentrated in vacuo. The crude material was purified by silica gel column (1:1 EtOAc/Hexanes) to yield 7-(Benzothiazole-6-carbonyl)-1,4-dioxa-spiro[4.5]decan-8-one (19B) (271 mg, 35%, light yellow solid).

Synthesis of 3-[2-(3-Benzothiazol-6-yl-3-oxo-propyl)-[1,3]dioxolan-2-yl]-propionic acid ethyl ester (19C, Ar2=benzothiazol-6-yl)

Under a nitrogen atmosphere, 7-(Benzothiazole-6-carbonyl)-1,4-dioxa-spiro[4.5]decan-8-one (271 mg, 0.85 mmol) was dissolved in ethanol (1 mL). 2.43 M sodium ethoxide solution (0.01 mL, 0.03 mmol) was added. After 12 hrs, reaction was concentrated in vacuo. The residue was diluted with 10 mL EtOAc/5 mL 10% citric acid. The layers were separated. The aqueous layer was further extracted with EtOAc (3×3 mL). The combined organic layers were washed with water (5 mL) and brine (5 mL), dried over Na$_2$SO$_4$, filtered and concentrated in vacuo. The crude material was purified by silica gel column (40% EtOAc/hexanes) to yield 3-[2-(3-Benzothiazol-6-yl-3-oxo-propyl)-[1,3]dioxolan-2-yl]-propionic acid ethyl ester (19C) (100 mg, 38%, light yellow oil).

Synthesis of 7-Benzothiaol-6-yl-4,7-dioxo-heptanoic acid ethyl ester (19D, Ar2=benzothiazol-6-yl)

Under a nitrogen atmosphere, 3-[2-(3-Benzothiazol-6-yl-3-oxo-propyl)-[1,3]dioxolan-2-yl]-propionic acid ethyl ester (19C) (100 mg, 0.28 mmol) was dissolved in THF (1 mL). 3N HCl was added and stirred at room temperature. After 12 hrs, the reaction was diluted with water and extracted with EtOAc (3 times). The combined organic layers were washed with brine, dried over Na$_2$SO$_4$, filtered and concentrated in vacuo to give 7-Benzothiaol-6-yl-4,7-dioxo-heptanoic acid ethyl ester (19D) (52 mg, 58%, dark red solid; ⅔ as ethyl ester, ⅓ as carboxylic acid).

Synthesis of 3-[5-Benzothiazol-6-yl-1-(4-carbamoyl-2-methylphenyl)-1H-pyrrol-2-yl]-propionic acid ethyl ester (19E, Ar2=benzothiazol-6-yl)

In a 4 mL vial, purged with nitrogen, 7-Benzothiaol-6-yl-4,7-dioxo-heptanoic acid ethyl ester (52 mg, 0.16 mmol) was dissolved in 2 mL ethanol. P-toluenesulfonic acid (9.9 mg, 0.05 mmol) and 4-amino-3-methyl benzamide (37 mg, 0.24 mmol) were added. The vial was capped tightly and heated to 80° C. in an oil bath. After the 12 hrs, the reaction was cooled and concentrated in vacuo. The crude material was dissolved in N,N-dimethylforamide (1 mL). Potassium carbonate (44 mg, 0.32 mmol) was added. Then iodoethane (0.01 mL, 0.17 mmol) was added. The reaction was stirred at room temperature for 12 hrs. The reaction was diluted with water and extracted with ethyl acetate. The combined organic layers were washed with water, brine and dried over Na$_2$SO$_4$, filtered and concentrated in vacuo. The crude product was purified by silica gel column (5% IPA/CH$_2$Cl$_2$) to give 3-[5-Benzothiazol-6-yl-1-(4-carbamoyl-2-methylphenyl)-1H-pyrrol-2-yl]-propionic acid ethyl ester (19E, Ar2=benzothiazol-6-yl) (42 mg, 73% over 2 steps, red solid).

Synthesis of 3-[5-Benzothiazol-6-yl-1-(4-carbamoyl-2-methylphenyl)-1H-pyrrol-2-yl]-propionic acid (19F, Ar2=benzothiazol-6-yl)

3-[5-Benzothiazol-6-yl-1-(4-carbamoyl-2-methylphenyl)-1H-pyrrol-2-yl]-propionic acid ethyl ester (19E) (42 mg, 0.10 mmol) was hydrolyzed according to the procedure described above in the final step of scheme 4, to give the title compound 3-[5-Benzothiazol-6-yl-1-(4-carbamoyl-2-methylphenyl)-1H-pyrrol-2-yl]-propionic acid (19F, Ar2=benzothiazol-6-yl) (23 mg, 59%, light tan powder).

Scheme 20: A general scheme for preparing GSNOR inhibitors with structure 20C

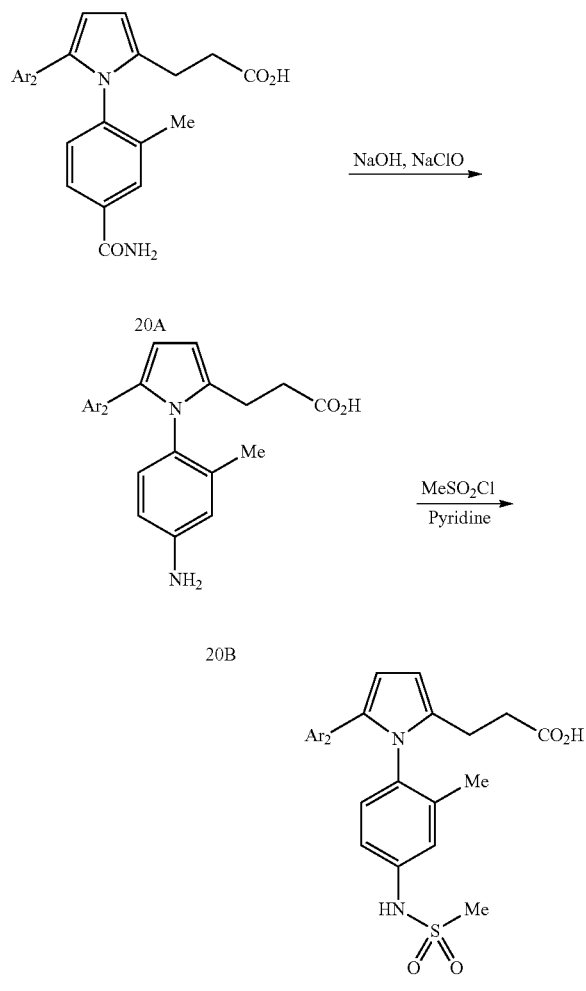

Representative procedure for Scheme 20: Synthesis of 3-(5-(4-(1H-imidazol-1-yl)phenyl)-1-(2-methyl-4-(methylsulfonamido)phenyl)-1H-pyrrol-2-yl)propanoic acid Synthesis of 3-(5-(4-(1H-imidazol-1-yl)phenyl)-1-(4-amino-2-methylphenyl)-1H-pyrrol-2-yl)propanoic acid (20B, Ar2=4-(1H-imidazol-1-yl)phenyl)

3-(5-(4-(1H-imidazol-1-yl)phenyl)-1-(4-carbamoyl-2-methylphenyl)-1H-pyrrol-2-yl)propanoic acid (20A, prepared according to Scheme 5, Ar2=4-carbamoyl-2-methylphenyl) (3.88 g, 9.37 mmol) was added to aq. NaOH (4.12 g, 103.09 mmol, dissolving in 50 mL). Then 11% aq. NaClO (28.83 g, 42.17 mmol) was added dropwise. The resulting mixture was kept at 0~10° C. for 1 h, at 35° C. for 1 h and at 75° C. for 30 min. After cooling to room temperature, the reaction was acidified with 10% hydrochloric acid to pH=7.0 and filtered to remove the solid impurity. The filtrate was further acidified with 10% hydrochloric acid to pH=5.0 and a new precipitate appeared. The precipitate was filtrated and dried to afford 20B, Ar2=4-(1H-imidazol-1-yl)phenyl as a gray powder (3.20 g, 88%).

Synthesis of 3-(5-(4-(1H-imidazol-1-yl)phenyl)-1-(2-methyl-4-(methylsulfonamido)phenyl)-1H-pyrrol-2-yl)propanoic acid (20C, Ar2=4-(1H-imidazol-1-yl)phenyl)

To a solution of pyridine (2 mL) and $CH_3SO_2Cl$/DCM (v/v=1/100, 5 mL) was added a solution of 3-(5-(4-(1H-imidazol-1-yl)phenyl)-1-(4-amino-2-methylphenyl)-1H-pyrrol-2-yl)propanoic acid (20B) (250 mg, 0.74 mmol) in pyridine (2 mL) at 0° C. The mixture was stirred at room temperature for 1 h. The solvents were removed under reduced pressure and the resulting solid was acidified with 10% hydrochloric acid to pH=5.0. The resulting precipitate was isolated by centrifuge, rinsed with water, dried under reduced pressure to afford 20C, Ar2=4-(1H-imidazol-1-yl)phenyl as a brown powder (40 mg, 13%).

Scheme 21: A general scheme for preparing GSNOR inhibitors with structure 21B

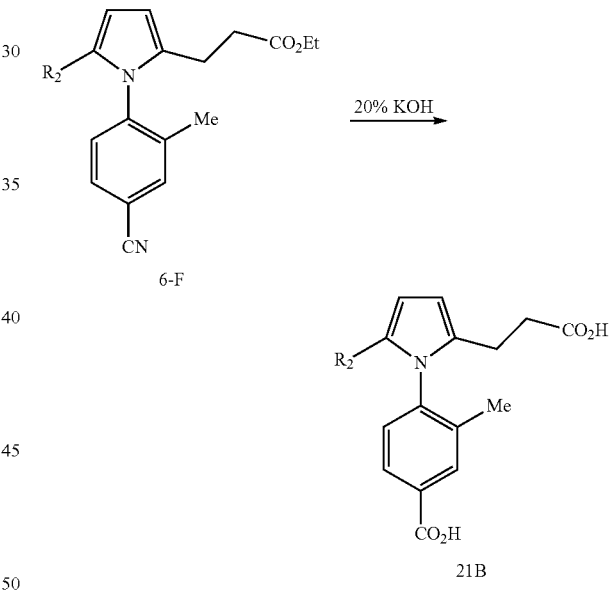

Representative procedure for Scheme 21: Synthesis of 4-(2-(benzo[d][1,3]dioxol-5-yl)-5-(2-carboxyethyl)-1H-pyrrol-1-yl)-3-methylbenzoic acid The mixture of ethyl 3-(5-(benzo[d][1,3]dioxol-5-yl)-1-(4-cyano-2-methylphenyl)-1H-pyrrol-2-yl)propanoate (prepared by Scheme 6, through intermediate 6F, where Ar2=benzo[d][1,3]dioxol-5-yl) (120 mg, 0.298 mmol) and 20% KOH (2 mL) was heated to 80° C. and stirred for 3 h. TLC and LC-MS showed that the reaction was completed. 10% Hydrochloric acid was added to acidify until pH=2. The suspension was centrifuged and dried in vacuum to afford 4-(2-(benzo[d][1,3]dioxol-5-yl)-5-(2-carboxyethyl)-1H-pyrrol-1-yl)-3-methylbenzoic acid as a white solid (85 mg, 73%).

Scheme 22: Preparation of ethyl 3-(1-(4-amino-2-methylphenyl)-5-(4-bromophenyl)-1H-pyrrol-2-yl)propanoate (22C)

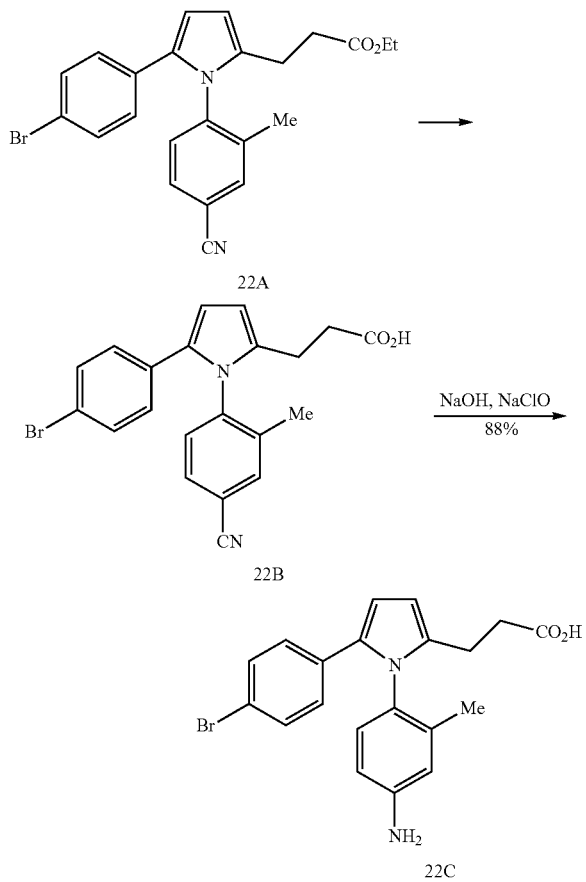

Scheme 23: Preparation of 3-(1-(4-carbomoyl-2-methylphenyl)-5-(4-methylsulfinyl)phenyl)-1H-pyrrol-2-yl)propanoate acid (23D)

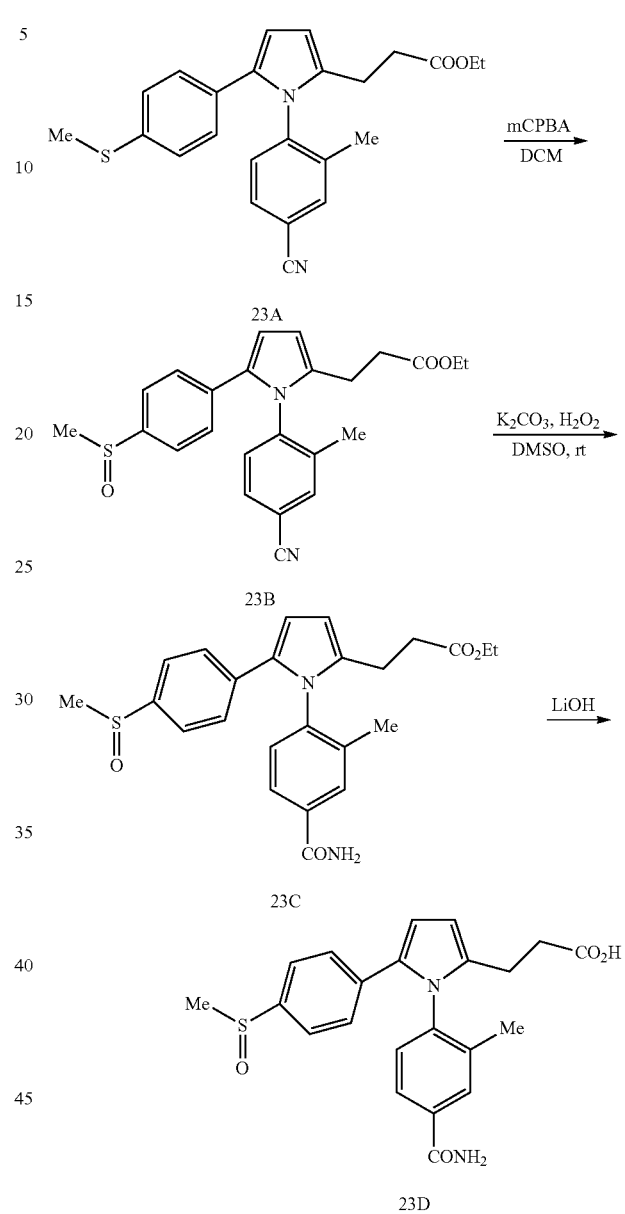

Synthesis of ethyl 3-(5-(4-bromophenyl)-1-(4-cyano-2-methylphenyl)-1H-pyrrol-2-yl)propanoate (22A)

22A was prepared following Scheme 5 through step 5C, where Ar1=4-carbamoyl-2-methylphenyl.

Synthesis of ethyl 3-(5-(4-bromophenyl)-1-(4-cyano-2-methylphenyl)-1H-pyrrol-2-yl)propanoate (22B)

Ethyl 3-(5-(4-bromophenyl)-1-(4-cyano-2-methylphenyl)-1H-pyrrol-2-yl)propanoate (22A) was hydrolyzed according to the procedure described in the final step of Scheme 5, to give the title compound.

Synthesis of ethyl 3-(1-(4-amino-2-methylphenyl)-5-(4-bromophenyl)-1H-pyrrol-2-yl)propanoate (22C)

Ethyl 3-(5-(4-bromophenyl)-1-(4-cyano-2-methylphenyl)-1H-pyrrol-2-yl)propanoate (22B) was converted from the nitrile to the amide following the same procedure described in Scheme 20, step 1 to give the desired title compound, ethyl 3-(1-(4-amino-2-methylphenyl)-5-(4-bromophenyl)-1H-pyrrol-2-yl)propanoate (22C).

Synthesis of ethyl 3-(1-(4-cyano-2-methylphenyl)-5-(4-(methylthio)phenyl)-1H-pyrrol-2-yl)propanoate (23A)

Ethyl 3-(1-(4-cyano-2-methylphenyl)-5-(4-(methylthio)phenyl)-1H-pyrrol-2-yl)propanoate 23A was prepared following Scheme 6 through 6F, where Ar2=4-(methylthio)phenyl.

Synthesis of ethyl 3-(1-(4-cyano-2-methylphenyl)-5-(4-(methylsulfinyl)phenyl)-1H-pyrrol-2-yl)propanoate (23B)

To a solution of ethyl 3-(1-(4-cyano-2-methylphenyl)-5-(4-(methylthio)phenyl)-1H-pyrrol-2-yl)propanoate (23A)

(98 mg, 0.23 mmol) in DCM (1 mL) was added m-CPBA below 0° C. by five portions. Then the reaction mixture was stirred at room temperature for 3 h. TLC showed that the reaction was complete. The mixture was diluted with DCM (10 mL) and washed with sat. NaHCO$_3$ (15 mL), dried over Na$_2$SO$_4$, filtered and concentrated to afford a yellow oil, which was purified by silica gel column chromatography to afford ethyl 3-(1-(4-cyano-2-methylphenyl)-5-(4-(methylsulfinyl)phenyl)-1H-pyrrol-2-yl)propanoate (23B) as a light yellow solid (65 mg, 65%).

Synthesis of ethyl 3-(1-(4-carbamoyl-2-methylphenyl)-5-(4-(methylsulfinyl)phenyl)-1H-pyrrol-2-yl)propanoate (23C)

Ethyl 3-(1-(4-cyano-2-methylphenyl)-5-(4-(methylsulfinyl)phenyl)-1H-pyrrol-2-yl)propanoate (23B) was converted to the amide following the second to last step of Scheme 6 to give compound ethyl 3-(1-(4-carbamoyl-2-methylphenyl)-5-(4-(methylsulfinyl)phenyl)-1H-pyrrol-2-yl)propanoate (23C).

Synthesis of 3-(1-(4-carbamoyl-2-methylphenyl)-5-(4-(methylsulfinyl)phenyl)-1H-pyrrol-2-yl)propanoic acid Ethyl 3-(1-(4-carbamoyl-2-methylphenyl)-5-(4-(methylsulfinyl)phenyl)-1H-pyrrol-2-yl)propanoate (23C) was then hydrolyzed following the final step of Scheme 6 to give the title compound, 3-(1-(4-carbamoyl-2-methylphenyl)-5-(4-(methylsulfinyl)phenyl)-1H-pyrrol-2-yl)propanoic acid (23D).

Scheme 24: Intentionally omitted

Scheme 25: A general scheme for preparing GSNOR inhibitors with structure 25E

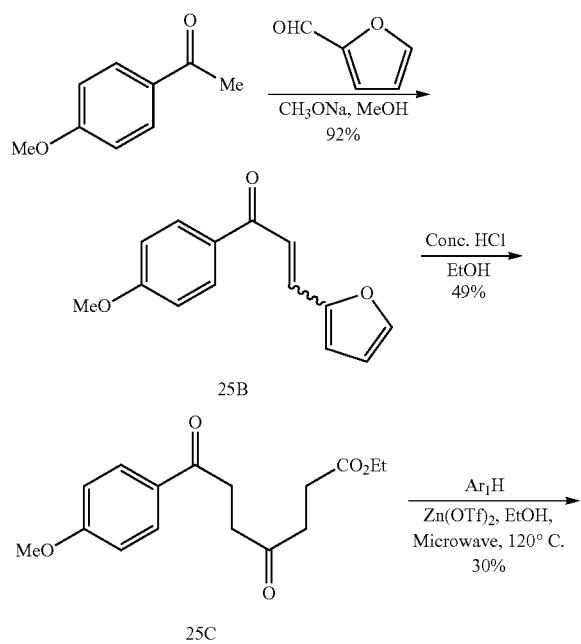

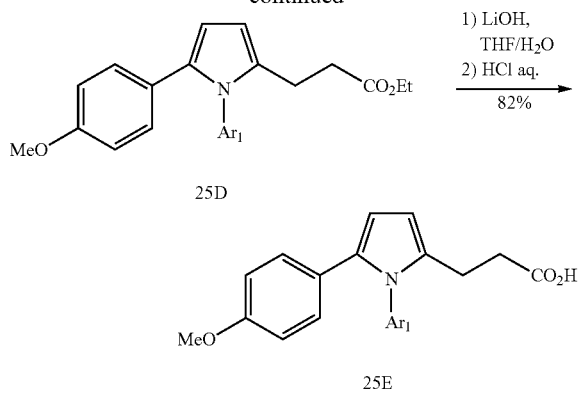

Representative procedure for Scheme 25: Synthesis of 3-(1-(4-(1H-imidazol-2-yl)-2-methylphenyl)-5-(4-methoxyphenyl)-1H-pyrrol-2-yl)propanoic acid (25E, Ar1=4-(1H-imidazol-2-yl)-2-methylphenyl)

Synthesis of 3-(furan-2-yl)-1-(4-methoxyphenyl)prop-2-en-1-one (25B)

To a solution of 1-(4-methoxyphenyl)ethanone (17.0 g, 113.0 mmol) in methanol (240 mL) was added a solution of 2-furaldehyde (12.0 g, 125.0 mmol) in methanol (240 mL) followed by the addition of sodium methoxide (6.10 g, 113.0 mmol). The reaction mixture was stirred at room temperature for 24 h, and then was neutralized with HCl aq. (6.0 M, 18.8 mL). The volatile was removed in vacuum. The residue was dissolved in ethyl acetate (500 mL), washed with water (250 mL) and brine (250 mL), dried over Na$_2$SO$_4$, filtered, concentrated and purified by silica gel column chromatography (PE:EA=5:1~3:1) to afford 3-(furan-2-yl)-1-(4-methoxyphenyl)prop-2-en-1-one (25B) as a yellow solid (23.80 g, 92%).

Synthesis of ethyl 7-(4-methoxyphenyl)-4,7-dioxoheptanoate (25C)

To a solution of compound 3-(furan-2-yl)-1-(4-methoxyphenyl)prop-2-en-1-one (8.0 g, 35.1 mmol) in ethanol (150 mL) was added conc. HCl (38.0 mL). The resulting mixture was refluxed for 14 h. Then the solution was neutralized with 10% Na$_2$CO$_3$ solution. The volatile was removed. The residue was diluted with DCM (750 mL), washed with water (200 mL) and brine (200 mL), dried over Na$_2$SO$_4$, filtered, concentrated and purified by silica gel column chromatography (PE:EA=8:1~4:1) to give ethyl 7-(4-methoxyphenyl)-4,7-dioxoheptanoate (25C) as a yellow solid (5.10 g, 49%).

Synthesis of ethyl 3-(1-(4-(1H-imidazol-2-yl)-2-methylphenyl)-5-(4-methoxyphenyl)-1H-pyrrol-2-yl)propanoate (25D, Ar1=4-(1H-imidazol-2-yl)-2-methylphenyl)

To a solution of 4-(1H-imidazol-2-yl)-2-methylaniline (Method #3) (1.0 g, 5.76 mmol) and ethyl 7-(4-methoxyphenyl)-4,7-dioxoheptanoate (25C) (2.03 g, 6.93 mmol) in EtOH (12 mL) was added Zn(OTf)$_2$ (6.30 g, 17.34 mmol). The mixture was heated by microwave at 120° C. for 5 h. The solvent was removed under reduced pressure and the residue was dissolved in EA, washed with water and brine, dried over MgSO$_4$, filtered, concentrated and purified by silica gel column chromatography (PE:EA=1:1) to afford ethyl 3-(1-(4-

(1H-imidazol-2-yl)-2-methylphenyl)-5-(4-methoxyphenyl)-1H-pyrrol-2-yl)propanoate as a brown solid (755 mg, 30%).

Synthesis of 3-(1-(4-(1H-imidazol-2-yl)-2-methylphenyl)-5-(4-methoxyphenyl)-1H-pyrrol-2-yl)propanoic acid (25E, Ar1=4-(1H-imidazol-2-yl)-2-methylphenyl)

To a solution of ethyl 3-(1-(4-(1H-imidazol-2-yl)-2-methylphenyl)-5-(4-methoxyphenyl)-1H-pyrrol-2-yl)propanoate (100 mg, 0.233 mmol) in THF/H$_2$O (v/v=1/1, 2 mL) was added lithium hydroxide monohydrate (15 mg, 0.350 mmol). The solution was stirred at room temperature overnight. THF was removed under reduced pressure and the resulting aqueous solution was acidified with 10% hydrochloric acid to pH=6.0. The resulting precipitate was isolated by centrifuge, rinsed with water, dried under reduced pressure to afford 3-(1-(4-(1H-imidazol-2-yl)-2-methylphenyl)-5-(4-methoxyphenyl)-1H-pyrrol-2-yl)propanoic acid as a brown powder (76 mg, 82%).

Synthesis of 3-[1-(4-carbamoyl-2-methyl-phenyl)-5-(4-cyano-phenyl)-1H-pyrrol-2-yl]-propionic acid ethyl ester (26A)

26A was prepared following Scheme 1 through 1C, where Ar1=4-carbamoyl-2-methylphenyl and Ar2=4-cyanophenyl.

Synthesis of 3-[1-(4-Carbamoyl-2-methyl-phenyl)-5-[4-(2H-tetrazol-5-yl)-phenyl]-1H-pyrrol-2-yl]-propionic acid ethyl ester (26B)

To 25 mL vial which contained 3-[1-(4-carbamoyl-2-methyl-phenyl)-5-(4-cyano-phenyl)-1H-pyrrol-2-yl]-propionic acid ethyl ester (26A) (50 mg, 0.12 mmoL) in DMF (4 mL) was added sodium azide (40 mg, 0.6 mmoL) and ammonium chloride (40 mg, 0.8 mmoL) at rt. The vial was sealed and the reaction mixture was heated to 100° C. and stirred for 16 h. The reaction mixture was cooled to rt and poured into 30 mL ice-water solution. The aqueous solution was acidified with aq HCl (1 N) to pH=1-2, the solid which formed was filtered Scheme 26: Preparation of 3-(5-(4-(2H-tetrazol-5-yl)phenyl)-1-(4-carbamoyl-2-methylphenyl)-1H-pyrrol-2-yl)propanoic acid (26C) and 4-(2-(4-(2H-tetrazol-5-yl)phenyl)-5-(2-carboxyethyl)-1H-pyrrol-1-yl)-3-methylbenzoic acid (26D)

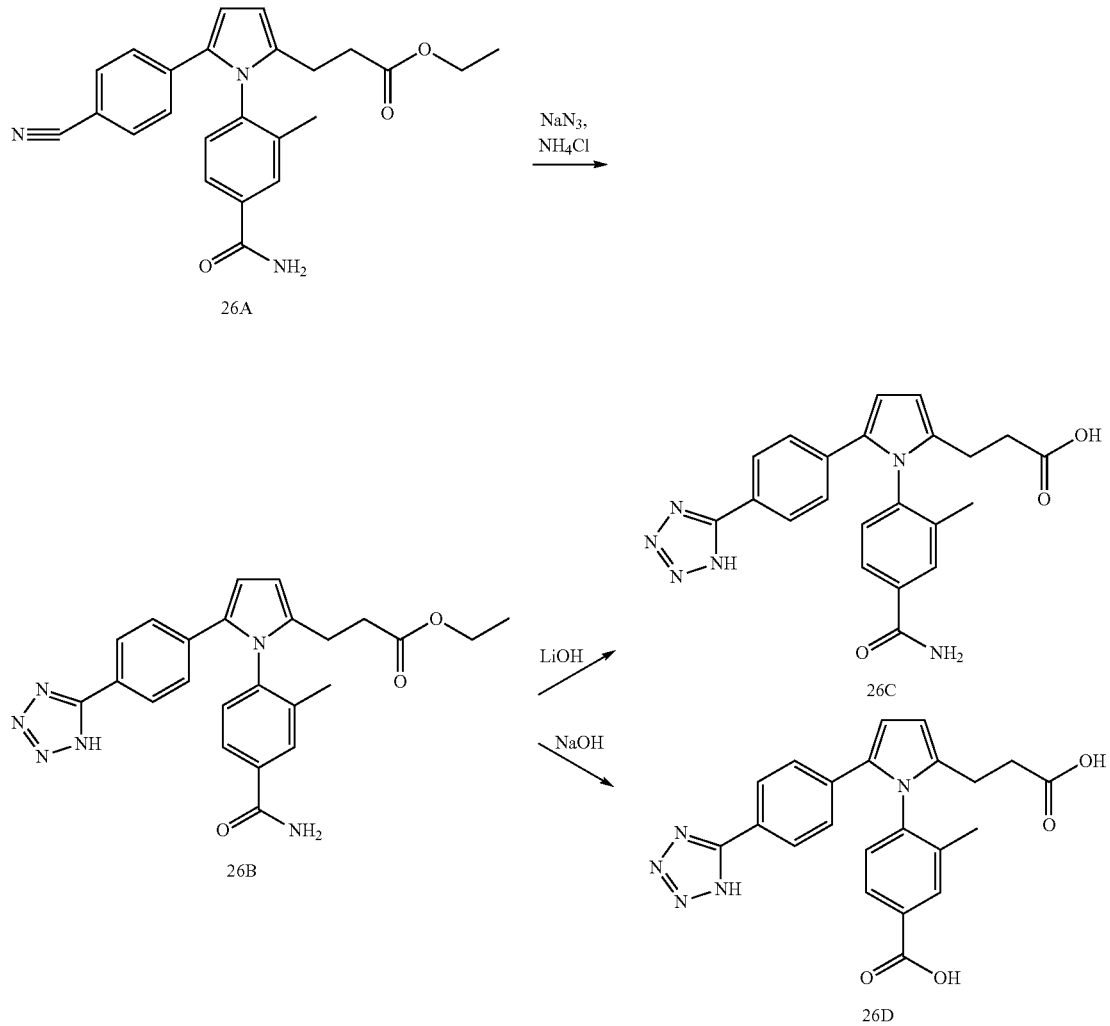

out, washed with water (25 mL), dried over air to afford the desired compound 3-{1-(4-Carbamoyl-2-methyl-phenyl)-5-[4-(2H-tetrazol-5-yl)-phenyl]-1H-pyrrol-2-yl}-propionic acid ethyl ester (26B) (27 mg, 50% yield).

Synthesis of 3-(5-(4-(2H-tetrazol-5-yl)phenyl)-1-(4-carbamoyl-2-methylphenyl)-1H-pyrrol-2-yl)propanoic acid (26C)

To 3-{1-(4-carbamoyl-2-methyl-phenyl)-5-[4-(2H-tetrazol-5-yl)-phenyl]-1H-pyrrol-2-yl}-propionic acid ethyl ester (26B) (16 mg, 0.035 mmoL) in 1:1 MeOH/THF (1.0 mL) was added aq. 1.0 N lithium hydroxide (2 eq). The reaction mixture was allowed to stir at rt for 16 h. The reaction mixture was poured into 10 mL ice-water solution which was extracted with diethyl ether. The aqueous layer was acidified with aq HCl (2 N) to pH=2, and then was extracted with diethyl ether. The combined organic layers were dried over $Na_2SO_4$. The solvent was removed under vacuum to yield the desired target 3-(5-(4-(2H-tetrazol-5-yl)phenyl)-1-(4-carbamoyl-2-methylphenyl)-1H-pyrrol-2-yl)propanoic acid (26C) (15 mg, 95%).

4-(2-(4-(2H-tetrazol-5-yl)phenyl)-5-(2-carboxyethyl)-1H-pyrrol-1-yl)-3-methylbenzoic acid (26D).

To 3-{1-(4-carbamoyl-2-methyl-phenyl)-5-[4-(2H-tetrazol-5-yl)-phenyl]-1H-pyrrol-2-yl}-propionic acid ethyl ester 26B (25 mg, 0.055 mmoL) in MeOH (2 mL) was added aq. sodium hydroxide (15%, 0.5 mL). The reaction mixture was allowed to stir at rt for 16 h. The reaction mixture was poured into 20 mL ice-water solution which was extracted with diethyl ether (2×10 mL). The aqueous layer was acidified with aq HCl (2 N) to pH=1-2, and then was extracted with diethyl ether (6×10 mL). The combined organic layers were dried over $Na_2SO_4$. The solvent was removed under vacuum to yield the desired target 4-(2-(4-(2H-tetrazol-5-yl)phenyl)-5-(2-carboxyethyl)-1H-pyrrol-1-yl)-3-methylbenzoic acid (26D) (15 mg, 65%).

Scheme 27: A general scheme for preparing GSNOR inhibitors with structure 27C

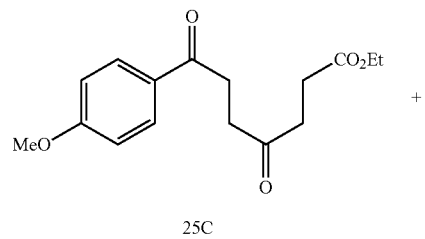

25C

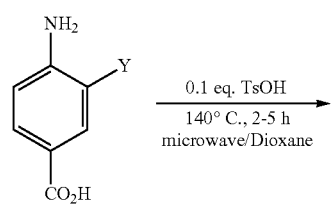

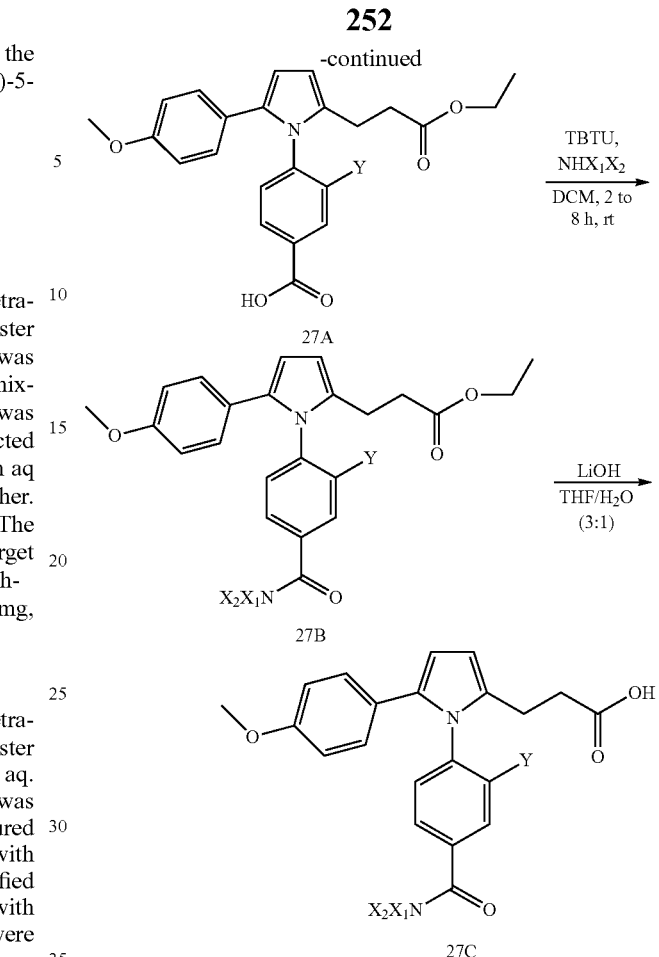

Representative procedure for Scheme 27: Synthesis of 3-(1-(4-(Dimethylcarbamoyl)-2-methylphenyl)-5-(4-methoxyphenyl)-1H-pyrrol-2-yl)propanoic acid ($Y=CH_3$, $X_1=X_2=CH_3$)

Synthesis of 4-(2-(3-Ethoxy-3-oxopropyl)-5-(4-methoxyphenyl)-1H-pyrrol-1-yl)-3-methylbenzoic acid (27A, $Y=CH_3$)

4-Amino-3-methylbenzoic acid (0.322 g) was mixed with ethyl 7-(4-methoxyphenyl)-4,7-dioxoheptanoate (25C, see scheme 25) (0.498 g) and p-toluenesulfonic acid (49 mg) in dioxane (3 mL). The mixture was heated at 140° C. via microwave over 2 hours. The resultant solution was diluted with EtOAc (20 mL) and washed with 0.5 N HCl (8 mL), Brine (8 mL) and dried over anhydrous Na2SO4. After removal of solvents under reduced pressure, the residue was purified by flash silica gel column chromatography, eluted with 10% MeOH in DCM, to afford 4-(2-(3-ethoxy-3-oxopropyl)-5-(4-methoxyphenyl)-1H-pyrrol-1-yl)-3-methylbenzoic acid (0.35 g) as a light yellow solid.

Synthesis of Ethyl 3-(1-(4-(Dimethylcarbamoyl)-2-methylphenyl)-5-(4-methoxyphenyl)-1H-pyrrol-2-yl)propanoate (27B, Y=methyl, $CH_3$, $X_1=X_2=CH_3$)

4-(2-(3-Ethoxy-3-oxopropyl)-5-(4-methoxyphenyl)-1H-pyrrol-1-yl)-3-methylbenzoic acid (44 mg) was treated with TBTU (42 mg), DPPA (10 μL) and dimethylamine HCl (14 mg) in DCM (4 mL) over 8 h at room temperature. The reaction mixture was diluted with EtOAc (15 mL), washed with 0.5 N HCl (8 mL), saturated NaHCO$_3$ (8 mL), and Brine (8 mL). After removal of solvents, the residue was purified by flash silcal gel chromatography to afford ethyl 3-(5-(4-methoxyphenyl)-1-(2-methyl-4-(methylcarbamoyl)phenyl)-1H-pyrrol-2-yl)propanoate (25 mg).

Synthesis of 3-(1-(4-(Dimethylcarbamoyl)-2-methylphenyl)-5-(4-methoxyphenyl)-1H-pyrrol-2-yl)propanoic acid (27C, Y=methyl, CH$_3$, X$_1$=X$_2$=CH$_3$)

Ethyl 3-(5-(4-methoxyphenyl)-1-(2-methyl-4-(methylcarbamoyl)phenyl)-1H-pyrrol-2-yl)propanoate (25 mg) was treated with LiOH.H$_2$O (6 mg) in THF (3 mL) and H2O (1 mL) over 12 h at room temperature. The basic solution was acidified with 1 NH$_4$Cl and the aqueous layer was extracted with EtOAc (15 mL). After removal of the solvents under reduced pressure, it afforded 3-(5-(4-methoxyphenyl)-1-(2-methyl-4-(methylcarba3-(5-(4-Methoxyphenyl)-1-(2-methyl-4-(methylcarbamoyl)phenyl)-1H-pyrrol-2-yl)propanoic acid (20 mg).

Scheme 28: Preparation of 3-(1-(4-carbamoyl-2-methylphenyl)-5-(4-(methylsulfonyl)phenyl)-1H-pyrrol-2-yl)propanoic acid (28D)

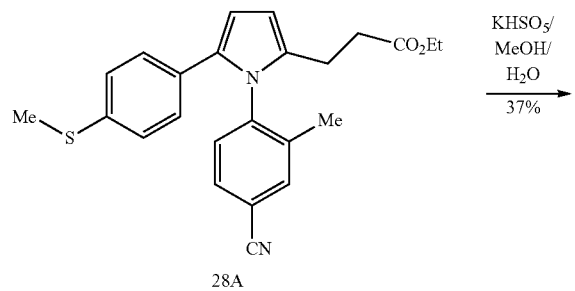

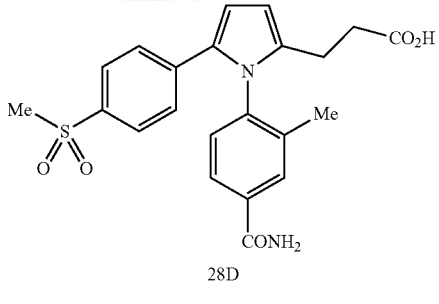

28D

Synthesis of ethyl 3-(1-(4-cyano-2-methylphenyl)-5-(4-(methylthio)phenyl)-1H-pyrrol-2-yl)propanoate (28A)

28A was prepared following Scheme 6 through 6F, where Ar2=4-(methylthio)phenyl.

Synthesis of ethyl 3-(1-(4-cyano-2-methylphenyl)-5-(4-(methylsulfonyl)phenyl)-1H-pyrrol-2-yl)propanoate (28B)

To a vigorously stirred solution of ethyl 3-(1-(4-cyano-2-methylphenyl)-5-(4-(methylthio)phenyl)-1H-pyrrol-2-yl) propanoate 28A (50 mg, 0.12 mmol) in methanol (1 mL) was added dropwise a solution of oxone (300 mg, 0.74 mmol) in water (5 mL) at 20° C. The mixture was stirred for 1 h, diluted with water (10 mL) and extracted with ethyl acetate (30 mL×3). The combined organic layers were washed with water and brine, dried over Na$_2$SO$_4$, filtered, concentrated and purified by silica gel flash chromatography (PE:EA=3:1) to afford ethyl 3-(1-(4-cyano-2-methylphenyl)-5-(4-(methylsulfonyl) phenyl)-1H-pyrrol-2-yl)propanoate (28B) as a brown solid (120 mg, 37%).

Synthesis of ethyl 3-(1-(4-carbamoyl-2-methylphenyl)-5-(4-(methylsulfonyl)phenyl)-1H-pyrrol-2-yl) propanoate (28C)

To a stirred suspension of ethyl 3-(1-(4-cyano-2-methylphenyl)-5-(4-(methylsulfonyl)phenyl)-1H-pyrrol-2-yl) propanoate (28B) (120 mg, 0.28 mmol) and potassium carbonate in DMSO (0.2 mL) was added dropwise 30% H$_2$O$_2$ at 0° C. The mixture was allowed to warm to room temperature and stirred 3 h. After water (2 mL) was added, some precipitate appeared, which was separated by centrifuge, rinsed with water (0.5 mL) and dried in vacuum to afford ethyl 3-(1-(4-carbamoyl-2-methylphenyl)-5-(4-(methylsulfonyl)phenyl)-1H-pyrrol-2-yl)propanoate (28C) as a white solid (100 mg, 80%).

Synthesis of 3-(1-(4-carbamoyl-2-methylphenyl)-5-(4-(methylsulfonyl)phenyl)-1H-pyrrol-2-yl)propanoic acid (28D)

To a solution of ethyl 3-(1-(4-carbamoyl-2-methylphenyl)-5-(4-(methylsulfonyl)phenyl)-1H-pyrrol-2-yl)propanoate (28C) (100 mg, 0.22 mmol) in THF/H$_2$O (v/v=1/1, 1 mL) was added lithium hydroxide monohydrate (18 mg, 0.44 mmol) and stirred overnight at room temperature. THF was evaporated in vacuum and the resulting aqueous solution was acidified with 10% hydrochloric acid to pH=4.0. The resulting precipitate was separated by centrifuge, rinsed with distilled water and purified by prep-HPLC to afford 3-(1-(4-carbamoyl-2-methylphenyl)-5-(4-(methylsulfonyl)phenyl)-1H-pyrrol-2-yl)propanoic acid (28D) as a light green solid (30 mg, 32%).

Scheme 29: A general scheme for preparing GSNOR inhibitors with structure 29C

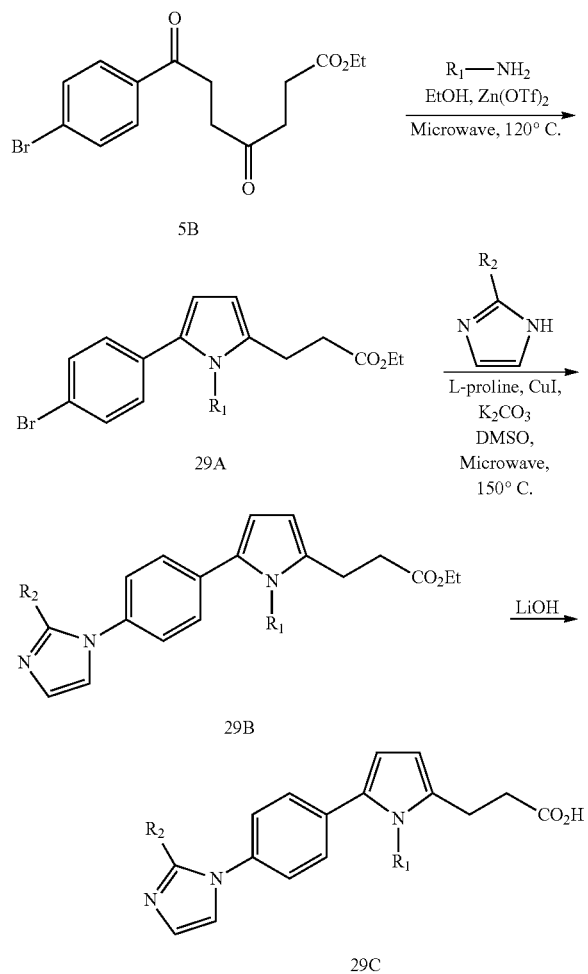

Representative procedure for Scheme 29: Synthesis of 3-(5-(4-(1H-imidazol-1-yl)phenyl)-1-(5-(1H-imidazol-1-yl)pyridin-2-yl)-1H-pyrrol-2-yl)propanoic acid, (29C, R1=5-(1H-imidazol-1-yl)pyridin-2-yl, R2=H)

Synthesis of ethyl 7-(4-bromophenyl)-4,7-dioxoheptanoate (5B)

Synthesis of 5B described in scheme 5, steps 1 and 2

Synthesis of ethyl 3-(1-(5-(1H-imidazol-1-yl)pyridin-2-yl)-5-(4-bromophenyl)-1H-pyrrol-2-yl)propanoate (29A, R1=5-(1H-imidazol-1-yl)pyridin-2-yl)

To a solution of ethyl 7-(4-bromophenyl)-4,7-dioxoheptanoate (5B) (2.56 g, 7.5 mmol) and 5-(1H-imidazol-1-yl) pyridin-2-amine (1.20 g, 7.5 mmol) in 15 mL of ethanol was added Zn(OTf)$_2$ (8.18 g, 22.5 mmol). The resultant mixture was heated at 120° C. for 4 h under microwave irradiation and then concentrated to dryness. The resultant residue was dissolved in EA, washed with water and brine, dried over MgSO$_4$, concentrated and purified by silica gel column chromatography (PE:EA=6:1) to afford ethyl 3-(1-(5-(1H-imidazol-1-yl)pyridin-2-yl)-5-(4-bromophenyl)-1H-pyrrol-2-yl)propanoate as a brown oil (250 mg, 7.1%).

Synthesis of ethyl 3-(5-(4-(1H-imidazol-1-yl)phenyl)-1-(5-(1H-imidazol-1-yl)pyridin-2-yl)-1H-pyrrol-2-yl)propanoate (29B, R1=5-(1H-imidazol-1-yl) pyridin-2-yl, R2=H)

To a mixture of ethyl 3-(1-(5-(1H-imidazol-1-yl)pyridin-2-yl)-5-(4-bromophenyl)-1H-pyrrol-2-yl)propanoate (29A) (200 mg, 0.43 mmol) and imidazole (35 mg, 0.516 mmol) in DMSO (5 mL) was added L-proline (19.8 mg, 0.172 mmol), CuI (16.4 mg, 0.086 mmol) and K$_2$CO$_3$ (119 mg, 0.86 mmol). The resultant mixture was heated at 150° C. for 5 h under microwave irradiation, poured into water and extracted with EA for 5 times. The combined organic layers were washed with brine, dried over MgSO$_4$, concentrated and purified by silica gel column chromatography (DCM:MeOH=20:1) to afford ethyl 3-(5-(4-(1H-imidazol-1-yl)phenyl)-1-(5-(1H-imidazol-1-yl)pyridin-2-yl)-1H-pyrrol-2-yl)propanoate as a brown oil (40 mg, 21%).

Synthesis of 3-(5-(4-(1H-imidazol-1-yl)phenyl)-1-(5-(1H-imidazol-1-yl)pyridin-2-yl)-1H-pyrrol-2-yl) propanoic acid (29C, R1=5-(1H-imidazol-1-yl)pyridin-2-yl, R2=H)

To a solution of ethyl 3-(5-(4-(1H-imidazol-1-yl)phenyl)-1-(5-(1H-imidazol-1-yl)pyridin-2-yl)-1H-pyrrol-2-yl)propanoate (29B) (40 mg, 0.088 mmol) in THF/H$_2$O (v/v=1/1, 2 mL) was added LiOH.H$_2$O (11 mg, 0.264 mmol). The solution was stirred at room temperature for 8 h. THF was removed under reduced pressure and the resultant aqueous solution was acidified with 10% hydrochloric acid to pH=5. The resultant precipitate was isolated by centrifuge, rinsed with water, dried in vacuo to afford 3-(5-(4-(1H-imidazol-1-yl)phenyl)-1-(5-(1H-imidazol-1-yl)pyridin-2-yl)-1H-pyrrol-2-yl)propanoic acid (12 mg, yield 32%) as a yellow powder.

Scheme 30: Preparation of 3-(5-(4-(1H-imidazol-1-yl)phenyl)-1-(4-(aminomethyl)-2-methylphenyl)-1H-pyrrol-2-yl)propanoic acid (30D)

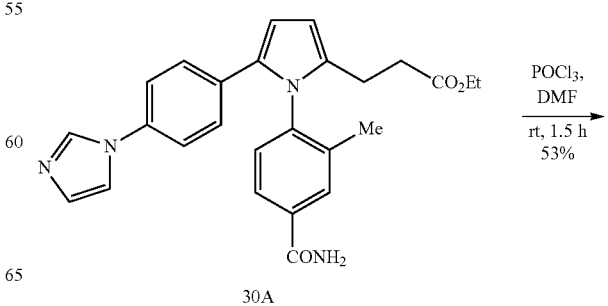

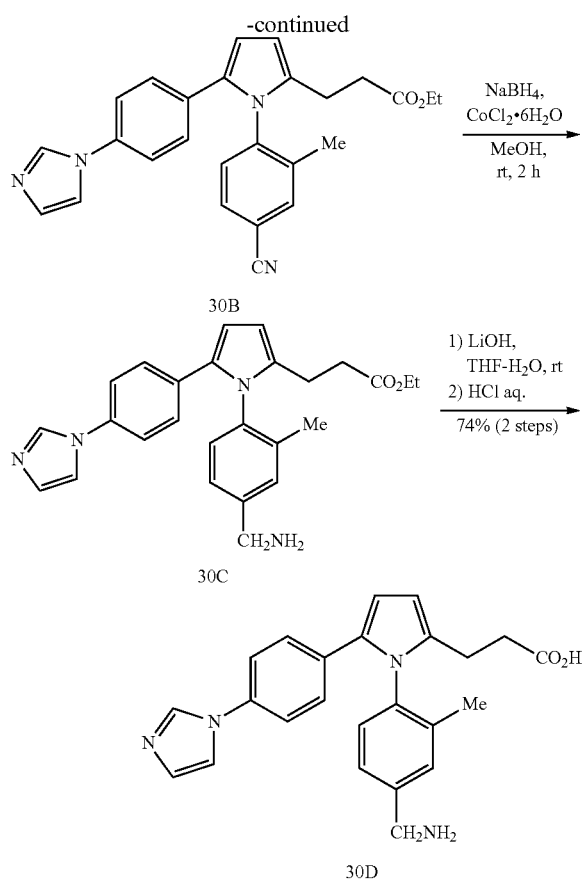

30B

30C

30D

Synthesis of ethyl 3-(5-(4-(1H-imidazol-1-yl)phenyl)-1-(4-carbamoyl-2-methylphenyl)-1H-pyrrol-2-yl)propanoate (30A)

30A was prepared following the first four steps of Scheme 5, where Ar1=4-carbamoyl-2-methylphenyl.

Synthesis of ethyl 3-(5-(4-(1H-imidazol-1-yl)phenyl)-1-(4-cyano-2-methylphenyl)-1H-pyrrol-2-yl)propanoate (30B)

To a solution of ethyl 3-(5-(4-(1H-imidazol-1-yl)phenyl)-1-(4-carbamoyl-2-methylphenyl)-1H-pyrrol-2-yl)propanoate (30A) (2.0 g, 4.52 mmol) in DMF (9 mL) was added POCl$_3$ (693 mg, 4.52 mmol) at 0° C., and then stirred at room temperature for 1.5 h. After cooling to room temperature, the reaction mixture was added to ice-water (20 mL). Sat. Na$_2$CO$_3$ was added to adjust pH=8 followed by extraction with ethyl acetate (50 mL×4). The combined organic layers were dried over Na$_2$SO$_4$, filtered, concentrated and purified by silica gel column chromatography (PE:EA=1:1) to afford ethyl 3-(5-(4-(1H-imidazol-1-yl)phenyl)-1-(4-cyano-2-methylphenyl)-1H-pyrrol-2-yl)propanoate (30B) (1.02 g, 53%), LC-MS: [M+H]$^+$ 425.

Synthesis of ethyl 3-(5-(4-(1H-imidazol-1-yl)phenyl)-1-(4-(aminomethyl)-2-methylphenyl)-1H-pyrrol-2-yl)propanoate (30C)

To a solution of ethyl 3-(5-(4-(1H-imidazol-1-yl)phenyl)-1-(4-cyano-2-methylphenyl)-1H-pyrrol-2-yl)propanoate (30B) (300 mg, 0.71 mmol) in methanol (10 mL) was added CoCl$_2$·6H$_2$O (337 mg, 1.41 mmol), then NaBH$_4$ (137 mg, 3.53 mmol) was added in portions within 30 min. The reaction mixture was stirred at room temperature for 2 h. 10% hydrochloric acid was added to adjust pH=2. After methanol was distilled, conc. NH$_3$.H$_2$O was added to adjust pH=8 followed by extraction with ethyl acetate (80 mL×3). The combined organic layers were dried over Na$_2$SO$_4$, filtered and concentrated to afford crude ethyl 3-(5-(4-(1H-imidazol-1-yl)phenyl)-1-(4-(aminomethyl)-2-methylphenyl)-1H-pyrrol-2-yl)propanoate (30C) (300 mg), which was used for the next step without further purification. LC-MS: [M+H]$^+$ 428.

Synthesis of 3-(5-(4-(1H-imidazol-1-yl)phenyl)-1-(4-(aminomethyl)-2-methylphenyl)-1H-pyrrol-2-yl)propanoic acid (30D)

To a solution of ethyl 3-(5-(4-(1H-imidazol-1-yl)phenyl)-1-(4-(aminomethyl)-2-methylphenyl)-1H-pyrrol-2-yl)propanoate (30C) (300 mg) in THF/H$_2$O (v/v=1/1, 6 mL) was added lithium hydroxide monohydrate (50.4 mg, 2.10 mmol). The solution was stirred at room temperature overnight. THF was removed under reduced pressure and the resulting solution was acidified with 10% hydrochloric acid to pH=6.0. The resulting precipitate was isolated by centrifuge, rinsed with water, dried under reduced pressure and purified by prep-HPLC to afford 3-(5-(4-(1H-imidazol-1-yl)phenyl)-1-(4-(aminomethyl)-2-methylphenyl)-1H-pyrrol-2-yl)propanoic acid (30D) (170 mg, 74%) as a yellow solid.

Scheme 31: A representative example of a simple acylation procedure

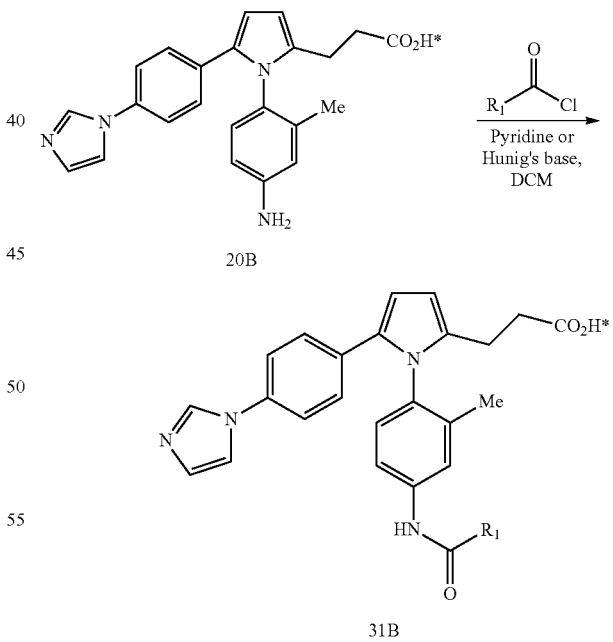

20B

31B

*In some cases 20B (see scheme 20) was treated with MeOH or EtOH and HCl to prepare the ester to aid in purification. In these cases after 31B was prepared as described, the compound was purified by normal phase column chromatography hexanes/ethyl acetate, followed by the necessary hydrolysis step (see final step of Scheme 6). The example below is with the acid; therefore no hydrolysis was necessary.

Representative procedure for Scheme 31: Synthesis of 3-(5-(4-(1H-imidazol-1-yl)phenyl)-1-(2-methyl-4-propionamidophenyl)-1H-pyrrol-2-yl)propanoic acid (R1=H, R2=ethyl)

To a solution of pyridine (1 mL) and C$_2$H$_5$COCl/DCM (v/v=1/100, 4.2 mL) was added a solution of 20B (see scheme 20) (150 mg, 0.389 mmol) in pyridine (1 mL) at 0° C. The mixture was stirred at room temperature overnight. The solvents were removed under reduced pressure and the resulting solid was acidified with 10% hydrochloric acid to pH=5.0. The resulting precipitate was isolated by centrifuge, rinsed with water, dried under reduced pressure to afford the crude product as a brown powder, After purification by prep-HPLC, 3-(5-(4-(1H-imidazol-1-yl)phenyl)-1-(2-methyl-4-propionamidophenyl)-1H-pyrrol-2-yl)propanoic acid (32 mg, 19%) was obtained as a brown oil.

Scheme 32: A representative example of a DCC coupling procedure

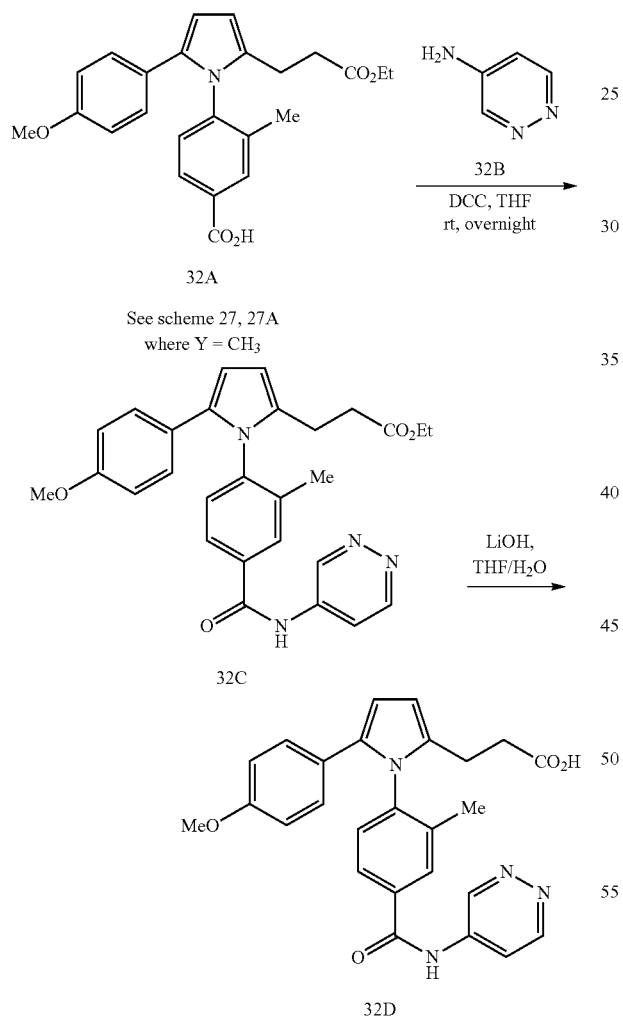

Synthesis of Compound 32C

To a mixture of 32A (200 mg, 0.49 mmol) and pyridazin-4-amine (56 mg, 0.59 mmol) in THF (3 mL) was added DCC (152 mg, 0.74 mmol) and the mixture was stirred at room temperature overnight. TLC showed the reaction was complete. Water (5 mL) was added and the mixture was extracted with ethyl acetate (5 mL×4). The combined organic layers were dried over Na$_2$SO$_4$, filtered, concentrated and purified by silica gel column chromatography (DCM:MeOH=15:1) to afford 32C as a yellow solid (137 mg, yield 58%).

Synthesis of Compound 32D

Hydrolysis of 32C completed following procedure described in the last step of Scheme 5.

Scheme 33: A general scheme for preparing GSNOR inhibitors with structure 33C

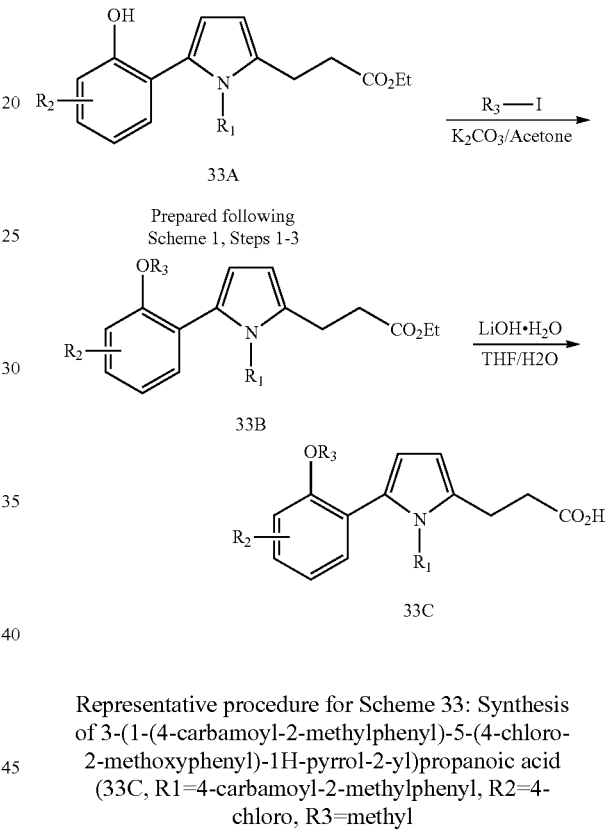

Representative procedure for Scheme 33: Synthesis of 3-(1-(4-carbamoyl-2-methylphenyl)-5-(4-chloro-2-methoxyphenyl)-1H-pyrrol-2-yl)propanoic acid (33C, R1=4-carbamoyl-2-methylphenyl, R2=4-chloro, R3=methyl Synthesis of 33A, R1=4-carbamoyl-2-methylphenyl, R2=4-chloro Prepared following scheme 1 thru 1C, R1=4-carbamoyl-2-methylphenyl, R2=4-chloro-2-hydroxyphenyl.

Synthesis of 33B, R1=4-carbamoyl-2-methylphenyl, R2=4-chloro, R3=methyl 33A (300 mg, 0.704 mmol) was dissolved in acetone. Potassium carbonate (146 mg, 1.056 mmol) and methyl iodide (299 mg, 2.112 mmol) was added and stirred at room temperature overnight. When TLC indicated that the reaction was complete, the mixture was filtered, evaporated in vacuo. The residue was partitioned between ethyl acetate (20 mL) and water (5 mL). The organic phase was dried with magnesium sulfate, filtered and concentrated to afford 33B (R1=4-carbamoyl-2-methylphenyl, R2=4-chloro, R3=methyl) as a yellow oil (295 mg, yield 95%).

Synthesis of 3-(1-(4-carbamoyl-2-methylphenyl)-5-(4-chloro-2-methoxyphenyl)-1H-pyrrol-2-yl)propanoic acid (33C, R1=4-carbamoyl-2-methylphenyl, R2=4-chloro, R3=methyl)

Hydrolysis completed following final step of Scheme 5.

Scheme 34: A general scheme for preparing GSNOR inhibitors with structure 34C

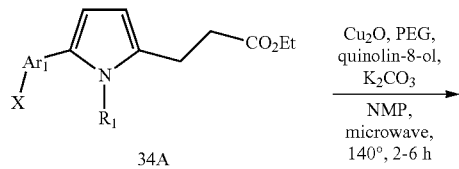

Prepared by Scheme 1, Steps 1-3

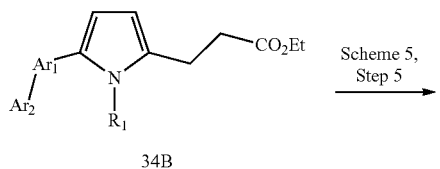

Representative procedure for Scheme 34: Synthesis of 3-(1-(4-carbamoyl-2-methylphenyl)-5-(4-(2-cyclopropyl-1H-imidazol-1-yl)phenyl)-1H-pyrrol-2-yl)propanoic acid (34C, Ar1-X=4-bromophenyl, Ar2 is 2-cyclopropyl-1H-imidazol-1-yl, R1=4-carbamoyl-2-methylphenyl)

Synthesis of ethyl 3-(5-(4-bromophenyl)-1-(4-carbamoyl-2-methylphenyl)-1H-pyrrol-2-yl)propanoate (34A, R1=4-carbamoyl-2-methylphenyl, Ar1-X=4-bromophenyl)

Prepared by Scheme 1 through step 1C.

Synthesis of ethyl 3-(1-(4-carbamoyl-2-methylphenyl)-5-(4-(2-cyclopropyl-1H-imidazol-1-yl)phenyl)-1H-pyrrol-2-yl)propanoate (34B, Ar1-X=4-bromophenyl, Ar2 is 2-cyclopropyl-1H-imidazol-1-yl, R1=4-carbamoyl-2-methylphenyl To a mixture of 34A (Ar2=4-bromophenyl) (455 mg, 1.0 mmol) and 2-cyclopropyl-1H-imidazole (see Method 14 for synthesis) (324 mg, 3.0 mmol, 3.0 eq) in NMP (4 mL) was added 8-hydroxyquinoline (22 mg, 0.15 mmol, 0.15 eq), Cu$_2$O (282 mg, 0.1 mmol) and K$_2$CO$_3$ (166 mg, 1.2 mmol) and PEG-2000 (50 mg). The resultant mixture under N$_2$ was irradiated under microwave at 128° C. for 6.0 h, cooled to room temperature and diluted with THF (10 mL) and water (10 mL). The mixture was filtered and the resultant aqueous layer was extracted with EA (30 mL×5). The combined organic layers were washed with brine (20 mL), dried over MgSO$_4$, filtered, concentrated and purified by silica gel column chromatography (MeOH:CH$_2$Cl$_2$=1:15) to afford the desired compound as a yellow solid (190 mg, yield 39%).

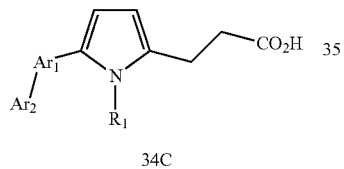

Synthesis of 3-(1-(4-carbamoyl-2-methylphenyl)-5-(4-(2-cyclopropyl-1H-imidazol-1-yl)phenyl)-1H-pyrrol-2-yl)propanoic acid (34C, Ar1-X=4-bromophenyl, Ar2 is 2-cyclopropyl-1H-imidazol-1-yl, R1=4-carbamoyl-2-methylphenyl)

Hydrolysis completed following final step of Scheme 5 to give the title compound.

Scheme 35: Preparation of 4-(1-(4-carbamoyl-2-methylphenyl)-5-(2-carboxyethyl)-1H-pyrrol-2-yl)benzoic acid (35-6) and 3-(1-(4-carbamoyl-2-methylphenyl)-5-(4-(hydroxycarbamoyl)phenyl)-1H-pyrrol-2-yl)propanoic acid (35-8)

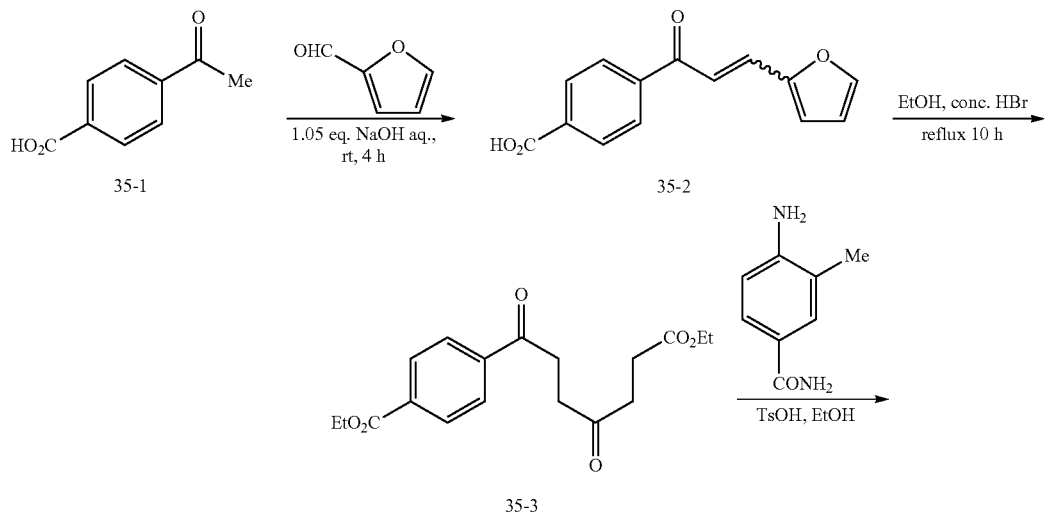

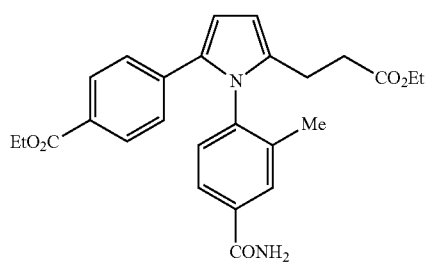

35-4

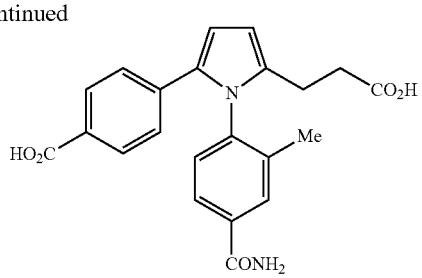

35-5

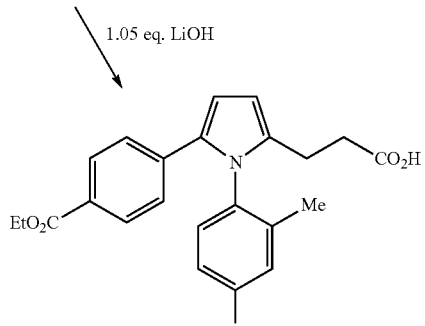

35-6

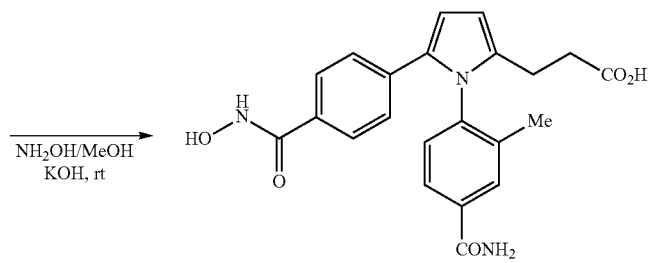

35-7

Synthesis of Compound 35-2

To a solution of NaOH (5.10 g, 127.6 mmol) in water (300 mL) was added 35-1 (20.0 g, 121.6 mmol). After the solid of 35-1 was dissolved, 2-furaldehyde (11.72 g, 121.6 mmol) was added and the mixture was stirred at room temperature for 4 h, then the resultant solid was filtered, washed with water (20 mL×2), suspended in water (120 mL) and acidified to pH=3 with 10% hydrochloric acid, extracted with EA (160 mL×3). The combined organic layers were dried over $Na_2SO_4$, filtered and concentrated to afford 35-2 as a yellow solid (21.65 g, yield 73%).

Synthesis of Compound 35-3

To a solution of compound 35-2 (11.40 g, 47.1 mmol) in ethanol (100 mL) was added conc. HBr (30 mL). The resultant mixture was refluxed for 14 h. Ethanol was evaporated in vacuo and the residue was extracted with ethyl acetate (80 mL×4). The combined organic layers were washed with sat. $NaHCO_3$ (100 mL) and brine (80 mL), dried over $Na_2SO_4$, filtered, concentrated and purified by silica gel column chromatography (PE:EA=10:1) to afford 35-3 as a yellow solid (1.40 g, yield 20%).

Synthesis of Compound 35-4

To a solution of compound B35-3 (1.845 g, 5.52 mmol) in anhydrous ethanol (20 mL) was added 4-amino-3-methylbenzamide (0.91 g, 6.06 mmol) and TsOH (211 mg, 1.11 mmol) and the mixture was heated under reflux overnight. TLC and LC-MS showed that the reaction was complete. Ethanol was evaporated in vacuo and the residue was purified by silica gel column chromatography (PE:EA=8:1) to afford 35-4 as a yellow solid (1.69 g, yield 70%).

Synthesis of 4-(1-(4-carbamoyl-2-methylphenyl)-5-(2-carboxyethyl)-1H-pyrrol-2-yl)benzoic acid (Compound 35-5)

To a mixture of compound B30-4 (140 mg, 0.31 mmol) in $THF/H_2O/MeOH$ (5 mL, v/v=2/2/1) was added lithium hydroxide monohydrate (65 mg, 1.56 mmol). The mixture was stirred at room temperature overnight. THF was evaporated in vacuo. The residue was acidified to pH=3 with 10% hydrochloric acid. The resultant precipitate was isolated by centrifuge and purified by prep-HPLC to afford 35-5 as a white powder (70 mg, yield 56%).

Synthesis of Compound 35-6

To the mixture of compound 35-5 (500 mg, 1.12 mmol) in $THF/H_2O/MeOH$ (10 mL, v/v/v=5/4/1) was added lithium hydroxide monohydrate (49 mg, 1.17 mmol). The mixture was stirred at room temperature overnight. THF was evaporated in vacuo. The residue was acidified to pH=4 with 5% hydrochloric acid, filtered and dried in vacuo to afford 35-6 as a white solid (469 mg, yield 100%).

Synthesis of 3-(1-(4-carbamoyl-2-methylphenyl)-5-(4-(hydroxycarbamoyl)phenyl)-1H-pyrrol-2-yl)propanoic acid (Compound 35-7)

To a mixture of compound 35-6 (469 mg, 1.12 mmol) in 1M hydroxylammonium methanol solution (11.2 mL, 11.2 mmol) was added potassium hydroxide (150 mg, 2.23 mmol). The mixture was stirred at 0° C. for 4 h and concentrated. The residue was dissolved in water (10 mL) and acidified to pH=4 with 10% hydrochloric acid. The resultant precipitate was isolated by centrifuge and purified by prep-HPLC to afford 35-7 as a white powder (130 mg, yield 29%).

265

Scheme 36: A general scheme for preparing GSNOR inhibitors with structure 36D

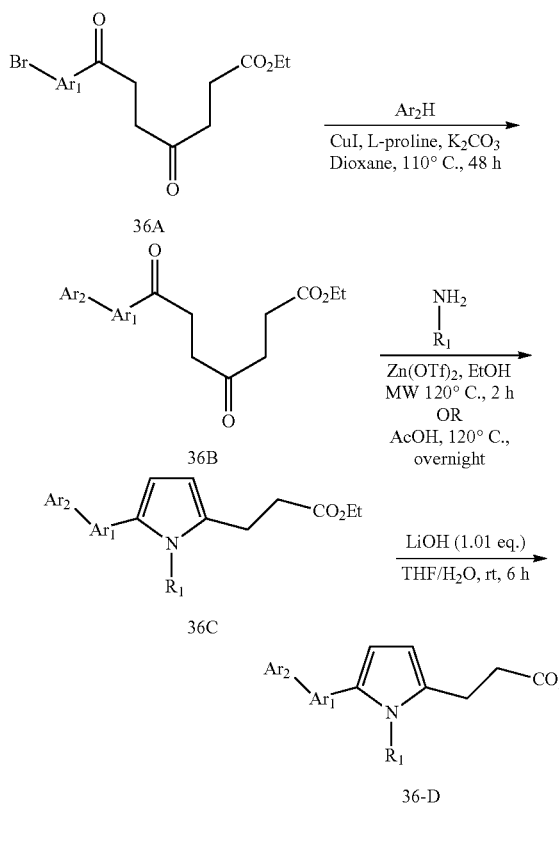

Representative procedure for Scheme 36: 3-(1-(4-carbamoyl-2-methylphenyl)-5-(4-(2-oxooxazolidin-3-yl)phenyl)-1H-pyrrol-2-yl)propanoic acid Synthesis of ethyl 4,7-dioxo-7-(4-(2-oxooxazolidin-3-yl)phenyl)heptanoate To a mixture of ethyl 7-(4-bromophenyl)-4,7-dioxoheptanoate ((36A, where Ar1-Br=4-bromophenyl, also see compound 5B, Scheme 5) (1.50 g, 4.4 mmol) and oxazolidin-2-one (575 mg, 6.6 mmol) in dioxane (5 mL) were added L-proline (50 mg, 0.44 mmol), CuI (42 mg, 0.22 mmol) and K$_2$CO$_3$ (1.22 g, 8.8 mmol). The resultant mixture was stirred under N$_2$ at 110° C. for 48 h and then evaporated. The residue was diluted with EA/water (40 mL/40 mL). The mixture was filtered and the resultant aqueous layer was extracted with EA (30 mL×5). The combined organic layers were washed with brine, dried over NaSO$_4$, concentrated and purified by silica gel column chromatography (pure DCM to DCM:MeOH=30:1) to afford titled compound as a white solid (158 mg, yield 10%).

Synthesis of ethyl 3-(1-(4-carbamoyl-2-methylphenyl)-5-(4-(2-oxooxazolidin-3-yl)phenyl)-1H-pyrrol-2-yl)propanoate To a solution of ethyl 4,7-dioxo-7-(4-(2-oxooxazolidin-3-yl)phenyl)heptanoate (158 mg, 0.43 mmol) and 4-amino-3-methylbenzamide (130 mg, 0.68 mmol) in EtOH (1 mL) was added Zn(OTf)$_2$ (313 mg, 0.86 mmoL). The mixture was heated to 120° C. under microwave for 2 h. After evaporation under reduced pressure, the crude product was purified by silica gel column chromatography (DCM:MeOH=20:1) to afford the titled compound as a yellow solid (77 mg, yield 39%).

Synthesis of 3-(1-(4-carbamoyl-2-methylphenyl)-5-(4-(2-oxooxazolidin-3-yl)phenyl)-1H-pyrrol-2-yl)propanoic acid To a solution of ethyl 3-(1-(4-carbamoyl-2-methylphenyl)-5-(4-(2-oxooxazolidin-3-yl)phenyl)-1H-pyrrol-2-yl)propanoate (67 mg, 0.15 mmol) in THF/H$_2$O (1 mL, v/v=1/1) was added lithium hydroxide monohydrate (7 mg, 0.15 mmol). The mixture was stirred at room temperature for 6 h. THF was evaporated in vacuo. The residue was acidified to pH=5 with 5% hydrochloric acid, concentrated and purified by prep-TLC to afford the titled compound as a brown solid (24 mg, yield 39%).

Scheme 36A: Alternative method for making for making Compound 36B-type intermediates (Scheme 36 above).

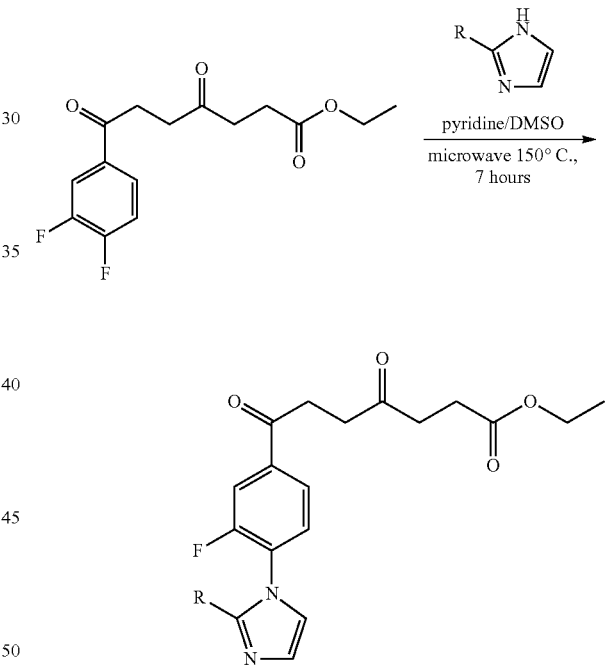

Representative procedure for Scheme 36A: Synthesis of ethyl 7-(3-fluoro-4-(1H-imidazol-1-yl)phenyl)-4,7-dioxoheptanoate (R=H)

Ethyl 7-(3,4-difluorophenyl)-4,7-dioxoheptanoate (351 mg) was treated with imidazole (241 mg) and pyridine (395 mg) in DMSO (3 mL) at 150° C. over 7 h with a micro-wave heating. The resultant mixture was diluted with water (12 mL) and was extracted with EtOAc (20 mL×3). After removal the solvents, the mixture was purified by flash silica gel chromatography, eluting with EtOAc, to afford the desired product -ethyl 7-(3-fluoro-4-(1H-imidazol-1-yl)phenyl)-4,7-dioxoheptanoate (279 mg, 68%) as light brown solids.

Scheme 36B: Another alternative method for making Compound 36B-type intermediates (Scheme 36 above).

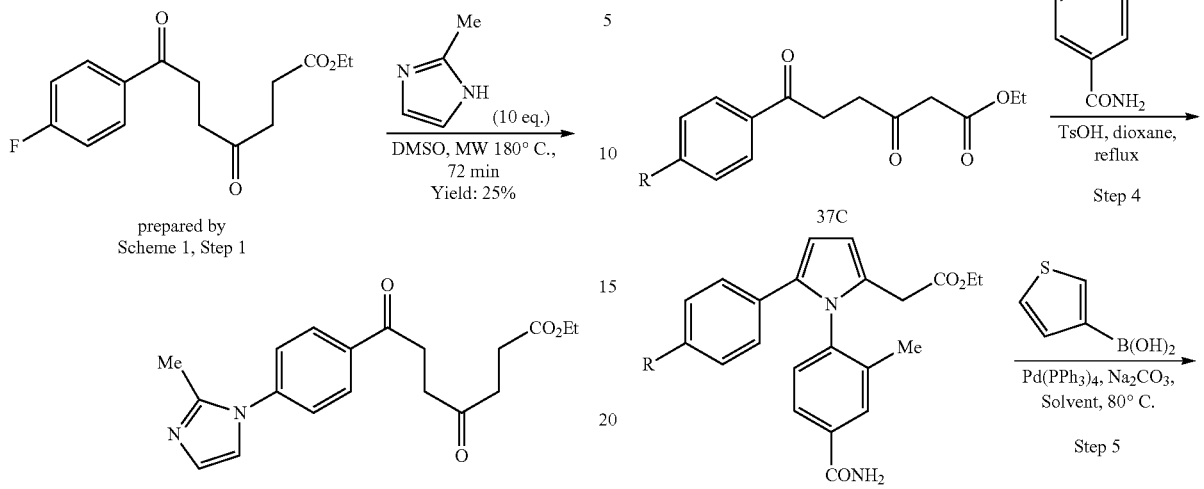

Representative procedure for Scheme 36B: Synthesis of ethyl 7-(4-(2-methyl-1H-imidazol-1-yl)phenyl)-4,7-dioxoheptanoate Ethyl 7-(4-fluorophenyl)-4,7-dioxoheptanoate (2.00 g, 7.1 mmol) and 2-methyl-1H-imidazole (7.0 g, 86 mmol) were taken up into DMSO (4 mL). The mixture was heated to 180° C. under microwave for 72 min. Water (100 mL) was added and the mixture was extracted with ethyl acetate (50 mL×3). The combined organic layers were washed with brine (40 mL), dried over $Na_2SO_4$, filtered, concentrated and purified by silica gel column chromatography (DCM to DCM:MeOH=25:1) to afford the title compound as a dark brown solid (660 mg, yield 25%).

Scheme 37: Preparation of 2-(1-(4-carbamoyl-2-methylphenyl)-5-(4-(thiophen-3-yl)phenyl)-1H-pyrrol-2-yl)acetic acid

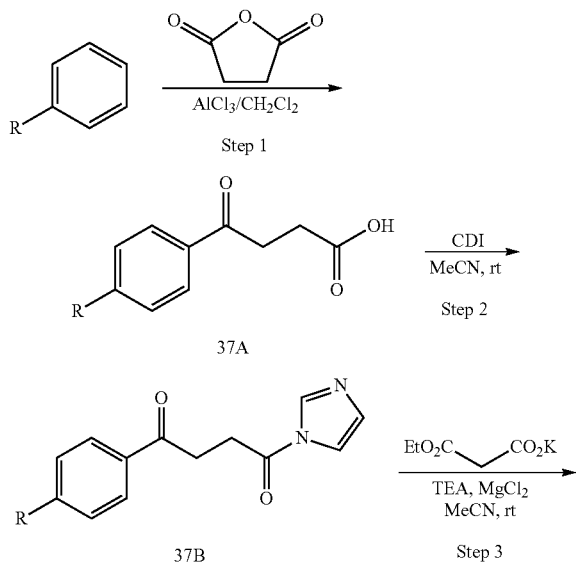

Step 1: Synthesis of 4-(4-bromophenyl)-4-oxobutanoic acid (37A, R═Br)

Anhydrous aluminum trichloride (29.1 g, 218 mmol) was suspended in dichloromethane (120 mL) and cooled to 0° C. Bromobenzene (35.1 g, 224 mmol) was added carefully. When the addition was complete, succinic anhydride (10.0 g, 100 mmol) was added in ten portions carefully. Then the mixture was warmed to room temperature and stirred for 4 h. TLC showed the reaction was complete, 6N HCl (50 mL) was added dropwise. The solid was filtered, washed with distilled water (10 mL×2) and dried in vacuo to afford 37A, R═Br as a white solid (22 g, yield 82%).

Step 2 and 3: Synthesis of 1-(4-bromophenyl)-4-(1H-imidazol-1-yl)butane-1,4-dione (37C, R═Br)

To a solution of 37A, R═Br (5.00 g, 18.6 mmol) in anhydrous MeCN (50 mL) was added CDI (3.91 g, 24.2 mmol).

The solution was stirred at room temperature for 2 h and turned red to give 37B, R=Br, which was used for the next step without any purification. To a suspension of potassium 3-ethoxy-3-oxopropanoate (6.32 g, 37.2 mmol) in anhydrous MeCN (200 mL) TEA (5.63 g, 55.8 mmol) and anhydrous magnesium dichloride (5.3 g, 55.8 mmol) was added gradually at 0° C. The mixture was stirred at room temperature for 2 h, to which the solution of 37B, R=Br was added in portions. The mixture was stirred at room temperature overnight. The volatiles were removed under reduced pressure and the residue was dissolved in EA (250 mL), washed with water (50 mL×2) and brine (30 mL), dried over $Na_2SO_4$, filtered, concentrated and purified by silica gel column chromatography (PE:EA=3:1) to afford ethyl 6-(4-bromophenyl)-3,6-dioxohexanoate (37C, R=Br) as a brown solid (5.3 g, yield 88%).

Step 4: Synthesis of ethyl 2-(5-(4-bromophenyl)-1-(4-carbamoyl-2-methylphenyl)-1H-pyrrol-2-yl)acetate (37D, R=Br, Ar1=4-carbamoyl-2-methylphenyl)

37C, R=Br was cyclized following step 3 of Scheme 1 with 4-amino-3-methylbenzamide with a different solvent, dioxane.

Step 5: Synthesis of ethyl 2-(1-(4-carbamoyl-2-methylphenyl)-5-(4-(thiophen-3-yl)phenyl)-1H-pyrrol-2-yl)acetate (37E, R=Br, Ar1=4-carbamoyl-2-methylphenyl Coupling with 37D, R=Br, Ar1=4-carbamoyl-2-methylphenyl and thiophen-3-ylboronic acid was performed under conditions described in Scheme 6, step 6 to give 37E, R=Br, Ar1=4-carbamoyl-2-methylphenyl.

Step 6: Synthesis of 2-(1-(4-carbamoyl-2-methylphenyl)-5-(4-(thiophen-3-yl)phenyl)-1H-pyrrol-2-yl)acetic acid (37F, R=Br, Ar1=4-carbamoyl-2-methylphenyl Hydrolysis of 37E was performed following the final step of Scheme 5 to give the desired compound, 37F, R=Br, Ar1=4-carbamoyl-2-methylphenyl.

Scheme 38: A general scheme for preparing GSNOR inhibitors with structure 38F

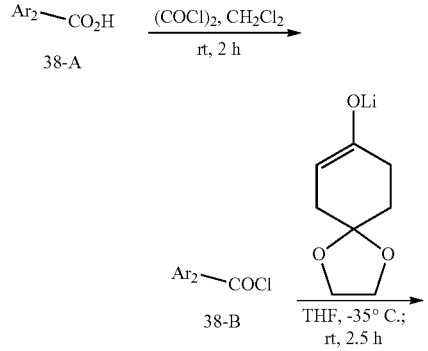

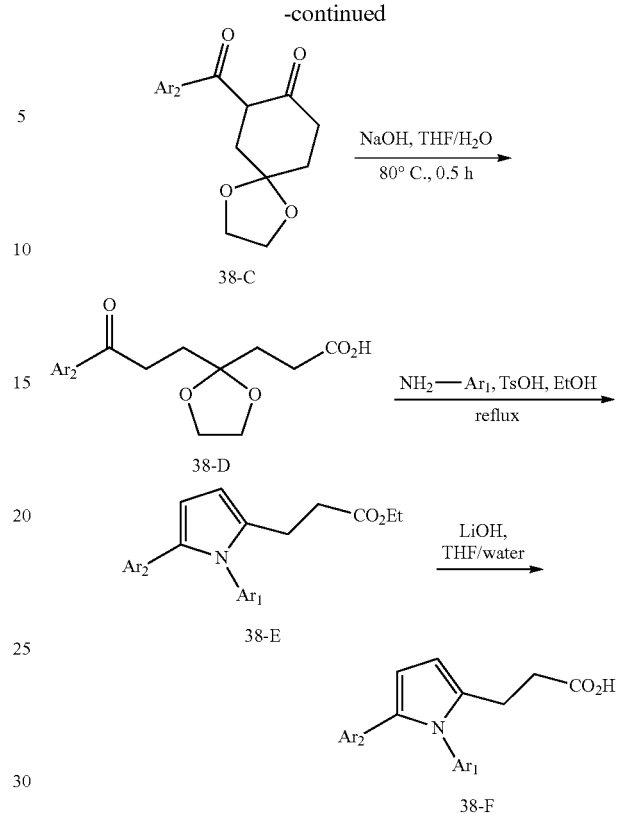

Representative procedure for Scheme 38: Synthesis of 3-(5-(5-bromofuran-2-yl)-1-(4-carbamoyl-2-methylphenyl)-1H-pyrrol-2-yl)propanoic acid Synthesis of 5-bromofuran-2-carbonyl chloride At 0° C., to a stirred solution of 5-bromofuran-2-carboxylic acid (3.00 g, 15.7 mmol) in DCM (30 mL) was added dropwise oxalyl dichloride (4.50 mL, 47.1 mmol). Then the resulted mixture was stirred at room temperature for 2 h. TLC and LC-MS showed no starting material. The volatile was removed under reduced pressure and the residual yellow solid was used without further purification (3.20 g, quant.)

Synthesis of 7-(5-bromofuran-2-carbonyl)-1,4-dioxaspiro[4.5]decan-8-one

Under $N_2$ at about −35° C., to a stirred solution of 1,4-cyclohexanedione monoethyleneacetal (2.57 g, 16.5 mmol) in THF (30 mL) was added a solution of LHMDS (20% in THF, 18 mL, 18.8 mmol) over about 1 h. After stirred for another 1 h, the resulted solution was added dropwise to the solution of 5-bromofuran-2-carbonyl chloride (3.20 g, 15.7 mmol) in THF (30 mL) at about −35° C. over about 0.5 h and then stirred without cooling for about 1 h. NaOH solution (2.51 g in 300 mL of water, 62.8 mmol) was added to the above solution, and the resultant mixture was heated under reflux for a further 0.5 h. The volatile was removed under reduced pressure and then the aqueous phase was acidified with 6N HCl to pH=5 at 0-10° C. and filtered. The collected solids were dried in vacuo and then recrystallized from ethanol to give 7-(5-bromofuran-2-carbonyl)-1,4-dioxaspiro[4.5]decan-8-one as a yellow solid (2.02 g, 36%), which was used without further purification.

Synthesis of 3-(2-(3-(5-bromofuran-2-yl)-3-oxopropyl)-1,3-dioxolan-2-yl)propanoic acid. 7-(5-bromofuran-2-carbonyl)-1,4-dioxaspiro[4.5]decan-8-one (2.00 g, 5.78 mmol), 4-amino-3-methylbenzamide (1.04 mg, 6.90 mmol) and TsOH (100 mg, 0.578 mmol) were taken up into EtOH (20 mL). The resulted mixture was heated to reflux for 61 h. After evaporation under reduced pressure, the crude product was purified by a silica gel column chromatography (EA:PE=1:1) to afford 3-(2-(3-(5-bromofuran-2-yl)-3-oxopropyl)-1,3-dioxolan-2-yl)propanoic acid as a yellow solid (760 mg, yield: 30%).

Synthesis of 3-(5-(5-bromofuran-2-yl)-1-(4-carbamoyl-2-methylphenyl)-1H-pyrrol-2-yl)propanoic acid To a solution of 3-(2-(3-(5-bromofuran-2-yl)-3-oxopropyl)-1,3-dioxolan-2-yl)propanoic acid (100 mg, 0.224 mmol) in THF/H$_2$O (v/v=2/1, 1.5 mL) was added lithium hydroxide monohydrate (19 mg, 0.449 mmol). The solution was stirred at room temperature for 8 h. THF was removed under reduced pressure and the resultant aqueous solution was purified by Prep-HPLC to afford 3-(5-(5-bromofuran-2-yl)-1-(4-carbamoyl-2-methylphenyl)-1H-pyrrol-2-yl)propanoic acid as a grey solid (45 mg, yield: 48%).

Synthesis of 39b-A

To a mixture of 16-4 (Method 16) (200 mg, 0.419 mmol), NaBH$_3$CN (53 mg, 0.838 mmol), 37% HCHO (1.5 mL, 2.095 mmol) in CH$_3$CN (5 mL) was added AcOH (0.5 mL). After stirred at rt overnight, the solution was concentrated and diluted with water (15 mL), extracted with ethyl acetate (10 mL×4). The organic phase was separated and dried, purified with prep-TLC (PE:EA=1:1) to afford 39b-A as a yellow oil (97 mg, 49%).

Synthesis of 39b-B

Followed the procedure described in the last two steps of Scheme 6 (steps 7 and 8), with a purification of the final product by prep-HPLC.

Scheme 39: Preparation of 3-(1-(4-carbamoyl-2-methylphenyl)-5-(4-chloro-2-(methylamino)phenyl)-1H-pyrrol-2-yl)propanoic acid and 3-(1-(4-carbamoyl-2-methylphenyl)-5-(4-chloro-2-(dimethylamino)phenyl)-1H-pyrrol-2-yl)propanoic acid

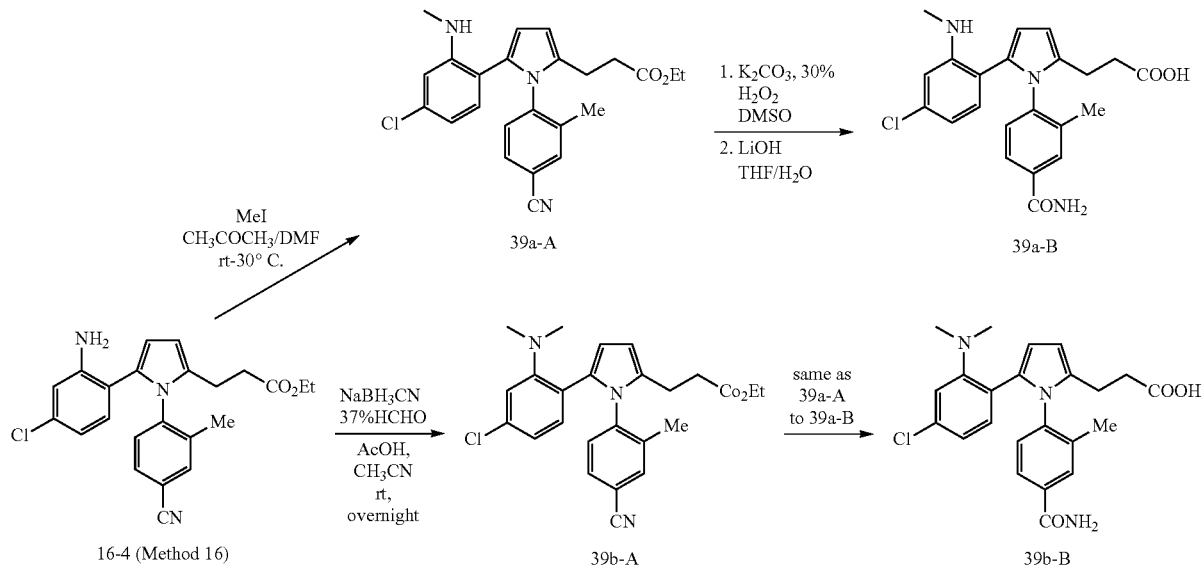

Synthesis of 39a-A

To a mixture of 16-4 (Method 16) (200 mg, 0.419 mmol) in acetone (5 mL) was added MeI (118 mg, 0.838 mmol). DMF (5 mL) was added after stirred at rt overnight. The mixture was heated to 30° C. overnight. The solution was concentrated and diluted with water (15 mL), extracted with ethyl acetate (10 mL×4). The organic phase was separated and dried, purified with prep-TLC (PE:EA=1:1) to afford 39a-A as a yellow oil (104 mg, 51%).

Synthesis of 39a-B

Followed the procedure described in the last two steps of Scheme 6 (steps 7 and 8), with a purification of the final product by prep-HPLC.

Scheme 40: A general scheme for preparing GSNOR inhibitors with structure 40B

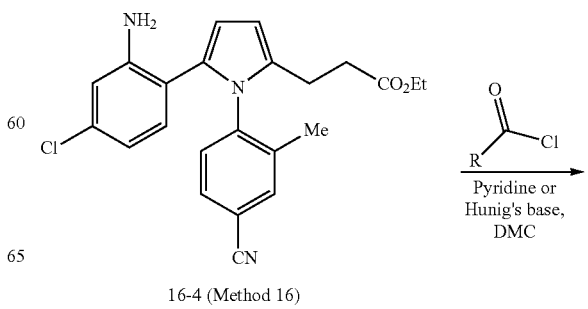

-continued

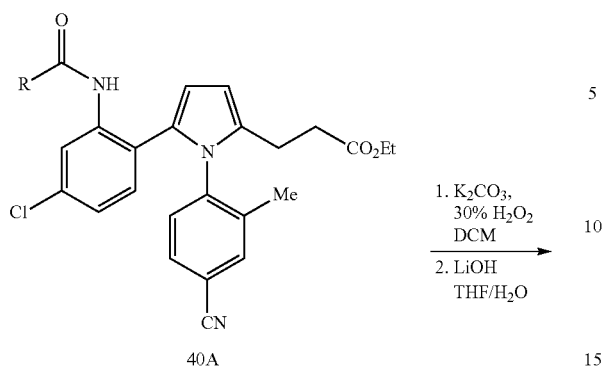

40A

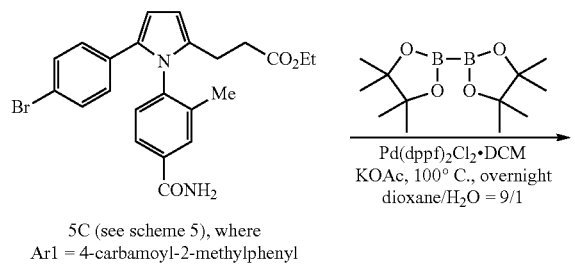

40B

Synthesis of 40A

See method described in Scheme 31.

Synthesis of 40B

See methodology described in the last steps of Scheme 6 (steps 7 and 8).

Scheme 41: Preparation of ethyl 3-(1-(4-carbamoyl-2-methylphenyl)-5-(4-thiazol-5-yl)phenyl)-1H-pyrrol-2-yl)propanoate (41B)

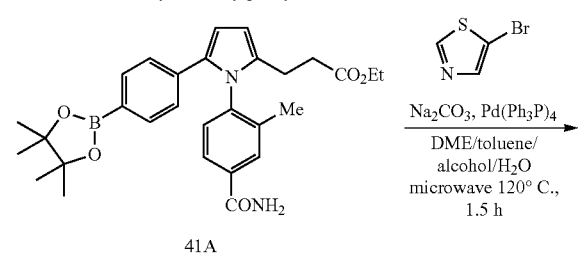

-continued

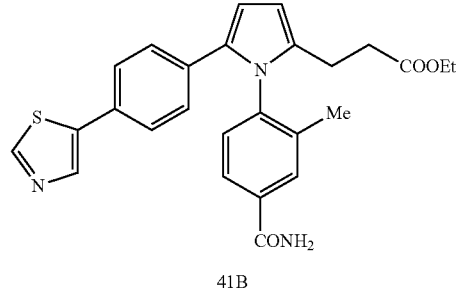

41B

Compound 41A

A solution of 5C (900 mg, 2 mmol), Bis(pinacolato)diboron (609 mg, 2.4 mmol), KOAc (344 mg, 4 mmol) and Pd(dppf)$_2$Cl$_2$DCM (326 mg, 0.4 mmol) in dioxane/H$_2$O (v/v=9/1) was stirred at 100° C. overnight. TLC showed that the reaction was complete. The mixture was evaporated to afford a brown oil. Water (6 mL) was added and the mixture was extracted with ethyl acetate (10 mL×3). The combined organic layers were dried over MgSO$_4$, filtered, concentrated and purified by silica gel column chromatography (PE:EA=1:1) to afford 41A as a yellow oil (730 mg, 73%).

Compound 41B

To a suspension of 41A (1.00 equivalent), 5-bromothiazole (0.92 equivalent), and sodium bicarbonate (3.15 equivalents) in solvents (DME/H$_2$O/Toluene/EtOH=10/1/6/3, 4 mL) was added Pd(PPh$_3$)$_4$ (0.2 equivalents). The reaction was degassed, purged with nitrogen and heated to reflux for 5 h. TLC showed that the reaction was complete. Water (4 mL) was added and the mixture was extracted with ethyl acetate (5 mL×3). The combined organic layers were dried over MgSO$_4$, filtered, concentrated and purified by silica gel column chromatography (DCM:MeOH=15:1) to afford 41B as a colorless oil.

Scheme 42: Preparation of 3-(5-(2-(1H-imidazol-1-yl)pyrimidin-5-yl)-1-(4-carbamoyl-2-methylphenyl)-1H-pyrrol-2-yl)propanoic acid

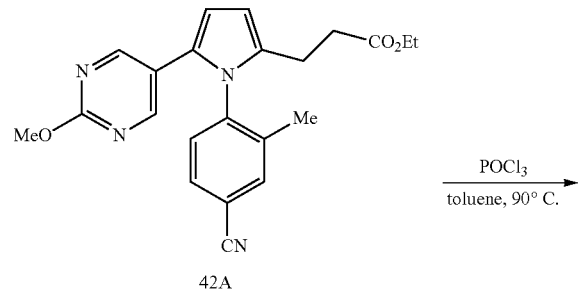

42A

Scheme 6, through 6F,
Ar2 = 2-methoxypyrimidin-5-yl/method # 11,

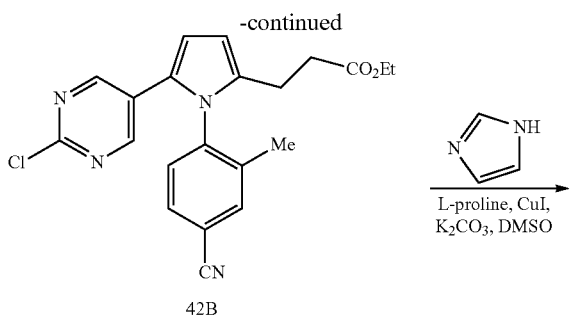

42B

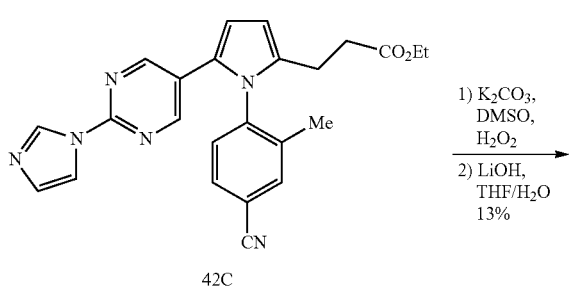

42C

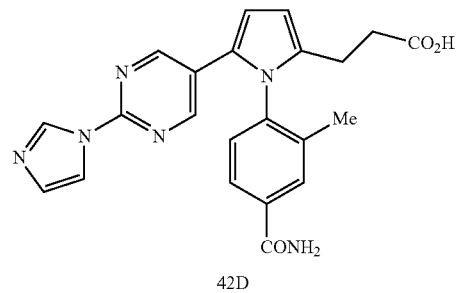

42D

Synthesis of 42A

Follow scheme 6 through 6F, where Ar2=2-methoxypyrimidin-5-yl, using the boronic acid intermediate described in Method 11.

Synthesis of 42B

To a solution of 42A (500 mg, 1.03 mmol) in toluene (5 mL) was added $POCl_3$ (0.3 mL, 6.0 mmol) at 0° C., and then stirred at 90° C. overnight. After cooling to room temperature, the reaction mixture was added to ice-water (20 mL). Sat. $Na_2CO_3$ was added to adjust pH=7 and extracted with ethyl acetate (50 mL×4). The combined organic layers were dried over $Na_2SO_4$, filtered, concentrated and purified by silica gel column chromatography (PE:EA=3:1) to afford 42B as a yellow solid (145 mg, 30%).

Synthesis of 42C

Followed the coupling procedure described in Scheme 5 with the conversion of 5C to 5D.

Synthesis of 42D

Followed the final two steps of Scheme 6, (6F to 6H) to give the desired compound, 3-(5-(2-(1H-imidazol-1-yl)pyrimidin-5-yl)-1-(4-carbamoyl-2-methylphenyl)-1H-pyrrol-2-yl)propanoic acid.

Scheme 43: Preparation of 3-(5-(4-methoxyphenyl)-1-(2-methyl-4-(pyridin-4-ylcarbamoyl)phenyl)-1H-pyrrol-2-yl)propanoic acid

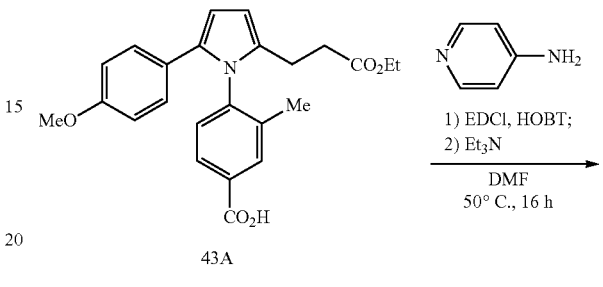

43A

See scheme 27, 27A where Y = $CH_3$

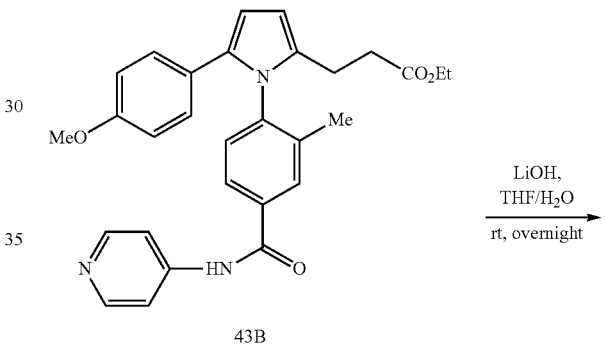

43B

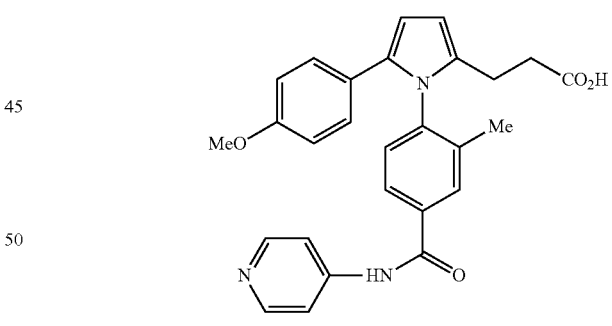

43C

Synthesis of Compound 43B 43A (500 mg, 1.23 mmol) was dissolved in DMF (7 mL). EDCI (592 mg, 1.85 mmol) and HOBT (250 mg, 1.85 mmol) were added and stirred the resultant mixture was stirred at 50° C. for 1 h. Pyridin-4-amine (121 mg, 1.29 mmol) was then added. After continual agitation at 50° C. overnight, brine (30 mL) was added and the resultant mixture was extracted with ethyl acetate (30 mL×3). The organic phase was washed with sat. $NaHCO_3$ (20 mL×2) and brine (20 mL), dried over MgSO$_4$, concentrated and purified by prep-TLC (MeOH:dichloromethane=1:15) to afford 43B as a yellow solid (243 mg, yield 41%).

Synthesis of Compound 43C. Hydrolysis of 43B completed following procedure described in the last step of Scheme 5

Scheme 44: Preparation of 3-(1-(4-carbamoyl-3-chlorophenyl)-5-(4-methoxyphenyl)-1H-pyrrol-2-yl)propanoic acid:

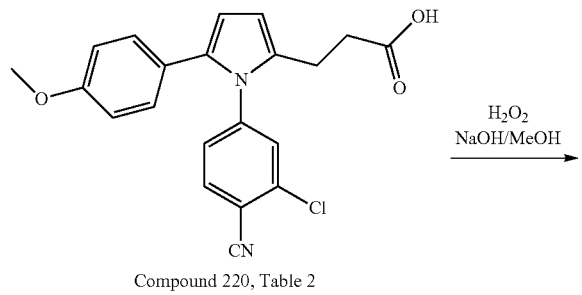

Compound 220, Table 2

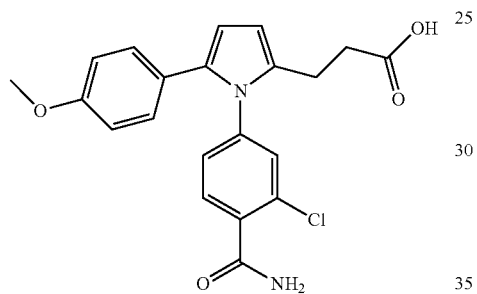

An 8 ml vial was loaded with a mixture of 30% H$_2$O$_2$ (50 uL), 3N NaOH (0.15 ml) and MeOH (0.125 ml). To this mixture 3-[1-(3-chloro-4-cyanophenyl)-5-(4-methoxyphenyl)-1H-pyrrol-2-yl]propanoic acid (40 mg, 0.105 mmol) was added at room temperature. The reaction mixture was stirred at rt for 45 minutes, TLC showed the starting material to be consumed. The reaction mixture was diluted with water, acidified to pH=2, stirred for 10 minutes, and filtered off. The solid was washed with water and dried to give 30 mg of 3-(1-(4-carbamoyl-3-chlorophenyl)-5-(4-methoxyphenyl)-1H-pyrrol-2-yl)propanoic acid, 73% yield.

Scheme 45: A general scheme for preparing GSNOR inhibitors with structure 45-2.

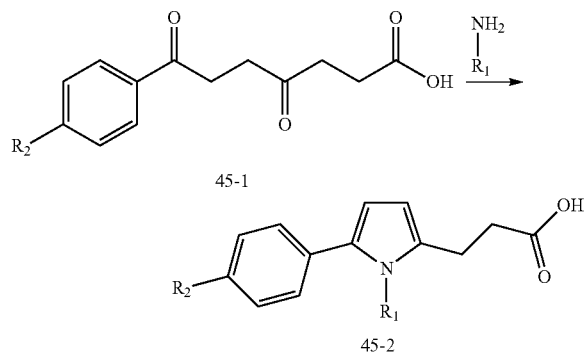

R$_2$ = H or OMe, commercial

Representative procedure for Scheme 45: Synthesis of 3-(1-(4-acetylphenyl)-5-phenyl-1H-pyrrol-2-yl) propanoic acid (45-2, R2=H, R1=4-acetylphenyl)

To a mixture of 4,7-dioxo-7-phenyl-heptanoic acid (150 mg, 0.64 mmol) in acetic acid (1.5 mL) was added 4-aminoacetophenone (87 mg, 0.64 mmol). The reaction was run using Microwave Biotage Initiator for 1 hour at 150° C. The solvent was removed in vacuo to provide the crude mixture, which was washed with water and filtered off. The solid was triturated with ether/methanol (98/2) to give 150 mg of 3-(1-(4-acetylphenyl)-5-phenyl-1H-pyrrol-2-yl)propanoic acid (45-2, R2=H, R1=4-acetylphenyl), 70% yield.

Scheme 46: Preparation of 3-(1-(4-hydroxy-3-(hydroxymethyl)phenyl)-5-phenyl-1H-pyrrol-2-yl)propanoic acid

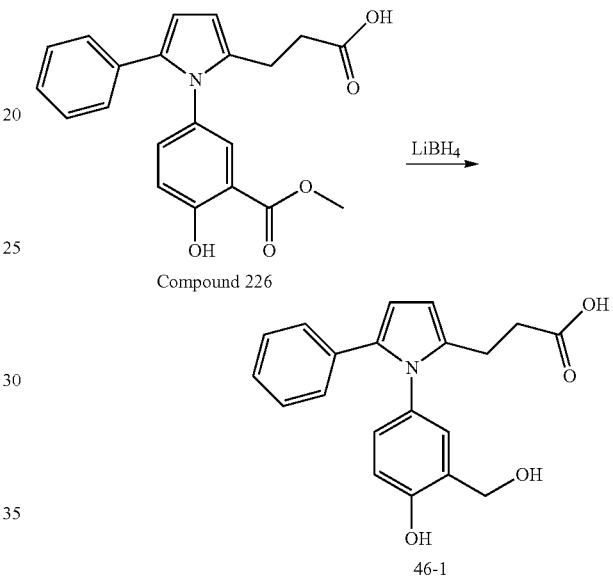

To a solution of 3-(1-(4-hydroxy-3-(methoxycarbonyl)phenyl)-5-phenyl-1H-pyrrol-2-yl)propanoic acid (40 mg, 0.109 mmol) in 2 ml anhydrous THF was added LiBH$_4$ (2M in THF, 0.14 ml, 2.5 eq.) via a syringe at 0° C. The reaction mixture was stirred at rt for 4 hours. Mixture was quenched with saturated sol. NH$_4$Cl, then acidified to pH=2 using 10% HCl solution. This was extracted several times using ethyl acetate. Combined organic layers were washed with brine, dried (Na$_2$SO$_4$) and concentrated. The crude was purified by preparative TLC using 1:1 ethyl acetate/hexane. 18 mg of 3-(1-(4-hydroxy-3-(hydroxymethyl)phenyl)-5-phenyl-1H-pyrrol-2-yl)propanoic acid was obtained, 47% yield.

Scheme 47: Preparation of 3-(1-(3-aminobenzo[d]isoxazol-6-yl)-5-(4-methoxyphenyl)-1H-pyrrol-2-yl)propanoic acid

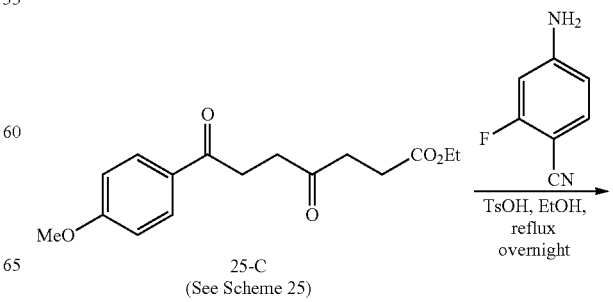

25-C
(See Scheme 25)

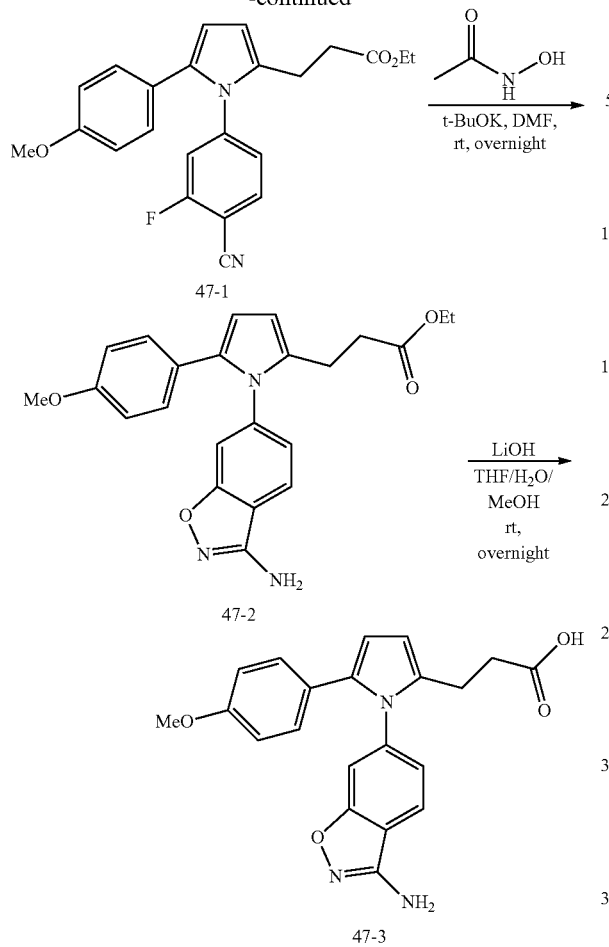

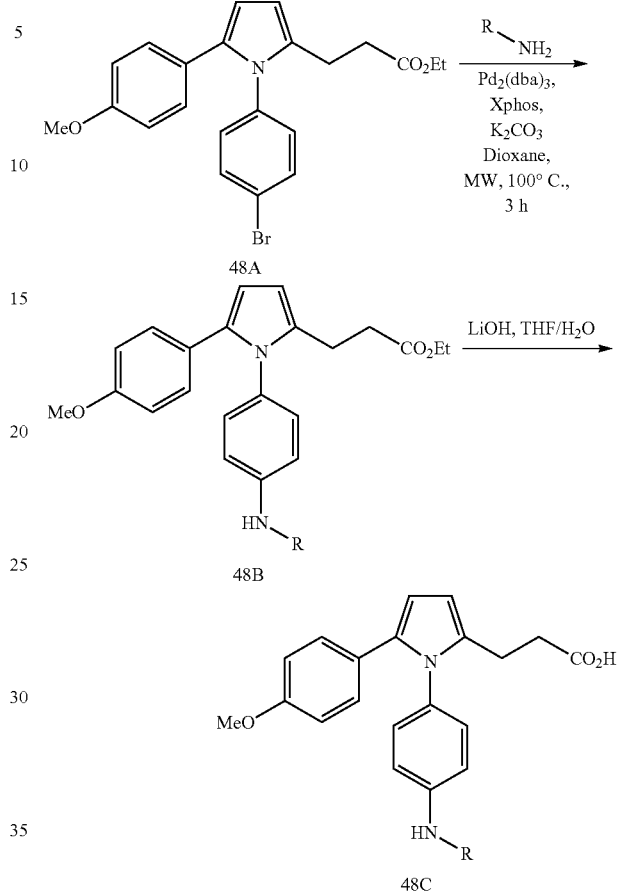

Scheme 48: A general scheme for preparing GSNOR inhibitors with structure 48C.

Synthesis of ethyl 3-(1-(4-cyano-3-fluorophenyl)-5-(4-methoxyphenyl)-1H-pyrrol-2-yl)propanoate (47-1)

Followed procedure described in Scheme 1, step 3.

Synthesis of ethyl 3-(1-(3-aminobenzo[d]isoxazol-6-yl)-5-(4-methoxyphenyl)-1H-pyrrol-2-yl)propanoate (47-2)

In 4 mL of dry DMF was dissolved acetohydroxamic acid (57 mg, 0.765 mmol), followed by potassium t-butoxide (86 mg, 0.765 mmol) at ambient temperature. After this mixture had been stirred for 30 min, compound 47-1 (200 mg, 0.510 mmol) was added and stirred overnight. The reaction mixture was poured into a mixture of brine (30 mL) and ethyl acetate (30 mL). The organic phase was separated, the aqueous layer was extracted EA (20 mL×3). The combined organic phase was washed with brine (30 mL), dried over anhydrous $Na_2SO_4$, filtered, concentrated and purified by silica gel column chromatography (PE:EA=1:1) to afford 47-2 as a yellow oil (80 mg, 39%).

Synthesis of 3-(1-(3-aminobenzo[d]isoxazol-6-yl)-5-(4-methoxyphenyl)-1H-pyrrol-2-yl)propanoic acid (47-3)

Followed procedure described in the last step of Scheme 25 to get the desired product, 47-3.

Representative procedure for Scheme 48: Synthesis of 3-(5-(4-methoxyphenyl)-1-(4-(pyridin-3-ylamino)phenyl)-1H-pyrrol-2-yl)propanoic acid (48-3, R2=H, R1=4-acetylphenyl)

Synthesis of ethyl 3-(1-(4-bromophenyl)-5-(4-methoxyphenyl)-1H-pyrrol-2-yl)propanoate (48A)

Prepared by Scheme 1, Step 1-Step 3, where R1=4-bromophenyl, R2=4-methoxy phenyl.

Synthesis of ethyl 3-(5-(4-methoxyphenyl)-1-(4-(pyridin-3-ylamino)phenyl)-1H-pyrrol-2-yl)propanoate (48B, R=pyridin-3-yl)

48A (500 mg, 1.17 mmol), pyridin-3-amine (121 mg, 1.28 mmol), $Pd_2(dba)_3$ (54 mg, 0.0600 mmol), XPhos (42 mg, 0.0870 mmol) and $K_2CO_3$ (485 mg, 3.50 mmol) were taken up into dioxane (4 mL). After being degassed and refilled with nitrogen, the resulted mixture was heated to 100° C. under microwave for 3 h. After evaporation under reduced pressure, the crude product was purified by silica gel column chromatography (MeOH:DCM=1:10) to afford 48B, R=pyridin-3-yl as a yellow oil (344 mg, yield: 44%).

Synthesis of 3-(5-(4-methoxyphenyl)-1-(4-(pyridin-3-ylamino)phenyl)-1H-pyrrol-2-yl)propanoic acid (48C, R=pyridin-3-yl)

Followed procedure described in the final step of Scheme 5 to give 48C, R=pyridin-3-yl as a white solid (45 mg, yield: 14%).

Scheme 49: Synthesis of 3-(1-(4-(2-hydroxyethylamino)phenyl)-5-(4-(2-methyl-1H-imidazol-1-yl)phenyl)-1H-pyrrol-2-yl)propanoic acid

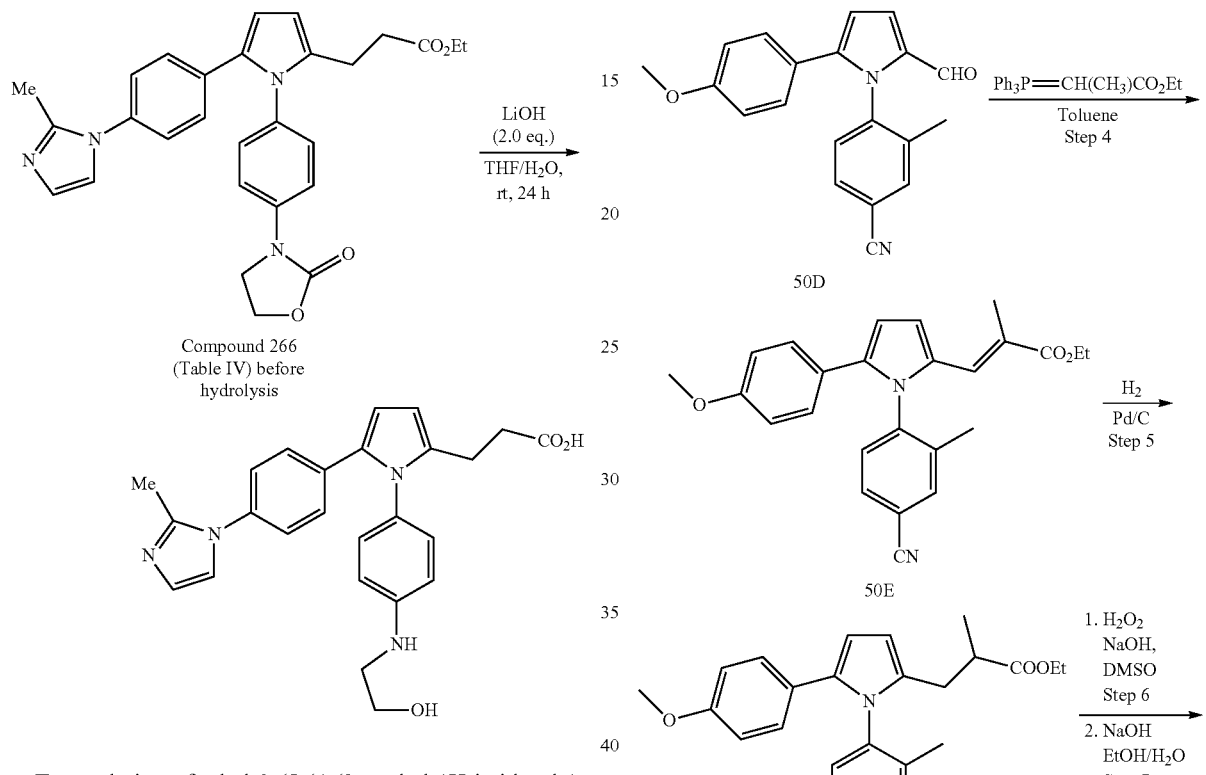

To a solution of ethyl 3-(5-(4-(2-methyl-1H-imidazol-1-yl)phenyl)-1-(4-(2-oxooxazolidin-3-yl)phenyl)-1H-pyrrol-2-yl)propanoate (see compound 266, Table IV) (105 mg, 0.22 mmol) in THF/H₂O (1 mL, v/v=1/1) was added 2 equivalents of lithium hydroxide monohydrate (19 mg, 0.43 mmol). The mixture was stirred at room temperature for 24 h. THF was evaporated in vacuo. The residue was acidified to pH=5 with 5% hydrochloric acid, concentrated and purified by prep-HPLC to afford the title compound as a brown solid (68 mg, yield 73%).

Scheme 50: Synthesis of 3-(1-(4-carbamoyl-2-methylphenyl)-5-(4-methoxyphenyl)-1H-pyrrol-2-yl)-2-methylpropanoic acid

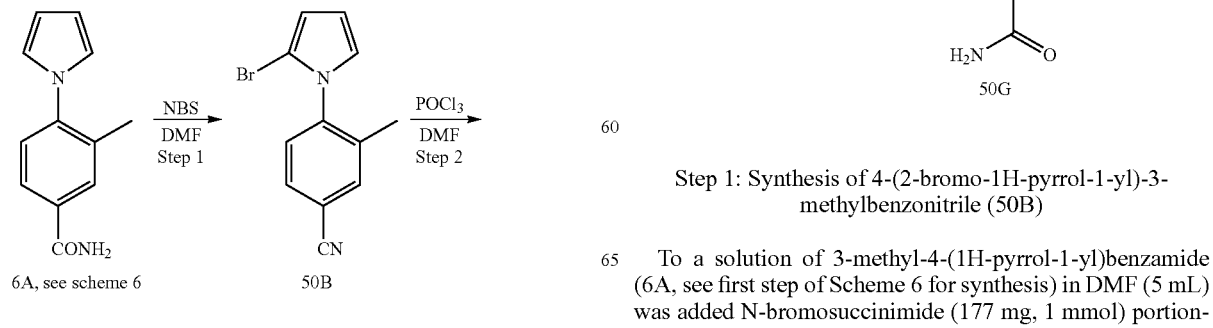

Step 1: Synthesis of 4-(2-bromo-1H-pyrrol-1-yl)-3-methylbenzonitrile (50B)

To a solution of 3-methyl-4-(1H-pyrrol-1-yl)benzamide (6A, see first step of Scheme 6 for synthesis) in DMF (5 mL) was added N-bromosuccinimide (177 mg, 1 mmol) portionwise at 0° C., after the addition was completed, the mixture was stirred at room temperature for 35 min. The reaction mixture was poured into water, and extracted with ethyl acetate (10 mL×3). The combined organic layers were washed with brine (25 mL×2), dried over anhydrous sodium sulfate, filtered, and concentrated under reduced pressure. The residue was purified by column chromatography on silica gel (petroleum ether/ethyl acetate=5:1) to afford 50B (100 mg, yield 36%).

Step 2: Synthesis of 4-(2-bromo-5-formyl-1H-pyrrol-1-yl)-3-methylbenzonitrile (50C)

DMF (0.1 mL) was added to phosphorus oxychloride (0.5 mL, 5.2 mmol) at 0° C., and the mixture was stirred at room temperature for 1.5 h. At 0° C., a solution of compound 50B (100 mg. 0.36 mmol) in DMF (2 mL) was added, and the resultant mixture was stirred at room temperature for 30 min. The reaction mixture was poured into ice-water, adjusted to pH=8 with saturated aqueous sodium carbonate solution, and extracted with ethyl acetate (10 mL×3). The combined organic layers were washed with brine (20 mL×2), dried over anhydrous sodium sulfate, filtered, and concentrated under reduced pressure. The residue was purified by preparative TLC to afford 50C (60 mg, yield 58%).

Step 3: Synthesis of 4-(2-formyl-5-(4-methoxyphenyl)-1H-pyrrol-1-yl)-3-methylbenzonitrile (50D)

A mixture of compound 50C (24 mg, 0.083 mmol), compound 4-methoxyphenylboronic acid (15.2 mg, 0.1 mmol) and sodium carbonate (17.6 mg, 0.166 mmol) in a mixture of DME (5 mL) and water (1 mL) was degassed, and [11'-bis(diphenlphospino)-ferrocene]dichloropalladium(II) (96 mg, 0.008 mmol) was added. The reaction mixture was heated at 90° C. for 10 hours, poured into water, and extracted with ethyl acetate (10 mL×3). The combine organic layers were washed with brine (20 mL×2), dried over anhydrous sodium sulfate, filtered, and concentrate under reduced pressure, and purified by preparative TLC to afford the compound 50D (15 mg, 57%).

Step 4: Synthesis of (E)-ethyl 3-(1-(4-cyano-2-methylphenyl)-5-(4-methoxyphenyl)-1H-pyrrol-2-yl)-2-methylacrylate (50E)

A mixture of compound 50D (300 mg, 0.9 mmol) and Ph3P=CH(CH3)CO2Et (360 mg, 0.99 mmol) in toluene (10 mL) was heated at 120° C. for 10 h. The reaction mixture was concentrated, and the residue was purified by column chromatography on silica gel (petroleum ether/ethyl acetate=15:1) to afford 50E (220 mg, 61% yield), which contained some of Ph₃OP and was used in the next step directly.

Step 5: Synthesis of ethyl 3-(1-(4-cyano-2-methylphenyl)-5-(4-methoxyphenyl)-1H-pyrrol-2-yl)-2-methylpropanoate (50F)

(E)-ethyl 3-(1-(4-cyano-2-methylphenyl)-5-(4-methoxyphenyl)-1H-pyrrol-2-yl)-2-methylacrylate (50E) was converted to the title compound (50F) following the same procedure described in Scheme 6, step 4.

Step 6 and Step 7: Synthesis of 3-(1-(4-carbamoyl-2-methylphenyl)-5-(4-methoxyphenyl)-1H-pyrrol-2-yl)-2-methylpropanoic acid (50G)

Ethyl 3-(1-(4-cyano-2-methylphenyl)-5-(4-methoxyphenyl)-1H-pyrrol-2-yl)-2-methylpropanoate (50F) was converted to the title compound (50G) following the same procedure described in Scheme 6, steps 7 and 8.

The following Methods describe the synthesis of intermediates/starting materials used in Schemes described above:

Method 1: Synthesis of 4-Amino-3-chloro-benzamide:

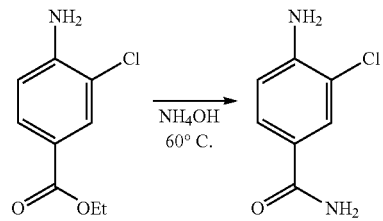

A 18 ml vial was loaded with 4-Amino-3-chloro-benzoic acid ethyl ester (350 mg, 1.88 mmole) and 5 ml of 30% NH₄OH. The vial was sealed and the mixture was heated at 50° C. for 3 days. The mixture was cooled down and concentrated to half. The suspension was filtered off, solid was washed with water and dried to give 200 mg product, 62.3% yield.

Method 2: Synthesis of 1-(6-imidazol-1-yl-pyridin-3-yl)-ethanone

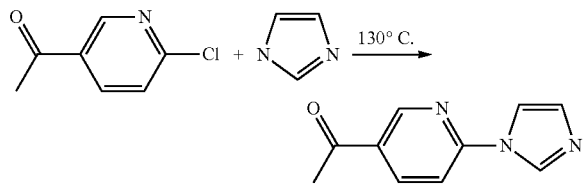

To a 25 mL vial which contained 1-(6-chloro-pyridin-3-yl)-ethanone (1.5 g, 10 mmoL) was added 1H-imidazole (3 g, 50 mmoL) at rt. The mixture was stirred at 120-130° C. for 2 h and cooled to rt. The contents were poured into 150 mL ice-water solution and extracted with EtOAc (3×100 mL). The combined organic layers was washed with water (3×50 mL), brine (50 mL) and dried over Na₂SO₄. The solvent was removed under vacuum to yield the crude which was purified by column to afford desired 1-(6-imidazol-1-yl-pyridin-3-yl)-ethanone (1.25 g, 67%).

Method 3: 4-(1H-imidazol-2-yl)-2-methylaniline

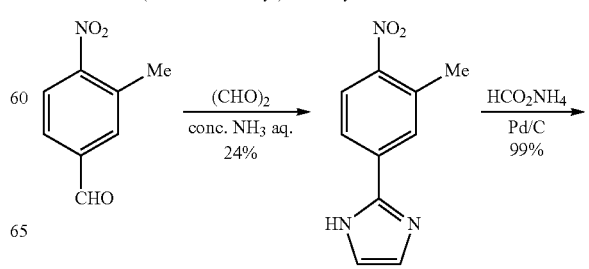

-continued

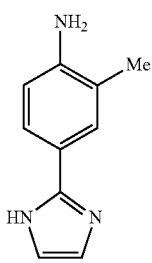

Step 1: Synthesis of 2-(3-methyl-4-nitrophenyl)-1H-imidazole

To a solution of 3-methyl-4-nitrobenzaldehyde (1.00 g, 6.06 mmol) in THF (6 mL) was added conc. NH₃ (4 mL), MeOH (5 mL) and 40% glyoxal (1.32 g, 9.09 mmol) at 0° C. The resulting mixture was stirred overnight at room temperature and evaporated under reduced pressure. The residue was rinsed with water (100 mL) and then purified by silica gel column chromatography (PE:EA=3:1) to afford 2-(3-methyl-4-nitrophenyl)-1H-imidazole as a brown solid (295 mg, 24%).

Step 2: Synthesis of 4-(1H-imidazol-2-yl)-2-methylaniline

To a mixture of 2-(3-methyl-4-nitrophenyl)-1H-imidazole (1.17 g, 5.76 mmol) and 10% Pd/C (0.8 g) in EtOH (5 mL) was added dropwise HCO₂NH₄ [3.63 g, 57.64 mmoL, dissolving in MeOH (50 mL)]. After 1 h, TLC showed the reaction was complete. Filtration and the filtrate was evaporated under reduced pressure. The residue was dissolved in DCM (30 mL) and filtrated. The filtrate was concentrated to afford 4-(1H-imidazol-2-yl)-2-methylaniline as a yellow solid (1.0 g, 99%).

Method 4: 2-methyl-4-(oxazol-2-yl)aniline

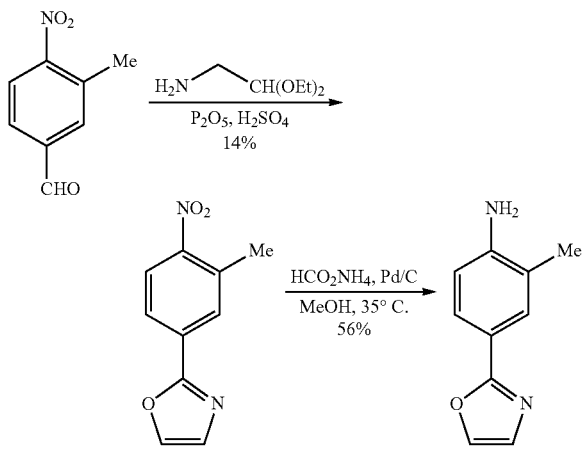

Step 1: Synthesis of 2-(3-methyl-4-nitrophenyl)oxazole

A mixture of 3-methyl-4-nitrobenzaldehyde (500 mg) and diethyl aminoacetal (404 mg, 3.03 mmol) was heated at 115° C. for 3 h. After cooling to room temperature, conc. H₂SO₄ (4.2 mL) was added by one portion and the mixture of P₂O₅ (1.44 g, 10.15 mmol) and H₂SO₄ (0.5 mL) was dropped into within 5 min. The resulting mixture was heated at 180° C. for 20 min and then poured into ice-water (100 mL), which was neutralized with ammonia. A precipitate was filtered and purified by prep-TLC (PE:EA=4:1) to afford 2-(3-methyl-4-nitrophenyl)oxazole as a white solid (91 mg, 14%).

Step 2: Synthesis of 2-methyl-4-(oxazol-2-yl)aniline

Under nitrogen atmosphere, 2-(3-methyl-4-nitrophenyl)oxazole (50 mg, 0.25 mmol), HCOONH₄ (32 mg, 5.90 mmol) and Pd/C (10%, 13 mg) were added into methanol (5 mL). After having been stirred at 35° C. for 6 h, the mixture was filtered, concentrated and purified by prep-TLC (DCM) to afford 2-methyl-4-(oxazol-2-yl)aniline as a yellow solid (24 mg, 56%).

Method 5: 5-Amino-2,3-dihydro-isoindol-1-one

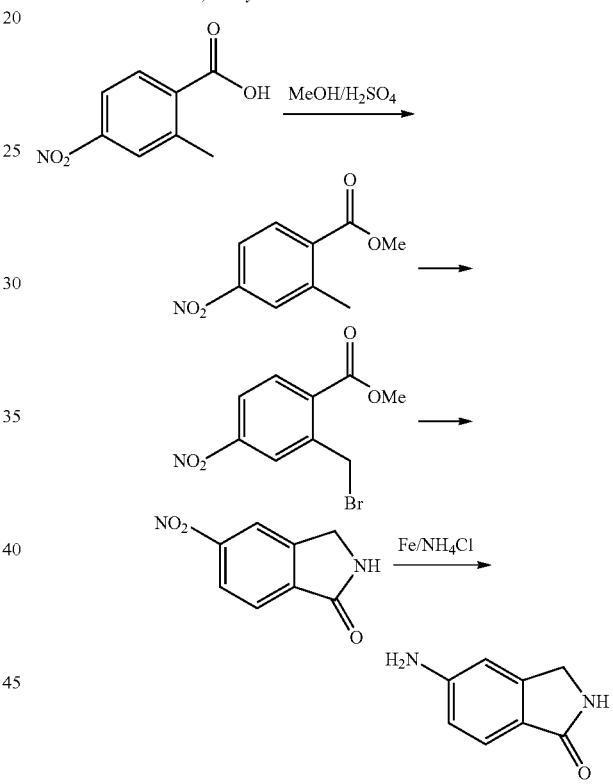

Step 1: Synthesis of 2-Methyl-4-nitro-benzoic acid methyl ester

To a solution of 2-methyl-4-nitro-benzoic acid (3 g, 16.56 mmole) in 30 ml methanol was added at 0° C. sulfuric acid (95-98%, 10 ml) slowly for ½ hr. The reaction mixture was stirred at 70° C. for 24 hrs. Mixture was cooled down, a solid precipitated out, then the mixture was concentrated, diluted with 50 ml water, stirred for 10 minutes, filtered off, the solid was washed with water, dried to afford 3.08 g of brown solid, 95.3% yield, pure by H NMR.

Step 2: Synthesis of 2-bromomethyl-4-nitro-benzoic acid methyl ester

To a solution of 2-Methyl-4-nitro-benzoic acid methyl ester (3.08 g, 15.79 mmole) in 125 ml carbontetrachloride was added NBS (3.1 g, 17.38 mmole) and AIBN (390 mg, 2.38 mmole). The reaction mixture was heated at reflux under light for 22 hours. The reaction mixture was cooled down, concentrated to half, filtered off, solid was washed with 25 ml carbontetrachloride. The filtrate was concentrated to give 4 g crude product, containing about 20% unreacted starting material. This was used for next step without purification.

Step 3: Synthesis of 5-Nitro-2,3-dihydro-isoindol-1-one

The crude from the previous step (4 g) was placed in a 100 ml round bottom flask, then a solution of 7N $NH_3$ in MeOH was added. The mixture was stirred at room temperature, overnight. The mixture was concentrated down to a solid residue, then triturated with 75 ml ethylacetate. The suspension was filtered off, solid was dried to give 1.8 g product, pure by HNMR, 64% over 2 steps yield.

Step 4: Synthesis of 5-Amino-2,3-dihydro-isoindol-1-one

To a suspension of Fe (1.1 g, 19.6 mmole), $NH_4Cl$ (1.5 g, 28 mmole) in a mixture of ethanol/water (30 ml/7 ml) at 80° C. was added a mixture of 5-Nitro-2,3-dihydro-isoindol-1-one (1 g, 5.6 mmole) in 10 ml ethanol. The reaction mixture was stirred at 80° C. for 2 hours. Mixture was cooled down, filtered off, solid was washed with 50 ml ethanol. The filtrate was concentrated, taken into 50 ml ethylacetate, washed with 20 ml water. Organic layer was dried over $Na_2SO_4$, filtered and concentrated to give about 900 mg crude. Trituration with methyl t-butylether gave 400 mg pure product, 48% yield.

Step 1: Synthesis of 6-Nitro-benzothiazol-2-yl)-carbamic acid tert-butyl ester

A 100 ml RBF was loaded with 2-amino-6-nitrobenzothiazole (3 g, 15.36 mmole) and 45 ml DMF. To this solution DMAP (936 mg, 7.68 mmole) and BOC anhydride (5 g, 23 mmole) were added. The solution was heated at 90° C. for 1 hour. After the mixture was allowed to cool to room temperature, a bulky solid formed. The suspension was filtered off, solid was washed with water and dried to give 2.5 g product. The filtrate was concentrated to half, diluted with MeOH. More solid precipitated out. The suspension was filtered off, the solid was washed with water and dried to give 1 g product, a total of 3.5 g, 87.5% yield.

Step 2: Synthesis of 6-Amino-benzothiazol-2-yl)-carbamic acid tert-butyl ester

A 250 ML RBF was loaded with 6-nitro-benzothiazol-2-yl)-carbamic acid tert-butyl ester (1.2 g, 4 mmole) and 20 ml THF. To this solution was added 10% Pd/C (400 mg, 0.37 mmole). The reaction mixture was stirred at 30-40 psi for about 2 hours. Mixture was diluted with 50 ml THF, filtered off trough a celite pad, washed with MeOH. Filtrate was concentrated to give 600 mg product, 60% yield.

Method 6: 5-Amino-pyridine-2-carboxylic acid amide:

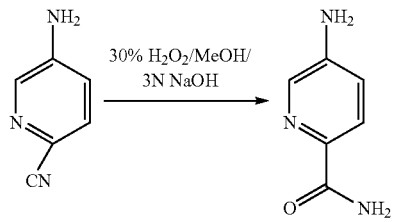

A 18 ml vial was loaded with a mixture of 30% $H_2O_2$ (1 ml), 3N NaOH (3 ml) and MeOH (2.5 ml). To this mixture 5-Amino-pyridine-2-carbonitrile (450 mg, 3.78 mmole) was added at room temperature. Reaction mixture was stirred at rt for 45 minutes, TLC showed the starting material to be consumed. The mixture was diluted with water and filtered; the solid was washed with water and dried to give 480 mg product, 92% yield.

Method 7: 6-Amino-benzothiazol-2-yl)-carbamic acid tert-butyl ester:

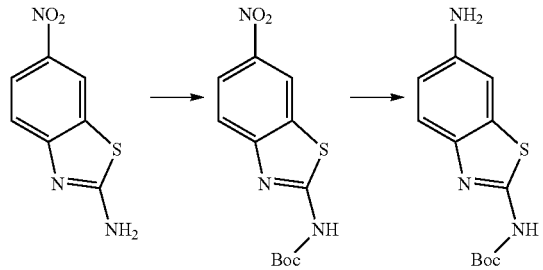

Method 8: 5-Amino-thiophene-2-carboxylic acid amide

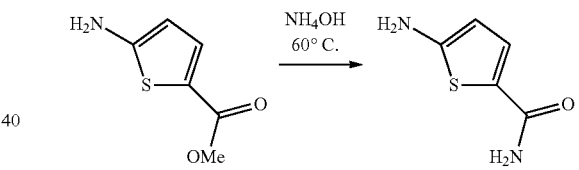

A 18 ml vial was loaded with 5-amino-thiophene-2-carboxylic acid methylester (250 mg, 1.59 mmole) and 5 ml of 30% $NH_4OH$. The vial was sealed and the mixture was heated at 60° C. for 24 hours. The mixture was cooled down and concentrated to give 200 mg crude product, 47.4% yield.

Method 9: 4-Amino-thiophene-2-carboxylic acid amide

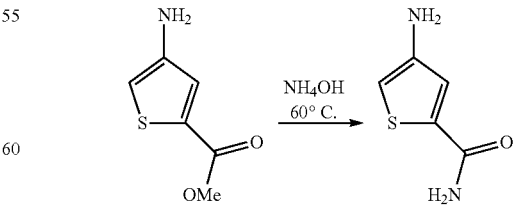

Followed same procedure as described in Method 8.

Method 10: Synthesis of 2-(2-Amino-thiazol-4-yl)-acetamide

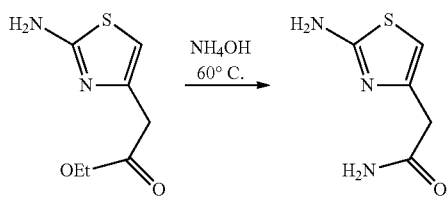

A 18 ml vial was loaded with (2-Amino-thiazol-4-yl)-acetic acid ethyl ester (500 mg, 2.68 mmole) and 5 ml of 30% NH₄OH. The vial was sealed and the mixture was heated at 50° C. for 3 days. The mixture was cooled down and concentrated to half. The suspension was filtered off, solid was washed with water and dried to give 200 mg product, 47.4% yield Method 11: Synthesis of 2-methoxy-5-(4,4,5,5-tetramethyl-1,3,2-dioxaborolan-2-yl)pyrimidine

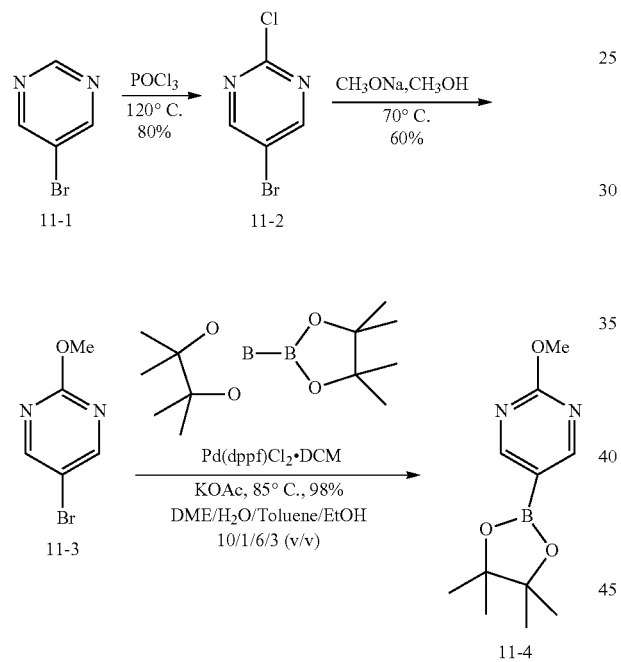

Synthesis of Compound 11-2

Compound 11-1 (5.0 g, 2.86 mmol) was added portionwise to POCl₃ (15 mL) at 0° C. during 10 min. The reaction mixture was stirred at 120° C. for 4 h, then cooled to room temperature and added to ice-water (100 mL). Sat. Na₂CO₃ was added to adjust pH=7 and extracted with ethyl acetate (200 mL×4). The combined organic layers were dried over Na₂SO₄, filtered and concentrated to afford 11-2, which was used in the next step without further purification (4.50 g, 80%).

Synthesis of Compound 11-3

To a solution of 11-2 (2.0 g, 10 mmol) in methanol (15 mL) was added CH₃ONa (2.16 g, 40 mmol). The resulting mixture was stirred at 70° C. overnight. Methanol was evaporated in vacuum. Water (10 mL) was added carefully to the residue and the mixture was extracted with ethyl acetate (300 mL×3). The combined organic layers were dried over Na₂SO₄, filtered and concentrated to afford 11-3 as a yellow solid (1.17 g, 60%).

Synthesis of Compound 11-4

To a solution of 11-3 (800 mg, 4.26 mmol) and potassium acetate (1.25 g, 12.77 mmol) in solvent (DME/H₂O/Toluenen/EtOH=10/1/6/3, 7 mL) was added Pd(dppf)Cl₂.DCM (700 mg, 0.85 mmol) and Bis(pinacolato)diboron (2.44 g, 9.6 mmol). After having been degassed and recharged with nitrogen, the reaction mixture was stirred at 85° C. overnight. TLC showed the reaction was complete. After cooling to room temperature, water (10 mL) was added and extracted with ethyl acetate (30 mL×3). The combined organic layers were dried over Na₂SO₄, filtered, concentrated and purified by silica gel column chromatography (PE:EA=5:1) to afford 11-4 as a yellow solid (1.0 g, 98%).

Method 12: Synthesis of 2-chloro-4-(4,4,5,5-tetramethyl-1,3,2-dioxaborolan-2-yl)aniline

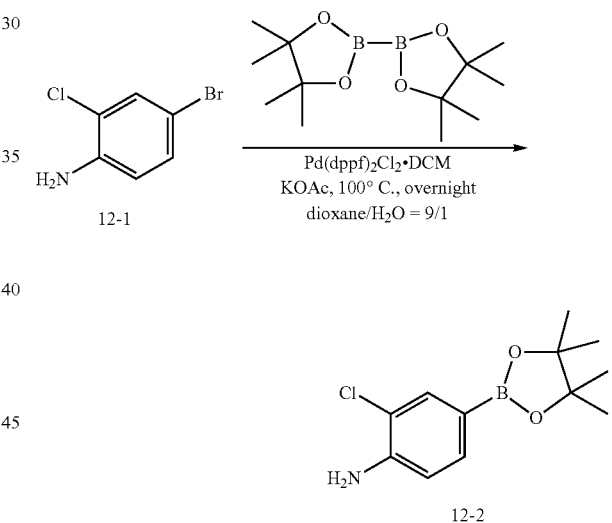

Compound 12-2

A solution of 12-1 (12.3 g, 0.06 mmol), Bis(pinacolato)diboron (18.3 g, 0.072 mol), KOAc (11.75 g, 0.12 mmol) and Pd(dppf)₂Cl₂DCM (2.0 g, 2.45 mmol) in dioxane/H₂O (v/v=9/1, 100 mL) was stirred at 80° C. overnight. TLC showed that the reaction was complete. The mixture was evaporated to afford a brown oil. Water (60 mL) was added and the mixture was extracted with ethyl acetate (60 mL×3). The combined organic layers were dried over MgSO₄, filtered, concentrated and purified by silica gel column chromatography (PE:EA=10:1) to afford 12-2 as a yellow solid (9.1 g, 60%).

Method 13: Synthesis of 2-methyl-4-(thiazol-2-yl)aniline

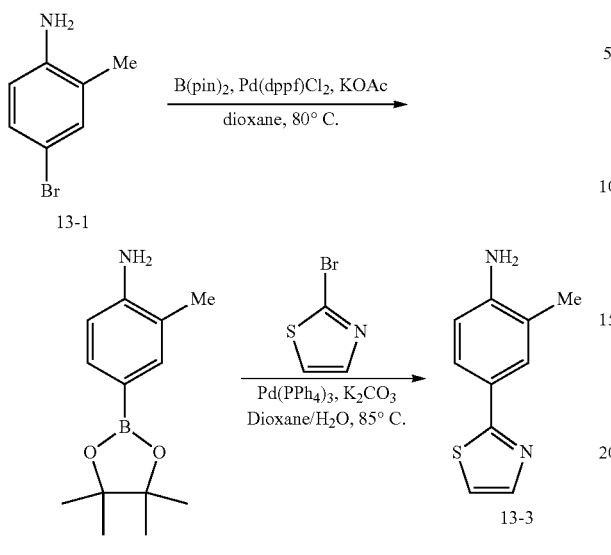

Compound 13-2

To a mixture of 4-bromo-2-methylbenzenamine (500 mg, 2.69 mmol), KOAc (1.32 g, 13.4 mmol) and bis(pinacolato)diboron (2.05 mg, 8.0 mmol) in dioxane (4 mL) was added Pd(dppf)Cl$_2$ (110 mg, 0.134 mmol). After having been degassed and recharged with nitrogen, the mixture was refluxed at 85° C. for 16 h. TLC showed that the reaction was complete. Water (20 mL) was added and the mixture was extracted with ethyl acetate (30 mL×3). The combined organic layers were dried over Na$_2$SO$_4$, filtered, concentrated and purified by silica gel column chromatography (DCM) to afford 13-2 as a white solid (485 mg, yield 77%).

Compound 13-3

To a mixture of 13-2 (257 mg, 1.57 mmol), K$_2$CO$_3$ (653 mg, 4.7 mmol) and 2-bromothiazole (367 mg, 1.57 mmol) in the mixed solvent (Dioxane/H$_2$O=2/1, 15 mL) was added Pd(PPh$_3$)$_4$ (182 mg, 0.157 mmol). After having been degassed and recharged with nitrogen, the mixture was refluxed at 85° C. for 11 h. TLC showed that the reaction was complete. Water (10 mL) was added and the mixture was extracted with ethyl acetate (20 mL×3). The combined organic layers were dried over Na$_2$SO$_4$, filtered, concentrated and purified by silica gel column chromatography (PE:Acetone=10:1) to afford 13-3 as a yellow oil (229 mg, yield 76%).

Method 14: Synthesis of 2-cyclopropyl-1H-imidazole

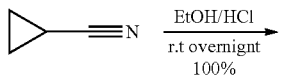

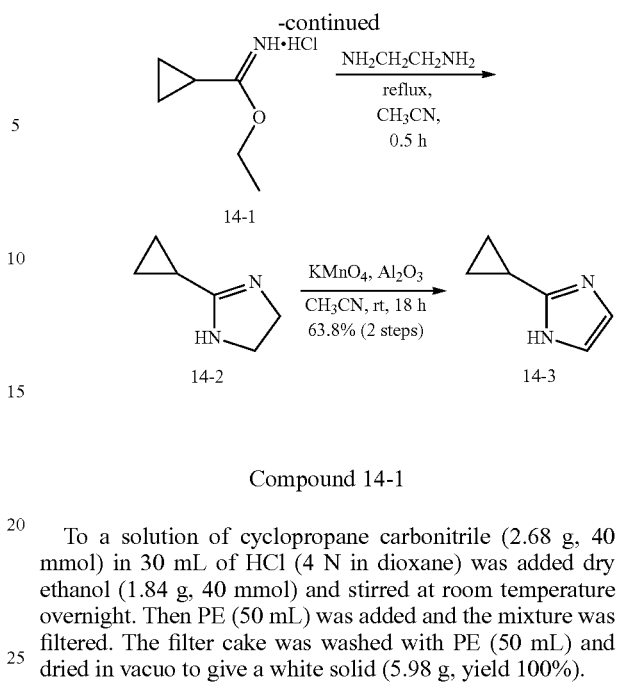

Compound 14-1

To a solution of cyclopropane carbonitrile (2.68 g, 40 mmol) in 30 mL of HCl (4 N in dioxane) was added dry ethanol (1.84 g, 40 mmol) and stirred at room temperature overnight. Then PE (50 mL) was added and the mixture was filtered. The filter cake was washed with PE (50 mL) and dried in vacuo to give a white solid (5.98 g, yield 100%).

Compound 14-2

To a mixture of 14-1 (2.50 g, 16.7 mmol, 1.0 eq) in CH$_3$CN (50 mL) was added ethane-1,2-diamine (1.2 g, 20.1 mmol, 1.2 eq). The mixture was heated under reflux for 0.5 h and cooled to room temperature. The reaction mixture was concentrated in vacuo to afford 14-2 (2.17 g) as a white solid, which was used for next step without purification.

Compound 14-3

To a mixture of 14-2 (2.17 g, 16.7 mmol, 1.0 eq) in CH$_3$CN (50 mL) was added KMnO$_4$ (1.58 g, 66.8 mmol, 4.0 eq) and silica gel (10.0 g, 200-300 mesh). The reaction mixture was stirred at room temperature overnight and methanol (about 5 mL) was added to the solution. The mixture was filtered and concentrated in vacuo to afford 14-3 as a white solid. (1.15 g, two steps yield 64%).

Method 15: Synthesis of 1-(4-bromo-2-methoxyphenyl)ethanone

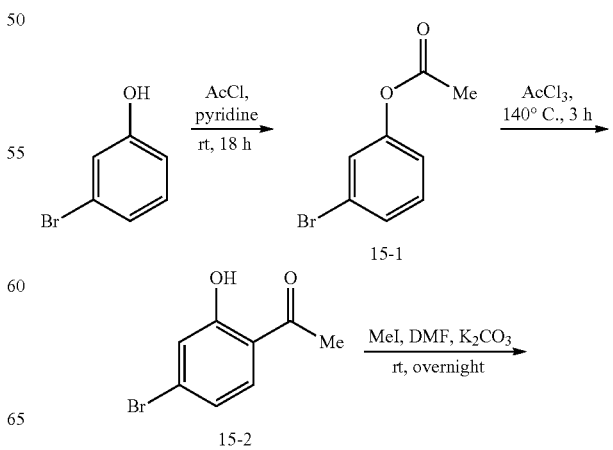

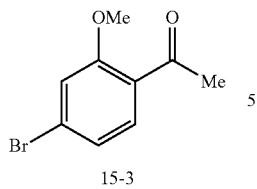

Compound 15-1

To a stirred suspension of 3-bromophenol (50 g, 0.29 mol) in pyridine (200 mL) and dichloromethane (100 mL) was added dropwise acetyl chloride (25 mL, 0.35 mol) at 0° C. and the mixture was stirred 18 h at room temperature. LC-MS showed that the reaction was complete. Pyridine and dichloromethane was evaporated in vacuo. Water (600 mL) was added and acidified with hydrochloric acid at pH 2. The reaction mixture was extracted with ethyl acetate (500 mL×3) and the organic phase was dried over anhydrous sodium sulfate, filtrated, concentrated and purified by column chromatography (PE:EA=60:1) to afford compound 15-1 as a colorless liquid (46 g, 74%).

Compound 15-2

To a stirred suspensions of compound 15-1 (46 g, 0.0.21 mol) and anhydrous aluminum chloride power (57 g, 0.42 mol) was heated to 160° C. for 3 h. The mixture reaction was cooled to room temperature and ice (200 g) and water (800 mL) was poured and purified with hydrochloric acid at pH 7. the reaction was extracted with ethyl acetate (500 mL×$_3$) and the organic phase was washed with saturated sodium bicarbonate, dried over anhydrous sodium sulfate, filtrated, concentrated and purified by column chromatography (PE:EA=60:1) to afford compound 15-2 as a light green solid (35.1 g, 76%).

Compound 15-3

To a suspensions of compound 15-2 (25 g, 0.12 mol) and potassium carbonate (24 g, 0.18 mol) in anhydrous DMF (20 mL) was added to MeI (22.6 mL, 0.23 mol) and the mixture reaction was stirred at room temperature overnight. LCMS showed that the reaction was complete. Then water (300 mL) was poured and the mixture was extracted with ethyl acetate and the organic phase was (200 mL×3) and the organic phase was washed saturated sodium chloride, dried over anhydrous sodium sulfate, filtrated, concentrated to afford compound 15-3 as a colorless solid (26.1 g, 98%).

Method 16: Synthesis of ethyl 3-(5-(2-amino-4-chlorophenyl)-1-(4-cyano-2-methylphenyl)-1H-pyrrol-2-yl)propanoate

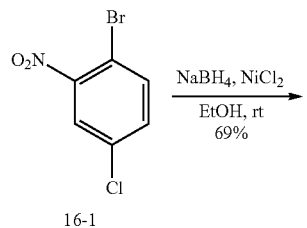

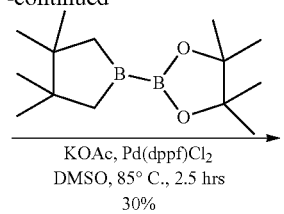

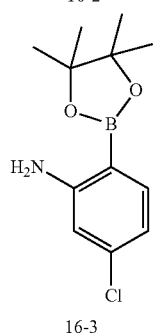

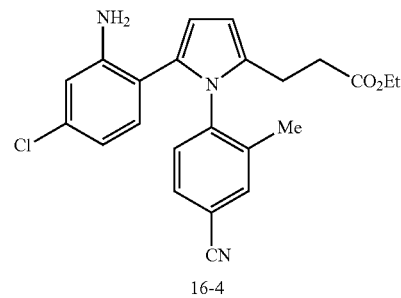

Compound 16-2

To a solution of 16-1 (6.50 g, 27.66 mmol) and NiCl$_2$ (7.80 g, 55.3 mmol) in EtOH (50 mL) was added NaBH$_4$ (5.60 g, 138.3 mmol) slowly. The resultant mixture was stirred at 0° C. for 2 h, filtered and concentrated under reduced pressure. The residue was dissolved with ethyl acetate (200 mL), washed with water (50 mL×3), dried over Na$_2$SO$_4$, concentrated and purified by silica gel column (PE:EA=5:1) to afford 16-2 as a dark solid (3.778 g, yield 67%).

Compound 16-3

A solution of 16-2 (3.778 g, 18.43 mmol), Bis(pinacolato)diboron (8.5 g, 33.17 mol), KOAc (3.2 g, 36.86 mmol) and Pd(dppf)$_2$Cl$_2$DCM (500 mg, 0.92 mmol) in DMSO (50 mL) was stirred at 85° C. for 2.5 h. TLC showed that the reaction was complete. Water (60 mL) was added and the mixture was extracted with ethyl acetate (60 mL×3). The combined organic layers were dried over Na$_2$SO$_4$, filtered, concentrated and purified by silica gel column (PE:EA=10:1) to afford 16-3 as a yellow solid (5.0 g, yield 100%).

Compound 16-4

To a solution of 16-3 (7.0 g, 27.7 mmol), Na$_2$CO$_3$ (11.75 g, 110.8 mmol) and 6E (ethyl 3-(5-bromo-1-(4-cyano-2-methylphenyl)-1H-pyrrol-2-yl)propanoate, see Scheme 6 for synthesis) (10 g, 21.4 mmol) in DMSO (30 mL) was added Pd(PPh$_3$)$_4$ (3.0 g, 8.31 mmol). After having been degassed and recharged with nitrogen, the reaction mixture was stirred at 80° C. overnight. TLC showed the reaction was complete. After cooling to room temperature, water (50 mL) was added and extracted with ethyl acetate (50 mL×4). The combined organic layers were dried over Na$_2$SO$_4$, filtered, concentrated and purified by silica gel column chromatography (PE:EA=3:1) to afford 16-4 as a yellow solid (3.10 g, yield 27%).

Method 17: Synthesis of 4-chloro-2-(methoxymethyl)phenylboronic acid

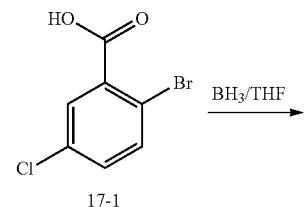

17-1

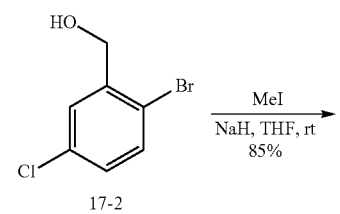

17-2

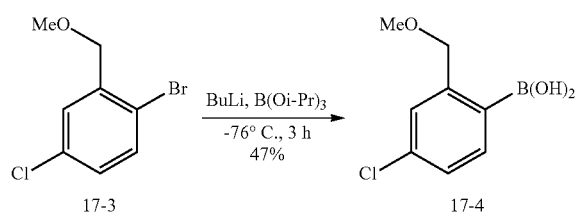

17-3                                    17-4

Compound 17-2

Compound 17-1 (5.0 g, 21.23 mmol) was added to BH$_3$/THF (1 M, 85 mL) under nitrogen atmosphere at 10° C. After addition, the mixture was stirred at room temperature overnight, quenched with methanol (30 mL) at 0° C. and concentrated to dryness. The residue was dissolved in methanol (100 mL) and concentrated to dryness again. This operation was repeated twice to afford 17-2 as a white solid (4.7 g, quantitative yield).

Compound 17-3

To a solution of compound 17-2 (8.0 g, 36.1 mmol) in THF (60 mL) was added NaH (60%, 1.88 g, 46.9 mmol) at 0° C. After addition, the reaction mixture was stirred at room temperature for 30 min. Iodomethane (10.25 g, 72.2 mmol) was added and stirred for another 30 min. The reaction was then quenched with sat. ammonium chloride (50 mL) and extracted with ethyl acetate (50 mL×3). The combined organic layers were washed with brine (60 mL), dried over Na$_2$SO$_4$, filtered, concentrated to afford 17-3 as a white solid (7.23 g, yield 85%).

Compound 17-4

To a mixture of 17-3 (3 g, 12.8 mmol) and triisopropyl borate (3.5 mL, 15.4 mmol) in THF (30 mL) at −76° C. was added n-BuLi (2.5 M in hexanes, 5.1 mL, 12.8 mmol) at a rate keeping the temperature below −69° C. The reaction was aged 20 min, allowed to warm to −20° C. and quenched with 2 M hydrochloric acid until the pH=4. The mixture was extracted with ethyl acetate (50 mL×3). The combined organic layers were dried over Na$_2$SO$_4$, filtered, concentrated to afford 17-4 as a pale white solid (1.2 g, 47%).

Method 18: Synthesis of 3-methoxy-4-(4,4,5,5-tetramethyl-1,3,2-dioxaborolan-2-yl)phenol

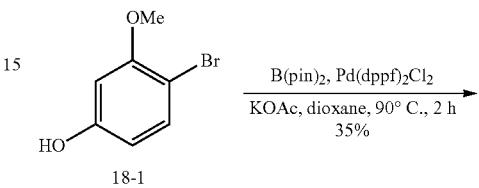

18-1

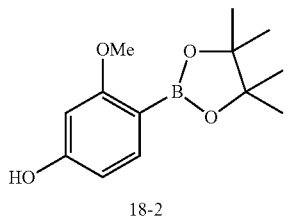

18-2

Compound 18-2

Prepared following the same procedure described in the first step of Method 13, with column purification using a different solvent system of (PE:EA=5:1) to give 35% yield of desired.

Method 19: Synthesis of 1-(5-bromothiophen-3-yl)ethanone

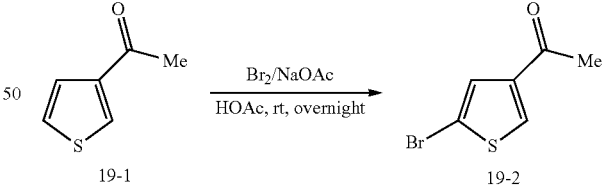

19-1                              19-2

Compound 19-2

To a solution of 3-acetylthiophene (2.52 g, 20 mmol, 1.0 eq) in HOAc (50 mL) was added NaOAc (2.46 g, 30 mmol, 1.5 eq) followed by bromine (3.2 g, 20 mmol, 1.0 eq) dropwise over 30 min. The mixture was allowed to stir at rt overnight. Water (150 mL) was added and the reaction mixture was stirred for 2 h. The resulting solid was collected by filtration, rinsed with water (10 mL) and PE (20 mL) and dried to afford 19-2 as a brown solid (1.52 g, yield 37%).

Method 20: Synthesis of N-(4-amino-3-methylphenyl)acetamide

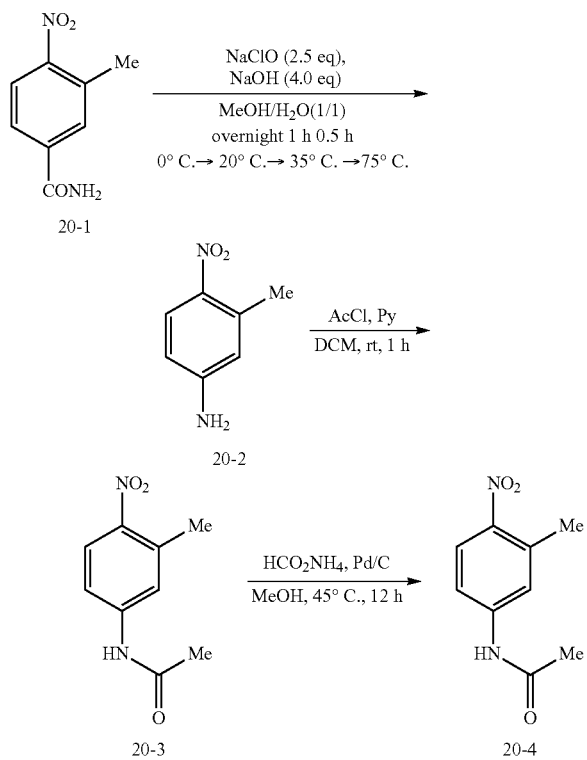

Compound 20-2

To an ice-cold solution of 20-1 (40 g, 222 mmol) in 400 mL of MeOH/$H_2O$ (v/v=1/1) was added NaOH (35.6 g, 888 mmol), stirred for 0.5 h, and NaClO (380 g, 556 mmol) was added drop wise at 0° C. The mixture was warmed to room temperature (20° C.), stirred for 18 h. Then the mixture was warmed to 35° C. stirred for 1 h, warmed to 75° C. stirred for 0.5 h. The mixture was cooled to room temperature, con. HCl was added to adjust pH=6.0 with brown precipitate appeared, filtrated and washed with water (200 mL×2) to afford 20-2 (29 g, 86%) as a tan powder.

Compound 20-3

To a solution of Pyridine (20 mL) and AcCl (6.158 g, 78.947) in DCM (100 mL) was added the solution of 20-2 (10 g, 65.789 mmol) in pyridine (20 mL) at 0° C. The mixture was stirred at room temperature for 3 h. The volatiles were removed under reduced pressure and the residue was washed with water (100 mL×3), dried under reduced pressure to afford 20-3 as yellow solid (12.5 g, yield: 97%).

Compound 20-4

To the solution of 20-3 (12 g, 61.86 mmol) in MeOH (200 mL) was added 10% Pd/C (1.5 g) purged with $N_2$. Then the solution of $HCO_2NH_4$ (39 g, 618.56 mmol) in MeOH (300 mL) was added gradually to the ice-cooled solution obtained. The mixture was warmed to 45° C., stirred at this temperature overnight. After filtrated, the filtrate was evaporated under reduced pressure. The residue was extracted with EA (200 mL×3), the organic layers were evaporated under reduced pressure, purified by silica gel column chromatography (PE: EA=1:2) to afford 20-4 as brown oil (3.1 g, yield: 30%).

Method 21: Synthesis of 1-(4-chloro-2-methoxyphenyl)ethanone

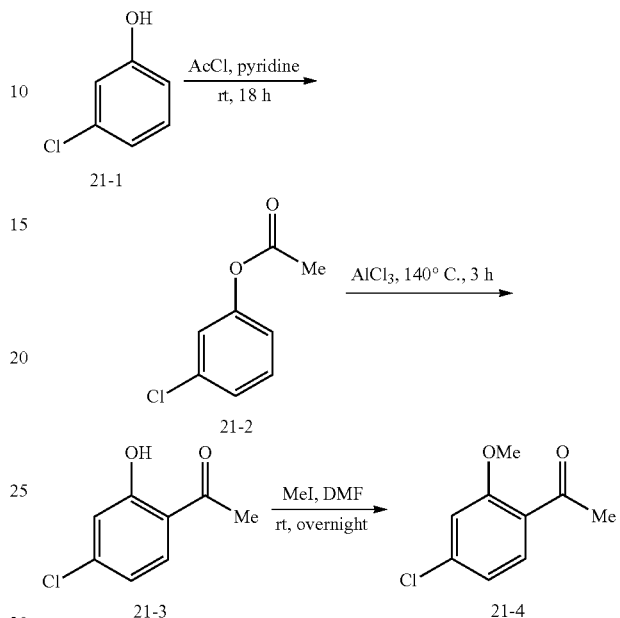

Synthesis of 21-4

Followed methods analogous to the three steps described in Method 15.

Method 22: Synthesis of 1-(4-bromothiazol-2-yl)ethanone

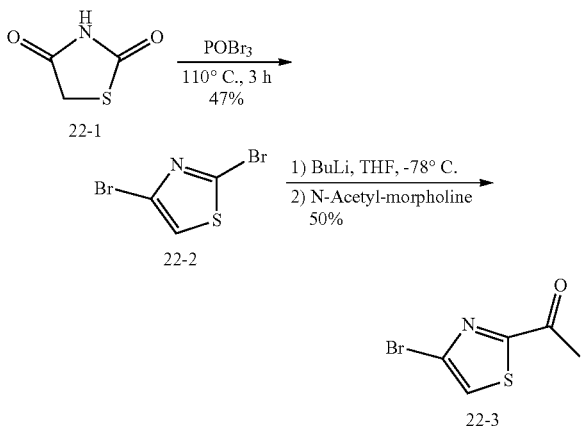

Compound 22-2

A mixture of 22-1 (5.0 g, 38.42 mmol) and $POBr_3$ (55.07 g, 192.09 mmol) was stirred at 110° C. for 3 h, then cooled to 55° C. and poured onto ice (300 g). Solid $Na_2CO_3$ (40 g) was added portionwise and the mixture was extracted with EA (150 mL×3). The combined organic layers were washed with brine (80 mL), dried over $Na_2SO_4$, filtered, concentrated and purified by silica gel column chromatography (pure PE to PE:EA=50:1) to afford 22-2 as a white solid (4.86 g, yield 47%).

Compound 22-3

To a solution of compound 22-2 (3.0 g, 12.35 mmol) in THF (25 mL) was added dropwise n-BuLi (2.5 M in hexane, 2.5 mL) at −78° C. After addition, the reaction mixture was stirred at −78° C. for 30 min. N-acetyl morpholine (1.9 mL, 16.06 mmol) was added dropwise during 15 min at −78° C. After addition, the reaction mixture was stirred at −78° C. for 4 h, then quenched with sat. NaHCO$_3$ (15 mL) and extracted with ethyl acetate (25 mL×4). The combined organic layers were washed with brine (30 mL), dried over Na$_2$SO$_4$, filtered, concentrated and purified by silica gel column chromatography (PE:EA=50:1 to 10:1) to afford 22-3-3 as a white solid (1.28 g, yield 50%).

Method 23: Synthesis of N-(4-aminophenyl)methanesulfonamide (23-3, R = H) and N-(4-amino-3-methylphenyl)methanesulfonamide (23-3, R = CH3)

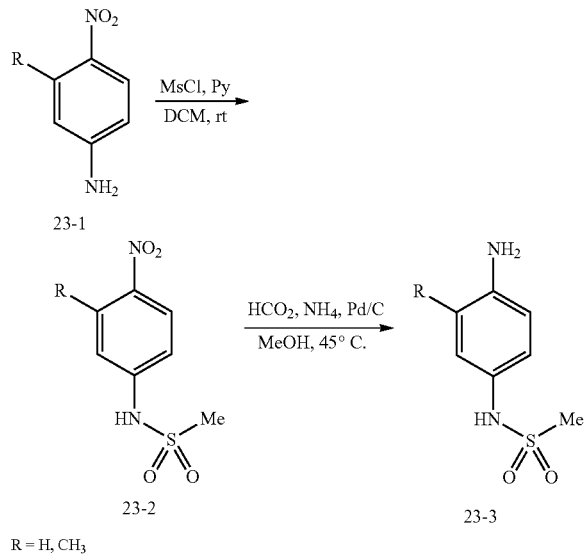

R = H, CH$_3$

Representative Example for Method 23: Synthesis of N-(4-aminophenyl)methanesulfonamide (23-3, R═H)

Compound 23-2, R═H

To a solution of pyridine (50 mL) and MsCl (15.86 g, 139.13 mmol) in DCM (150 mL) was added the solution of 4-nitrobenzenamine (16.0 g, 115.94 mmol) in pyridine (100 mL) at 0° C. The mixture was stirred at room temperature for 4 h. The volatiles were removed under reduced pressure. The residue was rinsed with water (200 mL×3) and dried under reduced pressure to afford the title compound as a yellow powder (23.20 g, yield 95%).

Compound 23-3, R═H

To a solution of 23-2, R═H (23.0 g, 106.48 mmol) in MeOH (100 mL) was added 10% Pd/C (3.0 g) purged with N$_2$. Then a solution of HCO$_2$NH$_4$ (67.0 g, 1.06 mol) in MeOH (500 mL) was added gradually under ice-water bath during 5 min. After addition, the mixture was warmed to 45° C. and stirred overnight and filtered. The filtrate was evaporated under reduced pressure to afford yellow solid which was washed with EA (500 mL×3). The combined organic layers were evaporated under reduced pressure, purified by silica gel column chromatography (PE:EA=1:2) to afford N-(4-aminophenyl)methanesulfonamide as a yellow solid (9.80 g, yield 49%).

Method 24: Synthesis of 1-(3-chlorothiophen-2-yl)ethanone

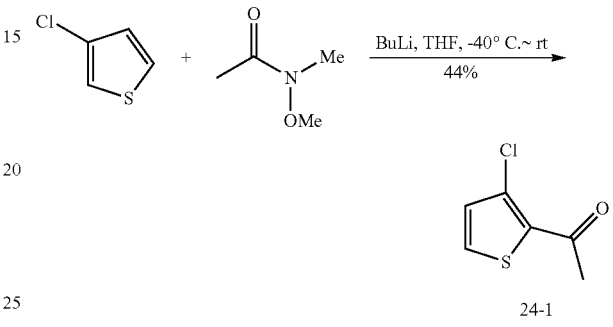

Compound 24-1

To a solution of 3-chlorothiophene (4.80 g, 40.48 mmol) in THF (50 mL) was added BuLi (2.5N in hexane, 17.9 mL) at −30° C. After addition, the mixture was stirred for 30 min at −10° C., and then cooled to −45° C. N-methoxy-N-methyl acetamide (55.0 g, 48.8 mmol) was added and allowed to warm to room temperature during 40 min and maintained for an additional 20 min. Brine (80 mL) was added to quench the reaction, extracted with EA (60 mL×3). The combined organic layers were dried over anhydrous Na$_2$SO$_4$, filtered, concentrated to afford 24-1 (~80% pure) as a yellow oil (6.80 g) which used for the next step directly.

Method 25: Synthesis of 1-(3-bromo-5-methoxythiophen-2-yl)ethanone

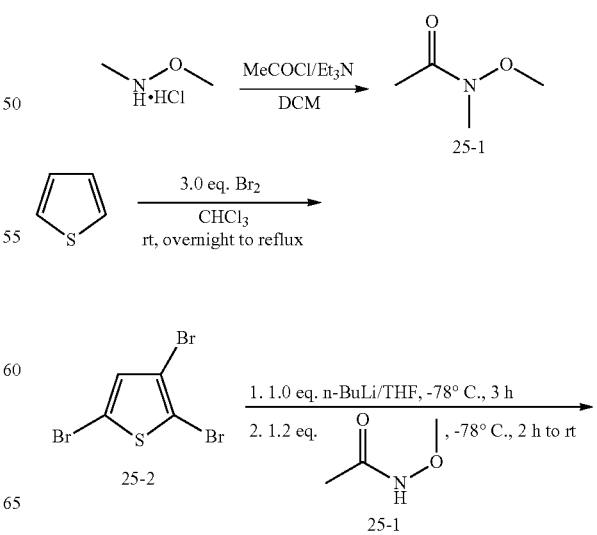

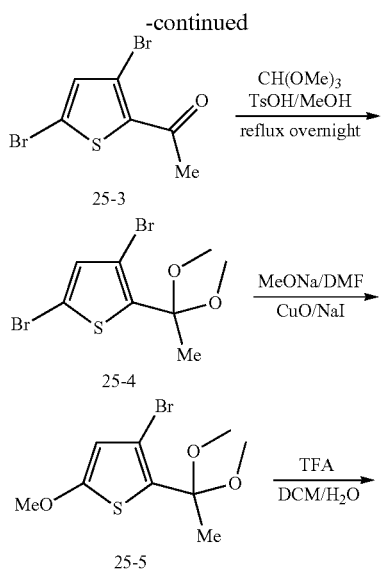

Compound 25-1

To a suspension of N,O-dimethylhydroamine hydrochloride (100 g, 1026 mmol) in DCM (1000 mL) was added triethylamine (300 mL, 2052 mmol) at 0° C. Acetyl chloride was added dropwise to the suspension for 2 h at 0° C. When the addition was complete, the mixture was allowed to warm to rt and stirred for 2 h. The mixture was washed with brine (1 L), 1 N HCl (500 mL), brine (200 mL) respectively and dried with magnesium sulfate, filtered and concentrated to afford brown oil, which was purified by distillation to afford 25-1 as a colourless liquid (65 g, 61%).

Compound 25-2

To a solution of thiophene (84 g, 1.0 mol) in chloroform (34 mL) was added dropwise bromine at rt for 3 h. When the addition was complete, the mixture was stirred at rt overnight. The mixture was heated to 50° C. for 3 h. The reaction mixture was washed with 1M NaOH (aq. 100 mL), brine (100 mL×2) respectively. The organic phase was dried with anhydrous sodium sulfate, filtered and concentrated to afford light yellow oil, which was solidified in methanol (100 mL). The solid was filtered and dried in vacuo to afford 25-2 (89 g, 56%).

Compound 25-3

25-2 (9.5 g, 30 mmol) was dissolved in anhydrous THF (100 mL) and cooled to −78° C. To the above solution was added dropwise n-BuLi (8 mL, 21 mmol) for 30 min and stirred for 30 min. 25-1 was added dropwise at −78° C., stirred for 30 min and allowed to warm to rt before quenching with saturated ammonium chloride. The organic phase was separated and washed with brine, dried with anhydrous Na$_2$SO$_4$, filtered and concentrated to afford yellow oil, which was purified by column chromatography (elution: PE/EA=10/1) afford 25-3 as a yellow solid (2.3 g, 28%).

Compound 25-4

To a solution of 25-3 (2.4 g, 8.5 mmol) in methanol (35 mL) was added trimethyl orthofomate (15 mL) and TsOH (300 mg, 1.7 mmol). The solution was heated to reflux for 10 h. Methanol was evaporated in vacuo and the residue was partitioned between EA (300 mL) and 5% sodium bicarbonate (100 mL). The organic phase was separated, dried with anhydrous sodium sulfate, filtered and concentrated to afford 25-4 as a yellow oil, which was used directly for next step (2.3 g, 82%).

Compound 25-5

To a solution of 25-4 (6.0 g, 18.3 mmol) in DMF (75 mL) was added sodium methoxide (9.9 g, 183 mmol), cuprous oxide (1.5 g, 18.3 mmol) and sodium iodide (2.8 g, 18.3 mmol). The mixture was heated to 100° C. for 4 h. TLC indicated that the reaction was complete and the reaction was quenched with brine (250 mL). The solid was filtered and the filtrate was extracted with ethyl acetate (100 mL×3). The combined organic layers were dried with anhydrous sodium sulfate, filtered and concentrated to afford brown oil, which was purified by column chromatography (elution: PE/EA=3/1) to afford 25-5 as a light yellow oil (1.2 g, 23%).

Compound 25-6

To a solution of 25-5 (1.2 g, 4.29 mmol) in DCM (8 mL) and water (10 mL) was added trifluoroacetic acid (10 mL). The reaction mixture was stirred at rt for 4 h. Saturated sodium bicarbonate (10 mL) was added and the organic phase was separated, dried with anhydrous sodium sulfate, filtered and concentrated to afford brown oil, which was purified by column chromatography (elution: PE/EA=10/1) to afford 25-6 as a light yellow solid (750 g, 74%).

Method 26: Synthesis of (1H-imidazol-2-yl)methanol

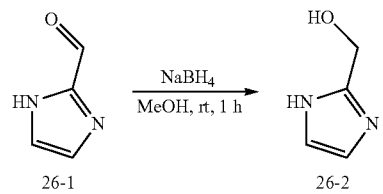

Compound 26-2

To a solution of 2-imidazolecarboxyaldehyde (26-1) (1.92 g, 20 mmol, 1.0 eq) was suspended in methanol (30 mL), NaBH$_4$ (1.52 g, 40 mmol, 2.0 eq) was added portion-wise. The reaction mixture was stirred at room temperature for 1 h under N$_2$. It was quenched with 5 mL of brine. The solvent was removed and the solid was purified with silica gel column chromatography (DCM:MeOH=20:1) to afford a white solid. (1.0 g, Yield: 51%).

Method 27: Synthesis of 4-amino-3-methylbenzenesulfonamide

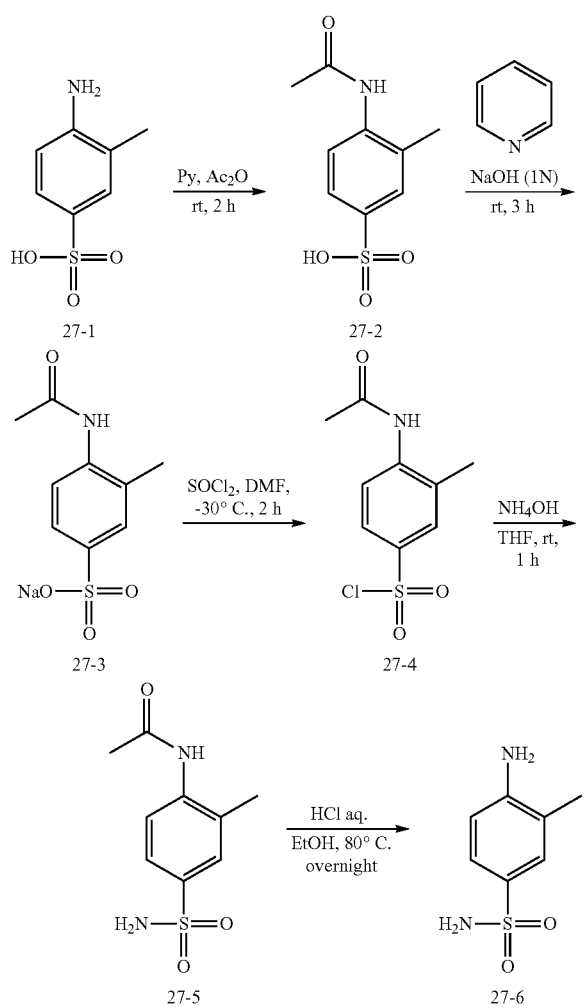

Compound 27-2

Ac$_2$O (16 ml, 0.16 mol) was added to the solution of 27-1 (20 g, 0.107 mol) in 80 ml of pyridine. The mixture was stirred at rt for 2 hours. Then EtOH (40 ml) was added and the solid was isolated by filtration and washed with EtOH to give 27-2 as a brown solid (10.3 g, yield 56%).

Compound 27-3

Compound 27-2 (10 g, 43.6 mmol) was added to a flask containing 1 N NaOH (36 ml) and the mixture was stirred at rt for 3 hours. The solvent was removed and the residue was washed with EtOH. 27-3 was isolated by filtration as a pale solid (8.8 g, yield 88%).

Compound 27-4

Compound 27-3 (16 g, 63.7 mmol) and DMF (20 ml) were added to a flask and then SOCl$_2$ (18.4 g, 155 mol) was added dropwise at −30-40° C. When the addition was complete, the mixture was stirred at rt for 2 hours. Then the mixture was added to ice slowly and solid appeared. The solid was isolated by filtration and dried to give 27-4 as a pale solid (6.0 g, yield 38%).

Compound 27-5

The solution of 27-4 (6.0 g, 24.2 mmol) in 50 ml of THF was added to 50 ml of NH$_4$OH at 0° C. dropwise. The mixture was stirred at rt for 1 h. The solvent was removed under reduced pressure and the residue was extracted with EA (30 ml×4). The organic layer was dried over Na$_2$SO$_4$ and filtered, concentrated to give 27-5 as a pale solid (5.1 g, yield 93%).

Compound 27-6

A mixture of 27-5 (5.1 g, 22.3 mmol), HCl (2 N, 76.5 ml) and EtOH (100 ml) was refluxed overnight. Then the mixture was neutralized with Na$_2$CO$_3$(aq) to PH=8. The mixture was extracted with EA (80 ml×4), dried over Na$_2$SO$_4$, and concentrated to give 27-6 as a pale solid (4.9 g, yield 100%).

Method 28: Synthesis of 1-(5-bromo-4-chlorothiophen-2-yl)ethanone (28-2) and 1-(4-chlorothiophen-2-yl)ethanone (28-3)

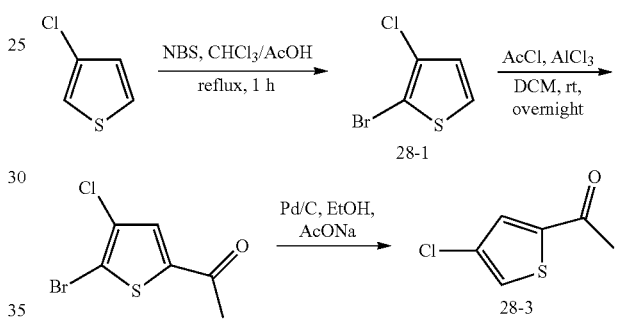

Compound 28-1

To a solution of 3-chlorothiophene (6.52 g, 55 mmol) in CHCl$_3$ (30 mL) and AcOH (30 mL) was added NBS (9.80 g, 55 mmol). The mixture was heated at reflux for 1.5 h, then cooled to room temperature. Water (70 mL) was added and the mixture was extracted with CHCl$_3$ (30 mL×2). The combined organic layers were washed with sat. NaHCO$_3$ (40 mL) and brine (30 mL), dried over anhydrous Na$_2$SO$_4$, filtered, concentrated to afford 28-1 as a brown oil (10.02 g, quantitive yield) which used for the next step directly.

Synthesis of 1-(5-bromo-4-chlorothiophen-2-yl)ethanone (28-2)

To a mixture of 28-1 (10.0 g, 50.6 mmol) and AlCl$_3$ (8.09 g, 60.7 mmol) in DCM (120 mL) was added dropwise acetyl chloride (4.76 g, 60.7 mmol) during 5 min at 0° C. After addition, the mixture was stirred overnight at room temperature, washed with diluted hydrochloride acid (1.2N, 150 mL) and brine (150 mL), dried over anhydrous Na$_2$SO$_4$, filtered, concentrated and purified by silica gel column chromatography (PE/EA=20/1 to 3/1) to afford 28-2 as a brown solid (8.0 mg, yield: 66%).

Synthesis of 1-(4-chlorothiophen-2-yl)ethanone (28-3)

To a solution of 28-2 (3.20 mg, 13.36 mmol) in EtOH (70 mL) was added 10% Pd/C (2.50 g) and AcONa (1.10 g, 13.36 mmol). The reaction mixture was stirred under a hydrogen atmosphere at room temperature for 3 h, filtered, and the filtrate was concentrated. The resultant residue was dissolved in EA (100 mL) washed with sat. NaHCO₃ (40 mL) and brine (30 mL), dried over anhydrous Na₂SO₄, filtered, concentrated and purified by silica gel column chromatography (PE/EA=30/1 to 5/1) to afford 28-3 as a yellow oil (1.32 g, yield: 62%).

Method 29: Synthesis of 1-amino-(2-methyl-4-(sulfamoylamino)phenyl)

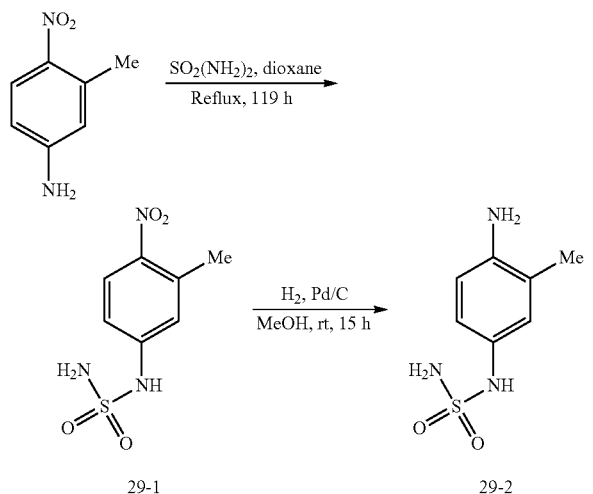

Compound 29-1

To a solution of 3-methyl-4-nitroaniline (4.50 g, 29.6 mmol) in dioxane (90 mL) was added sulfuric diamide (14.2 g, 428 mmol). The reaction mixture was heated to reflux for 119 h. After the removal of the volatile, the residual was dissolved in ethyl acetate (400 mL), and then washed with water (200 mL) and brine (200 mL), dried over Na₂SO₄, filtered, concentrated and purified by silica gel column chromatography (EA:PE=1:4) to afford 29-1 as a yellow solid (1.84 mg, yield: 27%).

Compound 29-2

To a suspend solution of Pd/C (10%, 200 mg) in methanol (20 mL) was added 29-1 (1.84 g, 7.95 mmol). After having been degassed and recharged with hydrogen gas, the mixture was stirred at room temperature for 15 h. TLC showed that the reaction was complete. The Pd/C solid was removed by filtration and then the solvent was evaporated. The obtained brown solid (550 mg, quant.) was used without further purification for the next step preparation.

Method 30: Synthesis of 5-methyl-1H-benzo[d]imidazol-6-amine (30-3A) and 5-methyl-1H-benzo[d]imidazol-4-amine (30-3B).

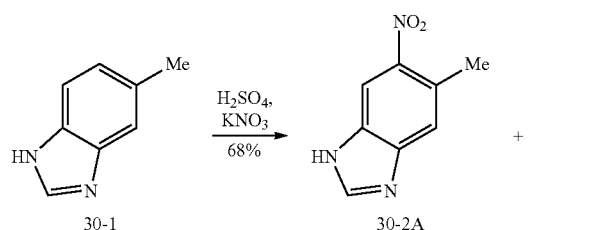

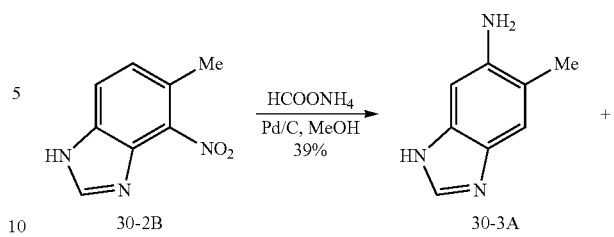

Compound 30-2A and 30-2B

5-Methylbenzimidazole (6.0 g, 45.40 mmol) was dissolved in concentrated H₂SO₄ (97.5 mL) and cooled to 0° C. Potassium nitrate (4.135 g, 40.90 mmol) was added portionwise. After stirring for 1 h, the reaction mixture was poured over ice and Na₂CO₃ was added to adjust pH>8. The aqueous layer was extracted with EtOAc. The combined organic layers were dried over Na₂SO₄, filtered and concentrated in vacuo. The resulting yellow solid was recrystallized from 50% MeOH/water (80 mL) to afford a mixture of 30-2A and 30-2B as a brown powder (5.5 g, 68%).

Compound 30-3A and 30-3B

To a mixture of 30-2A and 30-2B (5.5 g, 31.073 mmol) and 10% Pd/C (1.0 g) in EtOH (5 mL) was added dropwise the solution of HCO₂NH₄ (19.576 g, 310.73 mmol) in MeOH (200 mL). After 1 h, TLC showed the reaction was complete. Filtration and the filtrate was evaporated under reduced pressure. The residue was dissolved in DCM (100 mL) and filtrated. The filtrate was concentrated and purified by silica gel column chromatography (DCM:MeOH=10:1) to afford 30-3A (2.0 g, 44%) and 30-3B (1.8 g, 39%) as brown solids.

Method 31: Synthesis of isoquinolin-7-amine

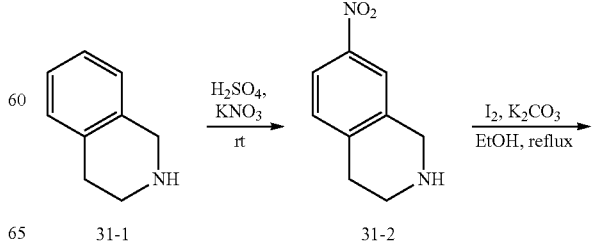

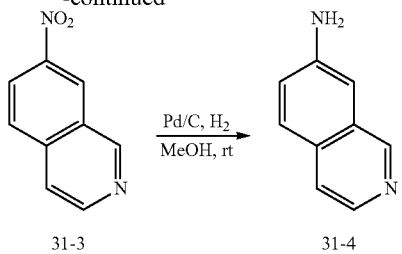

Synthesis of 7-nitro-1,2,3,4-tetrahydroisoquinoline (31-2)

1,2,3,4-Tetrahydroisoquinoline (4.0 g, 30.0 mmol) was dissolved in 10 N of sulfuric acid (6 mL, 30.0 mmol) and then evaporated to dryness to afford a solid residual. This sulfate was added slowly to a solution of potassium nitrate (3.34 g, 33.0 mmol) in sulfuric acid (15 mL), taking care that the temperature of the reaction mixture did not rise above 5° C. After being stirred at room temperature for a further 27 h, the reaction mixture was slowly poured into a con. ammonium solution (ca. 100 mL) under ice cooling. The resulted solution was extracted with dichloromethane (100 mL×3). The combined organic phase was washed with brine (150 mL), dried over $Na_2SO_4$, filtered, concentrated and purified by silica gel column chromatography (DCM:MeOH=100:1) to afford 31-2 as a brown solid (2.24 g, yield 41%).

Synthesis of 7-nitroisoquinoline (31-3)

Under refluxing, a solution of iodine (4.0 g, 15.9 mmol) in ethanol (56 mL) was added dropwise to a stirred solution of 31-2 (2.0 g, 9.34 mmol) in ethanol (24 mL) during 5 h. Then the resulted mixture was stirred for a further 66 h. The solvent was removed and the residual was loaded onto a silica gel chromatography column (PE:EA=6:1) to give 31-3 as a brown dark solid (602 mg, yield 36%).

Synthesis of isoquinolin-7-amine (31-4)

To a suspend solution of Pd/C (10%, 100 mg) in methanol (20 mL) was added 31-3 (200 mg, 1.15 mmol) in methanol (40 mL). After having been degassed and recharged with hydrogen, the mixture was then stirred at room temperature for 24.5 h. TLC showed that the reaction was complete. The Pd/C was removed by filtration and the solvent was evaporated. The residual was used without further purification (150 mg, yield 90%).

Method 32: Synthesis of isoquinolin-6-amine

Followed same procedure described in the synthesis of isoquinolin-7-amine, Method 31.

Method 33: Synthesis of N-(3-methoxy-4-(4,4,5,5-tetramethyl-1,3,2-dioxaborolan-2-yl)pheynl)formamide

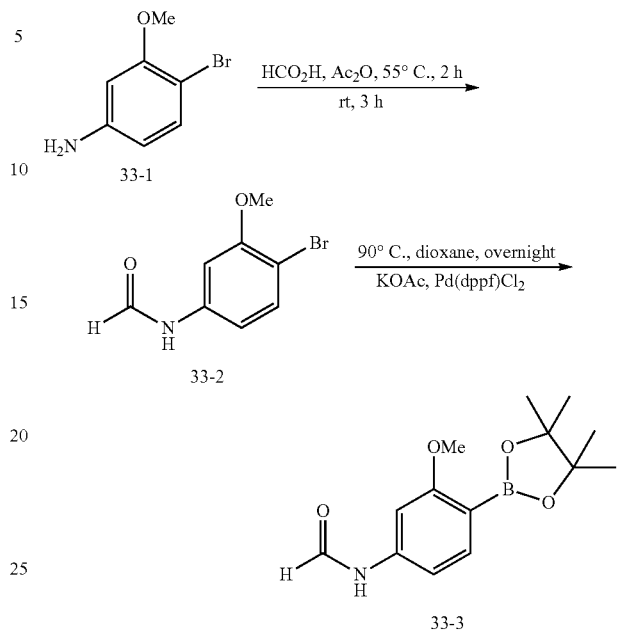

Compound 33-2

A mixture of $HCO_2H$ (644 mg, 14 mmol) and $Ac_2O$ (1.16 g, 11.4 mmol) was heated to 55° C. for 2 h and then cooled to room temperature. THF (1 mL) and 33-1 (880 mg, 4.38 mmol) in THF (1 mL) was added stepwise and the resultant mixture was continually stirred at room temperature for 3 h. After evaporation, the residue was extracted with EA (5 mL×3). The organic phase was successively washed with sat. aqueous sodium bicarbonate (10 mL) and sodium chloride (10 mL), dried over anhydrous sodium sulfate, filtrated and concentrated to afford 33-2 as a liquid (845 mg, yield: 85%), which was used directly for the next step.

Compound 33-3

To a mixture of 33-2 (845 mg, 4.38 mmol), KOAc (726 mg, 7.4 mmol), $B(pin)_2$ (1.41 g, 5.6 mmol) and dioxane was added $Pd(dppf)_2Cl_2$ (20 mg, 0.02 mmol). After having been degassed and recharged with nitrogen, the mixture was refluxed at 90° C. overnight. TLC showed that the reaction was complete. Water (10 mL) was added and the mixture was extracted with ethyl acetate (10 mL×3). The combined organic layers were dried over $Na_2SO_4$, filtered, concentrated and purified by silica gel column chromatography (PE:EA=4:1) to afford 33-3 as a colorless solid (220 mg, yield: 29%).

Method 34: Synthesis of 4-(pyridin-3-yloxy)aniline (34-2)

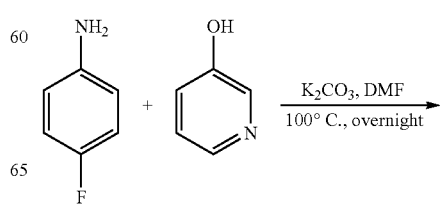

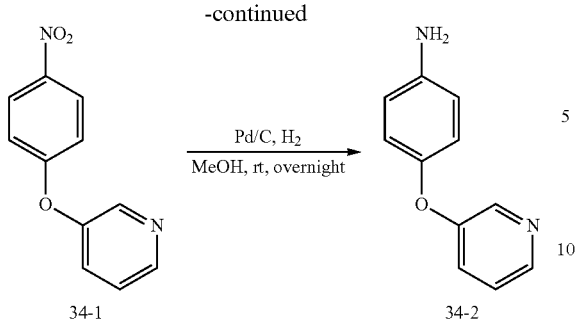

Synthesis of compound 34-1

To a solution of 4-fluorobenzenamine (6.746 g, 47.85 mmol) and pyridine-3-ol (5.0 g, 52.63 mmol) in 100 mL of DMF was added $K_2CO_3$ (13.21 g, 95.69 mmol). The mixture was heated to 100° C. overnight. Then it was dissolved in 500 mL of EA and washed with water (400 mL×2). The organic layer was concentrated under reduced pressure, the residue was purified by silica gel column (PE/EA=1/5) to afford 34-1 (7.8 g, 76%) as brown solid.

Synthesis of compound 34-2

To the solution of 34-1 (2.0 g, 9.259 mmol) in MeOH (20 mL) was added 10% Pd/C (0.2 g) purged with $N_2$. Then $H_2$ was added to remove $N_2$. The mixture was stirred at room temperature overnight. After filtrated, the filtrate was concentrated to dryness affording 34-2 (1.7 g, 99%) as brown solid.

Method 35: Synthesis of 4-amino-benzenesulfonamide

Followed procedure/scheme described in method 27, Synthesis of 4-amino-3-methylbenzenesulfonamide.

Method 36: Synthesis of N-(4-aminophenyl)acetamide

Step 1: Synthesis of N-(4-nitrophenyl)acetamide

To a solution of Pyridine (3 mL) and AcCl (1.017 g, 13.043) in DCM (15 mL) was added the solution of 4-nitrobenzenamine (1.5 g, 10.870 mmol) in pyridine (3 mL) at 0° C. The mixture was stirred at room temperature for 1 h. The volatiles were removed under reduced pressure and the residue was washed with water (10 mL×3), dried under reduced pressure to afford N-(4-nitrophenyl)acetamide as yellow powder (1.9 g, yield: 97%).

Step 2: Synthesis of N-(4-aminophenyl)acetamide

To the solution of N-(4-nitrophenyl)acetamide (1.9 g, 10.556 mmol) in MeOH (10 mL) was added 10% Pd/C (0.2 g) purged with $N_2$. Then the solution of $HCO_2NH_4$ (6.7 g, 106 mmol) in MeOH (20 mL) was added gradually to the ice-cooled solution obtained. The mixture was warmed to 45° C., stirred at this temperature overnight. After filtrated, the filtrate was removed in vacuo. The residue was extracted with EA (30 mL×3), the organic layer were evaporated under reduced pressure, purified by silica gel column chromatography (PE: EA=1:2) to afford N-(4-aminophenyl)aceta as a yellow powder (1.3 g, yield: 82%).

Method 37: Synthesis of 4-(1-methylpyrrolidin-3-yloxy)aniline

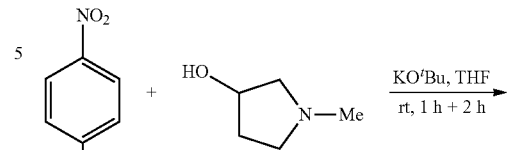

Step 1: Synthesis of 1-methyl-3-(4-nitrophenoxy)pyrrolidine

To a solution of potassium tert-butoxide (1.43 g, 12.9 mmol) in THF (6 mL) was added 1-methylpyrrolidin-3-ol (645 mg, 6.39 mmol). The reaction mixture was stirred at room temperature for 1 h. Then 1-fluoro-4-nitrobenzene (900 mg, 6.39 mmol) was added to the above solution and stirred for another 2 h. After the removal of the volatile, the residual was dissolved in ethyl acetate (40 mL), and then washed with water (20 mL) and brine (20 mL), dried over $Na_2SO_4$, filtered, concentrated and purified by silica gel column chromatography (EA:PE=1:4) to give desired product as a yellow oil (626 mg, 44%).

Step 2: Synthesis of 4-(1-methylpyrrolidin-3-yloxy)aniline

Followed same procedure described in final step of Method 34.

Method 38: Synthesis of 3-(4-aminophenyl)oxazolidin-2-one

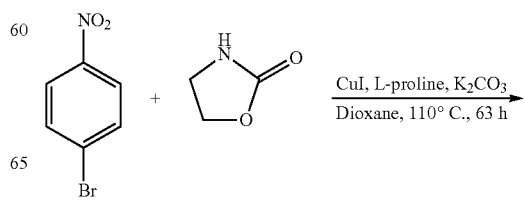

311

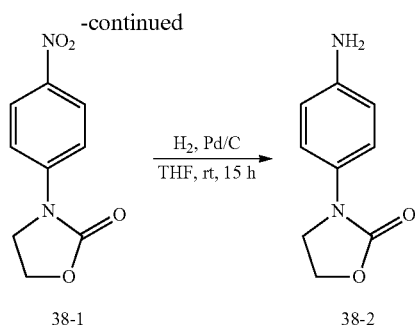

38-1          38-2

Step 1: Synthesis of
3-(4-nitrophenyl)oxazolidin-2-one (38-1)

To a mixture of 1-bromo-4-nitrobenzene (5.00 g, 25 mmol) and oxazolidin-2-one (3.23 g, 37 mmol) in dioxane (25 mL) were added L-proline (285 mg, 2.5 mmol), CuI (238 mg, 1.2 mmol) and $K_2CO_3$ (6.90 g, 50 mmol). The resultant mixture was stirred under $N_2$ at 110° C. for 63 h and then evaporated. The residue was diluted with EA/water (40 mL/40 mL). The mixture was filtered and the resultant aqueous layer was extracted with EA (30 mL×5). The combined organic layers were washed with brine, dried over $NaSO_4$, concentrated and purified by silica gel column chromatography (DCM to DCM:MeOH=50:1) to afford desired as a yellow solid (1.40 g, yield 27%).

Step 2: Synthesis of
3-(4-aminophenyl)oxazolidin-2-one (38-2)

To a solution of 3-(4-nitrophenyl)oxazolidin-2-one (800 mg, 3.8 mmol) in MeOH (10 mL) was added Pd/C (10%, 200 mg). After having been degassed and recharged with hydrogen from a balloon, the mixture was stirred at rt for 15 h. TLC showed no starting material existed. The solid Pd/C was separated by filtration and the crude product 3-(4-aminophenyl)oxazolidin-2-one was obtained by evaporation as a yellow solid (622 mg, yield 90%) and used directly for the next step.

Method 39: Synthesis of 5-aminobenzo[d]oxazol-2(3H)-one (39-2)

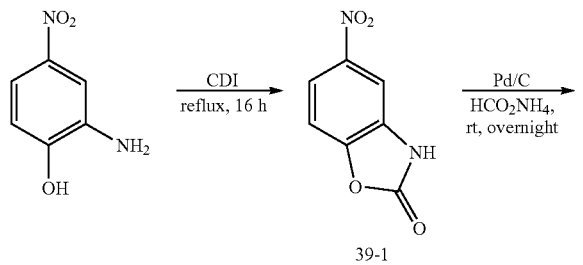

39-1

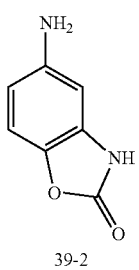

39-2

312

Synthesis of 5-nitrobenzo[d]oxazol-2(3H)-one (39-1)

The mixture of 2-amino-4-nitrophenol (5 g, 32.44 mmol) and CDI (6.3 g, 38.93 mmol) in THF (60 mL) was heated at refluxing for 16 h. Cooled to room temperature, the solvent was removed under reduced pressure, the residue was dissolved in DCM (100 mL) and poured into 2N HCl solution (200 mL) with stirring, after 30 min, collected the solid and washed with water (50 mL×2), dried in vacuo to get compound 39-1 as a yellow solid (5.1 g, yield 87%).

Synthesis of 5-aminobenzo[d]oxazol-2(3H)-one (39-2)

The mixture of 39-1 (5.1 g, 28.31 mmol), Pd/C (0.5 g) and $HCO_2NH_4$ (8.9 g, 141.57 mmol) in MeOH (200 mL) was stirred at room temperature overnight. Filtered with kiselguhr, concentrated in vacuo, the residue was added 5% $NaHCO_3$ solution, collected the solid and washed with water (50 mL), dried in vacuo to get compound 39-2 as a brown solid (4 g, yield 94%).

Method 40: Synthesis of 6-aminobenzo[d]oxazol-2(3H)-one (40-2).

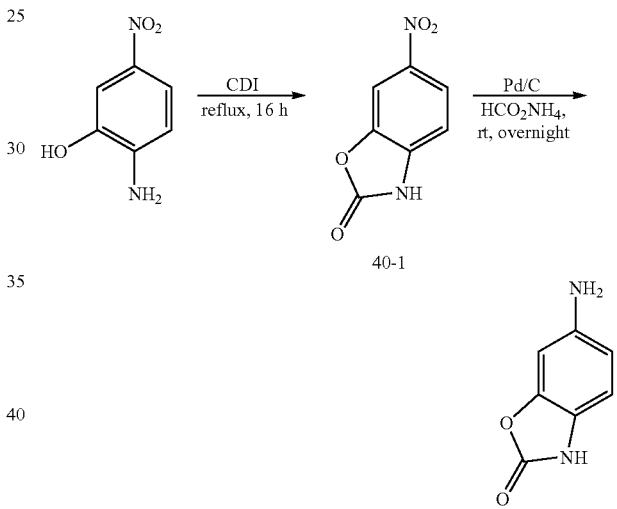

40-1

40-2

Followed the same 2 step procedure described for the synthesis of 5-aminobenzo[d]oxazol-2(3H)-one (39-2) in Method 39 above.

Method 41: Synthesis of 1-(5-bromo-2-methoxyphenyl)ethanone

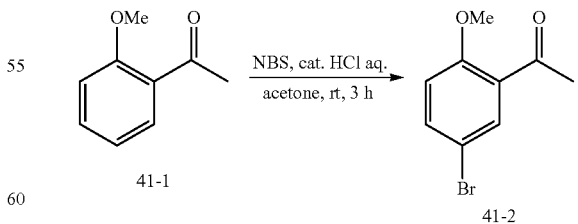

41-1          41-2

Compound 41-2

To a solution of 41-1 (2.0 g, 13.32 mmol) in acetone (25 mL) was added NBS (2.37 g, 13.32 mmol) and 1M HCl aq.

(0.13 mL, 0.13 mmol). The reaction mixture was stirred at room temperature for 3 h, and then concentrated to dryness under reduced pressure. The residue was dissolved with PE (40 mL) the resultant precipitate was filtered and dried in vacuum to afford 41-2 as a white solid (2.90 g, yield: 95%).

Example 2

GSNOR Assays

Various compounds were tested in vitro for their ability to inhibit GSNOR activity. Representative compounds and their corresponding GSNOR activity are described in a paragraph before Table 1 above. GSNOR expression and purification is described in *Biochemistry* 2000, 39, 10720-10729.

GSNOR Fermentation:

Pre-cultures were grown from stabs of a GSNOR glycerol stock in 2XYT media containing 100 ug/ml ampicillin after an overnight incubation at 37° C. Cells were then added to fresh 2XYT (4 L) containing ampicillin and grown to an OD ($A_{600}$) of 0.6-0.9 at 37° C. before induction. GSNOR expression was induced with 0.1% arabinose in an overnight incubation at 20° C.

GSNOR Purification:

E. coli cell paste was lysed by nitrogen cavitation and the clarified lysate purified by Ni affinity chromatography on an AKTA FPLC (Amersham Pharmacia). The column was eluted in 20 mM Tris pH 8.0/250 mM NaCl with a 0-500 mM imidazole gradient. Eluted GSNOR fractions containing the Smt-GSNOR fusion were digested overnight with Ulp-1 at 4° C. to remove the affinity tag then re-run on the Ni column under the same conditions. GSNOR was recovered in the flowthrough fraction and for crystallography is further purified by Q-Sepharose and Heparin flowthrough chromatography in 20 mM Tris pH 8.0, 1 mM DTT, 10 uM $ZnSO_4$.

GSNOR Assay:

GSNO and Enzyme/NADH Solutions are made up fresh each day. The Solutions are filtered and allowed to warm to room temperature. GSNO Solution: 100 mM $NaPO_4$ (pH 7.4), 0.480 mM GSNO. 396 μL of GSNO Solution is added to a cuvette followed by 8 μL of test compound in DMSO (or DMSO only for full reaction control) and mixed with the pipette tip. Compounds to be tested are made up at a stock concentration of 10 mM in 100% DMSO. 2 fold serial dilutions are done in 100% DMSO. 8 μL of each dilution are added to an assay so that the final concentration of DMSO in the assay is 1%. The concentrations of compounds tested range from 100 to 0.003 μM. Enzyme/NADH Solution: 100 mM $NaPO_4$ (pH 7.4), 0.600 mM NADH, 1.0 μg/mL GSNO Reductase. 396 μL of the Enzyme/NADH Solution is added to the cuvette to start the reaction. The cuvette is placed in the Cary 3E UV/Visible Spectrophotometer and the change in 340 nm absorbance/min at 25° C. is recorded for 3 minutes. The assays are done in triplicate for each compound concentration. IC50's for each compound are calculated using the standard curve analysis in the Enzyme Kinetics Module of SigmaPlot.

Final assay conditions: 100 mM NaPO4, pH 7.4, 0.240 mM GSNO, 0.300 mM NADH, 0.5 μg/mL GSNO Reductase and 1% DMSO. Final volume: 800 μL/cuvette.

Example 3

GSNOR Inhibition Assay in an In Vivo Animal Model

To demonstrate the influence of GSNOR inhibition, a mouse model of asthma was used that was similar to a model previously shown to be influenced by GSNO reductase and bioavailable SNO's (Que et al., *Science*, 2005). Que et al. demonstrated that following ova-albumin (OVA) challenge, wild type mice exhibiting bronchial reactivity have increased levels of GSNOR and have lungs that were depleted of SNO's. In contrast to wild-type mice, Que et al. demonstrated that mice with a genetic deletion of GSNOR increased lung SNO's and were protected from OVA induced airway hyperreactivity.

In an effort to determine if similar observations would manifest if GSNOR were inhibited pharmacologically by a GSNOR inhibitor, an OVA mouse model (i.e., the wild-type model of Que et al.) was used. In this study, OVA sensitized mice were administered 1 mg/kg, 10 mg/kg or 30 mg/kg of Compound 1 intravenously at 24 hours prior to being placed in a whole body plethysmograph (Buxco Research Systems, Wilmington, N.C.) and provided with fresh air.

Subject animals were then challenged with an aerosol of increasing dosages of the bronchoconstrictive agent methacholine, a pharmacologic agent commonly used in determining the degree of bronchial hyper-reactivity in experimental subjects. In this study mice were exposed to an increasing concentration of methacholine, each dose being presented for 3 minutes, during which time readings were taken. Doses of methacholine were 0 mg/ml, 5 mg/ml, 20 mg/ml, and 50 mg/ml. The degree of bronchial hyper-reactivity was measured as the 'Enhanced Pause' (Penh), a unit-less index of airway hyper-reactivity (Dohi et al., Lab Invest. 79(12):1559-1571, 1999).

The administration of Compound 1 produced lower broncho-constrictive responses in these test animals compared with vehicle-only dosed animals, These results are consistent with a greater level of bioactive SNO's available to counter the broncho-constrictive methacholine challenge.

Example 4

Efficacy of GSNORi in Experimental Asthma

Experimental Asthma Model

A mouse model of ovalbumin (OVA)-induced asthma was used to screen GSNOR inhibitors for efficacy against methacholine (MCh)-induced bronchoconstriction/airway hyperreactivity. This is a widely used and well characterized model that presents with an acute, allergic asthma phenotype with similarities to human asthma. Efficacy of GSNOR inhibitors were assessed using a prophylactic protocol in which GSNOR inhibitors were administered prior to challenge with MCh. Bronchoconstriction in response to challenge with increasing doses of MCh was assessed using whole body plethysmography ($P_{enh}$; Buxco). The amount of eosinophil infiltrate into the bronchoaveolar lavage fluid (BALF) was also determined as a measure of lung inflammation. The effect of GSNOR inhibitors were compared to vehicles and to Combivent (inhaled; IH) as the positive control.

Materials and Methods

Allergen Sensitization and Challenge Protocol

OVA (500 μg/ml) in PBS was mixed with equal volumes of 10% (w/v) aluminum potassium sulfate in distilled water and incubated for 60 min. at room temperature after adjustment to pH 6.5 using 10 N NaOH. After centrifugation at 750×g for 5 min, the OVA/alum pellet was resuspended to the original volume in distilled water. Mice received an intraperitoneal (IP) injection of 100 μg OVA (0.2 mL of 500 μg/mL in normal saline) complexed with alum on day 0. Mice were anesthetized by IP injection of a 0.2-mL mixture of ketamine and xylazine (0.44 and 6.3 mg/mL, respectively) in normal saline and were placed on a board in the supine position. Two hundred fifty micrograms (100 μl of a 2.5 mg/ml) of OVA (on day 8) and 125 μg (50 μl of 2.5 mg/ml) OVA (on days 15, 18, and 21) were placed on the back of the tongue of each animal.

Pulmonary Function Testing (Penh)

In vivo airway responsiveness to methacholine was measured 24 h after the last OVA challenge in conscious, freely moving, spontaneously breathing mice with whole body plethysmography using a Buxco chamber (Wilmington, N.C.). Mice were challenged with aerosolized saline or increasing doses of methacholine (5, 20 and 50 mg/mL) generated by an ultrasonic nebulizer for 2 min. The degree of bronchoconstriction was expressed as enhanced pause ($P_{enh}$), a calculated dimensionless value, which correlates with the measurement of airway resistance, impedance, and intrapleural pressure in the same mouse. $P_{enh}$ readings were taken and averaged for 4 min. after each nebulization challenge. $P_{enh}$ was calculated as follows: $P_{enh}=[(T_e/T_r-1)\times(PEF/PIF)]$, where $T_e$ is expiration time, $T_r$ is relaxation time, PEF is peak expiratory flow, and PIF is peak inspiratory flow×0.67 coefficient. The time for the box pressure to change from a maximum to a user-defined percentage of the maximum represents the relaxation time. The $T_r$ measurement begins at the maximum box pressure and ends at 40%.

Eosinophil Infiltrate in BALF

After measurement of airway hyper-reactivity, the mice were exsanguination by cardiac puncture, and then BALF was collected from either both lungs or from the right lung after tying off the left lung at the mainstem bronchus. Total BALF cells were counted from a 0.05 mL aliquot, and the remaining fluid is centrifuged at 200×g for 10 min at 4° C. Cell pellets were resuspended in saline containing 10% BSA with smears made on glass slides. Eosinophils were stained for 5 min. with 0.05% aqueous eosin and 5% acetone in distilled water, rinsed with distilled water, and counterstained with 0.07% methylene blue.

GSNOR Inhibitors and Controls

GSNOR inhibitors were reconstituted in phosphate buffered saline (PBS), pH 7.4, at concentrations ranging from 0.00005 to 3 mg/mL. GSNOR inhibitors were administered to mice (10 mL/kg) as a single dose either intravenously (IV) or orally via gavage. Dosing was performed from 30 min. to 24 h prior to MCh challenge. Effect of GSNOR inhibitors were compared to PBS vehicle dosed in the same manner.

Combivent was used as the positive control in all studies. Combivent (Boehringer Ingelheim) was administered to the lung using the inhaler device supplied with the product, but adapted for administration to mice, using a pipet tip. Combivent was administered 48 h, 24 h, and 1 h prior to MCh challenge. Each puff (or dose) of Combivent provided a dose of 18 μg ipatropium bromide (IpBr) and 103 μg albuterol sulfate or approximately 0.9 mg/kg IpBr and 5 mg/kg albuterol.

Statistical Analyses

Area under the curve values for $P_{enh}$ across baseline, saline, and increasing doses of MCh challenge were calculated using GraphPad Prism 5.0 (San Diego, Calif.) and expressed as a percent of the respective (IV or orally administered) vehicle control. Statistical differences among treatment groups and the respective vehicle control group within each study were calculated using one-way ANOVA, Dunnetts (JMP 8.0, SAS Institute, Cary, N.C.). A p value of <0.05 among the treatment groups and the respective vehicle control group was considered significantly different.

Results:

Compound 1 Results

Compound 1 administered intravenously (IV) was efficacious against experimental asthma as noted by attenuation of methacholine (MCh) induced bronchoconstriction and pulmonary inflammation. Significant efficacy with Compound 1 was observed with a single IV dose of 0.01 mg/kg at 24 h prior to MCh. The area under the curve (AUC) for Penh response reported as percent of vehicle control (AUC=100%) was 42.1±2.8% (p<0.0001). Eosinophil infiltration into the bronchoaveolar lavage fluid (BALF) was reduced by 98% (p<0.0001). Significant efficacy with Compound 1 was also observed as early as 1 h (AUC=76.4±6.6; p=0.0082) and up to 48 h (AUC=64.4±55; p=<0.0001) prior to MCh at a single IV dose of 0.1 mg/kg. The ED50, the dose of Compound 1 demonstrating 50% reduction in Penh response, was 0.011±0.003 mg/kg.

Compound 2 Results

Compound 2 administered intravenously (IV) was efficacious against experimental asthma as noted by attenuation of methacholine (MCh) induced bronchoconstriction. Significant efficacy with Compound 2 was observed with a single IV dose of 0.01, 0.1, and 1 mg/kg at 24 h prior to MCh. The area under the curve (AUC) for Penh response reported as percent of vehicle control (AUC=100%) was 65.3±6.5% (p=0.0002); 50.5±6.3% (p<0.0001); and 41.7±5.2% (p<0.0001) for 0.01, 0.1, and 1 mg/kg, respectively, of Compound 2.

Compound 3 Results

Compound 3 administered intravenously (IV) was efficacious against experimental asthma as noted by attenuation of methacholine (MCh) induced bronchoconstriction and pulmonary inflammation. Significant efficacy with Compound 3 was observed with a single IV dose of 1 mg/kg at 24 h prior to MCh. The area under the curve (AUC) for Penh response reported as percent of vehicle control (AUC=100%) was 71.0±8.6% (p=0.0051). Eosinophil infiltration into the bronchoaveolar lavage fluid (BALF) was reduced by 46% (p=0.0002).

Compound 9 Results

Compound 9 administered intravenously (IV) or orally was efficacious against experimental asthma as noted by attenuation of methacholine (MCh) induced bronchoconstriction and pulmonary inflammation. Significant efficacy with Compound 9 was observed with a single IV dose of 1 mg/kg at 24 h prior to MCh. The area under the curve (AUC) for Penh response reported as percent of vehicle control (AUC=100%) was 65.3±5.9% (p=0.0001). Eosinophil infiltration into the bronchoaveolar lavage fluid (BALF) was reduced by 92% (p<0.0001). Significant efficacy with Compound 9 was also observed with a single oral dose of 30 mg/kg at 24 h prior to MCh. The area under the curve (AUC) for Penh response reported as percent of vehicle control (AUC=100%) was 24.6±3.0% (p<0.0001). Eosinophil infiltration into the bronchoaveolar lavage fluid (BALF) was reduced by 100% (p=0.0004).

Compound 12 Results

Compound 12 administered intravenously (IV) was efficacious against experimental asthma as noted by attenuation of methacholine (MCh) induced bronchoconstriction. Significant efficacy with Compound 12 was observed with a single IV dose of 0.1 and 1 mg/kg at 24 h prior to MCh. The area under the curve (AUC) for Penh response reported as percent of vehicle control (AUC=100%) was 56.1±2.2% (p<0.0001) and 50.4±3.7% (p<0.0001) 0.1 and 1 mg/kg of Compound 7, respectively.

Compound 116 Results

Compound 116 administered intravenously (IV) or orally was efficacious against experimental asthma as noted by attenuation of methacholine (MCh) induced bronchoconstriction and pulmonary inflammation. Significant efficacy with Compound 116 was observed with a single IV dose of 0.1, 1, and 10 mg/kg at 24 h prior to MCh. The area under the curve (AUC) for Penh response reported as percent of vehicle control (AUC=100%) was 64.2±7.6% (p=0.0007); 60.2±7.9% (p=0.0002); and 40.7±2.4% (p<0.0001) for 0.1 mg/kg, 1 mg/kg, and 10 mg/kg, respectively, of Compound 116. Eosinophil infiltration into the bronchoaveolar lavage fluid (BALF) was reduced by 79% (p=0.0064); 100% (p=0.0007); and 100% (p=0.0007) for 0.1 mg/kg, 1 mg/kg, and 10 mg/kg, respectively, of Compound 116. Significant efficacy with Compound 116 was also observed as early as 30 min. (AUC=35.2±9.3; p<0.0001) prior to MCh at a single IV dose of 10 mg/kg. Eosinophil infiltration into the BALF was reduced by 94% (p<0.0001). Significant efficacy with Compound 116 was also observed with a single oral dose of 30 mg/kg at 24 h prior to MCh. The area under the curve (AUC) for Penh response reported as percent of vehicle control (AUC=100%) was 26.7±1.4% (p<0.0001). Eosinophil infiltration into the bronchoaveolar lavage fluid (BALF) was reduced by 100% (p=0.0019).

Compound 136 Results

Compound 136 administered intravenously was efficacious against experimental asthma as noted by attenuation of methacholine (MCh) induced bronchoconstriction and pulmonary inflammation. Significant efficacy with Compound 136 was observed with a single IV dose of 1 mg/kg at 24 h prior to MCh. The area under the curve (AUC) for Penh response reported as percent of vehicle control (AUC=100%) was 72.9±8.7% (p=0.0089). Eosinophil infiltration into the bronchoaveolar lavage fluid (BALF) was reduced by 61% (p<0.0001).

Compound 171 Results

Compound 171 administered intravenously (IV) was efficacious against experimental asthma as noted by attenuation of methacholine (MCh) induced bronchoconstriction and pulmonary inflammation. Significant efficacy with Compound 171 was observed with a single IV dose of 1 mg/kg at 24 h prior to MCh. The area under the curve (AUC) for Penh response reported as percent of vehicle control (AUC=100%) was 78.7±8.1% (p=0.0323). Eosinophil infiltration into the bronchoaveolar lavage fluid (BALF) was reduced by 63% (p<0.0001).

It will be apparent to those skilled in the art that various modifications and variations can be made in the methods and compositions of the present invention without departing from the spirit or scope of the invention.

The invention claimed is:

1. A method of treatment of pulmonary hypertension, ARDS, asthma, pneumonia, pulmonary fibrosis/interstitial lung diseases, cystic fibrosis, and chronic obstructive pulmonary disease (COPD) comprising administering a therapeutically effective amount of a compound of formula I or a pharmaceutically acceptable salt thereof:

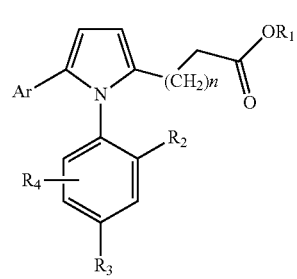

(I)

wherein

Ar is selected from the group consisting of aryl, substituted aryl, heteroaryl and substituted heteroaryl;

$R_1$ is selected from the group consisting of hydrogen, $C_1$-$C_6$ alkyl, $C_3$-$C_6$ cycloalkyl, aryl, substituted aryl, heteroaryl, and substituted heteroaryl;

$R_2$ is selected from the group consisting of halogen, $C_1$-$C_6$ alkyl, $C_3$-$C_6$ cycloalkyl, cyano, nitro, $CF_3$, carbamoyl, $C_1$-$C_6$ alkylcarbamoyl, amino, $C_1$-$C_6$ alkylamino, $C_1$-$C_6$ dialkylamino, $C_1$-$C_6$ alkoxyl, and $C_3$-$C_6$ cycloalkoxyl;

$R_3$ is selected from the group consisting of hydroxyl, carbamoyl, $C_1$-$C_6$ alkylcarbamoyl, sulfamoyl, $C_1$-$C_6$ alkylsulfamoyl, $C_3$-$C_6$ cycloalkyl, cyano, nitro, carboxyl, amino, aminomethyl, acetamido, acetamido-2-methyl, 2-methoxyacetamido, propionamido, tetrahydrofuran-2-ylmethoxy, $CF_3$, carboxyl, ureido, sulfamoylamino, $C_1$-$C_6$ alkylsulfonamido, 2-amino-2-oxoethyl, $C_1$-$C_6$ alkylamino, $C_1$-$C_6$ dialkylamino, arylamino, heteroarylamino, $C_1$-$C_6$ alkoxyl, $C_3$-$C_6$ cycloalkoxyl, 1H-imidazol-2-yl, oxazol-2-yl, thiazol-2-yl, methylcarbamoyl, dimethylcarbamoyl, methoxyethylcarbamoyl, hydroxyethylcarbamoyl, (dimethylamino)ethylcarbamoyl, pyridin-3-ylcarbamoyl, pyridin-4-yl-carbamoyl, 6-methoxypyridin-3-ylcarbamoyl, pyridazin-4-ylcarbamoyl, and pyrimidin-5-ylcarbamoyl;

$R_4$ is selected from the group consisting of hydrogen, hydroxyl, halogen, $C_1$-$C_6$ alkyl, $C_3$-$C_6$ cycloalkyl, cyano, nitro, carbamoyl, $C_1$-$C_6$ alkylcarbamoyl, sulfamoyl, $C_1$-$C_6$ alkyl sulfamoyl, amino, $C_1$-$C_6$ alkylamino, $C_1$-$C_6$ dialkylamino, $C_1$-$C_6$ alkoxyl, and $C_3$-$C_6$ cycloalkoxyl;

n is 0-3;

wherein Ar excludes substituted or unsubstituted indazol-3-yl and substituted or unsubstituted 1H-pyrazolo[3,4-b]pyridyl;

with the following provisos:

proviso Ia: when $R_3$ is carboxyl, methylsulfonamido, or sulfamoyl, then Ar cannot be phenyl, substituted or unsubstituted phenyl-($C_1$-$C_3$)-alkyl, or phenyl-($C_2$-$C_6$)-alkenyl; and proviso Ib: when $R_2$ and $R_3$ are both methoxy, then Ar cannot be phenyl, 4-methyl-phenyl, 4-methoxy-phenyl, 4-halo-phenyl, or thiophen-yl.

2. The method of claim 1 wherein:

Ar is selected from the group consisting of phenyl, substituted phenyl, thiophen-yl, substituted thiophen-yl, pyridinyl, substituted pyridinyl, thiazolyl, substituted thiazolyl, pyrimidinyl, substituted pyrimidinyl, furanyl, substituted furanyl, bicyclic aryl, substituted bicyclic aryl, bicyclic heteroaryl, and substituted bicyclic heteroaryl;

$R_1$ is selected from the group consisting of hydrogen and $C_1$-$C_6$ alkyl;

$R_2$ is selected from the group consisting of halogen, $C_1$-$C_6$ alkyl, and $CF_3$;

$R_3$ is selected from the group consisting of hydroxyl, carbamoyl, sulfamoyl, sulfamoylamino, $C_1$-$C_6$ alkoxy, amino, aminomethyl, acetamido, acetamido-2-methyl, 2-methoxyacetamido, propionamido, tetrahydrofuran-2-ylmethoxy, methylsulfamido, carboxyl, $C_1$-$C_6$ alkylamino, 1H-imidazol-2-yl, oxazol-2-yl, thiazol-2-yl, methylcarbamoyl, dimethycarbamoyl, methoxyethylcarbamoyl, hydroxyethylcarbamoyl, (dimethylamino) ethylcarbamoyl, pyridin-3-ylcarbamoyl, pyridin-4-ylcarbamoyl, 6-methoxypyridin-3-ylcarbamoyl, pyridazin-4-ylcarbamoyl, and pyrimidin-5-ylcarbamoyl;

$R_4$ is selected from the group consisting of hydrogen and $C_1$-$C_6$ alkyl; and n is 1.

3. The method of claim 2 wherein Ar is selected from the group consisting of phenyl, substituted phenyl, aryl-phenyl, substituted aryl-phenyl, heteroaryl-phenyl, substituted heteroaryl-phenyl, thiophen-yl, substituted thiophen-yl, aryl-thiophen-yl, substituted aryl-thiophen-yl, heteroaryl-thiophen-yl, substituted heteroaryl-thiophen-yl, pyridinyl, substituted pyridinyl, aryl-pyridinyl, substituted aryl-pyridinyl, heteroaryl-pyridinyl, substituted heteroaryl-pyridinyl, thiazolyl, substituted thiazolyl, aryl-thiazolyl; substituted aryl-thiozolyl; heteroaryl-thiazolyl; substituted heteroaryl-thiazolyl, pyrimidinyl, substituted pyrimidinyl, aryl-pyrimidinyl, substituted aryl-pyrimidinyl, heteroaryl-pyrimidinyl, substituted heteroaryl-pyrimidinyl, furanyl, substituted furanyl, aryl-furanyl, substituted aryl-furanyl, heteroaryl-furanyl, and substituted heteroaryl-furanyl.

4. The method of claim 2 wherein Ar is selected from the group consisting of phenyl, thiophen-yl, thiazolyl, pyridinyl, pyrimidinyl, or furanyl having 0, 1, 2, or 3 substitutions, wherein such substitutions are independently selected from the group consisting of hydrogen, hydroxyl, halogen, $C_1$-$C_6$ alkoxy, amino, cyano, $C_1$-$C_6$ alkyl, imidazolyl, methyl imidazolyl, ethyl imidazolyl, furanyl, methylthio, nitro, triazolyl, tetrazolyl, carbamoyl, pyrazolyl, trifluoromethoxy, trifluoromethyl, 2-amino-2oxoethoxy, ureido, morpholino, pyridinyl, pyrrolyl, methyl sulfonamido, carbamoyl phenyl, 6-oxo-1,6-dihydropyridinyl, 3,5-dimethylisoxazolyl, carboxymethoxy, hydroxyacetamido, methoxyacetamido, sulfamoyl, piperazinyl, oxoimidazolidinyl, methylsulfinyl, methylsulfonyl, pyrrolidinyl, piperidinyl, methylpyrazolyl, phenyl, thiazolyl, hydroxycarbamoyl, cyclopropylimidazolyl, carboxy, methylamino, methoxymethyl, dimethylamino, hydroxymethylimidazolyl, oxooxazolidinyl, formamido, hydroxyphenyl, and thiophen-yl.

5. The method of claim 2 wherein Ar is selected from the group consisting of 4-(1H-imidazol-1-yl)phenyl, 5-(1H-imidazol-1-yl)thiophen-2-yl, 4-(2-methyl-1H-imidazol-1-yl)phenyl, thiazol-5-yl, 4-hydroxyphenyl, 5-bromothiophen-2-yl, 4-methoxyphenyl, 4-aminophenyl, 4-bromophenyl, 4-(furan-3-yl)phenyl, phenyl, 3-chloro-4-methoxyphenyl, 3-fluoro-4-methoxyphenyl, 4-cyanophenyl, 3-chloro-4-hydroxyphenyl, 4-methoxy-3-methylphenyl, 4-iodophenyl, 3-methoxyphenyl, 6-methoxypyridin-3-yl, benzo[d]thiazol-6-yl, 4-(methylthio)phenyl, 4-nitrophenyl, 4-(4H-1,2,4-triazol-4-yl)phenyl, 4-(2H-tetrazol-5-yl)phenyl, benzo[d][1,3]dioxol-5-yl, 6-(1H-imidazol-1-yl)pyridin-3-yl, 5-carbamoylthiophen-2-yl, 4-(1H-pyrazol-4-yl)phenyl, 4-(trifluoromethoxy)phenyl, 4-carbamoylphenyl, 4-(trifluoromethyl)phenyl, 4-(1H-1,2,4-triazol-1-yl)phenyl, 4-(1H-pyrazol-1-yl)phenyl, 4-(2-amino-2-oxoethoxy)phenyl, 4-(1-methyl-1H-pyrazol-4-yl)phenyl, 4-(1H-tetrazol-1-yl)phenyl, 4-(4-methyl-1H-imidazol-1-yl)phenyl, 4-ureidophenyl, 4-morpholinophenyl, 4-(2H-tetrazol-5-yl)phenyl, 4-(pyridin-4-yl)phenyl, 4-(1H-pyrrol-1-yl)phenyl, 4-(methylsulfonamido)phenyl, 1H-1,2,3-triazol-1-yl)phenyl, naphthalen-2-yl, 3'-carbamoylbiphenyl-4-yl, 4-(6-oxo-1,6-dihydropyridin-3-yl)phenyl, 4-(3,5-dimethylisoxazol-4-yl)phenyl, 4-(pyridin-3-yl)phenyl, 4-(carboxymethoxy)phenyl, 4-(2-hydroxyacetamido) phenyl, 4-(2-methoxyacetamido)phenyl, 4-sulfamoylphenyl, 4-(piperazin-1-yl)phenyl, 4-(2-oxoimidazolidin-1-yl)phenyl, 4-ethoxyphenyl, 4-(methylsulfinyl)phenyl, 4-(2-ethyl-1H-imidazol-1-yl)phenyl, 4-(furan-2-yl)phenyl, 4-(methylsulfonyl)phenyl, 4-(pyrrolidin-1-yl)phenyl, 4-(piperidin-1-yl)phenyl, 4-(1-methyl-1H-pyrazol-5-yl)phenyl, 5-(2-methyl-1H-imidazol-1-yl)thiophen-2-yl, 4-(furan-3-yl)phenyl, 2-methoxypyrimidin-5-yl, 2-methyl-4-(methylsulfonamido)phenyl, 4-amino-3-chlorophenyl, 3,4-difluorophenyl, 2,4-difluorophenyl, 4-chlorophenyl, 4-bromothiophen-2-yl, biphenyl-4-yl, 2-(1H-imidazol-1-yl)pyrimidin-5-yl, 4-fluoro-3-methoxyphenyl, 3-cyano-4-fluorophenyl, 4-carbamoyl-2-methylphenyl, 4-methoxy-2-methylphenyl, 4-chloro-2-fluorophenyl, 4-fluorophenyl, 4-fluoro-2-methylphenyl, 4-chloro-2-(trifluoromethyl)phenyl, 4-chloro-2-methoxyphenyl, 4-cyano-3-fluorophenyl, 2-chloro-4-methoxyphenyl, 4-(1H-imidazol-1-yl)thiophen-2-yl, 3,5-dimethyl-4-nitrophenyl, 4-amino-3,5-dimethylphenyl, 2-(1H-imidazol-1-yl)thiazol-4-yl, 2-ethoxy-4-fluorophenyl, 4-methoxy-2-(trifluoromethyl)phenyl, 4-fluoro-2-methoxyphenyl, 4-(thiazol-5-yl)phenyl, 4-chloro-3-fluorophenyl, 4-(hydroxycarbamoyl)phenyl, 3-fluoro-4-(1H-imidazol-1-yl)phenyl, 3-fluoro-4-(2-methyl-1H-imidazol-1-yl)phenyl, 4-chloro-2-ethoxyphenyl, 5-bromo-2-methoxyphenyl, 4-(2-cyclopropyl-1H-imidazol-1-yl)phenyl, 4-(2-methyl-1H-imidazol-1-yl)thiophen-2-yl, 4-bromo-2-methoxyphenyl, 2-methoxy-4-(2-methyl-1H-imidazol-1-yl)phenyl, 4-chloro-2-hydroxyphenyl, 5-bromothiophen-3-yl, 4-hydroxy-3-methylphenyl, 2-carbamoyl-4-chlorophenyl, 2-acetamido-4-chlorophenyl, 2-methoxyphenyl, benzoic acid, 2,4-dimethoxyphenyl, 4-chloro-2-propoxyphenyl, 4-chloro-2-(2-methoxyacetamido)phenyl, 4-chloro-2-(methylsulfonamido)phenyl, 4-chloro-2-(methylamino)phenyl, 4-chloro-2-(methoxymethyl)phenyl, 4-hydroxy-2-methoxyphenyl, 4-chloro-2-(dimethylamino)phenyl, 4-(2-(hydroxymethyl)-1H-imidazol-1-yl)phenyl, 4-(2-oxooxazolidin-3-yl)phenyl)-1H-pyrrol-2-yl, 4-(1H-imidazol-1-yl)-2-methoxyphenyl, 5-(2-methyl-1H-imidazol-1-yl)thiophen-3-yl, 5-chlorothiophen-2-yl, 5-bromothiazol-2-yl, 4-bromothiazol-2-yl, 5-(2-ethyl-1H-imidazol-1-yl)thiophen-2-yl, 4-chloro-2-formamidophenyl, 3-chlorothiophen-2-yl, 4-formamido-2-methoxyphenyl, 3-bromo-5-methoxythiophen-2-yl, 5-(4-hydroxyphenyl)thiophen-2-yl, 4-(thiophen-3-yl)phenyl, 5-(1H-imidazol-1-yl)furan-2-yl, 4-chlorothiophen-2-yl, 5-bromo-4-chlorothiophen-2-yl, 5-(2-methyl-1H-imidazol-1-yl)furan-2-yl, and 5-bromofuran-2-yl.

6. The method of claim 2 wherein Ar is selected from the group consisting of 4-(1H-imidazol-1-yl)phenyl, 5-(1H-imidazol-1-yl)thiophen-2-yl, 4-(2-methyl-1H-imidazol-1-yl)phenyl, thiazol-5-yl, 4-hydroxyphenyl, 5-bromothiophen-2-yl, 4-methoxyphenyl, 4-aminophenyl, 4-bromophenyl, 4-(furan-3-yl)phenyl, 3-chloro-4-methoxyphenyl, 3-fluoro- 4-methoxyphenyl, 4-cyanophenyl, 3-chloro-4-hydroxyphenyl, 4-methoxy-3-methylphenyl, 4-iodophenyl, 3-methoxyphenyl, 6-methoxypyridin-3-yl, benzo[d]thiazol-6-yl, 4-(methylthio)phenyl, 4-nitrophenyl, 4-(4H-1,2,4-triazol-4-yl)phenyl, 4-(2H-tetrazol-5-yl)phenyl, benzo[d][1,3]dioxol-5-yl, 6-(1H-imidazol-1-yl)pyridin-3-yl, 5-carbamoylthiophen-2-yl, 4-(1H-pyrazol-4-yl)phenyl, 4-(trifluoromethoxy)phenyl, 4-carbamoylphenyl, 4-(trifluoromethyl)phenyl, 4-(1H-1,2,4-triazol-1-yl)phenyl, 4-(1H-pyrazol-1-yl)phenyl, 4-(2-amino-2-oxoethoxy)phenyl, 4-(1-methyl-1H-pyrazol-4-yl)phenyl, 4-(1H-tetrazol-1-yl)phenyl, 4-(4-methyl-1H-imidazol-1-yl)phenyl, 4-ureidophenyl, 4-morpholinophenyl, 4-(2H-tetrazol-5-yl)phenyl, 4-(pyridin-4-yl)phenyl, 4-(1H-pyrrol-1-yl)phenyl, 4-(methylsulfonamido)phenyl, 1H-1,2,3-triazol-1-yl)phenyl, naphthalen-2-yl, 3'-carbamoylbiphenyl-4-yl, 4-(6-oxo-1,6-dihydropyridin-3-yl)phenyl, 4-(3,5-dimethylisoxazol-4-yl)phenyl, 4-(pyridin-3-yl)phenyl, 4-(carboxymethoxy)phenyl, 4-(2-hydroxyacetamido)phenyl, 4-(2-methoxyacetamido)phenyl, 4-sulfamoylphenyl, 4-(piperazin-1-yl)phenyl, 4-(2-oxoimidazolidin-1-yl)phenyl, 4-ethoxyphenyl, 4-(methylsulfinyl)phenyl, 4-(2-ethyl-1H-imidazol-1-yl)phenyl, 4-(furan-2-yl)phenyl, 4-(methylsulfonyl)phenyl, 4-(pyrrolidin-1-yl)phenyl, 4-(piperidin-1-yl)phenyl, 4-(1-methyl-1H-pyrazol-5-yl)phenyl, 5-(2-methyl-1H-imidazol-1-yl)thiophen-2-yl, 4-(furan-3-yl)phenyl, 2-methoxypyrimidin-5-yl, 2-methyl-4-(methylsulfonamido)phenyl, 4-amino-3-chlorophenyl, 3,4-difluorophenyl, 2,4-difluorophenyl, 4-chlorophenyl, 4-bromothiophen-2-yl, biphenyl-4-yl, 2-(1H-imidazol-1-yl)pyrimidin-5-yl, 4-fluoro-3-methoxyphenyl, 3-cyano-4-fluorophenyl, 4-carbamoyl-2-methylphenyl, 4-methoxy-2-methylphenyl, 4-chloro-2-fluorophenyl, 4-fluorophenyl, 4-fluoro-2-methylphenyl, 4-chloro-2-(trifluoromethyl)phenyl, 4-chloro-2-methoxyphenyl, 4-cyano-3-fluorophenyl, 2-chloro-4-methoxyphenyl, 4-(1H-imidazol-1-yl)thiophen-2-yl, 3,5-dimethyl-4-nitrophenyl, 4-amino-3,5-dimethylphenyl, 2-(1H-imidazol-1-yl)thiazol-4-yl, 2-ethoxy-4-fluorophenyl, 4-methoxy-2-(trifluoromethyl)phenyl, 4-fluoro-2-methoxyphenyl, 4-(thiazol-5-yl)phenyl, 4-chloro-3-fluorophenyl, 4-(hydroxycarbamoyl)phenyl, 3-fluoro-4-(1H-imidazol-1-yl)phenyl, 3-fluoro-4-(2-methyl-1H-imidazol-1-yl)phenyl, 4-chloro-2-ethoxyphenyl, 5-bromo-2-methoxyphenyl, 4-(2-cyclopropyl-1H-imidazol-1-yl)phenyl, 4-(2-methyl-1H-imidazol-1-yl)thiophen-2-yl, 4-bromo-2-methoxyphenyl, 2-methoxy-4-(2-methyl-1H-imidazol-1-yl)phenyl, 4-chloro-2-hydroxyphenyl, 5-bromothiophen-3-yl, 4-hydroxy-3-methylphenyl, 2-carbamoyl-4-chlorophenyl, 2-acetamido-4-chlorophenyl, 2-methoxyphenyl, benzoic acid, 2,4-dimethoxyphenyl, 4-chloro-2-propoxyphenyl, 4-chloro-2-(2-methoxyacetamido)phenyl, 4-chloro-2-(methylsulfonamido)phenyl, 4-chloro-2-(methylamino)phenyl, 4-chloro-2-(methoxymethyl)phenyl, 4-hydroxy-2-methoxyphenyl, 4-chloro-2-(dimethylamino)phenyl, 4-(2-(hydroxymethyl)-1H-imidazol-1-yl)phenyl, 4-(2-oxooxazolidin-3-yl)phenyl)-1H-pyrrol-2-yl, 4-(1H-imidazol-1-yl)-2-methoxyphenyl, 5-(2-methyl-1H-imidazol-1-yl)thiophen-3-yl, 5-chlorothiophen-2-yl, 5-bromothiazol-2-yl, 4-bromothiazol-2-yl, 5-(2-ethyl-1H-imidazol-1-yl)thiophen-2-yl, 4-chloro-2-formamidophenyl, 3-chlorothiophen-2-yl, 4-formamido-2-methoxyphenyl, 3-bromo-5-methoxythiophen-2-yl, 5-(4-hydroxyphenyl)thiophen-2-yl, 4-(thiophen-3-yl)phenyl, 5-(1H-imidazol-1-yl)furan-2-yl, 4-chlorothiophen-2-yl, 5-bromo-4-chlorothiophen-2-yl, 5-(2-methyl-1H-imidazol-1-yl)furan-2-yl, and 5-bromofuran-2-yl.

7. The method of claim 4 wherein the compound of formula 1 is selected from the group consisting of:

3-(1-(4-carbamoyl-2-methylphenyl)-5-(thiazol-5-yl)-1H-pyrrol-2-yl)propanoic acid; 3-(1-(4-carbamoyl-2,6-dimethylphenyl)-5-(4-methoxyphenyl)-1H-pyrrol-2-yl)propanoic acid; 3-(5-(4-(1H-imidazol-1-yl)phenyl)-1-(4-hydroxy-2-methylphenyl)-1H-pyrrol-2-yl)propanoic acid; 3-(1-(4-carbamoyl-2-chlorophenyl)-5-(4-methoxyphenyl)-1H-pyrrol-2-yl)propanoic acid; 3-(5-(4-aminophenyl)-1-(4-carbamoyl-2-methylphenyl)-1H-pyrrol-2-yl)propanoic acid; 3-(1-(4-carbamoyl-2-methylphenyl)-5-(4-(furan-3-yl)phenyl)-1H-pyrrol-2-yl)propanoic acid; 3-(5-(4-methoxyphenyl)-1-(2-methyl-4-sulfamoylphenyl)-1H-pyrrol-2-yl)propanoic acid; 3-(1-(4-carbamoyl-2-methylphenyl)-5-phenyl-1H-pyrrol-2-yl)propanoic acid; 3-(1-(4-carbamoyl-2-methylphenyl)-5-(4-cyanophenyl)-1H-pyrrol-2-yl)propanoic acid; 3-(1-(4-carbamoyl-2-ethylphenyl)-5-(4-methoxyphenyl)-1H-pyrrol-2-yl)propanoic acid; 3-(1-(4-carbamoyl-2-methylphenyl)-5-(4-iodophenyl)-1H-pyrrol-2-yl)propanoic acid; 3-(1-(4-carbamoyl-2-methylphenyl)-5-(6-methoxypyridin-3-yl)-1H-pyrrol-2-yl)propanoic acid; 3-(5-(benzo[d]thiazol-6-yl)-1-(4-carbamoyl-2-methylphenyl)-1H-pyrrol-2-yl)propanoic acid; 3-(1-(4-carbamoyl-2-methylphenyl)-5-(4-(methylthio)phenyl)-1H-pyrrol-2-yl)propanoic acid; 3-(1-(4-carbamoyl-2-methylphenyl)-5-(4-nitrophenyl)-1H-pyrrol-2-yl)propanoic acid; 3-(5-(4-(1H-imidazol-1-yl)phenyl)-1-(4-amino-2-methylphenyl)-1H-pyrrol-2-yl)propanoic acid; 3-(5-(4-(4H-1,2,4-triazol-4-yl)phenyl)-1-(4-carbamoyl-2-methylphenyl)-1H-pyrrol-2-yl)propanoic acid; 3-(5-(4-(2H-tetrazol-5-yl)phenyl)-1-(4-carbamoyl-2-methylphenyl)-1H-pyrrol-2-yl)propanoic acid; 3-(1-(4-methoxy-2-methylphenyl)-5-(4-methoxyphenyl)-1H-pyrrol-2-yl)propanoic acid; 3-(5-(benzo[d][1,3]dioxol-5-yl)-1-(4-carbamoyl-2-methylphenyl)-1H-pyrrol-2-yl)propanoic acid; 3-(5-(4-bromophenyl)-1-(4-hydroxy-2-methylphenyl)-1H-pyrrol-2-yl)propanoic acid; 3-(5-(6-(1H-imidazol-1-yl)pyridin-3-yl)-1-(4-carbamoyl-2-methylphenyl)-1H-pyrrol-2-yl)propanoic acid; 3-(1-(4-carbamoyl-2-methylphenyl)-5-(5-carbamoylthiophen-2-yl)-1H-pyrrol-2-yl)propanoic acid; 3-(5-(4-(1H-pyrazol-4-yl)phenyl)-1-(4-carbamoyl-2-methylphenyl)-1H-pyrrol-2-yl)propanoic acid; 3-(1-(4-carbamoyl-2-methylphenyl)-5-(4-(trifluoromethoxy)phenyl)-1H-pyrrol-2-yl)propanoic acid; 3-(1-(4-carbamoyl-2-methylphenyl)-5-(4-carbamoylphenyl)-1H-pyrrol-2-yl)propanoic acid; 3-(1-(4-carbamoyl-2-methylphenyl)-5-(4-(trifluoromethyl)phenyl)-1H-pyrrol-2-yl)propanoic acid; 3-(5-(4-(1H-1,2,4-triazol-1-yl)phenyl)-1-(4-carbamoyl-2-methylphenyl)-1H-pyrrol-2-yl)propanoic acid; 3-(5-(4-(1H-pyrazol-1-yl)phenyl)-1-(4-carbamoyl-2-methylphenyl)-1H-pyrrol-2-yl)propanoic acid; 3-(5-(4-(2-amino-2-oxoethoxy)phenyl)-1-(4-carbamoyl-2-methylphenyl)-1H-pyrrol-2-yl)propanoic acid; 3-(1-(4-carbamoyl-2-methylphenyl)-5-(4-(1-methyl-1H-pyrazol-4-yl)phenyl)-1H-pyrrol-2-yl)propanoic acid; 3-(5-(4-(1H-tetrazol-1-yl)phenyl)-1-(4-carbamoyl-2-methylphenyl)-1H-pyrrol-2-yl)propanoic acid; 3-(1-(4-carbamoyl-2-methylphenyl)-5-(4-ureidophenyl)-1H-pyrrol-2-yl)propanoic acid; 4-(2-(benzo[d][1,3]dioxol-5-yl)-5-(2-carboxyethyl)-1H-pyrrol-1-yl)-3-methylbenzoic acid; 3-1-(4-amino-2-methylphenyl)-5-(4-bromophenyl)-1H-pyrrol-2-yl)propanoic acid; 3-(1-(4-carbamoyl-2-methylphenyl)-5-(4-morpholinophenyl)-1H-pyrrol-2-yl)propanoic acid;

4-(2-(4-(2H-tetrazol-5-yl)phenyl)-5-(2-carboxyethyl)-1H-pyrrol-1-yl)-3-methylbenzoic acid; 3-(1-(4-carbamoyl-2-methylphenyl)-5-(4-(pyridin-4-yl)phenyl)-1H-pyrrol-2-yl)propanoic acid; 3-(5-(4-(1H-pyrrol-1-yl)phenyl)-1-(4-carbamoyl-2-methylphenyl)-1H-pyrrol-2-yl)propanoic acid; 3-(1-(4-hydroxy-2,5-dimethylphenyl)-5-(4-methoxyphenyl)-1H-pyrrol-2-yl)propanoic acid; 3-(1-(4-carbamoyl-2-methylphenyl)-5-(4-(methylsulfonamido)phenyl)-1H-pyrrol-2-yl)propanoic acid; 3-(5-(4-(1H-1,2,3-triazol-1-yl)phenyl)-1-(4-carbamoyl-2-methylphenyl)-1H-pyrrol-2-yl)propanoic acid; 3-(1-(4-carbamoyl-2-methylphenyl)-5-(naphthalen-2-yl)-1H-pyrrol-2-yl)propanoic acid; 3-(1-(4-carbamoyl-2-methylphenyl)-5-(3'-carbamoylbiphenyl-4-yl)-1H-pyrrol-2-yl)propanoic acid; 3-(1-(4-carbamoyl-2-methylphenyl)-5-(4-(6-oxo-1,6-dihydropyridin-3-yl)phenyl)-1H-pyrrol-2-yl)propanoic acid; 3-(1-(4-carbamoyl-2-methylphenyl)-5-(4-(3,5-dimethylisoxazol-4-yl)phenyl)-1H-pyrrol-2-yl)propanoic acid; 3-(1-(4-carbamoyl-2-methylphenyl)-5-(4-(pyridin-3-yl)phenyl)-1H-pyrrol-2-yl)propanoic acid; 3-(1-(4-carbamoyl-2-methylphenyl)-5-(4-(carboxymethoxy)phenyl)-1H-pyrrol-2-yl)propanoic acid; 3-(1-(4-carbamoyl-2-methylphenyl)-5-(4-(2-hydroxyacetamido)phenyl)-1H-pyrrol-2-yl)propanoic acid; 3-(1-(4-carbamoyl-2-methylphenyl)-5-(4-(2-methoxyacetamido)phenyl)-1H-pyrrol-2-yl)propanoic acid; 3-(1-(4-carbamoyl-2-methylphenyl)-5-(4-sulfamoylphenyl)-1H-pyrrol-2-yl)propanoic acid; 3-(1-(4-carbamoyl-2-methylphenyl)-5-(4-(piperazin-1-yl)phenyl)-1H-pyrrol-2-yl)propanoic acid; 3-(1-(4-carbamoyl-2-methylphenyl)-5-(4-(2-oxoimidazolidin-1-yl)phenyl)-1H-pyrrol-2-yl)propanoic acid; 3-(1-(4-carbamoyl-2-methylphenyl)-5-(4-ethoxyphenyl)-1H-pyrrol-2-yl)propanoic acid; 3-(1-(4-carbamoyl-2-methylphenyl)-5-(4-(methylsulfinyl)phenyl)-1H-pyrrol-2-yl)propanoic acid; 3-(5-(4-(1H-imidazol-1-yl)phenyl)-1-(4-(aminomethyl)-2-methylphenyl)-1H-pyrrol-2-yl)propanoic acid; 3-(1-(4-(1H-imidazol-2-yl)-2-methylphenyl)-5-(4-methoxyphenyl)-1H-pyrrol-2-yl)propanoic acid; 3-(1-(4-carbamoyl-2-methylphenyl)-5-(4-(furan-2-yl)phenyl)-1H-pyrrol-2-yl)propanoic acid; 3-(1-(4-(dimethylcarbamoyl)-2-methylphenyl)-5-(4-methoxyphenyl)-1H-pyrrol-2-yl)propanoic acid; 3-(5-(4-methoxyphenyl)-1-(2-methyl-4-(methylcarbamoyl)phenyl)-1H-pyrrol-2-yl)propanoic acid; 3-(1-(4-(2-methoxyethylcarbamoyl)-2-methylphenyl)-5-(4-methoxyphenyl)-1H-pyrrol-2-yl)propanoic acid; 3-(1-(4-(2-hydroxyethylcarbamoyl)-2-methylphenyl)-5-(4-methoxyphenyl)-1H-pyrrol-2-yl)propanoic acid; 3-(5-(4-methoxyphenyl)-1-(2-methyl-4-(oxazol-2-yl)phenyl)-1H-pyrrol-2-yl)propanoic acid; 3-(1-(4-carbamoyl-2-methylphenyl)-5-(4-(methylsulfonyl)phenyl)-1H-pyrrol-2-yl)propanoic acid; 3-(1-(4-hydroxy-2-methylphenyl)-5-(4-methoxyphenyl)-1H-pyrrol-2-yl)propanoic acid; 3-(1-(2-chloro-4-hydroxyphenyl)-5-(4-methoxyphenyl)-1H-pyrrol-2-yl)propanoic acid; 3-(1-(4-hydroxy-2,3-dimethylphenyl)-5-(4-methoxyphenyl)-1H-pyrrol-2-yl)propanoic acid; 3-(1-(4-carbamoyl-2-methylphenyl)-5-(4-(pyrrolidin-1-yl)phenyl)-1H-pyrrol-2-yl)propanoic acid; 3-(1-(4-carbamoyl-2-methylphenyl)-5-(4-(piperidin-1-yl)phenyl)-1H-pyrrol-2-yl)propanoic acid; 3-(1-(4-carbamoyl-2-methylphenyl)-5-(4-(1-methyl-1H-pyrazol-5-yl)phenyl)-1H-pyrrol-2-yl)propanoic acid; ethyl 3-(5-(4-(1H-imidazol-1-yl)phenyl)-1-(4-carbamoyl-2-methylphenyl)-1H-pyrrol-2-yl)propanoate; ethyl 3-(1-(4-carbamoyl-2-methylphenyl)-5-(4-(2-methyl-1H-imidazol-1-yl)phenyl)-1H-pyrrol-2-yl)propanoate; ethyl 3-(1-(4-carbamoyl-2-methylphenyl)-5-(5-(2-methyl-1H-imidazol-1-yl)thiophen-2-yl)-1H-pyrrol-2-yl)propanoate; ethyl 3-(1-(4-carbamoyl-2-methylphenyl)-5-(4-(furan-3-yl)phenyl)-1H-pyrrol-2-yl)propanoate; ethyl 3-(1-(4-carbamoyl-2-methylphenyl)-5-(4-cyanophenyl)-1H-pyrrol-2-yl)propanoate; ethyl 3-(1-(4-carbamoyl-2-methylphenyl)-5-(4-(furan-2-yl)phenyl)-1H-pyrrol-2-yl)propanoate; 3-(1-(4-carbamoyl-2-methylphenyl)-5-(2-methoxypyrimidin-5-yl)-1H-pyrrol-2-yl)propanoic acid; 3-(5-(4-(1H-imidazol-1-yl)phenyl)-1-(4-acetamido-2-methylphenyl)-1H-pyrrol-2-yl)propanoic acid; 3-(1-(4-hydroxy-2-(trifluoromethyl)phenyl)-5-(4-methoxyphenyl)-1H-pyrrol-2-yl)propanoic acid; 3-(5-(4-methoxyphenyl)-1-(4-((tetrahydrofuran-2-yl)methoxy)-2-(trifluoromethyl)phenyl)-1H-pyrrol-2-yl)propanoic acid; 3-(1-(4-carbamoyl-2-(trifluoromethyl)phenyl)-5-(4-methoxyphenyl)-1H-pyrrol-2-yl)propanoic acid; 3-(5-(4-(1H-imidazol-1-yl)phenyl)-1-(2-methyl-4-propionamidophenyl)-1H-pyrrol-2-yl)propanoic acid; 3-(5-(4-(1H-imidazol-1-yl)phenyl)-1-(4-(2-methoxyacetamido)-2-methylphenyl)-1H-pyrrol-2-yl)propanoic acid; 3-(5-(biphenyl-4-yl)-1-(4-carbamoyl-2-methylphenyl)-1H-pyrrol-2-yl)propanoic acid; 3-(1-(4-carbamoyl-2-fluorophenyl)-5-(4-methoxyphenyl)-1H-pyrrol-2-yl)propanoic acid; 3-(5-(2-(1H-imidazol-1-yl)pyrimidin-5-yl)-1-(4-carbamoyl-2-methylphenyl)-1H-pyrrol-2-yl)propanoic acid; 3-(1-(4-carbamoyl-2-methylphenyl)-5-(3-cyano-4-fluorophenyl)-1H-pyrrol-2-yl)propanoic acid; 3-(5-(4-methoxyphenyl)-1-(2-methyl-4-(thiazol-2-yl)phenyl)-1H-pyrrol-2-yl)propanoic acid; 3-(1-(4-carbamoyl-2-methylphenyl)-5-(4-chloro-2-(trifluoromethyl)phenyl)-1H-pyrrol-2-yl)propanoic acid; 3-(1-(4-carbamoyl-2-methylphenyl)-5-(4-cyano-3-fluorophenyl)-1H-pyrrol-2-yl)propanoic acid; 3-(1-(4-(2-(dimethylamino)ethylcarbamoyl)-2-methylphenyl)-5-(4-methoxyphenyl)-1H-pyrrol-2-yl)propanoic acid; 3-(1-(4-carbamoyl-2-methylphenyl)-5-(3,5-dimethyl-4-nitrophenyl)-1H-pyrrol-2-yl)propanoic acid; 3-(5-(4-amino-3,5-dimethylphenyl)-1-(4-carbamoyl-2-methylphenyl)-1H-pyrrol-2-yl)propanoic acid; 3-(5-(2-(1H-imidazol-1-yl)thiazol-4-yl)-1-(4-carbamoyl-2-methylphenyl)-1H-pyrrol-2-yl)propanoic acid; 3-(5-(4-bromophenyl)-1-(2-methyl-4-(pyridin-3-ylcarbamoyl)phenyl)-1H-pyrrol-2-yl)propanoic acid; 3-(5-(4-bromophenyl)-1-(4-(6-methoxypyridin-3-ylcarbamoyl)-2-methylphenyl)-1H-pyrrol-2-yl)propanoic acid; 3-(5-(4-methoxyphenyl)-1-(4-(6-methoxypyridin-3-ylcarbamoyl)-2-methylphenyl)-1H-pyrrol-2-yl)propanoic acid; 3-(1-(4-carbamoyl-2-methylphenyl)-5-(4-(thiazol-5-yl)phenyl)-1H-pyrrol-2-yl)propanoic acid; 3-(1-(4-carbamoyl-2-methylphenyl)-5-(4-(hydroxycarbamoyl)phenyl)-1H-pyrrol-2-yl)propanoic acid; 3-(5-(4-bromophenyl)-1-(2-methyl-4-(pyridin-4-ylcarbamoyl)phenyl)-1H-pyrrol-2-yl)propanoic acid; 3-(5-(4-methoxyphenyl)-1-(2-methyl-4-(pyridazin-4-ylcarbamoyl)phenyl)-1H-pyrrol-2-yl)propanoic acid; 3-(5-(4-methoxyphenyl)-1-(2-methyl-4-(pyridin-3-ylcarbamoyl)phenyl)-1H-pyrrol-2-yl)propanoic acid; 3-(5-(4-methoxyphenyl)-1-(2-methyl-4-(pyrimidin-5-ylcarbamoyl)phenyl)-1H-pyrrol-2-yl)propanoic acid; 3-(1-(4-carbamoyl-2-methylphenyl)-5-(4-(2-cyclopropyl-1H-imidazol-1-yl)phenyl)-1H-pyrrol-2-yl)propanoic acid; 3-(1-(4-acetamido-2-methylphenyl)-5-(4- bromophenyl)-1H-pyrrol-2-yl)propanoic acid; 3-(5-(4-bromophenyl)-1-(4-(2-methoxyacetamido)-2-methylphenyl)-1H-pyrrol-2-yl)propanoic acid; 3-(5-(2-acetamido-4-chlorophenyl)-1-(4-carbamoyl-2-methylphenyl)-1H-pyrrol-2-yl)propanoic acid; 4-(1-(4-carbamoyl-2-methylphenyl)-5-(2-carboxyethyl)-1H-pyrrol-2-yl)benzoic acid; 3-(1-(4-carbamoyl-2-methylphenyl)-5-(4-chloro-2-(2-methoxyacetamido) phenyl)-1H-pyrrol-2-yl)propanoic acid; 3-(1-(4-carbamoyl-2-methylphenyl)-5-(4-chloro-2-(methylsulfonamido)phenyl)-1H-pyrrol-2-yl) propanoic acid; 3-(1-(4-carbamoyl-2-methylphenyl)-5-(4-chloro-2-(methylamino)phenyl)-1H-pyrrol-2-yl) propanoic acid; 3-(1-(4-carbamoyl-2-methylphenyl)-5-(4-chloro-2-(methoxymethyl)phenyl)-1H-pyrrol-2-yl) propanoic acid; 3-(1-(4-carbamoyl-2-methylphenyl)-5-(4-(2-(hydroxymethyl)-1H-imidazol-1-yl)phenyl)-1H-pyrrol-2-yl)propanoic acid; 3-(1-(4-carbamoyl-2-methylphenyl)-5-(4-(2-oxooxazolidin-3-yl)phenyl)-1H-pyrrol-2-yl)propanoic acid; 3-(5-(5-bromothiazol-2-yl)-1-(4-carbamoyl-2-methylphenyl)-1H-pyrrol-2-yl)propanoic acid; 3-(1-(4-acetamido-2-methylphenyl)-5-(4-chloro-2-methoxyphenyl)-1H-pyrrol-2-yl) propanoic acid; 3-(5-(4-bromothiazol-2-yl)-1-(4-carbamoyl-2-methylphenyl)-1H-pyrrol-2-yl)propanoic acid; 3-(5-(5-bromothiophen-2-yl)-1-(2-methyl-4-(methylsulfonamido)phenyl)-1H-pyrrol-2-yl)propanoic acid; 3-(1-(4-acetamido-2-methylphenyl)-5-(4-(2-methyl-1H-imidazol-1-yl)phenyl)-1H-pyrrol-2-yl)propanoic acid; 3-(5-(4-chloro-2-methoxyphenyl)-1-(2-methyl-4-(methylsulfonamido)phenyl)-1H-pyrrol-2-yl)propanoic acid; 3-(1-(4-carbamoyl-2-methylphenyl)-5-(5-(4-hydroxyphenyl)thiophen-2-yl)-1H-pyrrol-2-yl)propanoic acid; 3-(5-(4-bromothiophen-2-yl)-1-(2-methyl-4-(methylsulfonamido)phenyl)-1H-pyrrol-2-yl) propanoic acid; 2-(1-(4-carbamoyl-2-methylphenyl)-5-(4-(thiophen-3-yl)phenyl)-1H-pyrrol-2-yl)acetic acid; 3-(5-(4-bromophenyl)-1-(2-methyl-4-(methylsulfonamido)phenyl)-1H-pyrrol-2-yl)propanoic acid; 3-(5-(5-(1H-imidazol-1-yl)furan-2-yl)-1-(4-carbamoyl-2-methylphenyl)-1H-pyrrol-2-yl)propanoic acid; 3-(5-(4-chloro-2-methoxyphenyl)-1-(2-methyl-4-sulfamoylphenyl)-1H-pyrrol-2-yl)propanoic acid; 3-(5-(4-methoxyphenyl)-1-(2-methyl-4-(pyridin-4-ylcarbamoyl)phenyl)-1H-pyrrol-2-yl)propanoic acid; 3-(1-(4-carbamoyl-2-methylphenyl)-5-(5-(2-methyl-1H-imidazol-1-yl)furan-2-yl)-1H-pyrrol-2-yl)propanoic acid; 3-(5-(5-bromofuran-2-yl)-1-(4-carbamoyl-2-methylphenyl)-1H-pyrrol-2-yl)propanoic acid; 3-(5-(4-bromophenyl)-1-(2-methyl-4-(sulfamoylamino) phenyl)-1H-pyrrol-2-yl)propanoic acid; 3-(5-(4-methoxyphenyl)-1-(2-methyl-4-(sulfamoylamino) phenyl)-1H-pyrrol-2-yl)propanoic acid; 3-(5-(4-chloro-2-methoxyphenyl)-1-(2-methyl-4-(sulfamoylamino) phenyl)-1H-pyrrol-2-yl)propanoic acid; and 3-(1-(4-carbamoyl-2-methylphenyl)-5-(4-methoxyphenyl)-1H-pyrrol-2-yl)butanoic acid.

8. The method of claim 1 comprising a pharmaceutical composition comprising a therapeutically effective amount of a compound according to claim 1 together with a pharmaceutically accepted carrier or excipient.

9. A method of treatment of pulmonary hypertension, ARDS, asthma, pneumonia, pulmonary fibrosis/interstitial lung diseases, cystic fibrosis, and chronic obstructive pulmonary disease (COPD) comprising administering a therapeutically effective amount of a compound of formula II or a pharmaceutically acceptable salt thereof:

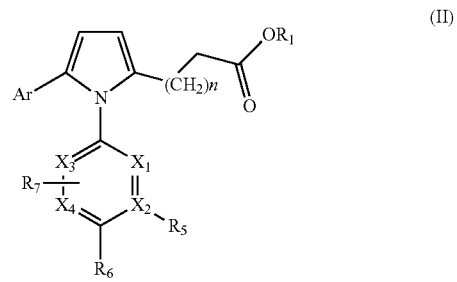

(II)

wherein
Ar is selected from the group consisting of aryl, substituted aryl, heteroaryl and substituted heteroaryl;
$R_1$ is selected from the group consisting of hydrogen, $C_1$-$C_6$ alkyl, $C_3$-$C_6$ cycloalkyl, aryl, substituted aryl, heteroaryl, and substituted heteroaryl;
$X_1$-$X_4$ is independently selected from the group consisting of C and N;
$R_5$ is selected from the group consisting of hydrogen, hydroxyl, halogen, $C_1$-$C_6$ alkyl, $C_3$-$C_6$ cycloalkyl, cyano, nitro, carbamoyl, $C_1$-$C_6$ alkylcarbamoyl, carboxyl, $C_1$-$C_6$ alkylhydroxy, sulfamoyl, $C_1$-$C_6$ alkylsulfamoyl, amino, $C_1$-$C_6$ alkylamino, $C_1$-$C_6$ dialkylamino, $C_1$-$C_6$ alkoxyl, and $C_3$-$C_6$ cycloalkoxyl;
$R_6$ is selected from the group consisting of halogen, hydroxyl, carbamoyl, substituted carbamoyl, $C_1$-$C_6$ alkylcarbamoyl, sulfamoyl, $C_1$-$C_6$ alkylsulfamoyl, $C_1$-$C_6$ alkyl, $C_3$-$C_6$ cycloalkyl, cyano, nitro, amino, $CF_3$, carboxyl, ureido, sulfamoylamino, 2-amino-2-oxoethyl, $C_1$-$C_6$ alkylamino, $C_1$-$C_6$ dialkylamino, arylamino, heteroarylamino, $C_1$-$C_6$ alkoxyl, $C_3$-$C_6$ cycloalkoxyl, 1H-imidazol-1-yl, and 2-methyl-1H-imidazol-1-yl;
or alternatively $R_5$ and $R_6$ together form a substituted or unsubstituted 5 or 6 membered heterocyclic ring containing up to 2 heteroatoms chosen from O, N or S;
$R_7$ is selected from the group consisting of hydrogen, hydroxyl, halogen, $C_1$-$C_6$ alkyl, $C_3$-$C_6$ cycloalkyl, cyano, nitro, carbamoyl, $C_1$-$C_6$ alkylcarbamoyl, sulfamoyl, $C_1$-$C_6$ alkylsulfamoyl, amino, $C_1$-$C_6$ alkylamino, $C_1$-$C_6$ dialkylamino, $C_1$-$C_6$ alkoxyl, and $C_3$-$C_6$ cycloalkoxyl;
n is 0-3;
wherein $R_5$ can be hydrogen only when at least one of $X_1$-$X_4$ is N;
and further wherein, $X_1$ and $X_3$ must be CH or N unless $R_5$ and $R_6$ together form a 5 or 6 membered heterocyclic ring or at least one of $X_1$-$X_4$ is N;
and wherein Ar excludes substituted or unsubstituted indazol-3-yl and substituted or unsubstituted 1H-pyrazolo[3,4-b]pyridyl;
with the following provisos:
proviso IIa: when all X are C and one of $R_5$, $R_6$, or $R_7$ are carboxyl, methylsulfonamido, or sulfamoyl, then Ar cannot be phenyl, substituted or unsubstituted phenyl-($C_1$-$C_3$)-alkyl, or phenyl-($C_2$-$C_6$)-alkenyl; and
proviso IIb: when all X are C and one of $R_5$, $R_6$, or $R_7$ are independently selected from the group consisting of halogen or methyl, then Ar cannot be 4-hydroxyphenyl or 4-$C_1$-$C_6$ acyl-oxy-phenyl; and
proviso IIc: when all X are C and $R_5$ is methyl, Cl, hydroxyl, trifluoromethyl and $R_6$ is methyl, methyoxy, carboxyethyl, Cl, or carboxypropyl, and n is 1, then Ar cannot be phenyl, 4-methyl-phenyl, 4-methoxy-phenyl, 4-halo-phenyl, or thiophen-yl; and proviso IId: when all X are C and $R_5$ and $R_6$ together form a heterocyclic ring and the resulting bicyclic ring system is benzo[d]thiazol substituted at the 2 position with $C_1$-$C_3$ alkyl, then Ar cannot be phenyl, 4-F-phenyl, 4-methoxy-phenyl, or thiophen-yl.

10. The method of claim 9 wherein:

Ar is selected from the group consisting of phenyl, substituted phenyl, thiophen-yl, substituted thiophen-yl, pyridinyl, substituted pyridinyl, thiazolyl, and substituted thiazolyl.

11. The method of claim 9 wherein the compound of formula II is selected from the group consisting of:

3-(5-(4-methoxyphenyl)-1-(1-oxoisoindolin-5-yl)-1H-pyrrol-2-yl)propanoic acid; 3-(1-(4-carbamoyl-3-methoxyphenyl)-5-(4-methoxyphenyl)-1H-pyrrol-2-yl)propanoic acid; 3-(1-(1H-benzo[d]imidazol-6-yl)-5-(4-methoxyphenyl)-1H-pyrrol-2-yl)propanoic acid; 3-(1-(4-carbamoyl-3-hydroxyphenyl)-5-(4-methoxyphenyl)-1H-pyrrol-2-yl)propanoic acid; 3-(1-(5-carbamoylpyridin-2-yl)-5-(4-methoxyphenyl)-1H-pyrrol-2-yl)propanoic acid; 3-(1-(3-chloro-4-hydroxyphenyl)-5-(4-methoxyphenyl)-1H-pyrrol-2-yl) propanoic acid; 3-(1-(6-carbamoylpyridin-3-yl)-5-(4-methoxyphenyl)-1H-pyrrol-2-yl)propanoic acid; 3-(5-(4-methoxyphenyl)-1-(1-oxo-1,3-dihydroisobenzofuran-5-yl)-1H-pyrrol-2-yl)propanoic acid; 3-(1-(1H-benzo[d]imidazol-6-yl)-5-phenyl-1H-pyrrol-2-yl)propanoic acid; 3-(1-(1,3-dioxoisoindolin-5-yl)-5-(4-methoxyphenyl)-1H-pyrrol-2-yl)propanoic acid; 3-(1-(1H-indazol-5-yl)-5-(4-methoxyphenyl)-1H-pyrrol-2-yl)propanoic acid; 3-(5-(4-methoxyphenyl)-1-(6-oxo-1,6-dihydropyridin-3-yl)-1H-pyrrol-2-yl)propanoic acid; 3-(1-(2-aminobenzo[d]thiazol-6-yl)-5-(4-methoxyphenyl)-1H-pyrrol-2-yl)propanoic acid; 3-(1-(4-hydroxy-3-methylphenyl)-5-(4-methoxyphenyl)-1H-pyrrol-2-yl)propanoic acid; 3-(1-(1H-indazol-6-yl)-5-(4-methoxyphenyl)-1H-pyrrol-2-yl)propanoic acid; 3-(1-(2-oxo-2,3-dihydro-1H-benzo[d]imidazol-5-yl)-5-phenyl-1H-pyrrol-2-yl)propanoic acid; 3-(5-(4-methoxyphenyl)-1-(2-oxo-2,3-dihydro-1H-benzo[d]imidazol-5-yl)-1H-pyrrol-2-yl)propanoic acid; 3-(5-(4-methoxyphenyl)-1-(quinolin-6-yl)-1H-pyrrol-2-yl)propanoic acid; 3-(1-(4-hydroxy-3,5-dimethylphenyl)-5-(4-methoxyphenyl)-1H-pyrrol-2-yl)propanoic acid; 3-(5-(4-(1H-imidazol-1-yl)phenyl)-1-(5-(1H-imidazol-1-yl)pyridin-2-yl)-1H-pyrrol-2-yl)propanoic acid; 3-(5-(4-(1H-imidazol-1-yl)phenyl)-1-(5-methyl-1H-benzo[d]imidazol-6-yl)-1H-pyrrol-2-yl)propanoic acid; 3-(1-(3-chloro-4-cyanophenyl)-5-(4-methoxyphenyl)-1H-pyrrol-2-yl)propanoic acid; 3-(1-(4-carbamoyl-3-chlorophenyl)-5-(4-methoxyphenyl)-1H-pyrrol-2-yl) propanoic acid; 3-(1-(isoquinolin-6-yl)-5-(4-methoxyphenyl)-1H-pyrrol-2-yl)propanoic acid; 3-(1-(isoquinolin-7-yl)-5-(4-methoxyphenyl)-1H-pyrrol-2-yl)propanoic acid; 3-(1-(1H-indol-5-yl)-5-(4-methoxyphenyl)-1H-pyrrol-2-yl)propanoic acid; 3-(1-(2-oxoindolin-5-yl)-5-phenyl-1H-pyrrol-2-yl) propanoic acid; 3-(1-(3-cyano-4-fluorophenyl)-5-(4-methoxyphenyl)-1H-pyrrol-2-yl)propanoic acid; 3-(1-(4-hydroxy-3-(methoxycarbonyl)phenyl)-5-phenyl-1H-pyrrol-2-yl)propanoic acid; 3-(1-(4-hydroxy-3-(methoxycarbonyl)phenyl)-5-(4-methoxyphenyl)-1H-pyrrol-2-yl)propanoic acid; 3-(1-(3-fluoro-4-hydroxyphenyl)-5-(4-methoxyphenyl)-1H-pyrrol-2-yl) propanoic acid; 3-(1-(4-hydroxy-3-(hydroxymethyl) phenyl)-5-phenyl-1H-pyrrol-2-yl)propanoic acid; 3-(1-(3-aminobenzo[d]isoxazol-6-yl)-5-(4-methoxyphenyl)-1H-pyrrol-2-yl)propanoic acid; 5-(2-(2-carboxyethyl)-5-phenyl-1H-pyrrol-1-yl)-2-hydroxybenzoic acid; 3-(1-(3-aminobenzo[d]isoxazol-5-yl)-5-(4-methoxyphenyl)-1H-pyrrol-2-yl)propanoic acid; 3-(1-(4-hydroxy-3-(hydroxymethyl)phenyl)-5-(4-methoxyphenyl)-1H-pyrrol-2-yl)propanoic acid; 3-(5-(4-(2-methyl-1H-imidazol-1-yl)phenyl)-1-(2-oxo-2,3-dihydrobenzo[d]oxazol-5-yl)-1H-pyrrol-2-yl) propanoic acid; and 3-(5-(4-(2-methyl-1H-imidazol-1-yl)phenyl)-1-(2-oxo-2,3-dihydrobenzo[d]oxazol-6-yl)-1H-pyrrol-2-yl)propanoic acid.

12. The method of claim 9 comprising a pharmaceutical composition comprising a therapeutically effective amount of a compound according to claim 9 together with a pharmaceutically accepted carrier or excipient.

13. A method of treatment of pulmonary hypertension, ARDS, asthma, pneumonia, pulmonary fibrosis/interstitial lung diseases, cystic fibrosis, and chronic obstructive pulmonary disease (COPD) comprising administering a therapeutically effective amount of a compound of formula III or a pharmaceutically acceptable salt thereof:

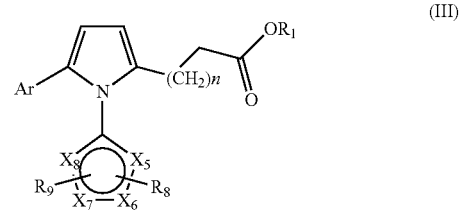

(III)

Ar is selected from the group consisting of aryl, substituted aryl, heteroaryl and substituted heteroaryl;

$R_1$ is selected from the group consisting of hydrogen, $C_1$-$C_6$ alkyl, $C_3$-$C_6$ cycloalkyl, aryl, substituted aryl, heteroaryl, and substituted heteroaryl;

$X_5$-$X_8$ are independently selected from the group consisting of N, C and S, wherein at least one X must be N or S;

$R_8$ and $R_9$ are independently selected from the group consisting of hydrogen, halogen, hydroxyl, carbamoyl, substituted carbamoyl, sulfamoyl, substituted sulfamoyl, $C_1$-$C_6$ alkyl, $C_3$-$C_6$ cycloalkyl, cyano, nitro, amino, $CF_3$, carboxyl, ureido, sulfamoylamino, 2-amino-2-oxoethyl, $C_1$-$C_6$ alkylamino, $C_1$-$C_6$ dialkylamino, arylamino, heteroarylamino, $C_1$-$C_6$ alkoxyl, $C_3$-$C_6$ cycloalkoxyl, aryl, aryloxyl, substituted aryl, heteroaryl, substituted heteroaryl, and null if $X_5$-$X_8$ are all N;

n is 0-3;

wherein Ar excludes substituted or unsubstituted indazol-3-yl and substituted or unsubstituted 1H-pyrazolo[3,4-b]pyridyl.

14. The method of claim 13 wherein Ar is selected from the group consisting of phenyl, substituted phenyl, thiophen-yl, substituted thiophen-yl, pyridinyl, substituted pyridinyl, thiazolyl, substituted thiazolyl, bicyclic aryl, substituted bicyclic aryl, bicyclic heteroaryl, and substituted bicyclic heteroaryl.

15. The method of claim 13 wherein the compound of formula III is selected from the group consisting of:

3-(1-(5-carbamoylthiophen-2-yl)-5-(4-methoxyphenyl)-1H-pyrrol-2-yl)propanoic acid;

3-(1-(5-carbamoylthiazol-2-yl)-5-(4-methoxyphenyl)-1H-pyrrol-2-yl)propanoic acid;

3-(1-(4-carbamoylthiophen-2-yl)-5-(4-methoxyphenyl)-1H-pyrrol-2-yl)propanoic acid;
3-(1-(5-carbamoylthiophen-3-yl)-5-(4-methoxyphenyl)-1H-pyrrol-2-yl)propanoic acid;
3-(1-(4-(2-amino-2-oxoethyl)thiazol-2-yl)-5-(4-methoxyphenyl)-1H-pyrrol-2-yl)propanoic acid; and 3-(1-(4-carbamoylthiazol-2-yl)-5-(4-methoxyphenyl)-1H-pyrrol-2-yl)propanoic acid.

16. A method of treatment of pulmonary hypertension, ARDS, asthma, pneumonia, pulmonary fibrosis/interstitial lung diseases, cystic fibrosis, and chronic obstructive pulmonary disease (COPD) comprising administering a therapeutically effective amount of a compound of formula IV or a pharmaceutically acceptable salt thereof:

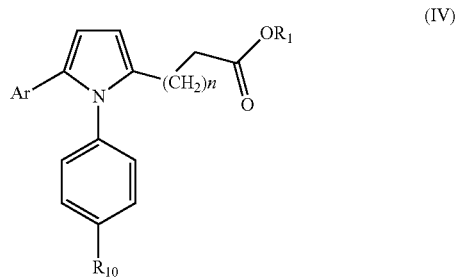

(IV)

Ar is selected from the group consisting of aryl, substituted aryl, heteroaryl and substituted heteroaryl;

$R_1$ is selected from the group consisting of hydrogen, $C_1$-$C_6$ alkyl, $C_3$-$C_6$ cycloalkyl, aryl, substituted aryl, heteroaryl, and substituted heteroaryl;

$R_{10}$ is hydroxyl, carbamoyl, ureido, sulfamoylamino, 2-amino-2-oxoethyl, hydroxyethyl, pyridin-3-ylamino, piridin-4-ylamino, 1-methylpyrrolidin-3-yloxy, trifluoroacetyl, imidazol-1-yl, acetamido, methylsulfamido, 2-oxooxazolidin-3-yl, 2-hydroxyethylamino, and methylcarbamoyl;

n is 0-3;

wherein Ar excludes substituted or unsubstituted indazol-3-yl and substituted or unsubstituted 1H-pyrazolo[3,4-b]pyridyl;

with the following proviso:

proviso IVa: when $R_{10}$ is hydroxyl or carbamoyl, Ar cannot be phenyl, 4-methyl-phenyl, 4-methoxy-phenyl, 4-halophenyl, or thiophen-yl when n is 0 or 1.

17. The method of claim 16 wherein Ar is selected from the group consisting of phenyl, substituted phenyl, thiophen-yl, substituted thiophen-yl, pyridinyl, substituted pyridinyl, thiazolyl, and substituted thiazolyl.

18. The method of claim 16 wherein Ar is selected from phenyl, 3-methoxyphenyl, 4-methoxyphenyl, 4-chloro-2-methoxyphenyl, 2-methoxy-4-(2-methyl-1H-imidazol-1-yl)phenyl, 1H-imidazol-1-yl-phenyl, 2-methyl-1H-imidazol-1-yl-phenyl, 1H-imidazol-1-yl-thiophen-2-yl, and 2-methyl-1H-imidazol-1-yl-thiophen-2-yl.

19. The method of claim 16 wherein the compound of formula IV is selected from the group consisting of: 3-(1-(4-carbamoylphenyl)-5-(3-methoxyphenyl)-1H-pyrrol-2-yl)propanoic acid; 3-(5-phenyl-1-(4-ureidophenyl)-1H-pyrrol-2-yl)propanoic acid; 3-(5-phenyl-1-(4-(sulfamoylamino)phenyl)-1H-pyrrol-2-yl)propanoic acid; 3-(1-(4-(2-amino-2-oxoethyl)phenyl)-5-phenyl-1H-pyrrol-2-yl)propanoic acid; 3-(1-(4-(2-amino-2-oxoethyl)phenyl)-5-(4-methoxyphenyl)-1H-pyrrol-2-yl)propanoic acid; 3-(5-(4-methoxyphenyl)-1-(4-(methylcarbamoyl)phenyl)-1H-pyrrol-2-yl)propanoic acid; 3-(1-(4-hydroxyphenyl)-5-(4-(2-methyl-1H-imidazol-1-yl)phenyl)-1H-pyrrol-2-yl)propanoic acid; 2-(1-(4-hydroxyphenyl)-5-(4-methoxyphenyl)-1H-pyrrol-2-yl)acetic acid; 3-(5-(4-(1H-imidazol-1-yl)phenyl)-1-(4-hydroxyphenyl)-1H-pyrrol-2-yl)propanoic acid; 3-(5-(5-(1H-imidazol-1-yl)thiophen-2-yl)-1-(4-hydroxyphenyl)-1H-pyrrol-2-yl)propanoic acid; 3-(1-(4-(1-hydroxyethyl)phenyl)-5-phenyl-1H-pyrrol-2-yl)propanoic acid; 3-(1-(4-hydroxyphenyl)-5-(4-(2-methyl-1H-imidazol-1-yl)thiophen-2-yl)-1H-pyrrol-2-yl)propanoic acid; 3-(5-(4-methoxyphenyl)-1-(4-(pyridin-3-ylamino)phenyl)-1H-pyrrol-2-yl)propanoic acid; 3-(5-(4-methoxyphenyl)-1-(4-(1-methylpyrrolidin-3-yloxy)phenyl)-1H-pyrrol-2-yl)propanoic acid; 3-(5-(4-methoxyphenyl)-1-(4-(pyridin-4-ylamino)phenyl)-1H-pyrrol-2-yl)propanoic acid; 3-(5-phenyl-1-(4-(2,2,2-trifluoroacetyl)phenyl)-1H-pyrrol-2-yl)propanoic acid; 3-(5-(4-methoxyphenyl)-1-(4-(2,2,2-trifluoroacetyl)phenyl)-1H-pyrrol-2-yl)propanoic acid; 3-(1-(4-(1H-imidazol-1-yl)phenyl)-5-(4-methoxyphenyl)-1H-pyrrol-2-yl)propanoic acid; 3-(5-(4-chloro-2-methoxyphenyl)-1-(4-hydroxyphenyl)-1H-pyrrol-2-yl)propanoic acid; 3-(1-(4-acetamidophenyl)-5-(4-chloro-2-methoxyphenyl)-1H-pyrrol-2-yl)propanoic acid; 3-(1-(4-carbamoylphenyl)-5-(4-chloro-2-methoxyphenyl)-1H-pyrrol-2-yl)propanoic acid; 3-(5-(4-chloro-2-methoxyphenyl)-1-(4-(methylsulfonamido)phenyl)-1H-pyrrol-2-yl)propanoic acid; 3-(5-(4-(2-methyl-1H-imidazol-1-yl)phenyl)-1-(4-(2-oxooxazolidin-3-yl)phenyl)-1H-pyrrol-2-yl)propanoic acid; 3-(5-(4-(2-methyl-1H-imidazol-1-yl)thiophen-2-yl)-1-(4-(methylsulfonamido)phenyl)-1H-pyrrol-2-yl)propanoic acid; 3-(1-(4-acetamidophenyl)-5-(4-(2-methyl-1H-imidazol-1-yl)phenyl)-1H-pyrrol-2-yl)propanoic acid; 3-(5-(2-methoxy-4-(2-methyl-1H-imidazol-1-yl)phenyl)-1-(4-(methylsulfonamido)phenyl)-1H-pyrrol-2-yl)propanoic acid; 3-(1-(4-acetamidophenyl)-5-(4-(2-methyl-1H-imidazol-1-yl)thiophen-2-yl)-1H-pyrrol-2-yl)propanoic acid; 3-(5-(4-(2-methyl-1H-imidazol-1-yl)phenyl)-1-(4-(methylsulfonamido)phenyl)-1H-pyrrol-2-yl)propanoic acid; 3-(1-(4-(2-hydroxyethylamino)phenyl)-5-(4-(2-methyl-1H-imidazol-1-yl)phenyl)-1H-pyrrol-2-yl)propanoic acid; and 3-(1-(4-hydroxyphenyl)-5-(5-(2-methyl-1H-imidazol-1-yl)thiophen-2-yl)-1H-pyrrol-2-yl)propanoic acid.

* * * * *